US011203629B2

(12) United States Patent
Heiland

(10) Patent No.: US 11,203,629 B2
(45) Date of Patent: Dec. 21, 2021

(54) LAMP CONSTRUCTS

(71) Applicant: Immunomic Therapeutics, Inc, Rockville, MD (US)

(72) Inventor: Teri Heiland, New Market, MD (US)

(73) Assignee: Immunomic Therapeutics, Inc., Rockville, MD (US)

( * ) Notice: Subject to any disclaimer, the term of this patent is extended or adjusted under 35 U.S.C. 154(b) by 0 days.

(21) Appl. No.: 16/607,082

(22) PCT Filed: Apr. 22, 2018

(86) PCT No.: PCT/US2018/028753
§ 371 (c)(1),
(2) Date: Oct. 21, 2019

(87) PCT Pub. No.: WO2018/195527
PCT Pub. Date: Oct. 25, 2018

(65) Prior Publication Data

US 2020/0377570 A1 Dec. 3, 2020

Related U.S. Application Data

(60) Provisional application No. 62/549,033, filed on Aug. 23, 2017, provisional application No. 62/549,119, filed on Aug. 23, 2017, provisional application No. 62/488,741, filed on Apr. 22, 2017.

(51) Int. Cl.
*A61K 39/00* (2006.01)
*C07K 14/705* (2006.01)
*A61P 35/00* (2006.01)

(52) U.S. Cl.
CPC .. *C07K 14/70596* (2013.01); *A61K 39/00115* (2018.08); *A61P 35/00* (2018.01); *A61K 2039/55522* (2013.01); *A61K 2039/57* (2013.01); *A61K 2039/575* (2013.01); *A61K 2039/6031* (2013.01); *C07K 2319/02* (2013.01); *C07K 2319/03* (2013.01); *C07K 2319/40* (2013.01)

(58) Field of Classification Search
None
See application file for complete search history.

(56) References Cited

U.S. PATENT DOCUMENTS

2007/0269457 A1 11/2007 Niazi et al.
2016/0185831 A1 * 6/2016 Hearl .................... A61K 39/35 424/275.1

FOREIGN PATENT DOCUMENTS

WO 2011046996 A2 4/2011
WO 2015200357 A2 12/2015

OTHER PUBLICATIONS

Arruda et al. Dendritic Cell-Lysosomal-Associated Membrane Protein (LAMP) and LAMP-1-HIV-1 Gag Chimeras Have Distinct Cellular Trafficking Pathways and Prime T and B Cell Responses to a Diverse Repertoire of Epitopes. The Journal of Immunology, 2006, 177: 2265-2275.*

De Arruda et al. DNA vaccine encoding human immunodeficiency virus-1 Gag, targeted to the major histocompatibility complex II compartment by lysosomal-associated membrane protein, elicits enhanced long-term memory response. Immunology. May 2004; 112(1):126-33.*

Zhang et al. (2014) Enhancement of Antitumor Immunity Using a DNA-Based Replicon Vaccine Derived from Semliki Forest Virus. PLoS ONE 9(3): e90551.*

International Preliminary Report of Patentability dated Oct. 31, 2019 and received in PCT /US2018/028753.

Arruda et al., "Dendritic Cell-Lysosomal-Associated Membrane Protein (LAMP) and LAMP-1-HIV-1 Gag Chimeras Have Distinct Cellular Trafficking Pathways and Prime T and B Cell Responses to a Diverse Repertoire of Epitopes", The Journal of Immunology, vol. 177, No. 4, pp. 2265-2275, (2006).

Carlssons, et al., "Structure of Human Lysosomal Membrane Glycoprotein 1, Assignment of Disulfide Bonds and Visualization of its Domain Arrangement", J. Biol. Chem, vol. 264, No. 34, pp. 20526-205311, Retrieved from the Internet:URL:http://www.jbc.org/content/264/34/2052, (1989).

Godinho et al., "Regulation of HIV-Gag Expression and Targeting to the Endolysosomal/Secretory Pathway by the Luminal Domain of Lysosomal-Associated Membrane Protein (LAMP-1) Enhance Gag-Specific Immune Response", Plos One, vol. 9, Issue 6, p. e99887, (2014).

Wimer-Mackin et al., "Transmembrane Domain Mutations Influence the Cellular Distribution of Lysosomal Membrane Glycoprotein A", Biochemical and Biophysical Research Communications, vol. 229, No. 2, pp. 472-478, (1996).

Written Opinion and International Search Report dated Jun. 26, 2018 in PCT/US2018/028753.

Zhou et al., "Lamp-2a Facilitates MHC Class II Presentation of Cytoplasmic Antigens", Immunity, vol. 22, No. 5, pp. 571-581 (2005).

(Continued)

*Primary Examiner* — Nianxiang Zou
(74) *Attorney, Agent, or Firm* — McNeill Baur PLLC

(57) ABSTRACT

The present invention provides improved LAMP Constructs comprising specific fragments of the LAMP lumenal domain to deliver antigens to immune cells for enhanced processing. These LAMP Constructs can be used for the treatment of disease and in particular, allergies, infectious disease, diabetes, hyperproliferative disorders and/or cancer. The improved LAMP Constructs allow for presentation of properly configured three dimensional epitopes for production of an immune response when administered to a subject. The improved LAMP Constructs can be multivalent molecules, and/or can be provided as part of a multivalent vaccine containing two or more LAMP Constructs. The improved LAMP Constructs as described herein can also be used to generate antibodies when administered to a non-human vertebrate.

23 Claims, 42 Drawing Sheets

Specification includes a Sequence Listing.

(56) References Cited

OTHER PUBLICATIONS

Official foreign office action issued for the corresponding EP Patent Application No. 18726576.4 dated Nov. 16, 2020.

* cited by examiner

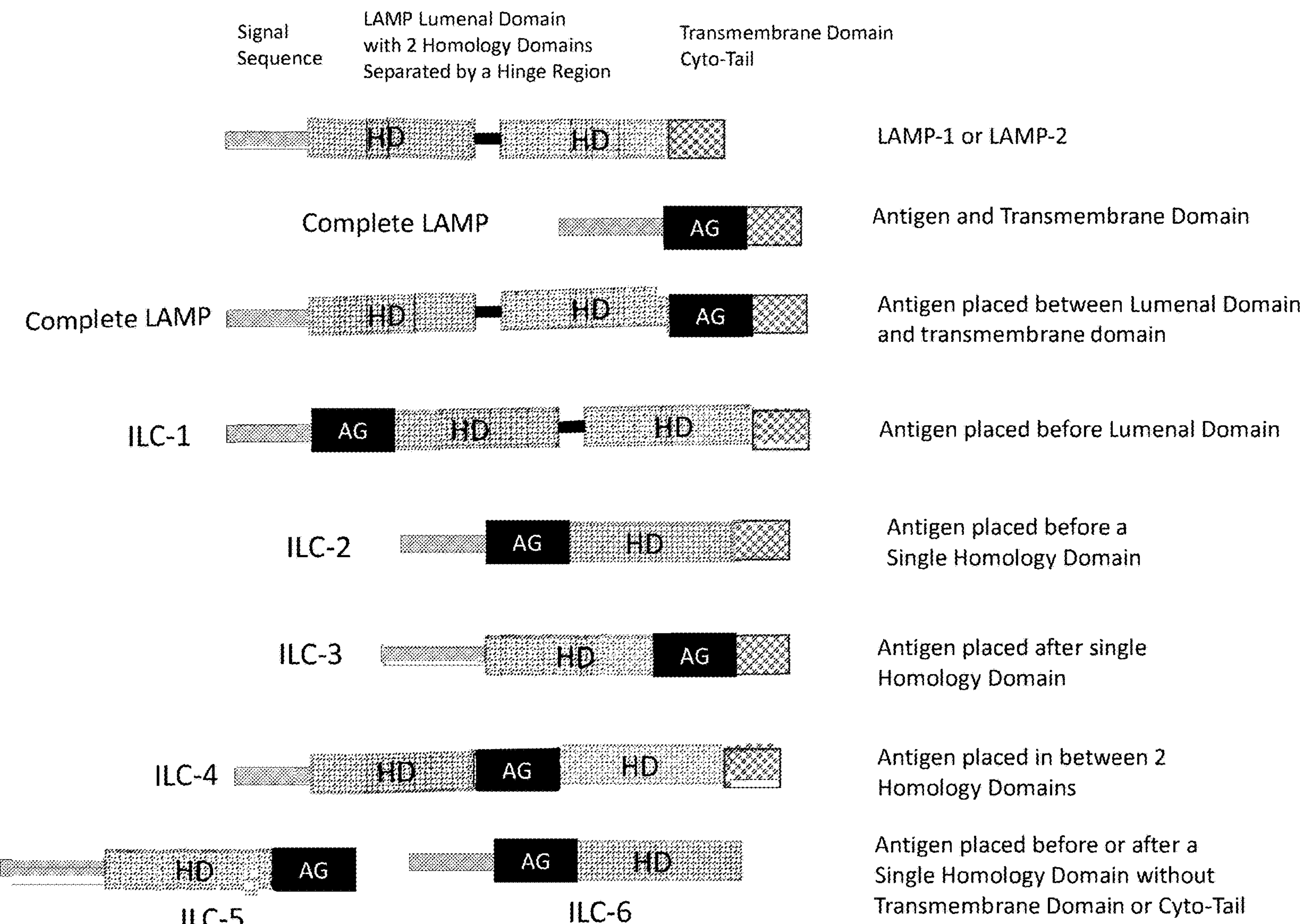
Figure 1
Signal Sequence
LAMP Lumenal Domain with 2 Homology Domains Separated by a Hinge Region
Transmembrane Domain Cyto-Tail
HD
HD
LAMP-1 or LAMP-2
Complete LAMP
AG
Antigen and Transmembrane Domain
Complete LAMP
HD
HD
AG
Antigen placed between Lumenal Domain and transmembrane domain
ILC-1
AG
HD
HD
Antigen placed before Lumenal Domain
ILC-2
AG
HD
Antigen placed before a Single Homology Domain
ILC-3
HD
AG
Antigen placed after single Homology Domain
ILC-4
HD
AG
HD
Antigen placed in between 2 Homology Domains
HD
AG
ILC-5
AG
HD
ILC-6
Antigen placed before or after a Single Homology Domain without Transmembrane Domain or Cyto-Tail

Figure 2A

| Gene Name Accession No. | Alternative Names | SEQ ID NO. | Orthologs | Signal Sequence | Lumenal Domain: First Homologous domain | Lumenal Domain: Hinge Region | Lumenal Domain: Second Homologous Domain | Transmembrane Domain | Cytoplasmic Tail |
|---|---|---|---|---|---|---|---|---|---|
| h. LAMP-1 NP_005552.3 | CD107a; LAMPA; LGP120 | 1 | SEQ ID NO: 6-24 | 1-28 | 29-194 | 195-227 | 228 to 381 or 382 | 382 or 383 to 405 | 406-417 |
| h. LAMP-2 NP_002285.1 | CD107b; LAMPB; LGP110 | 2 | SEQ ID NO:25-43 | 1-28 | 29-192 | 193-228 | 229-375 | 376-399 | 400-410 |
| h. LAMP-3 NP_055213.2 | CD208; DC LAMP; DC-LAMP; DCLAMP; TSC403 | 3 | SEQ ID NO:44-55 | 1-27 | 28-219 | 220-234 | 235-381 | 382-402 | 403-416 |
| LIMP-2 Q14108 | AMRF; EPM4; LGP85; CD36L2; HLGP85; LIMPII; SR-BII; SCARB2 | 4 | SEQ ID NO:56-66 | *5-27 Transmem. *Uncleavable | 28-433 | | | 434-459 | 460-478 |
| h. Endolyn NP_006007.2 | Sialomucin CD164 MUC-24 | 5 | SEQ ID NO:73-79 | 1-23 | 24-162 | | | 163-183 | 184-197 |
| Macrosailin NP_001242.2 | CD68 | 80 | SEQ ID NO: 81-92 | 1-21 | 22-319 | | | 320-344 | 345-354 |

Figure 2A cont.

| | | | | | | | |
|---|---|---|---|---|---|---|---|
| LAMP5<br>NP 036393 | BD-LAMP | 93 | SEQ ID NO: 94-101 | 1-29 | 30-235 | 236-256 | 257-280 |
| h. LIMBIC<br>NP_002329.2 | LSAMP<br>IGLON3 | 67 | SEQ ID NO: 68-72 and 102-113 | 1-28 | 29-315 | 316-338 | No tail |

FIGURE 3: HUMAN LAMP-1 ALIGNMENT WITH ORTHOLOGOUS SEQUENCES
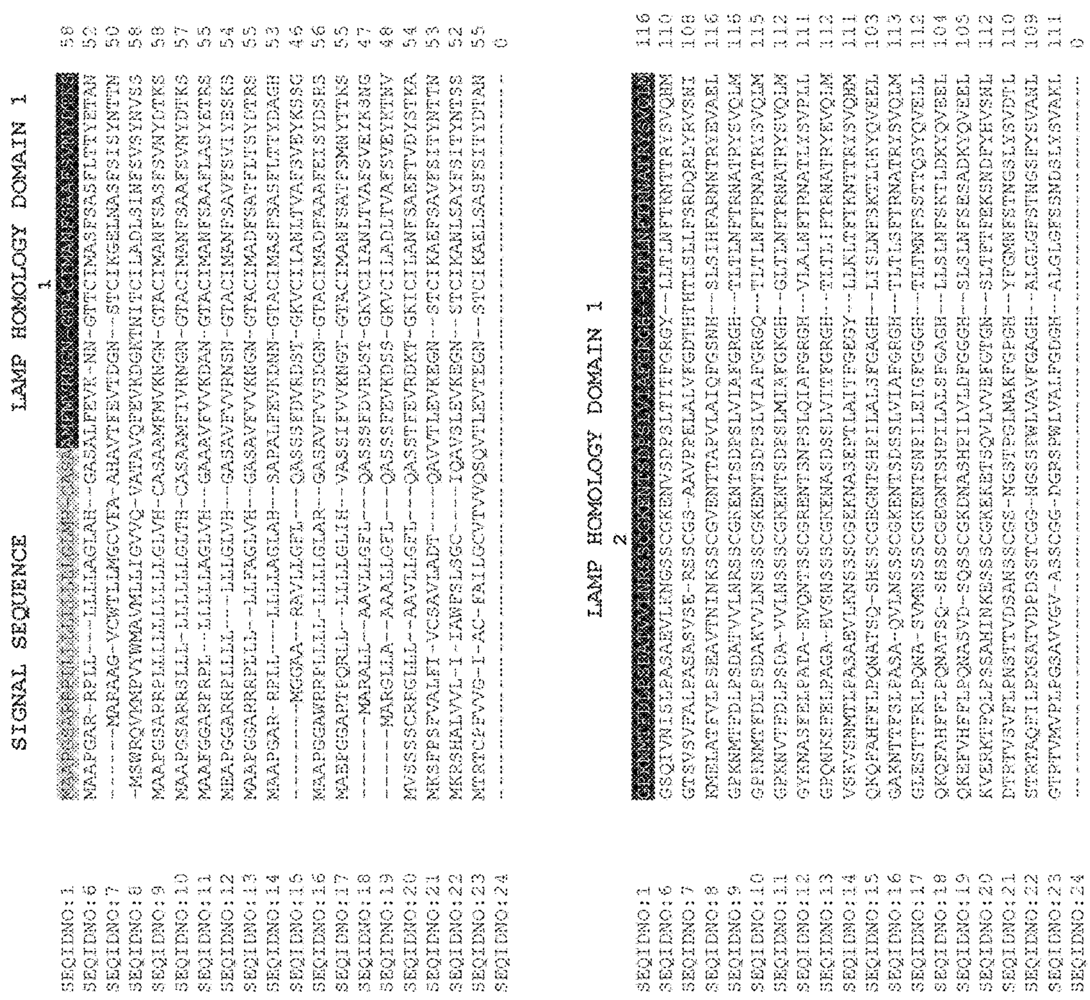

FIGURE 3 (cont.)

LAMP HOMOLOGY DOMAIN 1

```
                                                       3
SEQIDNO:1     SFVYNLSDTHLFPNASSK-EIKT-VESITDIRADIDKKYRCVSGTQVHMNN-VTVTLHDA   173
SEQIDNO:6     YFTYNLSDTEHFPNAISK-EIYT-MDSTTDIKADINKAYRCVSDIRVYMKN-VTVVLRDA   167
SEQIDNO:7     SLQYNLSDGDIFPQSSSAGVQSVMASVSEIMSARLNSTYRCVSSSSISLSAAVNLTLSGV   168
SEQIDNO:8     VMSYNLSDKIIFPNASENGTKTV-STNKTAVLAENDTVYKCMNPHLIRMDN-ANATFHDI   174
SEQIDNO:9     SFVYNLSDTHLFPNASSK-EIKT-VESITDIRADIDKKYRCVSGTQVHMNN-VTVTLHDA   173
SEQIDNO:10    SFVYNLSDTHLFPNASSK-EIKT-VESITDIRADIDKKYRCVSGTQVHMNN-VTVTLHDA   172
SEQIDNO:11    SFIYNLSDTQIFPNASSK-ETKT-VESATDIRADINKKYRCVSNTQIHMHN-VTVTFHDV   169
SEQIDNO:12    SFVYNLSDSDLFPNASSK-DIKT-VGSTTDIKADIDKRYRCVSDSKVPMGN-VTVTLQDA   168
SEQIDNO:13    RFAYNLSDTDTFPNSSST-GVKT-VESATDIKADINKTYRCVSETQVNMDN-VTVTLRDA   169
SEQIDNO:14    YFTYNLSDTQFFPNASSK-GEDT-VDSTTDIKADINKTYRCVSDIRVYMKN-VTIVLWDA   168
SEQIDNO:15    TFHYNLSDETLFPNATEG-KVMV-ATQKSVIQARIGTEYRCINSKYVRMKH-VNITFSNV   160
SEQIDNO:16    TLVYNLSDAEFFPSASSK-GTKT-VAASTDIRADLNTKYRCVSNSQVHLLN-VTVTLGNA   170
SEQIDNO:17    SFSYNLSDATLFPNASKGSEESS-VKSKTDIQADIRKKYRCVSSNRITMSN-VTIVLSDV   170
SEQIDNO:18    TFHYNLSDETLFPNASEG-KVME-VTQKSVIQARIGTEYRCINSKYIYIRH-VNITFSNV   161
SEQIDNO:19    VFHYNLSDATLFPNSSTG-GMKT-VSHKSIIQAHMGTQYRCINSKHINMKN-VNVTFSNV   162
SEQIDNO:20    TFSYNLSDSSFFPNSSG--GQRE-VSRAGDIQANINTTYRCRSNHRVNMTN-VTVLFSNV   168
SEQIDNO:21    FLRYNLSDASLFPEANSSGPVDFELSASVGIWAPTNTTYRCLSPTTITITR-PSVTFSEM   169
SEQIDNO:22    TLQYNLSDASVFPDANSSGVVTV-VSSSVGIWAAVNTTYRCLSSVLFQVGG-ATVTFSDM   167
SEQIDNO:23    TLQYNLSDVSNFPEANSTDVVTVE-TTSVGMVARVNTTYRCISASPVIVGG-ATVTFSNV   169
SEQIDNO:24    ------------------------------------------------------------   0
```

```
              LAMP HOMOLOGY DOMAIN 1              Hinge Region
                          4
SEQIDNO:1     TIQAYLSNSSFSRGETRCEQDRPSPTTAPPAP-----------PSP-SP---SPVPKSPS   218
SEQIDNO:6     TIQAYLSSGNFSKEETHCTQDGPSPTTGP--------------PSP-SP---PLVPTNPT   209
SEQIDNO:7     QMEAYMSSANLSADESVCSADQPSTTVAPPPSTT---------------TSPPPIPPVPE   213
SEQIDNO:8     RLEAYLKQSNFSQKVSTCSEDITPTSAPA-PV--T-----T------TAPVPAP-VPDPP   219
SEQIDNO:9     TIQAYLSNSSFSRGETRCEQDRPSPTTAPPAP-----------PSP-SP---SPVPESPS   218
SEQIDNO:10    TIQAYLSNSSFSREETRCEQDRPSPTTAPPAP-----------PSP-SP---SPVPESPS   217
SEQIDNO:11    TIQAYLANSNFSKEETRCEQDGPFPTTAPPPP-----------PHP-SP---SPAPESPS   214
SEQIDNO:12    TIQAYLWNNSFSQAESRCRQDMPSPTTAPPAPPVP-----PSPPSP-SP---PPKPESPS   219
SEQIDNO:13    AIQAYLSSSNFSREETRCEQDLPT----------P-----TTPPQP-AP---TPAPASPA   210
SEQIDNO:14    TIQAYLPSSNFSKEETRCPQDQPSPTTGP--------------PSP-SP---PLVPTNPS   210
SEQIDNO:15    TLEAYPTNDTFSANKTECREDMVSTTTVAPTTPKH-----ATSQVPTTSPAPTAAPSSPA   215
SEQIDNO:16    TIQAYLANNSFSQQETRCEQDKPSP-------PTP-----TAPPTP-TP---TPAPTSPV   214
SEQIDNO:17    TIQAYLSNNTFSKEETRCSQDTPSPSPVPTTHPTT-----IPVPTP-TPTRPPTPAEIPP   224
SEQIDNO:18    TLEAYPTNGTFSTNKTECSEDMVSTTTVAPTTPKH-----ITSQVPATSPAPTAAPSNPA   216
SEQIDNO:19    TLEAYLTNGTLSVNKTECAEDRVSTTTMVPTTPKQ-----TTSQSPTTGPAPTS-PPNPT   216
SEQIDNO:20    TLEAYLPNNAFSKNDSVCAEDKTSTVA--PPITTH-----IPTTTSLAPPT-PPPTDTPK   220
SEQIDNO:21    KLEAYMPGNDFSPAERVCAADQTTTGAPTTTT---------SAATP-TT-PSPTPAGTPE   218
SEQIDNO:22    PLEAYMPGNDLSPRESFCAADQTTTAPPTTTAAP----TTTAATTM-AP-PAPTPPGTPV   221
SEQIDNO:23    TMEAFMTGEDLSPNESVCTADQSFTTAPPPPPS--------TTTAA-PA-PVPTPPGTPS   219
SEQIDNO:24    -------------MVQICRVQSWFVGVTPLLIFATVLHQGPATVAP-PTPAPHKEPGRPE   46
                               *  :                                  *
```

FIGURE 3 (cont.)

```
                    Hinge          LAMP HOMOLOGY DOMAIN 2

                                1                                         2
SEQIDNO:1     VDKYNVSGTNGT-CLLASMGLQLNLTYE-RKDNTTVTRLLNINPNKTSASGSCGAHLVTL  276
SEQIDNO:6     VSKYNVTGNNGT-CLLASMALQLNITYL-KKDNKTVTRAFNISPNDT-SSGSCGINLVTL  266
SEQIDNO:7     KGNYSVTDGNGTVCVLALMGLQLNITHT-TTQNQSVSELMNLQPNQTTVSGSCGVTESSL  272
SEQIDNO:8     VVQYSVNRSSEP-CLLAKVGLQMNITYT-TKDGKNGSYVFNIESKGVTVDGNCTNTTAYL  277
SEQIDNO:9     VDKYNVSGTNGT-CLLASMGLQLNLTYE-RKDNTTVTRLLNINPNKTSASGSCGAHLVTL  276
SEQIDNO:10    VDKYNVSGTNGT-CLLASMGLQLNLTYE-RKDNTTVTRLLNINPNKTLASGSCGAHLVTL  275
SEQIDNO:11    VHKYNVSGANGT-CLLASMGLQLNVTYK-KKDNTTVVKVVSINPNKTTAGGSCGAQLVTL  272
SEQIDNO:12    VSRYNVSDGNAT-CLLASMGLQLNLTYV-HRDNATVTRVFNINPNKTKPSGHCGAQQVTL  277
SEQIDNO:13    VFRYNVSGSNGT-CLLASMGLQLNVTYR-RVDNKTVTREFNVNPNKTTFGGNCSATLATL  268
SEQIDNO:14    VSKYNVTGDNGT-CLLASMALQLNITYM-KKDNTTVTRAFNINPSDK-YSGTCGAQLVTL  267
SEQIDNO:15    VGKYNVTGANGT-CVLASMGLQLNITYV-KKDEKMGLDLLNFIPHNTSASGMCESTSAFL  273
SEQIDNO:16    VSRYNVSGANGT-CLLASMGLQLNVTYR-TKDNTTVTRGLNINPNKTTFGGSCSAQLVTL  272
SEQIDNO:17    IFKYNVSDANGT-CLLASMGLQLNITYA-KKDNSSARIIWNINPNKTVAGGSCSPQVAIL  282
SEQIDNO:18    VGKYNVTGANGT-CVLASMGLQLNITYL-KKDGKTGLDLLNFVPHNTNASGTCENTSAFL  274
SEQIDNO:19    VGKYNVTGPNGT-CVLAYMGLQLNITYQ-QKDEKMGLDLLNFVPHNTTSSGRCDNTSALL  274
SEQIDNO:20    IGRYNVTGLHGI-CLLATMGLQVNVTYS-TKNKTSKSELLNLPP-TAEVSGTCENSSITL  277
SEQIDNO:21    QGSYSVKNASGTVCLMAKMGVQLNVSYFSQSQNKTVQELLNLTPNLTSSSGLCGGTNATL  278
SEQIDNO:22    RGTYSVVNGNDTTCLLAQMGLQLNVSYFSRSQNKTVQSLVNLTPNLTNSTGSCEKGSATL  281
SEQIDNO:23    QGSYSVSNSNGTVCLLARMALQLNISHFSASQNKTIQEVVNLLPNQTTSSGSCDPTSATL  279
SEQIDNO:24    RGYYNVTNHNGTICLMAYMGLQLNISYNSTSQKKVVQDVMNLQPNLTKHSGLCDSDIASL  106
                 *,*        *::* :.:*:*:::     :        ..         * *     *

                                  LAMP HOMOLOGY DOMAIN 2

SEQIDNO:1     ELHS-EGSTVLLFQFGMNASSSRFFLQGIQLNTTLP-DARDPAFKAANGSLRALQATVGN  334
SEQIDNO:6     KVEN-K-NRALELQFGMNASSSLFFLQGVRLNMTLP-DALVPTFSISNHSLKALQATVGN  323
SEQIDNO:7     RLSD--ETTNLTFSFTMNSTTQKYYLSAVSVSALWP-DMS-VVFEAGNTSLSALQCSVGR  328
SEQIDNO:8     SLST-GS-IDLPENFTLNSSLEVFYLDGVSLSTGLPADANDTHFEAANSSLNYMQTNVHK  335
SEQIDNO:9     ELHS-EGSTVLLFLFGMNASSSRFFLQGIQLNTTLP-DARDPAFKAANGSLRALQATVGN  334
SEQIDNO:10    ELHS-EGSTVLLFQFGMNASSSRFFLQGIQLNTTLP-DARDPAFKAANSSLRALQATVGN  333
SEQIDNO:11    ELRS-ESVTLLAFQFGMNASTSRFFLQGIQLNMTLP-DARDPTFKAGNNSLRALQATIGN  330
SEQIDNO:12    ELQS-ERSTVLVFQFGMNASSGQYFLQGVLLNTTLP-DAREPAFSASNSSLRALQATLGN  335
SEQIDNO:13    ELHS-ENLLLLALQFVMNESSSRVFLQGVQLNLTLP-DAKEGSFTATNSSLRALQATAGN  326
SEQIDNO:14    KVGN-K-SRVLELQFGMNATSSLFFLQGVQLNMTLP-DAIEPTFSTSNYSLKALQASVGN  324
SEQIDNO:15    NLAF-EK-TKITFHFVLNASSEKFFLQGVNVSTTLPSEAKAPTFEASNDSMSESRATVGN  331
SEQIDNO:16    ELQG-ESLRLLALQFALNTSSSRVFLQGVQLNMTLP-DARDPSFSAANSSLRALQATAGN  330
SEQIDNO:17    ELQT-EN-STLAFSFGMNATTSKFFLREIRFHKFFP-DAKDPAFGAVNSSLKELQATVGN  339
SEQIDNO:18    NLAF-EK-TKITFHFVLNASSEKFFLQGVNVSTTLPSEAKAPMFEASNDSMSELRATVGN  332
SEQIDNO:19    NLTF-EK-TRVIFQFALNATAEKFFLQGVSVSTTLPSEAKNPKFEATNNSMSELRASVGN  332
SEQIDNO:20    NLTS-ES-TSLSFQFSQNTSTEKYFLQGIIVTANLPPEATEKNISYSNHTLNALKTSVGK  335
SEQIDNO:21    VLAQ-EETTVLSFLFTVNSTSNKYHLSGITLQANWT-DMM-SPFSASNTSLDYLRSSLGH  335
SEQIDNO:22    ILTQ-Q-TTILIFTFSINSTSSKYHLSGLSLQANWS-DMA-AAFSASNASLSYLRSTFGH  337
SEQIDNO:23    VLTQ-ANATNLSFLFTLNSTSNPYHLTGLSVVAAWS-DMT-APFNTSNSSLDYQRGSLGR  336
SEQIDNO:24    NLTVDAVKTNLTFVFTMNSTSNKYHLSEVTVSAAWP-EMK-EPVSVHNSSLDYLRGTVGY  164
               :          : : *  * :    ,* : .         :     .    * ::   : ,
```

FIGURE 3 (cont.)

```
                     LAMP HOMOLOGY DOMAIN 2           Trans. Domain
              3                                 4
SEQIDNO:1     SYKCNAEEHVRVTKAFSVNIFKVWVQAFKVEGGQFGSVEECLLDENSMLIPIAVGGALAG  394
SEQIDNO:6     SYKCNTEEHIFVSKMLSLNVFSVQVQAFKVDSDRFGSVEECVQDGNNMLIPIAVGGALAG  383
SEQIDNO:7     SYVCSAQQMLSVTPVFSINTFRLQLQPFNITANRFSTAEECRVDQENMLIPIIVGAALAG  388
SEQIDNO:8     SFKCNSKQTLQITDPFTVNTYHLQVQAFNSD-NTFASAVECSLDENGMLVPIVVGAALAG  394
SEQIDNO:9     SYKCNAEEHVRVTKAFSVNIFKVWVQAFKVEGGQFGSVEECVLDENNMLIPIAVGGALAG  394
SEQIDNO:10    SYKCNAEEHVRVTKAFSVNIFKVWVQAFKVEGGQFGSVEECLLDENNMLIPIAVGGALAG  393
SEQIDNO:11    SYKCNAGEHVQVTEAFSVNIIKVWVQAFQVQGDKFGSVEECQLDENSMLIPIAVGGALAG  390
SEQIDNO:12    SYKCNSEEHVRVTPAFSLSIFKVWVQAFQVKGDRFGSVEECLLDQDSMLIPIAVGGALAG  395
SEQIDNO:13    SYKCNAEQRLPVTSSFSLNMFRVWLQAFRVDGDKFGPVEECQLDENSMLIPIAVGGALAG  386
SEQIDNO:14    SYKCNSEEHIFVSKALALNVFSVQVQAFRVESDRFGSVEECVQDGNNMLIPIAVGGALAG  384
SEQIDNO:15    SYKCSAEENFQVTDKALVNVFNVQVQAFKVDGDKFGAMEECQLDENNMLIPIIVGAALAG  391
SEQIDNO:16    SYKCRSEQRLQVTEAFALNVFQVRVQAFRVDGDKFGPAEECQLDENSMLIPIAVGGALAG  390
SEQIDNO:17    SYKCNAEENVHVTDGFSVNIFRVRVQAFKVEGDKFGSVEECLLDENNMLIPIAVGGALAG  399
SEQIDNO:18    SYKCSAEENLQVTDKALVNVFNVQVQAFKVDGDRFGAVEECQLDENNMLIPIIVGAALAG  392
SEQIDNO:19    SYKCSSEENLQVTDQALVNVFNVQVQIFKIDGDKFGPVEECQLDENNMLIPIIVGAALAG  392
SEQIDNO:20    SYKCIAEESIWISGKAAVNIFNIQLQAFKIPGDKFGAVEECQLDENNMLIPIIVGAALAG  395
SEQIDNO:21    SYMCNAEQTLPVVSTFSINMFELQVQPFGVTSTQFASAEVCQIDQDQMLIPIIVGAALAG  395
SEQIDNO:22    SYMCNAEQILAVTPVFSLNTFSLQIQPFGVTTNQFAAAEECQMDQDQMLIPIIVGASLAG  397
SEQIDNO:23    SYMCISEQTLVVDQNFSLNTFQLQVQPFGITRGQFAQAEECQLDQDNMLIPIVVGAALAG  396
SEQIDNO:24    SYFCRDEQTLNVAQNLSINTFQLQVQPFAVKGDQFGAAEECQLDEDDMLIPIVVGAALAG  224
              *: *   : . :     :.   : :* *       *.     *  * : **:** **.:***

                      Cytoplasmic Tail

SEQIDNO:1     LVLIVLIAYLVGRKRSHAGYQTI   417
SEQIDNO:6     LVLIVLIAYLIGRKRSHAGYQTI   406
SEQIDNO:7     LVLIVLVAYLIGRKRTHAGYQTI   411
SEQIDNO:8     LVLIVLIAYLIGRKRSHAGYQTI   417
SEQIDNO:9     LVLIVLIAYLVGRKRSHAGYQTI   417
SEQIDNO:10    LVLIVLIAYLVGRKRSHAGYQT-   415
SEQIDNO:11    LVLIVLIAYLIGRKRSHAGYQTI   413
SEQIDNO:12    LVLVVLIAYLIGRKRSHAGYQT-   417
SEQIDNO:13    LVLIVLLAYLIGRKRSHAGYQTI   409
SEQIDNO:14    LVLIVLIAYLIGRKRSHAGYQTI   407
SEQIDNO:15    LVLIVLIAYLIGRKRSHAGYQTI   414
SEQIDNO:16    LVLVVLMAYLVGRKRSHAGYQTI   413
SEQIDNO:17    LVLIVLIAYLIGRKRSHAGYQTI   422
SEQIDNO:18    LVLIVLIAYLIGRKRSHAGYQTI   415
SEQIDNO:19    LVLIVLIAYLIGRKRSHAGYQTI   415
SEQIDNO:20    LVLIVLIAYLIGRKRSHAGYQTI   418
SEQIDNO:21    LVLIVLIAYLIGRKRSHAGYQTI   418
SEQIDNO:22    LVLIVLIAYLIGRKKSHAGYQTI   420
SEQIDNO:23    LVLIVLIAYLIGRKRSHAGYQTI   419
SEQIDNO:24    LVVIVLLAYLIGRKRSHAGYQSI   247
              **::**:***:***::*****:
```

FIGURE 3 (cont.)

| LAMP-1 | | | | | |
|---|---|---|---|---|---|
| Accession No. | *Species* | SEQ ID NO: | Accession No. | *Species* | SEQ ID NO: |
| NP_005552.3 | *H. sapiens* | 1 | NP_990614.1 | *G. gallus* | 15 |
| NP_034814.2 | *M. musculus* | 6 | NP_001011507.1 | *S. scrofa* | 16 |
| NP_955996.1 | *D. rerio* | 7 | XP_001374132.1 | *M. domestica* | 17 |
| NP_001087042.1 | *X. laevis* | 8 | XP_003203252.1 | *M. gallopavo* | 18 |
| NP_001233491.1 | *P. troglodytes* | 9 | XP_002191607.2 | *T. guttate* | 19 |
| XP_001087801.1 | *M. mulatta* | 10 | XP_003218797.1 | *A. carolinensis* | 20 |
| XP_534193.2 | *C. lupus familiaris* | 11 | XP_004067118.1 | *O. latipes* | 21 |
| XP_002723509.1 | *O. cuniculus* | 12 | XP_003969941.1 | *T. rubripes* | 22 |
| NP_001068592.1 | *B. taurus* | 13 | NP_001158846.1 | *S. salar* | 23 |
| NP_036989.1 | *R. novegicus* | 14 | XP_003452974.1 | *O. niloticus* | 24 |

FIGURE 4: HUMAN LAMP-2 ALIGNMENT WITH ORTHOLOGOUS SEQUENCES

```
SEQIDNO:2        ------------------------------------------------------------  0
SEQIDNO:25       ------------------------------------------------------------  0
SEQIDNO:26       ------------------------------------------------------------  0
SEQIDNO:27       ------------------------------------------------------------  0
SEQIDNO:28       ------------------------------------------------------------  0
SEQIDNO:29       ------------------------------------------------------------  0
SEQIDNO:30       ------------------------------------------------------------  0
SEQIDNO:31       ------------------------------------------------------------  0
SEQIDNO:32       ------------------------------------------------------------  0
SEQIDNO:33       ------------------------------------------------------------  0
SEQIDNO:34       ------------------------------------------------------------  0
SEQIDNO:35       ------------------------------------------------------------  0
SEQIDNO:36       ------------------------------------------------------------  0
SEQIDNO:37       MAMKNFTLQQERDTSVALIIRTYVRAFLKVYTKVPKPQRCHNQW---QSLNIEGIEGIEI  57
SEQIDNO:38       ------------------------------------------------------------  0
SEQIDNO:39       -----------------------------MECREGEVTRCKQENNLFSGIN-DDISGAKQ  30
SEQIDNO:40       ------------------------------------------------------------  0
SEQIDNO:41       ------------------------------------------------------------  0
SEQIDNO:42       ------------------------------------------------------------  0
SEQIDNO:43       ------------------------------------------------------------  0

SEQIDNO:2        ------------------------------------------------------------  0
SEQIDNO:25       ------------------------------------------------------------  0
SEQIDNO:26       ------------------------------------------------------------  0
SEQIDNO:27       ------------------------------------------------------------  0
SEQIDNO:28       ------------------------------------------------------------  0
SEQIDNO:29       ------------------------------------------------------------  0
SEQIDNO:30       ------------------------------------------------------------  0
SEQIDNO:31       ------------------------------------------------------------  0
SEQIDNO:32       ------------------------------------------------------------  0
SEQIDNO:33       ------------------------------------------------------------  0
SEQIDNO:34       ------------------------------------------------------------  0
SEQIDNO:35       ------------------------------------------------------------  0
SEQIDNO:36       ------------------------------------------------------------  0
SEQIDNO:37       VKGSKWR---SALETIITIQVKRK---------------SQVQKYHPPSLHSECQKTNQE  99
SEQIDNO:38       ------------------------------------------------------------  0
SEQIDNO:39       AKQRQCTPQKPPKRATATLPLQRPPRGIPGPAPAAVAAAVAADRITPSGSHQTRPPEAAR  90
SEQIDNO:40       ------------------------------------------------------------  0
SEQIDNO:41       ------------------------------------------------------------  0
SEQIDNO:42       ------------------------------------------------------------  0
SEQIDNO:43       ------------------------------------------------------------  0
```

FIGURE 4 (cont.)

```
SEQIDNO:2    --------------------------------------------------------MVCF  4
SEQIDNO:25   -----------------------------------------------------------M  1
SEQIDNO:26   --------------------------------------------------------MGDT  4
SEQIDNO:27   ------------------------------------------------------------  0
SEQIDNO:28   --------------------------------------------------------MVCF  4
SEQIDNO:29   --------------------------------------------------------MVCF  4
SEQIDNO:30   --------------------------------------------------------MVCF  4
SEQIDNO:31   --------------------------------------------------------MVCF  4
SEQIDNO:32   --------------------------------------------------------MVCF  4
SEQIDNO:33   --------------------------------------------------------MVCF  4
SEQIDNO:34   --------------------------------------------------------MVCF  4
SEQIDNO:35   --------------------------------------------------------MVCF  4
SEQIDNO:36   ----------------------------------------------------------MR  2
SEQIDNO:37   G---TGGVATVIADECLLWPSIPFSTLAQKVNLGSCEAFSIIGYSVFALFIYLKPNMLDF  156
SEQIDNO:38   ------------------------------------------------------------  0
SEQIDNO:39   DERPVRDPRNRAAAPSGHWPRAGGPQRHR------HHR-----------HRRHGPAPLHR  133
SEQIDNO:40   ------------------------------------------------------------  0
SEQIDNO:41   ------------------------------------------------------------  0
SEQIDNO:42   ------------------------------------------------------------  0
SEQIDNO:43   ------------------------------------------------------------  0


                     SIGNAL SEQUENCE        LAMP HOMOLOGY DOMAIN 1
                                                    1
SEQIDNO:2    -RL----FPVPGSGLVLVCLVLGAVQ--SYALEINLTDSGKATCLYAKWQMNFTVRYETT  57
SEQIDNO:25   -CL---SPVKGAKLILIFLFLGAVQ---SNALIVNLTDS-KGTCLYAEWEMNFTITYETT  53
SEQIDNO:26   GAM--ERCACPAAVLLLSLVL---MG--ATAFEVEIKDDKNATCIYAKLSVNITVQYETD  57
SEQIDNO:27   ---------MAVRGFLPLLFILLSGIVHADDMMTSPLPS----------------TAELK  35
SEQIDNO:28   -RL----FPVPGSGLVLVCLVLGAVQ--SYALEINLTDSGKATCLYAKWQMNFTVRYETT  57
SEQIDNO:29   -RL----FPVPGSGLVLVCLVLGAVQ--SYALELNLTDSGKATCLYAKWQMNFTVRYETT  57
SEQIDNO:30   -RL----FPVPGSGLVLVCLVLGAVR--SHALEINEADSAIN------------------  39
SEQIDNO:31   -RL----SPAPGSGLVLLCLVLGAVS--SYALEVNVTDSEKATCLYAKWQMNFTIQYNTT  57
SEQIDNO:32   -RL----SPVPGSGLVLLCLVLGAVS--SYALELNLTDSEKALCLYAKWQMNFTIPYETT  57
SEQIDNO:33   -RL----APVPGSGFLLLCLVLGAVS--SYALEINLTDSSNATCLYAKWQMNFTIRYETT  57
SEQIDNO:34   -RL----SPVPGSGLLMLCLVLGAVS--SYALELNLTNSEKATCLYAKWQMNFTIRYETT  57
SEQIDNO:35   -RL----APVPGCGFLLFCLVLGTVS--SYALEINLTDSSKATCLYAKWQMNFTIRYETT  57
SEQIDNO:36   -LL----SPVTGSKLVLLFLFLGAVR--SDALKLNLTDS-KGTCLYAEWEMNFTITYEAL  54
SEQIDNO:37   IELAELMLSTETQLLEPTRVCCGICQ--SYALEINLTDSKNATCLYSKWQMTFTINYETT  214
SEQIDNO:38   --MAPPRCPAGLALLLLLLGACGFFQ--SYAVEVDVKDASNFTCLYAQWMMKFLIKYETN  56
SEQIDNO:39   LLLRPPP-PAA-----AAARFLGFFQ--SYAVEVDIKDASNATCLYADWMMRFLIKYESN  185
SEQIDNO:40   ---M---ERCACPAALLLLLSLVL---MG---AMAFDVEIKDDKNATCIYAKLSVNVTVQYETN  51
SEQIDNO:41   ----------MF-RCAPLILFLALGNELHLSHGTEVSVNNTENKLCLYANLMVNFSVTYEVG  51
SEQIDNO:42   -----MKVSHATAGLVVWFVVLGCIDAVT----L-EVKESNTTCIKADLSASFSIIYNTT  50
SEQIDNO:43   ------------------------------------------------------------  0
```

FIGURE 4 (cont.)

```
                    LAMP HOMOLOGY DOMAIN 1
                              2
SEQIDNO:2     NKTYKTVTISDH--GTVTYNGSICGDDQNGPKIAVQFGPGFS-WIANFTKAA---STYSI   111
SEQIDNO:25    NQTNKTITIAVP--DKATHDGSSCGDDPNSAKIMIQFGFAVS-WAVNFTKEA---SHYSI   107
SEQIDNO:26    TSSSKNITFPVP---SDVTTNGSSCGSDGKAPLLVINFGNSQS-WSLNFTRNN----STYSG  111
SEQIDNO:27    ---T----ANLP--LVIQTTSSTTSTTTT-SPP--SSTSTHSTLTTEPAA----------   73
SEQIDNO:28    NKTYKTVTISDR---GTVTYNGSICGDDQNGPKIAVQFGPGFS-WIANFSKAA----STYSI 111
SEQIDNO:29    NKTYKTVTISDR---GTVTYNGSICGDDQNGPKIAVQFGPGFS-WIANFSKAA----STYSI 111
SEQIDNO:30    CSKCKTVTISDH--GTVTYNGSICGDDQNGPKIAVQFGPGFS-WIANFTKAA---STYSI   93
SEQIDNO:31    SKNFKTATISDF--STATYNGSVCGNDQNNPKIVVQFGSGFS-WIVNFTKKE---SAYLI   111
SEQIDNO:32    SKSYKTVTISNF---GTPTYNGSICGDNQNGSRIAVQFGSGFS-WIVNFTKSV----SVYSI 111
SEQIDNO:33    DKHNKTVPISDL---GAATYNGSFCGDDQNGPKIAVQFGSGFS-WIVNFTKEAASPSTYLV  114
SEQIDNO:34    NNSHKTVSISDF--GAATYNGSFCGDDHNDPQIVMQFGSGFS-WIVNFAKES---SSYLI   111
SEQIDNO:35    DKHNKTVTISDF--DAAAYNGSVCGDDQNGPKIAVQFGSGFS-WIVNFTKEASSTSTYLV  114
SEQIDNO:36    K-VNETVTITVP--DKVTYNGSSCGDDKNGAKIMIQYGSTLS-WAVNFTKEA---SQYFI  107
SEQIDNO:37    GNETKNVTVTVP--ENVTYDGSSCGDNQTVPQIAVQFGLGYS-WHLNFTKKEN--NSYSF  269
SEQIDNO:38    SSDYKNASLDLT--STVTHNGSICGSDTQAALLAVQFGDGHS-WSINFTKNN----ETYRA 110
SEQIDNO:39    SGDYKTTTLNLS---SSVTHNGSVCGNDTQAALVAVQFGEGHS-WSINITKNN----ETYQG 239
SEQIDNO:40    TSSTKNVTFSVP---SEVTTNGSSCGSNGKAPILVINFGNGHS-WSLNFTRND----SMYSG 105
SEQIDNO:41    VNKNETVIFVLP--ENVTTEGSTCDNTTSTLKL--SFGHGHS-WTVEFTKKN----KTYQV  103
SEQIDNO:42    HAER-TVQVLLPNSTTVDTANSTCGKDGSSPRLVAVFGSGY-TLGLNFSTNG----TLYQV  105
SEQIDNO:43    -------------------------------------------------------------   0

                    LAMP HOMOLOGY DOMAIN 1
                                        3
SEQIDNO:2     DSVSFSYNTGDNTTFPDAEDKGI-LTVDELLAIKIPLNDLFRCNSLSTLEKNDVVQHYWD  170
SEQIDNO:25    HDIVLSYNTSDSTVFPGAVAKGV-HTVKNPENFKVPLDVIFKCNSVLTYNLTPVVQKYWG  166
SEQIDNO:26    SALIFTYNTNDTILFPDALRKGLIS-STAMFLGPVPLNSTYKCISREVVVSENVTQIIND 170
SEQIDNO:27    ---------------------------KTTTARTTVTTSA----PTSTQSTSSSSTSATVTTLAP 107
SEQIDNO:28    DSISFSYNTGDNTTFPDAEDKGI-ITVDELLAIKIPLNDLFRCNSLSTLEKNDVVQNYWD  170
SEQIDNO:29    DSISFSYNTGDNTTFPDAEDKGI-ITVDELLAIKIPLNDLFRCNSLSTLEKNDVVQNYWD  170
SEQIDNO:30    DSISFSYNTGDNTTFPDAEDKGI-LTVDELLAIKIPLNDLFRCNSLSTLEKNDVVQHYWD  152
SEQIDNO:31    DSISFSYNLSDNATFPDAKEKGI-LTVHDIVGFRIPLNNIFRCNSLSTLEKNGVVQYYWD  170
SEQIDNO:32    DSISFSYNTGDNTTFPDAKDKGI-LTVNESVAFKIPLNDIFRCNSLSSLVKNGVVQNYWD  170
SEQIDNO:33    DTISFSYNTNDNKTFPDAKEKEV-FTVNNKVALKIPLNDIFRCNSLSTLENRDVVQHYWD  173
SEQIDNO:34    NSISFSYNTSDTTTFPDAKKKGV-LTVNDSVGFQVPLNDIFRCNSLSTLEKDNVVQHYWD  170
SEQIDNO:35    DSISFSYNTNDNATFPDAKEKGV-FTVNNRVALKIPLNDIFRCNSLSTLEKSDVVQHYWD  173
SEQIDNO:36    NNITLSYNTNDTKTFPGAVPKGI-LTVIIPVGSQLPLGVIFKCSSVLTFNLSPVVQHYWG  166
SEQIDNO:37    DTIVFTYNTSDNETFPEAKEKGQVLSVFEFRYARIPLNKIFRCHSEESLIGDKATHHYWE 329
SEQIDNO:38    EFITFTYNTNDTAVFPDARRQGPVTIVVKDAMHPIQLNNVFVCHHTTSLEAENVTQIFWN 170
SEQIDNO:39    DFITLTYNTNDTAVFPDAKPKGPITVLVRDPSRPIQLNTVFVCHNSFVIEAENTTQIFWN 299
SEQIDNO:40    GALIFTYNTNDSTLFPDALKEGLIS-STAAFLGPIPLNSTYKCISSEVVVSENVTQIISD 164
SEQIDNO:41    DTIVFSYNLNDSSVFPNSTSKETKFVTVKSIITNVSVDTYYSCKSENVLTVESVIQTLYD 163
SEQIDNO:42    SSLTLQYNLSDTSVFPNATISGVVTLVSASVGIEANVNTTYKCASPTVIDVATAKVNFTD 165
SEQIDNO:43    ------------------------------------------------MTQIGGVQPVFLA  13
```

FIGURE 4 (cont.)

```
                    LAMP HOMOLOGY DOMAIN 1          Hinge Region
                                  4
SEQIDNO:2     VLVQAFVQNGTVSTNEFLCDKDKTS---TVAPTIHTTVPS-------PTTTPT--PKEKPE  219
SEQIDNO:25    IHLQAFVQNGTVSHNEQVCEEDQTP---TTVAPTIHTTAPSTTTTLTPTSTPTPTPTPTPT  224
SEQIDNO:26    VKLEAFMANGTLGK-EIICDADKPS--PVPSPTQPST-----TASTAIPAPTSKPLDKPT  222
SEQIDNO:27    TTTGHNTTNSTTEPPTTTGHNTTNS--TTDAPTTTHTNAT----VAPTPPPTTPSVPKPT  161
SEQIDNO:28    VLVQAFVQNGTVSTNEFLCDEDKTS----TVAPTIHTTVPS-------PTTTPT--PKEKPE  219
SEQIDNO:29    VLVQAFVQNGTVSTNEFLCDEDKTS---TVAPTIHTTVPS-------PTTTPT--PKEKPE  219
SEQIDNO:30    VLVQAFVQNGTVSTNEFLCDKDKTS---TVAPTVHTTVPS-------PTTTPT--RIP---  198
SEQIDNO:31    VFVQAFVQNGTVSTKEFLCEKDKTS--TTVVPTISTTTPS-------PTTTPT--PKEKPE  220
SEQIDNO:32    VHVQAFVQNGTVSTNEYLCEKDNTT--TTVAPIVPTTVPSPTTTSSPTTTPS--PKEKPD  226
SEQIDNO:33    VHVQAFVQNGTVSTTEFLCDKDKTV--TTAVPIVPTTLPS-------PT----------KPV  216
SEQIDNO:34    VHVQAFVQNGTVSTKEFLCDKDKTL--TTTVPVIPTSVPS-------PTTTPT--PKEKPE  220
SEQIDNO:35    VHVQAFVQNGTVSTTEFLCDKDKTV--TTAMPIVPTTAPS-------PT---------KPV  216
SEQIDNO:36    IHLQAFVQNGTVSKHEQVCKEDKTA--TTVAPIIHTTVPSPTTTLTPTSI-----PVPTPT  220
SEQIDNO:37    TVVQAFIQNGTISKEEFICSKDPAS--TTVAPVTTQVVPS---------TTATPVPQDKPY  379
SEQIDNO:38    VTMQPFVQNGTISKKESRCYADTPTAAPTVLPTVANVTTAS-TTISPAPTTAPKPAENPV  229
SEQIDNO:39    VTMQAFVQNGTVSKKESRCPADTPTSEPTVPPTIANVTTASTTTLSPAPTTAPKPVENPV  359
SEQIDNO:40    VKLEAFMQNGTLGK-EVSCDADKPS--PTPT-TNPST-----TASTTTPTPTSKPLDNPT  215
SEQIDNO:41    VALQAFVINGSKSDTDTVCSADMTS--TTVAPTT----TV----TSTAAPTSTPTLPTPT  213
SEQIDNO:42    MRLEAYMPGNELSPNETVCPADQTS--TTPSPTTVSTTAV------PTQT------P--PGTPQ  213
SEQIDNO:43    VTVHLIL-----------ATV--LHQTP--AT----VTPPVTTA----VPHK----E--PGRPD  48

          Hinge                    LAMP HOMOLOGY DOMAIN 2
                     1                                     2
SEQIDNO:2     AGTYSVNNG--NDTCLLATMGLQLNITQ-------DKVASVININPNTTHSTGSCRSHTAL  271
SEQIDNO:25    VGNYSIRNG--NTTCLLATMGLQLNITE--------EKVPFIFNINPATTNETGSCQPQSAQ  276
SEQIDNO:26    MGNYTVSDA--SGICLLASMGLQINTSLL--SEGKNIWRPFNIDPLGIKTNGTCTNQTGT  278
SEQIDNO:27    VGNYSVKTD-NVSDCLLAKMGLQFSFKIS-----GNASLQTVNLDPNVTKVNGTCGSGGSD  216
SEQIDNO:28    AGTYSVNNG--NDTCLLATMGLQLNITQ-------DKVASVININPNTTHSTGSCRSHTAL  271
SEQIDNO:29    AGTYSVNNG--NETCLLATMGLQLNITQ--------DKVASVININPNTTHSTGSCRSHTAL  271
SEQIDNO:30    ------------------------------------PKVASVININPNTTHSTGSCRSHTAL  224
SEQIDNO:31    VGSYSVNNS--NGTCLLATMGLQLNITH-------NKVASVININPNTTDFTGSCQPQTAL  272
SEQIDNO:32    VGSYLVKNG--SDTCLLATMGLQLNVTH-------DKVASVININPNVTGYSGSCHPQTAL  278
SEQIDNO:33    VGSYSVVNS--NGTCLLATMGLQLNITH--------DKVASVFNINPNTTNATGSCQPQTAL  268
SEQIDNO:34    TGSYSVTSS--NGTCLLANMGLQLNITQ-------DKVASVININPNTTNATGNCHSKTAL  272
SEQIDNO:35    VGSYSVVNS--NGTCLLATMGLQLNITH-------DKVASVFNINPNTTNATGSCQPQTAL  268
SEQIDNO:36    VGNYTISNG--NATCLLATMGLQLNITE--------EKVPFIFNINPATTNFTGSCQPQTAQ  272
SEQIDNO:37    PGKYAVKNG--NDTCLLATMGLQLNVTQ-------NKVNSVININPNVTDFTGSCSNETAE  431
SEQIDNO:38    TGNYSLKTG--NKTCLLATVGLQLNISQ-------DK-PLLINIDPKTTHADGTCGNTSAT  280
SEQIDNO:39    TGNYSLKSG--NKTCFLATVGLQLNVSQ-------EK-PLLININPKTTVADGACGNTTAT  410
SEQIDNO:40    TGNYSVSDV--NGTCLLASMGLQINTSLL--SEGKNIWTAFNIDPTAMSKNGTCSNQTGT  271
SEQIDNO:41    TGKYSIAPDVNSTACLMATFGLQIGYKQG----D--KEETINLVPNITEVGGACGANSS-  266
SEQIDNO:42    QGNYTVKDA-NDTICLLAKMGLQLNVSYT--SQNKTVQDVLNLNPNVTNSTGSCGASSAT  270
SEQIDNO:43    QGDYQVTSS-NGTVCFLASMGLQLNITPNSTSQNKTLQEVINIQPNRTKSSGSCDTSSAL  107
                                                   .*:  *          * *       .
```

FIGURE 4 (cont.)

```
                                    LAMP HOMOLOGY DOMAIN 2

SEQIDNO:2      LRLNS-STIKYLDFVFAVKNE----NRFYLKEVNISMY-LVNGSV-FSIANNNLSYWDAP  324
SEQIDNO:25     LRLNN-SQIKYLDFIFAVKNE----KRFYLKEVNVYMY-LANGSA-FNISNKNLSFWDAP  329
SEQIDNO:26     LILTE--NRTIIEFTFALKNK----NHFYLEEVNITLI---NGSAFSSRQNQNLSIWEAS  329
SEQIDNO:27     SSLFLTS--KDITVHFVFTNDS---QKFRLHALTLTVD-LGNG-NIFNDSNTNLSLWEAS  269
SEQIDNO:28     LRLNS-STIKYLDFVFAVKNE----NRFYLKEVNVSMY-LVNGSV-FSIANNNLSYWDAP  324
SEQIDNO:29     LRLNS-STIKYLDFVFAVKNE----NRFYLKEVNVSMY-LVNGSV-FSIANNNLSYWDAP  324
SEQIDNO:30     LRLNS-STIKYLDFVFAVKNE----NRFYLKEVNISMY-LVNGSV-FSIANNNLSYWDAP  277
SEQIDNO:31     LRLNS-SNIKYLDFVFAVKNE----NRFYLKEVNVSMY-LVNGSV-FSIANNNLSYWDAP  325
SEQIDNO:32     LRLNS-SNIKYLDFVFAVKNE----NRFYLKEVNVSMY-LANGSV-FSFANNNLSYWDAP  331
SEQIDNO:33     LRLSS-SNIKYLDFVFAVKNE----NRFYLKEVNVSMI-LVNGSV-YSISNTNLSYWDAP  321
SEQIDNO:34     LRLSG-SNIKYLDFVFAVKND----NRFYLKEVNVSVY-LVNGSV-FSIANNNLSYWDAP  325
SEQIDNO:35     LRLSS-SNIKYLDFVFAVKNE----NRFYLKEVNVSMI-LVNGSV-YSISNTNLSYWDAP  321
SEQIDNO:36     LRLNN-SQIKYLDFTFAVKNE----KRFYLKEVNVNMY-LANGSA-FHVSNNNLSFWDAP  325
SEQIDNO:37     LRLSG-SNVKYIDFIFAVKNG----NRFYLKEVNVSIS-FVNASD-LNVANNNLSYWDAP  484
SEQIDNO:38     LKLND-GNRTLIDFTFIV-NASASVQKFYLREVNVTLLNYQNGSVILSADNNNLSKWDAS  338
SEQIDNO:39     LKLND-GNSTLIGFTFAVKNTSASVQKFYLREVNVTLLNRLNGSVISSADNSNLSIWDAF  469
SEQIDNO:40     LILTD--NSTVIEFTLALKNK----NHFYLKEVNVALI---NGSASSTRQNQNLSAWEAS  322
SEQIDNO:41     -DLILTS--DTITIMFTFSNDG---KKFHLHALKVTVK-PATG-DFVIAVNNNMSIWAAA  318
SEQIDNO:42     LVLTQ-TQSTILTFNFTLNSTT---NKYHLSGVTLIAN-WFDS-AHFSMSNNSLNYLRST  324
SEQIDNO:43     LTLTTDAEKTNLTFVFALNTTS---NKYHLSEVSLSAA-LSDMKETFVAQNHSLDYLRGT  163
                *        : . : . .      ::: *  :.:                * .:.    .

                 LAMP HOMOLOGY DOMAIN 2                          Trans. Domain
                    3                                 4
SEQIDNO:2      LGSSYMCNKEQTVSVSGAFQINTFDLRVQPFNVTQGKYSTAQDCSADD-DNFLVPIAVGA  383
SEQIDNO:25     LGSSYMCNKEQVLSVSRAFQINTFNLKVQPFNVTKGQYSTAQECSLDDD-TILIPIIVGA  388
SEQIDNO:26     VDSSYMCHKEQQIKVSEDLFINAFDVRVQPFGVNNGTFATAEDCFAD-Q-NFIVPIVVGA  387
SEQIDNO:27     VGSSYMCRKEQSYNISDKLTLNTFELQVQPFDVKKNSFSTAHECSLDDT-SLLIPIIVGA  328
SEQIDNO:28     LGSSYMCNKEQTVSVSGAFQINTFDLRVQPFNVTQGKYSTAEECSADSDLNFLIPVAVGV  384
SEQIDNO:29     LGSSYMCNKEQTVSVSGAFQINTFDLRVQPFNVTQGKYSTAQDCSADD-DNFLVPIAVGA  383
SEQIDNO:30     LGSSYMCNKEQTVSVSGAFQINTFDLRVQPFNVTQGKYSTAEECSADSDLNFLIPVAVGV  337
SEQIDNO:31     LGSSYMCNKEQTVSVSGAFQINTFDLRVQPFNVMEGKYSTAQECSLDDD-TILIPIIVGA  384
SEQIDNO:32     LGSSYMCNKEQTVSVSGEFQINTFDLRVQPFNVKDGKYSTAQDCRADD-DNFLVPIAVGA  390
SEQIDNO:33     LGSSYMCNKEQTVSVSGAFQINTFDLRVQPFSVTEGKYSTAQECSLDDD-TILIPIIVGA  380
SEQIDNO:34     LGSSYMCNKEQTVSVSGAFQINTFNLRVQPFSVMEGKYSTAQDCSADD-DNFIVPIAVGA  384
SEQIDNO:35     LGSSYMCNKEQTVSVSGALQINTFDLRVQPFSVTEGKYSTAEECSADSDLNFLIPVAVGV  381
SEQIDNO:36     LGSSYMCNKEQVVSVSRTFQINTFNLKVQPFNVTKGEYSTAQDCSADED-NFIVPIAVGA  384
SEQIDNO:37     LGSSYMCNKEQTLALADSLQINTFNLRVQPFSVVAGKYSTAEDCSADDD-NFIVPIAVGA  543
SEQIDNO:38     LGNSYMCRKEQTLEINENLQVHTFNLWVQPFLVKENKFSIAEECFADSDLNFLIPVAVGM  398
SEQIDNO:39     LGSSYMCRKEQTLQINENVQVHTFNLWIQPFLVEANKFATAEECIADSDLNFLIPIAVGV  529
SEQIDNO:40     VGSSYMCHNEQQIKVSEDLVINSFDVRVQLFGVKNETFATAQQCSLDDD-SIVIPIVVGA  381
SEQIDNO:41     VGSSYMCNKEQTLNVTDTLTLYTFELRVQPFEVNKGEFATAHECSLDDT-SILIPIIVGA  377
SEQIDNO:42     LGYSYMCNAEQTLFVTPSFSINTFDLQVQPFGVKSGRFATAEECQMDQN-QMIIPIIVGA  383
SEQIDNO:43     LGFSYMCRERQTLGVTPDFAINTFQVQVQPFGVTGKQFAAAEECQLDKD-DMLIPIIVGA  222
               :. ****. .*    :    . : :*:: :* * *    :: *.:*  *    :::*: **
```

FIGURE 4 (cont.)

```
                              Cytoplasmic Tail

SEQIDNO:2      ALAGVLILVLLAYFIGLKHHH-AGYEQF   410
SEQIDNO:25     GLSGLIIVIVIAYLIGRRKTY-AGYQTL   415
SEQIDNO:26     ALGVLVVLVMVAYFIGRRKQSSAGYEQM   415
SEQIDNO:27     ALAGLIFIVVIAYVIGRRPTY-VGYQTL   355
SEQIDNO:28     ALGFLIIVVFISYMIGRRKSR-TGYQSV   411
SEQIDNO:29     ALAGVLILVLLAYFIGLKRHH-AGYEQF   410
SEQIDNO:30     ALGFLIIVVFISYMIGRRKSR-TGYQSV   364
SEQIDNO:31     GLSGLIIVIVIAYLIGRRKSY-AGYQTL   411
SEQIDNO:32     ALAGVLILVLLAYFIGLKRHH-AGYEQF   417
SEQIDNO:33     GLSGLIIVIVIAYLIGRRKSY-AGYQTL   407
SEQIDNO:34     ALAGVLILVLLAYFIGLKRHH-AGYEQF   411
SEQIDNO:35     ALGFLIIVVFISYMIGRRKSR-TGYQSV   408
SEQIDNO:36     ALGGVLILVLLAYFIGLKRHH-TGYEQF   411
SEQIDNO:37     ALGGLVILVLMAYFVGRKRRA-TGYEQF   570
SEQIDNO:38     ALGFLIIILVFISYIIGRRKSR-TGYQSV   425
SEQIDNO:39     ALGFLIILVFISYIIGRRKSR-TGYQSV   556
SEQIDNO:40     ALAGLIVIIVIAYLIGRRKGY-SGYQTL   408
SEQIDNO:41     ALAGLILIVVIAYVIGRRKTY-VGYQTL   404
SEQIDNO:42     ALAGLVLITLIAYLIGKRRSH-AGYQAI   410
SEQIDNO:43     ALAALVLIVLSAYLIGRKRSH-AGYQSI   249
               .*. ::.: . :*.:* ::     **: .
```

| | LAMP-2 | | | | |
|---|---|---|---|---|---|
| Accession No. | *Species* | SEQ ID NO: | Accession No. | *Species* | SEQ ID NO: |
| NP_002285.1 | *H. sapiens* | 2 | NP_001231184.1 | *S. scrofa* | 34 |
| NP_034815.2 | *M. musculus* | 25 | XP_004022401.1 | *O. aries* | 35 |
| NP_001087881.1 | *X. laevis* | 26 | NP_058764.2 | *R. norvegicus* | 36 |
| NP_001013551.1 | *D. rerio* | 27 | XP_001510101.2 | *O. anatinus* | 37 |
| XP_003918270.1 | *P. Anubis* | 28 | NP_001001749.1 | *G. gallus* | 38 |
| XP_003918270.1 | *M. mulatta* | 29 | XP_002191794.1 | *T. guttata* | 39 |
| XP_003317709.1 | *P. traglodytes* | 30 | NP_001116192.2 | *X. tropicalis* | 40 |
| XP_005641822.1 | *C. lupus familiaris* | 31 | NP_001133282.1 | *S. salar* | 41 |
| XP_001493687.3 | *E. caballus* | 32 | XP_003445830.1 | *O. niloticus* | 42 |
| NP_001029742.1 | *B. Taurus* | 33 | XP_003961835.1 | *T. rubripes* | 43 |

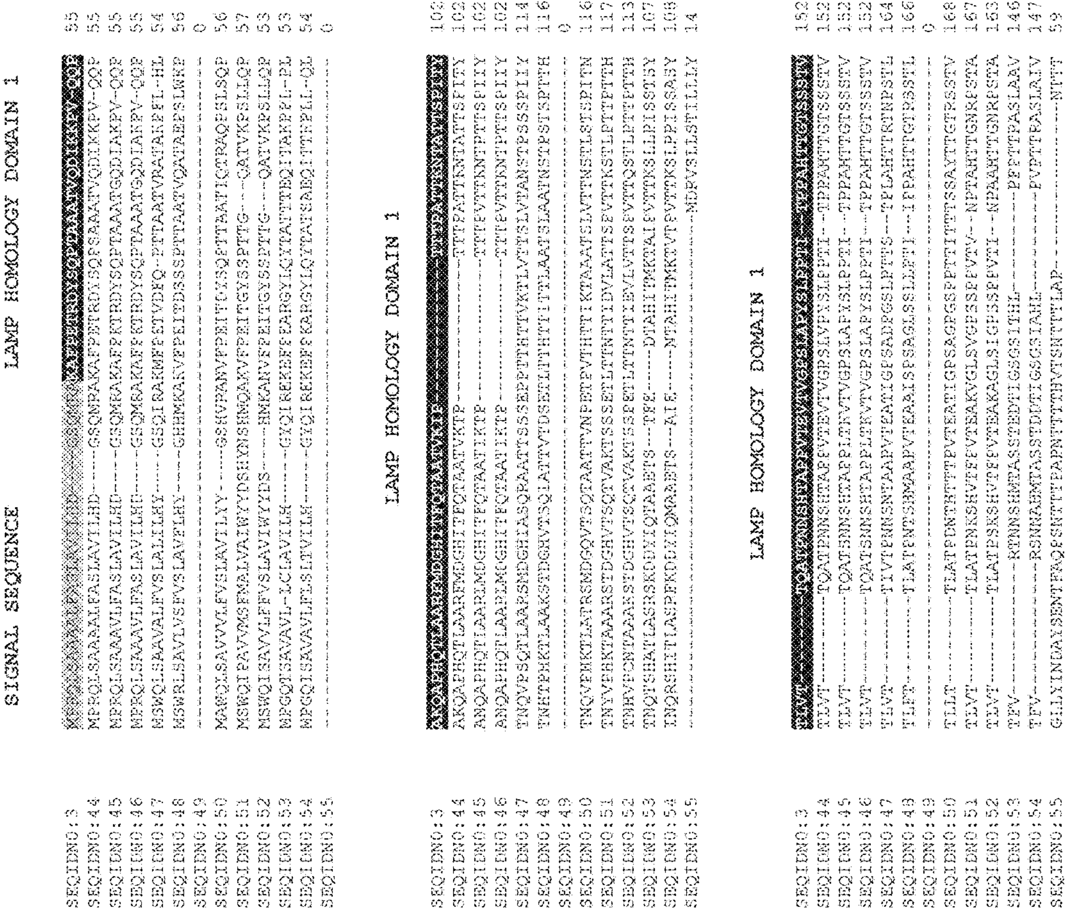
FIGURE 5: HUMAN LAMP-3 ALIGNMENT WITH ORTHOLOGOUS SEQUENCES

FIGURE 5 (cont.)

```
                                LAMP HOMOLOGY DOMAIN 1

SEQIDNO:3      SHTTGNTTQPSNQTTLPATLSIALHKSTTGQKPVQP---THAPGTTAAAHNTTRTAAPAS   209
SEQIDNO:44     SHTTGNTTQPSNQTTLPATLSIALHKSTTGQKPVQP---THAPGTTAAAHNTTRTAAPAS   209
SEQIDNO:45     NHTTGNATQPSNQTTLPATLSIALHKSTTGQKPVQP---THAPGTTAAAHNTTRTAAPAS   209
SEQIDNO:46     NHTTGNATQPSNQTTLPATLSIAPHKSTTGQKPVQP---THAPGTTAAAHNTTRTAAPAS   209
SEQIDNO:47     SHKTRKITHFGNQTTLPATLSTSTHKSTSSHKSAQS---THAPGPTTAAHNTTQTASPAT   221
SEQIDNO:48     SPTAGKTTQPSNQTTLPATLSTSPHNSTASQKPTHP---NHTPGPTTGAHNTTQTASPAT   223
SEQIDNO:49     ------MTQSSRSVLLIMLSSLHCLGSSLESNPKDPSVLAEAPGQN------KRDSDISL   48
SEQIDNO:50     SHTTGKTTQLSNQTTLPATLSTSPHNSTTSQNPAHS----THTPGPTTGTCNTTQTASPTT   225
SEQIDNO:51     SHTTGKTTQLSNQTTLPATLSTSPHNITTSQKPTQP----THTPGPTTATYNTTQTASPAT   224
SEQIDNO:52     SHTTGKTTQLSNQTTLPATLSTSPHNITTSQKPTQP---THTPGPTTAANNTTHTASPAT   220
SEQIDNO:53     NHITGRSTQLGGQTTLPKALFTPSHESTTTQRPTLS----TI-VSELTPTGKDRSTTSSVP   202
SEQIDNO:54     NYITGRATQLGGQTTLPKTFFTASHKSTTNQRPTLS---TNVLGTSTPTHKDRSTTSPVP   204
SEQIDNO:55     THVTSNTTTLA------PNTTTTHITSNTTTIAPNTT----TTLAPNTTTTHSVTTTKTAST   111
                      *  .                  :

                         Hinge            LAMP HOMOLOGY DOMAIN 2
                                          1
SEQIDNO:3      TVPGPTLAPQPSSVKTGIYQVLN-GSRLCIKAEMGIQLIVQDKESVFSPRRYFNLDPNAT   268
SEQIDNO:44     TVPGPTLAPQPSSVKTGIYQVLN-GSRLCIKAEMGIQLIVQDKESVSWGHRTITLSS---K   266
SEQIDNO:45     TVPGSTLAPQPSSVKTGIYQVLN-GSRLCIKAEMGIQLIVQDKESVFSPRRYFNLDPNAT   268
SEQIDNO:46     TVPGSTLAPQPSSIKTGIYQVLN-GSRLCIKAEMGIQLIVQDKESVFSPRRYFNLDPNAT   268
SEQIDNO:47     PASGPTLAPQPSSPKTGIYQVLN-GSRLCIKAEMGIELMVQDTKSVFSPQRYFNIDPNAT   280
SEQIDNO:48     IAPGPTLAPQPSSAKTGIYQVLN-GSKLCIKAEMGIELTVQDTQSVFSPQRYFNIDPNTT   282
SEQIDNO:49     VPQMPVLQPKETAPPLVTYTIRNPQGKVCVRASFGVEFVVREN-----KKKYYFNLTPNSA   104
SEQIDNO:50     TAPGPTLAPQPSSAKTGMYQILN-GSKLCIKAEMGIQLTVQDTKSASPPQGYFNIDPNTT   284
SEQIDNO:51     IAPRPTLAPQPLSPKTGIYQVHN-GSKLCIKAEMGIQLTVQDSVSVFSPQKYFNIDPNAT   283
SEQIDNO:52     IAPRPTLAPQPLSPKTGLYQVLN-GSKLCIKAEMGIQLTVQDSVSVFSPQKYFNIDPNAT   279
SEQIDNO:53     LVPRPTFVTWSSPAKIGTYEVLN-GSRLCIKAEMGIALIVQEKGLDSATQRHFNIDPSLT   261
SEQIDNO:54     LVPRPTLVTWSSPAKIGTYEVLN-GSRLCIKAEMGLALIVQEKDLDSATQRYFNIDPSLT   263
SEQIDNO:55     TTPTPTLEPKPSPPETGNYTVKI-KNEFCIEALMGLELELTNS----TKTQQYFNIVPSQI   167
                    .:              * :     ...*:.* :*: : : :.        :  :.:

                                LAMP HOMOLOGY DOMAIN 2
                      2
SEQIDNO:3      QASGNCGTRK-----SNLLLNFQGGFVNLTFTKDEESYYISEVGAYLTVS------DPETIY   319
SEQIDNO:44     SLSGGCLARNEHSPHPLFLFFEKGPPSVTQAEDEESYYISEVGAYLTVS------DPETIY   321
SEQIDNO:45     QASGNCGTRN-----SNLLLNFQGGFVNLTFTKDEGSYYISEVGACLTVS------DPETIY   319
SEQIDNO:46     QASGNCGTRN-----SNLLLNFQGGFVNLTFTKDEGSYYISEVGACLTVS------DPETIY   319
SEQIDNO:47     QTSGNCGSQK------SNLLLNFQGGFVNLTFLKDENSYYINEVGAYIAVS-------NPEKIY   331
SEQIDNO:48     QASGNCGSRK------SKLLLNFQGGFVNLTFTKDENSYYVSGVGAYLTVS-------NPEKVY   333
SEQIDNO:49     PATGYCANQK----TVLSLEFSGGNLEFTFIKDGDQSYVKTVKGSLRAAPPCKNCPSKIY   160
SEQIDNO:50     QVSGICGSRK----SNLLLNFWGGFVNLTFTKDENSYYISEVGAYLTVS-----NPEKTY   335
SEQIDNO:51     QASGNCGSRK----SNLLLNFQGGFVNLTFTKGEKSYYISEVEAYLTVS-----NPAKVY   334
SEQIDNO:52     QASGNCGSRK----SNLLLNFQGGFVNLTFIKDENSYYISEVEAYLTVS-----NPAKVY   330
SEQIDNO:53     HASGKCGSQN-----SNLFLNFQGGSVNVTFTKEENLYYVSEVGAYLTIS------NTEKTY   312
SEQIDNO:54     HASGKCDSQK----SNLFLNFQGGSVNITFTKEENLYYISEVGAYLTIS-----NTEKTY   314
SEQIDNO:55     NSNGTCEKSK----ANLNLTFANSYINFVFAQDDNSYYLDNVTVYFNLT------RSESWY   218
                 .* *   :       * * *  .  ...  :      *:. *  :  :        . *
```

FIGURE 5 (cont.)

```
                    LAMP HOMOLOGY DOMAIN 2
                    3                                                4
SEQIDNO:3     QGIKHAVVMFQTAVGHSFKCVSEQSLQLSAHLQVKTTDVQLQAFDFEDDHFGNVDECSSD  379
SEQIDNO:44    QGIKHAVVMFQTAVGHSFKCVSEQSLQLSAHLQLKTTDVQLQAFDFEDDHFGNVDECSSD  381
SEQIDNO:45    QGMKHAVVMFQTAVGHSFKCVSEQSLQLSAHLQLKTTNVQLQAFDFEDDHFGNVDECSSD  379
SEQIDNO:46    QGMKHAVVMFQTVVGHSFKCVSEQSLQLSAHLQLKTTNVQLQAFDFEDDHFGNVDECSSD  379
SEQIDNO:47    QGMKSSVVMFETGVGHSFKCVSEQSIQLSTHLQLKTMNVQFQAFDFEDDHFGNVDECSSD  391
SEQIDNO:48    QGMKNAVVMFETMIGHSFKCVSEQSIQLSPHLQLNTMNVQLQAFDFEDDHFGNVDECSSD  393
SEQIDNO:49    VGLVDNEKLFKAKNGLSFNCKSETMLILADYFRLKLVPLQIQAFDLVNGAFGKEVECWAD  220
SEQIDNO:50    QGMKSPVVMFETVIGHSFKCVSEQSLELSTQLHLKTTNVQLQAFDFEDDNFGNVDECSSD  395
SEQIDNO:51    QGLKHAMMMFETVVGHSFKCVSEQSIQLSTYLQLKTMNVQLQAFDFEDDHFGNADECISD  394
SEQIDNO:52    QGMKYAMMMFETVVGHSFKCVSEQSIQLSNHLQLKTVNVQLQAFDFEDDRFGNADECISD  390
SEQIDNO:53    QGKS-TMMMFETVVGHSFKCVSEQSIQLSAQLQMKTMNIHLQAFDFEGDSFGIVDECLSD  371
SEQIDNO:54    QGKKNTLMMFETVVGHSFKCVSEQSIQLSAQLQMKTMNIHLQAFDFEGDSFGNVNECLSD  374
SEQIDNO:55    GNAT-NQKLLKTENGYSVKCKNTPKIQLGDTMNLVMTNVKLQVFNFKDNSFGKETTCKYD  277
              .    ::::  * *.:* .   : *.  :.:     :::*.*:: .. **     *  *

              Trns Memb.        Cyto. Tail

SEQIDNO:3     YTIV-LPV-IGAIVVGLCLMGMGVYKIRLRCQSSGYQRI      416
SEQIDNO:44    YTIV-LPV-IGAIVVGLCLMGMGVYKIRLRCQSSGYQRI      418
SEQIDNO:45    YTIV-LPV-IGAIVVGLCLVGIGVYKIRLRCQSSGYQRI      416
SEQIDNO:46    YTIV-LPV-IGAIVVGLCLVGMGVYKIRLRCQSSGYQRI      416
SEQIDNO:47    YTVV-LPV-IGAIVLGLCAVGLIVYGIHLRRESSGYQRI      428
SEQIDNO:48    YTIV-LPV-IGAIVLGLCAVGLIVYGIRLKRESSEYQRI      430
SEQIDNO:49    YNKRMIPIILGAVAAAICLIAILTYVLVREIRNQGYEQL      259
SEQIDNO:50    YTVV-LPV-IGAIVLGLFAVGLIVYGVRVRREASGYQRI      432
SEQIDNO:51    RNRREIPVAVGLSIAVLLAVLLTACLVTRKRPSRGYERM      433
SEQIDNO:52    RNRREIPVAVGLSIAVLLAVLLTACLVTRKRPSRGYERM      429
SEQIDNO:53    YTVV-LPV-VGIIVVVLCVVGLGIYKIRQRRQSSAYQRI      408
SEQIDNO:54    YTVV-LPM-VAIIVVVICVVGLSVYKIRQRHQSSAYQRI      411
SEQIDNO:55    HNFG-LMI-AGIVIVVIVVLGVIIYFIWHKRKSSGYQRI      314
               .   : :  .      :  : :    :  .     *:::
```

| | LAMP-3 | | | | |
|---|---|---|---|---|---|
| Accession No. | *Species* | SEQ ID NO: | Accession No. | *Species* | SEQ ID NO: |
| NP_055213.2 | *H. sapiens* | 3 | XP_001496333.1 | *E. caballus* | 50 |
| XP_001155195.3 | *P. troglodytes* | 44 | NP_001095605.1 | *B. Taurus* | 51 |
| XP_003894825.1 | *P. Anubis* | 45 | XP_004003158.1 | *O. aries* | 52 |
| NP_001028044.1 | *M. mulatta* | 46 | NP_001012015.1 | *R. norvegicus* | 53 |
| XP_848889.2 | *C. lupus familiaris* | 47 | NP_796330.2 | *M. musculus* | 54 |
| XP_003358746.1 | *S. scrofa* | 48 | XP_002936919.2 | *X. tropicalis* | 55 |
| XP_001342688.2 | *D. rerio* | 49 | | | |

FIGURE 6: HUMAN LIMP-2 ALIGNMENT WITH ORTHOLOGOUS SEQUENCES

```
                                                                  SIGNAL SEQUENCE
SEQIDNO:4      ----------------------------------------------MGRCCFYTAGTLS 13
SEQIDNO:56     ----------------------------------------------MGRCCFYTAGTLS 13
SEQIDNO:57     ----------------------------------------------MGRCCFYTAGTLS 13
SEQIDNO:58     ----------------------------------------------MGRCCFYTVGTLS 13
SEQIDNO:59     ----------------------------------------------MGRCCFYAVGTLS 13
SEQIDNO:60     ----------------------------------------------MGRCCFYTAGTLS 13
SEQIDNO:61     --------------------------------------------MTRRSCTIYATGIVC 15
SEQIDNO:62     ----------------------------------------------MARCCFYTAGTLS 13
SEQIDNO:63     ----------------------------------------------MRSLCLVTVGVLA 13
SEQIDNO:64     ----------------------------------------------MVKWAVFGTAAVS 13
SEQIDNO:65     MQLDDILHINNCKADCSSLSTTPNPKTDLVNMNGPKHKPCTKLSSTYLPKWWITIV--VA 58
SEQIDNO:66     --------------------------------MYGRSNRLCAKLSSAFLRKWWFVIA--FA 27
                                                                  .  .  ..

                                       LAMP HOMOLOGY DOMAIN

SEQIDNO:4      LLLLVTSVTLLVARVFQKAVDQSIEKKIVLRNGTEAFDSWEKPPLPVYTQFYFFNVTNPE 73
SEQIDNO:56     LLLLVTSVTLLVARVFQKAVDQSIEKKIVLRNGTEAFDSWEKPPLPVYTQFYFFNVTNPE 73
SEQIDNO:57     LLLLVTSVTLLVARVFQKAVDQSIEKKIVLRNGTEAFDSWEKPPLPVYTQFYFFNVTNPE 73
SEQIDNO:58     LLLLVTSIALLVARVFQKAVDQTIEKNIVLRNGSETFDSWKKPPLPVYAQFYFFNVTNPE 73
SEQIDNO:59     LLLLVTSITLLVARVFQKAVDQTIEKNIVLRNGSETFDSWKKPPLPVYTQFYFFNVTNPE 73
SEQIDNO:60     LLLLVTSVTLLVARVFQKAVDQTIEKNMVLQNGTKVFNSWEKPPLPVYIQFYFFNVTNPE 73
SEQIDNO:61     AHLLILGIALLLAQVFQTMIQERIKKEITLAENSRVLDGWINPPPPVYMQYFFFNVTNPD 75
SEQIDNO:62     LLLLVTSVTLLVARVFQKAVDQTIEKNMVLQNGTKVFDSWEKPPLPVYIQFYFFNVTNPE 73
SEQIDNO:63     LTLLIASISLLVAHVFQTVVDLQVKQGTVLKNGTETFEAWEDPPPPVYMQFYFFNVTNPL 73
SEQIDNO:64     VTLLIVSIVLLLTHTFMDIVEGQVKQAIVLKNESEVFEDWANPPPPVYMQFYFFNVTNPL 73
SEQIDNO:65     AALIIG---GIVVACEPTVLIDAVVDRMVALRPGAKTFGWWAKPPVEPRISLYIYNVTNAD 116
SEQIDNO:66     LSLLVL---GALVTFGPTAFIRTIIDHQVALRVGGQSFGWWSRPPVEPIIRIFVYNVTNAD 85
                 *::     :::  *    :    :.:   .*     . :   *   **        :.:****

                                  LAMP HOMOLOGY DOMAIN

SEQIDNO:4      EILRGE-TPRVEEVGPYTYRELRNKANIQFGDNGTTISAVSNKAYVFERDQSVGDPKIDL 132
SEQIDNO:56     EILRGE-TPRVEEVGPYTYRELRNKANIQFGDNGTTISAVSNKAYVFERDQSVGDPKIDL 132
SEQIDNO:57     EILRGE-TPRVEEVGPYTYRELRNKANVQFGDNGTTISAVSNKAYVFERDQSVGDPKIDL 132
SEQIDNO:58     EILRGE-IPRLEEVGPYTYPELRDKADIQFGDNGTTISAVSNKAYVFERNQSVGDPKTDL 132
SEQIDNO:59     EILNGE-TPRLEEVGPYTYRELRNKDDIQFGDNGTTISAVSNKAYVFERDKSVGDPKIDL 132
SEQIDNO:60     EILQGE-IPLLEEVGPYTYRELRNKANIQFGENGTTISAVTNKAYVFERNQSVGDPNVDL 132
SEQIDNO:61     EFLAGKEKAKVTQMGPYTYREYRPRENVTYLENGTKIFATNPKSFVFLRNMSAGDPEVDR 135
SEQIDNO:62     EILQGE-IPLLEEVGPYTYRELRNKANVQFGENGTTISAVTNKAYIFERNQSVGDPTVDL 132
SEQIDNO:63     EVLQGA-TPLVEEKGPYTYREYRPRVHVQFLDNGTKVSALNPKTYVFEPEKSVGNPEVDL 132
SEQIDNO:64     EVLSGE-KPFVDEIGPYTYREYRPRENITFSVNGTEVSAVTPKTYVFEPEKSIGDPKVDL 132
SEQIDNO:65     DFLSNGSKAIVDEVGPYVYSETWEKVNIVENDNGTL-SYNLRKIISFREDLSVG-PEDDV 174
SEQIDNO:66     EFLNNGTKPILDELGPYVYVQTWEKVNIKENPNGTI-SYNQKRVYIFNEDLSGG-LEDDV 143
               :.* .       : : ***.* :    : .:     ***         : : *  : * *     *
```

FIGURE 6 (cont.)

LAMP HOMOLOGY DOMAIN

```
SEQIDNO:4     IRTLNIPVLTVIEWSQ-V-HFLREIIEAMLKAYQQKLFVTHTVDELLWGYKDEILSLIHV 190
SEQIDNO:56    IRTLNIPVLTVIEWSQ-V-RFLREIIEAMLKAYQQKLFVTHTVDELLWGYKDEILSLIHV 190
SEQIDNO:57    IRTLNIPVLTVIEWSQ-V-HFLREIIEAMLKAYQQKLFVTHTVDELLWGYKDEILSLIHV 190
SEQIDNO:58    IRTLNIPAVTAMEWAH-L-HFFRELIEALLKAYQQTLFVTHTVDELLWGYKDEILSLINV 190
SEQIDNO:59    LRTLNIPALTAMEWTQ-L-PLLRDIIEALLKAYRQKLFVTHTVDELLWGYKDETLSLINT 190
SEQIDNO:60    IRTINIPLLTVVDLAQ-L-TLLRELIEAMLKAYQQKLFVIHTVHELLWGYKDETLSLVHI 190
SEQIDNO:61    VTTVNIPMIAVMNELNSYSFFVRTAVSMYMGSMGMGLFMNPTVHEILWGFKDPLLTKLHA 195
SEQIDNO:62    IRTINIPLLTVVEMAQ-Q-PFLREIIEAMLKAYQQTLFVTHTVHELLWGYKDEVLSLVHI 190
SEQIDNO:63    IRTINVPAVTAMEWTR-A-TSLQFATEVLLLLYQESLFTVRTVHELLWGYKDKLLSTIHV 190
SEQIDNO:64    IRTVNIPLVTILEMTK-DSSLLRPFIIAALKTYKEGMFVTRTVDELLWGYKDAVLSILHF 191
SEQIDNO:65    VIVPNIPMLSATSQSKHAARFLRLAMASIMDILKIKPFVQVSVGQLLWGYEDPLLKLAKD 234
SEQIDNO:66    VIVPNIPMLSATSQSKHAARFLRLAMASIMDILKIKPFVEVSVGQLLWGYEDPLLKLAKD 203
              : . *:* ::  .   .      .:       :        *    :* ::***::* :*.   :
```

LAMP HOMOLOGY DOMAIN

```
                                                                        1
SEQIDNO:4     FRPDI-----SPYFGLFYENNGTNDGDYVFLTGEDSYLNFTKIVEWNGKTSLDWWITDKCN 246
SEQIDNO:56    FRPDI-----SPYFGLFYEKNGTNDGDYVFLTGEDSYLNFTKIVEWNGKTSLDWWITDKCN 246
SEQIDNO:57    FRPDI-----SPYFGLFYEKNGTNDGDYVFLTGEDNYLNFTKIVEWNGKTSLDWWITDKCN 246
SEQIDNO:58    FKPEI-----SPYFGLYYGKNGTNDGDYVFLTGEDNYLNFSKIVEWNGKTSLDWWTTDKCN 246
SEQIDNO:59    FKHDV-----SPYFGLFYGKNGTNDGDYVFLTGEDNYLNFSKIVEWNGKTSLDWWTADECN 246
SEQIDNO:60    FKPDV-----SPNFGLFYERNGTNDGEYVFLTGEDNYLNFSKIVEWNGKTSLDWWTTDTCN 246
SEQIDNO:61    MRPEV------DEHFGLMYNKNGTHEGEFVFHTGEKNYMNYGKIDTWNGISQMNWWSSNQSN 251
SEQIDNO:62    FRPDV-----SPNFGLFYERNGTNDGEYVFLTGEDNYLNFTKIVEWNGKTSLDWWTTDTCN 246
SEQIDNO:63    LHPEI-----DPVFGPFNKMNGTDDGEYVFLSGEMNYLNFSRIVEWKGKESLNWWTTKTCN 246
SEQIDNO:64    FKKNI-----SITFGLFYKMNTTDDGEYIFLSGEKDYLEFTQIAEWKGQKALNWWTTETCN 247
SEQIDNO:65    VVPKEQKLPYEEFGLLYGKNGTSSDRVTVNTGVDDIRRYGIIDNFNGPTHLPHWTTDACN 294
SEQIDNO:66    VVPKEQKLPYEEFGLMYGKNSTSKDTVTVWTGVDDITQYGIIDKYNGRSHQTHWLSEQCN 263
              .   .           **:     * *  ..    . :*   .   .:   *   ::*       * :. .*
```

LAMP HOMOLOGY DOMAIN

```
                                         2
SEQIDNO:4     MINGTDGDSFHPLITKDEVLYVFPSDFCRSVYITFSDYES-VQGLPAFRYKVPAEILANT 305
SEQIDNO:56    MINGTDGDSFHPLITKDEVLYVFPSDFCRSVYITFSDYES-VQGLPAFRYKVPAEILANT 305
SEQIDNO:57    MINGTDGDSFHPLITKDEVLYVFPSDFCRSVYITFSDYES-VQGLPAFRYKVPAEILANT 305
SEQIDNO:58    MINGTDGDSFHPLIDKDEILYVFPSEFCRSVYITFSDFKS-VQGIPAFRYKVPGEVLANT 305
SEQIDNO:59    MINGTDGDTFHPLITRDEVLYVFPSDFCRSVYITFSDFES-VQGLPALRYKVPAEILANT 305
SEQIDNO:60    MINGTDGDSFHPLISKDEVLYLFPSDLCRSVHITFSSFEN-VEGLPAFRYKVPAEILANT 305
SEQIDNO:61    MINGTDGSVFHTFLSRKELLYIFAADLCRSIHLGYVRDME-VKGIPAFRFAPPSDVLAPP 310
SEQIDNO:62    MINGTDGDSFHPLISKDETLYIFPSDFCRSVYITFSSFEN-VEGLPAFRYKVPAEILANS 305
SEQIDNO:63    MINGTDGTSFHPLISKDENIYIFSSDFCRSLYLVYDSSGS-VAGVPTYRFVPSPMVFANT 305
SEQIDNO:64    MINGTDGTSFHPLLNKDDTIYMFSSDLCRSIYAVYESSEN-IKDISVFRFSPPASVFANV 306
SEQIDNO:65    TLAGTDGSIFPPHIDHDRILHVYDKDLCRLLPLVFEKEVMTSNEVPGYRFTPPEWVFADV 354
SEQIDNO:66    RLNGTDGSIFPPRITKNSTLHVYEKDLCRLLPLSFEKEVTVRGGVKGYRFTPSPDVFASV 323
               : ****  *    : :.  :::: ::** :   :            :   *:      ::*
```

FIGURE 6 (cont.)

```
                        LAMP HOMOLOGY DOMAIN
                    3    4        5
SEQIDNO:4     ----SDNAGFCIPE-GNCLGSGVLNVSICKNGAPIIMSFPHFYQADERFVSAIEGMHP-NQ 360
SEQIDNO:56    ----SDNAGFCIPE-GNCLGSGVLNVSICKNGAPIIMSFPHFYQADERFVSAIEGMHP-NK 360
SEQIDNO:57    ----SDNAGFCIPE-GNCLGSGVLNVSICFNGAPIIMSFPHFYQADERFVSAIEGMHP-NK 360
SEQIDNO:58    ---SDNAGFCVPK-GNCLGSGVLNISICKNGAPIIISFPHFYEADKKFVSAIDGMRP-NK 360
SEQIDNO:59    ---SDNAGFCIPK-GNCLGSGVLNVSVCKNGAPIIMSFPHFYQADEKFVSAIGGMHP-NK 360
SEQIDNO:60    ---SENAGFCIPE-GNCMDSGVLNISICKNGAPIIMSFPHFYQADEKFVSAIKGMHP-NK 360
SEQIDNO:61    DENPANAGFCVPA-GDCLGKGVLKVSVCRQGAPIVVSFPHFYQADERYINAIEGMNP-NE 368
SEQIDNO:62    ---SENAGFCIPE-GNCMDAGVLNVSICKNGAPIIMSFPHFYQADEKFVSAIKGMRP-NK 360
SEQIDNO:63    TVNPDNAGFCVPP-GNCPGAGVLNVSICKQGAPIFLSAPHFYQADQKFVSDIEGMHP-TK 363
SEQIDNO:64    SVNPQNKGFCVPE-GNCLPSGLLNVSICKEGAPIVLSSPHFYQADENVINSIRGMKP-VK 364
SEQIDNO:65    DSHPDNMCFCPAGKPSCSPNGLFNVSLCQYDSPIMLSFPHFYLADESLRTQVEGISPPMK 414
SEQIDNO:66    DKNPNNMCYCPAG-PPCAPHGLFNVSLCQYDSPILLSFPHFYMADQTLRTAVEGISPPEK 382
                  *  :*      *   *::::*:*: .:**.:* **** **:    . : *: *  :
```

```
                        LAMP HOMOLOGY DOMAIN

SEQIDNO:4     EDHETFVDINPLTGIILKAAKRFQINIYVKKLDDFVETGDIRTMVFPVMYLNESVHIDKE 420
SEQIDNO:56    EDHETFVDINPLTGIILKAAKRFQINIYVKKLDDFVETGDIRTMVFPVMYLNESVHIDKE 420
SEQIDNO:57    EDHETFVDINPLTGIILKAAKRFQINIYVKNLDDFVETGDIPTMVFPVMYLNESVLIDKE 420
SEQIDNO:58    DYHETFVDINPLTGIILRAAKRFQINVYVKKLDDFIETGNIPTMVFPVMYINESVLIDKD 420
SEQIDNO:59    EYHETFVDINPLTGIILRAAKRFQINVYVPKLDDFVETGNIQTLVFPVMYINESVLIDKE 420
SEQIDNO:60    EEHESFVDINPLTGIILRGAKRFQINTYVRKLDDFVETGDIPTMVFPVMYLNESVLIDKE 420
SEQIDNO:61    EEHETYLDINPTTGVPIRACKPAQLNIILKRVRGFPNTKFLNETIFPIMYVNETATIDDE 428
SEQIDNO:62    EEHESFVDINPLTGIILRGAKRFQINTYVKKLDDFVETGNIRTMVFPVMYLNESVLIDKE 420
SEQIDNO:63    EYHETFVDINPLTGLVLQAAKRMQINIHVRKLPEFFETGNIRTLIFPVMYINESVLIDEA 423
SEQIDNO:64    EHHMTFLDINPLTGTLIQAAKRIQVNVYVRKINVYLITQDTQTLFFPVMHLNESVLIDDK 424
SEQIDNO:65    EKHQFFFDVQPKMGTTLRVRARIQINLAVSQVFDIKQVANFPDIIFPILWFEEGIDNLPD 474
SEQIDNO:66    DKHQLFIDVQPEMGTALRAPARIQINLAVSQVVDIKQVANFPDIVFPILWFEEGIDSLPD 442
              : *  :.*::*  *  ::    * *:*  : ::      .  :   .**:: .:*
```

```
                             Trans. Domain       Cytoplasmic Tail

SEQIDNO:4     TASRLKSMINTTLIITNI----PYIIMALGVFFGLVFTWLACKGQGSMDEGTADEPAPLI 476
SEQIDNO:56    TASRLKSMINTTLIITNI----PYIIMALGVFFGLVFTWLACKGQGSMDEGTADEPAPLI 476
SEQIDNO:57    TASRLKSVINTTLIITNI----PYIIMALGVFFGFVFTWLACKGQGSMDEGTADEPAPLI 476
SEQIDNO:58    TASPLKSVINTTLIITNI----PYIVMALGVFFGLIFTWLACPGQGSMDEGTPDEPAPLI 476
SEQIDNO:59    TASRLKSVINTTLIVTNI----PYIIMALGVFFGLIFTWLACRGQGSTDEGTADEPAPLI 476
SEQIDNO:60    TANQLKSVINTTLVVTNI----PYIIMALGVFFGLVFTWLACRGQGSMDEGTADERAPLI 476
SEQIDNO:61    SAAQMRMLLLIVTVVSNF----PVIILALGVILLVVLIFLVCRNRQRKNEVKRIDFTEAF 484
SEQIDNO:62    TASQLKSVINTTLIVTNI----PYIIMALGVFFGLIFTWLACRGQGSTDEGTADERAPLI 476
SEQIDNO:63    SANKLKHVLLEASVVTGI----PFVIMAIGIVFGIVFSVLVCRAQGAREESTEEERSPLI 479
SEQIDNO:64    SAGRLRSILFQGRVVANI----PFIIMGLGIILAFLFTTLSCLQKPSRDEGTEEERGPLI 480
SEQIDNO:65    EVTDL--MPFAEQVPPKIRVALIVGLCALGVILLLLSTF--CLIRNSHRQSTLHLEGSNY 530
SEQIDNO:66    EILDL--MKVATNIPPRAKFILTIALFGLGGFLFVVAVI--CLVRKSHRQSTLHLEGSNY 498
                  :  :     :              :  .:* .: .:      *  :     : .
```

FIGURE 6 (cont.)

```
SEQIDNO:4     RT---------------------------------------------     478
SEQIDNO:56    RT---------------------------------------------     478
SEQIDNO:57    RT---------------------------------------------     478
SEQIDNO:58    RT---------------------------------------------     478
SEQIDNO:59    RT---------------------------------------------     478
SEQIDNO:60    RT---------------------------------------------     478
SEQIDNO:61    HSFATTKDETAYTQVSNQAEDSPENPNNQPLRNGSYIAMSPVEAQKC     531
SEQIDNO:62    RT---------------------------------------------     478
SEQIDNO:63    RT---------------------------------------------     481
SEQIDNO:64    RAS--------------------------------------------     483
SEQIDNO:65    LATA------------QVDMNKKQNKDNQPAPY--------------     551
SEQIDNO:66    LATA------------SVDQAKKKAKMDNGMSSKSN-----------     522
               :
```

| LIMP-2 | | | | | |
|---|---|---|---|---|---|
| Accession No. | *Species* | SEQ ID NO: | Accession No. | *Species* | SEQ ID NO: |
| NP_005497.1 | *H. sapiens* | 4 | NP_775366.1 | *D. rerio* | 61 |
| XP_517214.2 | *P. troglodytes* | 56 | NP_446453.1 | *R. norvegicus* | 62 |
| XP_001096458.1 | *M. mulatta* | 57 | XP_420593.1 | *G. gallus* | 63 |
| XP_005639134.1 | *C. lupus familiaris* | 58 | NP_001016557.1 | *X. tropicalis* | 64 |
| NP_001095623.1 | *B. Taurus* | 59 | NP_726504.2 | *D. Melanogaster* | 65 |
| NP_031670.1 | *M. musculus* | 60 | XP_314345.2 | *A.gambiae* | 66 |

FIGURE 7: HUMAN LIMBIC/SLAMP ALIGNMENT WITH ORTHOLOGOUS SEQUENCES

```
                  SIGNAL SEQUENCE            LAMP HOMOLOGY DOMAIN
                                                          1
SEQIDNO:67     -MVRRVQPDRKQLPLV-LLRLLCL-LPTGLPVRSVDFNRGTDNITVRQGDTAILRCVVED  57
SEQIDNO:68     -MVRRVQPDRKQLPLV-LLRLLCL-LPTGLPVRSVDFNRGTDNITVRQGDTAILRCVVED  57
SEQIDNO:69     -MGARVQPDRKQLPLV-LLRLLCL-LPTGLPVRSVDFNRGTDNITVRQGDTAILRCVVED  57
SEQIDNO:70     -MVGRVQPDRKQLPLV-LLRLLCL-LPTGLPVRSVDFNRGTDNITVRQGDTAILRCVVED  57
SEQIDNO:71     -MVGRSQSDRNQLPLF-LLRLLCL-LPTGLPVRSGDFNRSTDNMTVRQGDTAILRCFVED  57
SEQIDNO:72     -----MSCLWIHSVFIPGFF--LLF-GFEGFPVISVESQRSTDNITIRQGDTTVIRCYVDD  53
SEQIDNO:102    -MVGRVQPDRKQLPLV-LLRLLCL-LPTGLPVRSVDFNRGTDNITVRQGDTAILRCVVED  57
SEQIDNO:103    -MVGRVQPDRKQLPLV-LLRLLCL-LPTGLPVRSVDFNRGTDNITVRQGDTAILRCVVED  57
SEQIDNO:104    -MVARVQPDRKQLPLV-LLRLLCL-LPTGLPVRSVDFNRGTDNITVRQGDTAILRCVVED  57
SEQIDNO:105    -MVARVQPDRKQLPLV-LLRLLCL-LPTGLPVRSVDFNRGTDNITVRQGDTAILRCVVED  57
SEQIDNO:106    --------------MSFAGEAA-------SQILNKAEPLFISRSEAFKFAVGDTITLPCEVAS  42
SEQIDNO:107    --------MRPCLLHSIWMLGFVLCLLSLQGLPVRSGDFNRSTDNITVRQGDTAILRCFVED  54
SEQIDNO:108    -MLGARRPPRSQLPLV-LLRLLCL-LPTGLPVRSVDFNRGTDNITVRQGDTAILRCVVED  57
SEQIDNO:109    -MVGRVHPDRKQLPLV-LLRLLCL-LPTGLPVRGVDFTRGTDNITVRQGDTAILRCYVED  57
SEQIDNO:110    -MVARAQPDRKQLPLV-LLRLLCL-LPTGLPVRSVDFTRGTDNITVRQGDTAILRCFVED  57
SEQIDNO:111    -----MRTYW-LHSIWVL-GFFLSLF-SLQGLPVRSVDFTRGTDNITVRQGDTAILRCYVED  54
SEQIDNO:112    --------MRPCLLHSIWMLGFVLCLLSLQGLPVRSGDFNRSTDNITVRQGDTAILRCFVED  54
SEQIDNO:113    MQVGRKSCWRQ---LQASFFRLLCL-IPTGFPVRSVDMQRATDNITIRQGDTAIIRCYVDD  57
                                        :          :: :..  ***  : * * .

                              LAMP HOMOLOGY DOMAIN
                                                          2
SEQIDNO:67     KN-SKVAWLNRSGIIFAGHDKWSLDPRVELEKRHSLEYSLRIQKVDVYDEGSYTCSVQTQ  116
SEQIDNO:68     KN-SKVAWLNRSGIIFAGHDKWSLDPRVELEKRHSLEYSLRIQKVDVYDEGSYTCSVQTQ  116
SEQIDNO:69     KN-SKVAWLNRSGIIFAGHDKWSLDPRVELEKRHSLEYSLRIQKVDVYDEGSYTCSVQTQ  116
SEQIDNO:70     KN-SKVAWLNRSGIIFAGHDKWSLDPRVELEKRHALEYSLRIQKVDVYDEGSYTCSVQTQ  116
SEQIDNO:71     KS-SKVAWLNRSGIIFAVDDKWSLDPRVELEKRSPFEYSLRIQKVDVSDEGPYICSVQTN  116
SEQIDNO:72     KV-SKVAWLNRSNIIFAGEDKWSLDPRVELVTQGQLEYSLRIQKVDVFDEGPYTCSIQTK  112
SEQIDNO:102    KN-SKVAWLNRSGIIFAGHDKWSLDPRVELEKRHALEYSLRIQKVDVYDEGSYTCSVQTQ  116
SEQIDNO:103    KN-SKVAWLNRSGIIFAGHDKWSLDPRVELEKRHSLEYSLRIQKVDVYDEGSYTCSVQTQ  116
SEQIDNO:104    KN-SKVAWLNRSGIIFAGHDKWSLDPRVELEKRHSLEYSLRIQKVDVYDEGSYTCSVQTQ  116
SEQIDNO:105    KN-SKVAWLNRSGIIFAGHDKWSLDPRVELEKPHSLEYSLRIQKVDVYDEGSYTCSVQTQ  116
SEQIDNO:106    PGTYVLAWKRGIAILTAGSVKVTPDPRVRLVN------GYSLQIRDAVPQDAGDYICQIAML  98
SEQIDNO:107    RS-SRVAWLNRSGIIFAGDDKWSLDPRVELEKRSLLEYSLRIQKVDVSDEGPYTCSVQTK  113
SEQIDNO:108    KN-SKVAWLNRSGIIFAGHDKWSLDPRVELEKRHSLEYSLRIQKVDVYDEGSYTCSVQTQ  116
SEQIDNO:109    KS-SKVAWLNRSGIIFAGHDKWSLDPRVELEKRTALEYSLRIQKVDVYDEGSYTCSVQTQ  116
SEQIDNO:110    RS-SKVAWLNRSGIIFAGEDKWSLDPRVELEKRSPLEYSLRIQKVDVYDEGSYTCSVQTQ  116
SEQIDNO:111    RS-SKVAWLNRSGIIFAGEDKWSLDPRVELEKRNPLEYSLRIQKVDVYDEGSYTCSVQTQ  113
SEQIDNO:112    RS-SRVAWLNRSGIIFAGDDKWSLDPRVELEKRSLLEYSLRIQKVDVSDEGPYTCSVQTK  113
SEQIDNO:113    KV-SKVAWLNRSNIIFAGQDKWSLDPRVDLVTKGQLEYSLRIQKVDVYDEGSYTCSIQTK  116
                  :**  .    *: *    * : **** * .     ***:*:..    * * * *.:
```

FIGURE 7 (cont.)

LAMP HOMOLOGY DOMAIN
3

```
SEQIDNO:67    HEPKTSQVYLIVQVPPKISNISS--DVTVNEGSNVTLVCMANGRPEPVITWRHLTP---T  171
SEQIDNO:68    HEPKTSQVYLIVQVPPKISNISS--DVTVNEGSNVTLVCMANGRPEPVITWRHLTP---T  171
SEQIDNO:69    HEPKTSQVYLIVQVPPKISNISS--DVTVNEGSNVTLVCMANGRPEPVITWRHLTP---T  171
SEQIDNO:70    HEPKTSQVYLIVQVPPKISNISS--DVTVNEGSNVTLVCMANGRPEPVITWRHLTP---L  171
SEQIDNO:71    QHTKTMQVYLIVQVPPKISNISA--DITVNEGSNVTLMCIAYGRPEPMITWRHLTP---T  171
SEQIDNO:72    QQSKTSQVYLIVQVPAIIYKVSE--DITVNEGSNVALTCLANGRPDPAITWRLLNP---S  167
SEQIDNO:102   HEPKTSQVYLIVQVPPKISNISS--DVTVNEGSNVTLVCMANGRPEPVITWRHLTP---L  171
SEQIDNO:103   HEPKTSQVYLIVQVPPKISNISS--DVTVNEGSNVTLVCMANGRPEPVITWRHLTP---T  171
SEQIDNO:104   HEPKTSQVYLIVQVPPKISNISS--DVTVNEGSNVTLVCMANGRPEPVITWRHLTP---T  171
SEQIDNO:105   HEPKTSQVYLIVQVPPKISNISS--DVTVNEGSNVTLVCMANGRPEPVITWRHLTP---T  171
SEQIDNO:106   DPR-EITHSVEILVPPKITHVTSGGHLQVRKGSPVRLECSATGNPMPNITWTRKNNLLPN  157
SEQIDNO:107   QHTKTTQVYLIVQVPPKISNISA--DITVNEGSNVTLMCIAYGRPEPMITWRHLTP---T  168
SEQIDNO:108   HEPKTSQVYLIVQVPPKISNISS--DVTVNEGSNVTLVCMANGRPEPVITWRHLTP---T  171
SEQIDNO:109   HQPKTSQVYLIVQVPPKISNISS--DVTVNEGSNVTLVCMANGRPEPVITWRHLTP---T  171
SEQIDNO:110   HHPKTSQVYLIVQVPPKISNISS--DITVNEGSNVTLVCMANGRPEPVITWRHLTP---T  171
SEQIDNO:111   HHPKTSQVYLIVQVPPKISNISS--DITVNEGSNVTLVCMANGRPEPVITWRHLTP---T  168
SEQIDNO:112   QHTKTTQVYLIVQVPPKISNISA--DITVNEGSNVTLMCIAYGRPEPMITWRHLTP---T  168
SEQIDNO:113   QQPKTSQVYLIVQVPASIYQVSN--DITVNEGSNVTLSCLANGRPDPAITWRLLNP---S  171
              .         : : **   * :::   .: *.:** * * * * *.* * ***    .
```

LAMP HOMOLOGY DOMAIN
4

```
SEQIDNO:67    GREFEGEEEYLEILGITREQSGKYECKAANEVSSADVKQVKVTVNYPPTITESKS       230
SEQIDNO:68    GREFEGEEEYLEILGITREQSGKYECKAANEVSSADVKQVKVTVNYPPTITESKS-NEAT  230
SEQIDNO:69    GREFEGEEEYLEILGITREQSGKYECKAANEVSSADVKQVKVTVNYPPTITESKS-NEAT  230
SEQIDNO:70    GREFEGEEEYLEILGITREQSGKYECKAANEVSSADVKQVKVTVNYPPTITESKS-NEAT  230
SEQIDNO:71    ARDFEGEEEFLEIQGITREQSGRYECKAANEVASADVKQVRVTVNYPPIITESNS-NEAT  230
SEQIDNO:72    AEALDV-GEYLEISGVVRSQAGRYECKASNDVSTPDVKYVNVVVNYPPYIKDVRS-SETA  225
SEQIDNO:102   GREFEGEEEYLEILGITREQSGKYECKAANEVSSADVKQVKVTVNYPPTITESKS-NEAT  230
SEQIDNO:103   GREFEGEEEYLEILGITREQSGKYECKAANEVSSADVKQVKVTVNYPPTITESKS-NEAT  230
SEQIDNO:104   GRELEGEEEYLEILGITREQSGKYECKAANEVSSADVKQVKVTVNYPPTITESKS-NEAT  230
SEQIDNO:105   GREFEGEEEYLEILGITREQSGKYECKAANEVSSADVKQVKVTVNYPPTITESKS-NEAT  230
SEQIDNO:106   GEEQFT-NPVYVIENMDRHKGGTYICTANNGVGQVATSQIILHVLYPPEISVENPTVYSG  216
SEQIDNO:107   ARDFEGEEEFLEIQGITREQSGRYECKAANEVASADVKQVRVTVNYPPIITESKS-NEAT  227
SEQIDNO:108   GREFEGEEEYLEILGITREQSGKYECKAANEVSSADVRQVKVTVNYPPTITESKS-NEAT  230
SEQIDNO:109   GREFEGEEEYLEILGITREQSGKYECKAANEVSSADVKQVKVTVNYPPTITESKS-NEAT  230
SEQIDNO:110   GKEFEGEEEYLEILGITREQSGKYECKAANEVASADVKQVRVTVNYPPTITESKS-NEAA  230
SEQIDNO:111   GKEFEGEEEYLEILGITREQSGKYECKAANEVASADVKQVRVTVNYPPTITESKS-NEAA  227
SEQIDNO:112   ARDFEGEEEFLEIQGITREQSGRYECKAANEVASADVKQVRVTVNYPPIITESKS-NEAT  227
SEQIDNO:113   AEPLDG-EEYLDIIGIMRTQAGRYECKASNDVATPDVKYVNVIVNYPPTIKKTQS-SETP  229
              ..           * .: * :.* * *.* * *.     .   : : * *** *.   .    :
```

FIGURE 7 (cont.)

LAMP HOMOLOGY DOMAIN

```
                 5                                                     6
SEQIDNO:67     TGRQASLKCEASAVPAPDFEWYRDDTRINSANGLEIKSTEGQSSLTVTNVTEEHYGNYTC  290
SEQIDNO:68     TGRQASLKCEASAVPAPDFEWYRDDTRINSANGLEIKSTEGQSSLTVTNVTEEHYGNYTC  290
SEQIDNO:69     TGRQASLKCEASAVPAPDFEWYRDDTRINSANGLEIKSTEGQSSLTVTNVTEEHYGNYTC  290
SEQIDNO:70     TGRQASLKCEASAVPAPDFEWYRDDTRINSANGLEIKSTEGQSSLTVTNVTEEHYGNYTC  290
SEQIDNO:71     TGKQAILRCEASAVPAPDFEWYKDDTRINSAQGLEIRNTGSRSVLMVANVTEEHYGNYTC  290
SEQIDNO:72     VGQAGVLHCEASAVPQPEFEWYRDERRLSSSQSLTIQVSGSRTVLVVANVTEEDYGNYTC  285
SEQIDNO:102    TGRQASLKCEASAVPAPDFEWYRDDTRINSANGLEIKSTEGQSSLTVTNVTEEHYGNYTC  290
SEQIDNO:103    TGRQASLKCEASAVPAPDFEWYRDDTRITSANGLEIKSTEGQSSLTVANVTEEHYGNYTC  290
SEQIDNO:104    TGRKASLKCEASAVPAPDFEWYRDDTRINSANGLEIKSTEGQSSLTVTNVTEEHYGNYTC  290
SEQIDNO:105    TGRKASLKCEASAVPAPDFEWYRDDTRINSANGLEIKSTEGQSSLTVTNVTEEHYGNYTC  290
SEQIDNO:106    EGQEAMLVCIVHGESQPEVLWHKDTMQIDQTERHVIENRGARHTLIIRKVHPQDFGNYSC  276
SEQIDNO:107    TGKQAILRCEASAVPAPDFEWYKDDTRINSAQGLEIRNTGSRSVLMVANVTEEHYGNYTC  287
SEQIDNO:108    TGRKASLKCEASAVPAPDFEWYRDDTRINSANGLEIKSTEGQSSLTVTNVTEEHYGNYTC  290
SEQIDNO:109    TGRQASLKCEASAVPAPDFEWYRDDTRINSANGLEIKSIEGQSLLMVTNVTEEHYGNYTC  290
SEQIDNO:110    TGRQALLRCEASAVPTPDFEWYRDDTRINSANGLEIKSTGSQSLLMVANVTEEHYGNYTC  290
SEQIDNO:111    TGRQALLRCEASAVPTPDFEWYRDDTRINSANGLEIKSTGSQSLLMVANVTEEHYGNYTC  287
SEQIDNO:112    TGKQAILRCEASAVPAPDFEWYKDDTRINSAQGLEIRNTGSRSVLMVANVTEEHYGNYTC  287
SEQIDNO:113    VGRNGTLRCEVTAVPTPEFEWYRDDKRLANTQSITIQTSGTTTSLTIANITEEDYGNYTC  289
                *: . * * . .   *:. *::*  :: .::   *.       * : ::  :.:***:*
```

Trns Memb.

```
SEQIDNO:67     VAANKLGVTNASLVLFRPGSVRGINGSISLAVPLWLLAASLLCLL-SKC------------  338
SEQIDNO:68     VAANKLGVTNASLVLFRPGSVRGINGSISLAVPLWLLAASLLCLL-SKC------------  338
SEQIDNO:69     VAANKLGVTNASLVLFRPGSVRGINGSISLAVPLWLLAASLLCLL-SKC------------  338
SEQIDNO:70     VAANKLGVTNASLVLFSKYAKTEPDSMQVIE-FLHIDLKSIRHPL-KVNPIQK-------  341
SEQIDNO:71     VAANKLGITNTSLYLYI-GPGTPIDNATSLAASLWLMANILLCLF-CTC------------  337
SEQIDNO:72     VATNRLGVHNASVFLYKPGMGRDINSAGCICQSLWLLLLCVSSAL-LQC------------  333
SEQIDNO:102    VAANKLGVTNASLVLFRPGSVRGINGSISLAVPLWLLAASLFCLL-SKC------------  338
SEQIDNO:103    VAANNLGVTNASLVLFRPGSVRGINGSISLAVPLWLLAASLLCLL-SKC------------  338
SEQIDNO:104    VAANNLGVTNASLVLFRPGSVRGINGSISLAVPLWLLAASLLCLL-SKC------------  338
SEQIDNO:105    VAANNLGMTNASLVLFRPGSVRGINGSISLAVPLWLLAASLICLL-SKC------------  338
SEQIDNO:106    IADNQLGKTRKTVTLTGKPKTAVF---RSVPNSQWKDKYNISWIVDSHSPIEEFKLYYRQ  333
SEQIDNO:107    VAANKLGITNTSLYLYI-GPGTPIDSATSLAASLWLMANLLFCLF-CTC------------  334
SEQIDNO:108    VAANNLGVTNASLVLFRPGSVRGINGSISLAVPLWLLAASLLCLL-SKC------------  338
SEQIDNO:109    VAANKLGVTNASLILFRPGSVRGINGSISLAVPLWLLAASLFCLL-SKC------------  338
SEQIDNO:110    VAANKLGVTNASLYLYRPGTGRVDNGSVSLAVPLWLLAASLLCLL-SKC------------  338
SEQIDNO:111    VAANKLGVTNASLYLYRPGTGRVDNGSMSLAVPLWLLAASLLCLL-SKC------------  335
SEQIDNO:112    VAANKLGITNTSLYLYI-GPGTPIDSATSLAASLWLMANLLFCLF-CTC------------  334
SEQIDNO:113    VASNRLGVQNASLFLYRPGTGRDINGSACVSQSLWLLLASFACLF-LKC------------  337
               :* *.**  . :: *               :          .    .
```

FIGURE 7 (cont.)

```
SEQIDNO:67     ------------------------------------------------------------   338
SEQIDNO:68     ------------------------------------------------------------   338
SEQIDNO:69     ------------------------------------------------------------   338
SEQIDNO:70     ------------------------------------------------------------   341
SEQIDNO:71     ------------------------------------------------------------   337
SEQIDNO:72     ------------------------------------------------------------   333
SEQIDNO:102    ------------------------------------------------------------   338
SEQIDNO:103    ------------------------------------------------------------   338
SEQIDNO:104    ------------------------------------------------------------   338
SEQIDNO:105    ------------------------------------------------------------   338
SEQIDNO:106    MTFSIGQLQPLQTDWRDTVLPAFFYSHHYTQGMSYLIRGLEPDQQYEARVQSRNRYGWSD   393
SEQIDNO:107    ------------------------------------------------------------   334
SEQIDNO:108    ------------------------------------------------------------   338
SEQIDNO:109    ------------------------------------------------------------   338
SEQIDNO:110    ------------------------------------------------------------   338
SEQIDNO:111    ------------------------------------------------------------   335
SEQIDNO:112    ------------------------------------------------------------   334
SEQIDNO:113    ------------------------------------------------------------   337

SEQIDNO:67     ------------------------   338
SEQIDNO:68     ------------------------   336
SEQIDNO:69     ------------------------   338
SEQIDNO:70     ------------------------   341
SEQIDNO:71     ------------------------   337
SEQIDNO:72     ------------------------   333
SEQIDNO:102    ------------------------   338
SEQIDNO:103    ------------------------   338
SEQIDNO:104    ------------------------   338
SEQIDNO:105    ------------------------   338
SEQIDNO:106    FSESFLFTTSNTGKWMCQCCTNPG   417
SEQIDNO:107    ------------------------   334
SEQIDNO:108    ------------------------   338
SEQIDNO:109    ------------------------   338
SEQIDNO:110    ------------------------   338
SEQIDNO:111    ------------------------   335
SEQIDNO:112    ------------------------   334
SEQIDNO:113    ------------------------   337
```

| LIMBIC/LSAMP | | | | | |
|---|---|---|---|---|---|
| Accession No. | Species | SEQ ID NO: | Accession No. | Species | SEQ ID NO: |
| NP_002329.2 | *H. sapiens* | 67 | NP_001192297.1 | *B. Taurus* | 105 |
| XP_516662.2 | *P. troglodytes* | 68 | XP_312298.5 | *A.gambiae* | 106 |
| XP_002716722.1 | *O. cuniculus* | 69 | NP_001096385.1 | *X.tropicalis* | 107 |
| NP_780757.1 | *M. musculus* | 70 | XP_003434117.1 | *C. lupus familiaris* | 108 |
| NP_001086181.1 | *X. laevis* | 71 | XP_001362972.1 | *M. domestica* | 109 |
| NP_001034921.1 | *D. rerio* | 72 | NP_990205.1 | *G. gallus* | 110 |
| NP_058938.1 | *R. norvegicus* | 102 | XP_002190582.1 | *T. guttate* | 111 |
| XP_001502710.1 | *E. caballus* | 103 | NP_001096385.1 | *X. tropicalis* | 112 |
| NP_001231626.1 | *S. scrofa* | 104 | XP_003449349.1 | *O. niloticus* | 113 |

FIGURE 8: HUMAN ENDOLYN ALIGNMENT WITH ORTHOLOGOUS SEQUENCES

```
                    SIGNAL SEQUENCE              LAMP HOMOLOGY DOMAIN

SEQIDNO:5     MSRLSRSLLWAATCLGVLCVLSADKNTTQH-PNVTTLAPISNVTSAP-----V-TSLPLV 53
SEQIDNO:73    MSGSSRRLLWAATCLAVLCVSAAQPNITTLAPNVTPVPT-----TT-----TKVVPTTQM 50
SEQIDNO:74    MSRLSRSLLWAVTCLAVLCVLSAEENPTPH-TNVTSLAPTSNITSAP-----V-TSLPLV 53
SEQIDNO:75    MLGLSRQLLWAVGCLAALCVLTAAKNSTIL-PPSTTTPWLSPPTTQT-----TSAPPKTL 54
SEQIDNO:76    MSGLSRPLLLAVGCLAALCVITAAGNTTLA-PNVTTASS-PPPTTTTVPVSPTTLSPLPV 58
SEQIDNO:77    MSGLSRPLLLAVGYLAALCVITAARNTTVT-PNVTTPSS-PPPTTATVPVSPTTLTPPPV 58
SEQIDNO:78    MSGLSPQLCWAAACLAALCALTAAQSPSSD-PNGTTTTQATTDAAT----TRVTTAAPA 55
SEQIDNO:79    MSGASRGLFWAATCLAALCLSAAQSNS-SASPNVTDPPT-----TT-----SKVVPTTLT 49
              *   ** *  *.  *..**  :*  .         *         :
```

```
                                LAMP HOMOLOGY DOMAIN
                   1    2 3          4   5     6      7     8
SEQIDNO:5     TTPAPETCEGRNSCVSCFNVSVV-NTTCFWIECKD--ESYCSHNSTVSDCQVGNTTDFCS 110
SEQIDNO:73    PTVLPETCASFNSCVSCVNATFTNNITCFWLHCQEANKTYCAN-EPLSRCSQVNRTDLCS 109
SEQIDNO:74    TTPAPETCEGRNSCVSCFNASTV-NTTCFWIECKD--ESYCSHNSTVSDCQVGNTTDFCS 110
SEQIDNO:75    PTPAPEICENRNSCISCFDA-----NNTCFWIECKG--KSYCSDNSTVSDCRVVNGTDFCS 108
SEQIDNO:76    TTPAPDICGSRNSCVSCVDG-----NATCFWIECKG--KSYCSDNSTAGDCKVVNTTGFCS 112
SEQIDNO:77    TTPAPDICGSRNSCISCVDG-----NATCFWIECKG--KSYCSDNSTVSDCKVVNTTGFCA 112
SEQIDNO:78    TTPAPDPCDNRNSCVSCVNTSVD-ATACSWIECKE--KSYCSHNTTVSDCQVVNSTQLCS 112
SEQIDNO:79    TTKPPETCESFNSCVSCVNATLTNNITCVWLDCHEANKTYCSS-ELVSNCTQNTSTDSCS 108
               *   *; *  . ***;**.;          :* *;.*;    ::**;       .:*    . *   *:
```

```
                                LAMP HOMOLOGY DOMAIN

SEQIDNO:5     VST-ATPVPTANSTAKPTVQPSPSTT-SKTVTTSGTTNNTVTPTSQPVRKSTFDAASFIG 168
SEQIDNO:73    VIPPTTPVPT-NSTAKPTTRPSSPTPTPSVVTSAGTTNTTLTPTSQPERKSTFDAASFIG 168
SEQIDNO:74    VPT-ATLVPTANSTAKPTVQPSPSTT-SKTVTTSGTTNTTVTPTSQPVRKSTFDAASFIG 168
SEQIDNO:75    GPT-VTPLPT-NSTAKTTTLPSPSSA-STTATTSGTTNTTLAPTTQPMRKSTFDAASFIG 165
SEQIDNO:76    VPT-TTPTPT-NSTAKTTTLPSTTTT-STTATTSGTTNTTLSPTIQPTRKSTFDAASFIG 169
SEQIDNO:77    VPT-TTPTPT-NSTAKTTTLPSTTTT-STTATTSGTANTTLTPTIQPMRKSTFDAASFIG 169
SEQIDNO:78    APE-PTMMPT-NSTAKTTTQPSSSTA-TTTATTSGTTNITLSPTSQPGPKSTFDAASFIG 169
SEQIDNO:79    VIP-TTPVPT-NSTAKPTTRPSSPTPTPSVVTSAGATNTTVTPTSQPERKSTFDAASFIG 166
                  *  ** ***** *. **   :    ...*::*;:* *:;** ** ************
```

```
              Trns Memb.  Cytoplasmic Tail

SEQIDNO:5     GIVLVLGVQAVIFFLYKFCKSKERNYHTL 197
SEQIDNO:73    GIVLVLGVQAVIFFLYKFCKSKERNYHTL 197
SEQIDNO:74    GIVLVLGVQAVIFFLYKFCKSKERNYHTL 197
SEQIDNO:75    GIVLVLGVQAVIFFLYKFCKSKERNYHTL 194
SEQIDNO:76    GIVLVLGVQAVIFFLYKFCKSKERNYHTL 198
SEQIDNO:77    GIVLVLGVQAVIFFLYKFCKSKERNYHTL 198
SEQIDNO:78    GIVLILGVQAVIFFLYKFCKSKERNYHTL 198
SEQIDNO:79    GIVLVLGVQAVIFFLYKFCKSKERNYHTL 195
              ****:************************
```

FIGURE 8 (cont.)

| | Endolyn | | | | |
|---|---|---|---|---|---|
| Accession No. | *Species* | SEQ ID NO: | Accession No. | *Species* | SEQ ID NO: |
| NP_006007.2 | *H. sapiens* | 5 | NP_001039506.1 | *B. taurus* | 76 |
| NP_058594.1 | *M. musculus* | 73 | XP_004011265.1 | *O. aries* | 77 |
| XP_001091286.1 | *M. mulatta* | 74 | XP_532256.2 | *C. lupus familiaris* | 78 |
| XP_001924661.2 | *S. scrofa* | 75 | NP_114000.1 | *R. norvegicus* | 79 |

FIGURE 9: HUMAN MACROSAILIN ALIGNMENT WITH ORTHOLOGOUS SEQUENCES

```
                    SIGNAL SEQUENCE          LAMP HOMOLOGY DOMAIN 1
                                         1
SEQIDNO:80     MRLAVLFSGALLGL-LAAQGTGNDCPHKKSATLLPSFTVTPTVTEST----GTTSHRTTK 55
SEQIDNO:81     MRLAVLFSGALLGL-LAAQGTGNDCPHKKSATLLPSFTVTPTVTEST----GTTSHRTTK 55
SEQIDNO:82     MRLAVFFSGALLGL-LAAQGTGNDCPHKKSATLLPSFTVTPTATESTPS-PGTTSHRTTK 58
SEQIDNO:83     MRLPVCL---ILLGP-LIAQGTEEDCPHKKAVTLLPSFTMTPTATESTAS-PTTSHRPTTT 56
SEQIDNO:84     MRLAVLFLGALLGL-LAAQGTGNDCPHKKSATLLPSFTVTPTATEST----GTTSHRTTK 55
SEQIDNO:85     MRFPVCL--TLLVL-LVAQGTGKDCPHKKAATLLPSFTETPTTTGSTAS-PTTTHRPTTT 56
SEQIDNO:86     MPPAVFFLGALVGL-LAAQGTRSDCPHKRSATLLPSFTVTPTATESTGS-PGTTSHSTTT 58
SEQIDNO:87     MRLAVLFSGALLGL-LAAQETGNDCPHKKSATLLPSFTVTPTATESTAS-PGTTSHQTTQ 58
SEQIDNO:88     MRLPVLFLA-LLGL-HAA-------------------------------S-SGTTSHRTTK 27
SEQIDNO:89     MTLAVLFLGALLGL-LAESTTSH-------------------------------------- 22
SEQIDNO:90     MRLAVLFSGALLGL-LAAQGTGNDCPHKKSATLLPSFTVTPTATEST----GTTSHRTTK 55
SEQIDNO:91     MRLSLLLSGILLGL-LAEQGAGDKCPQEKSVTLVPSFTVTTIATEPSTTSPETTTSSGS- 58
SEQIDNO:92     ---------MGLTLPLPAQGSQCRANCPHKKSATLVPSFTVTPTATSG-----PTTTAHQTTT 49
                       :

                             LAMP HOMOLOGY DOMAIN 1

SEQIDNO:80     SHKTTTHRTTT---------TGTTSHGPTTATHNPTTTSHGNVTVHPTSNSTATSQGPSTAT 108
SEQIDNO:81     SHKTTTHRTTT---------TGTASHGPTTATHNPTTTSHGNVTVHPTSNSTATSQGPSTAT 108
SEQIDNO:82     SHRTTTWRISTTTHTTNTTGTTSSESPTATHSPA---------------------------- 92
SEQIDNO:83     SHGNVTVH----------T-----SSGPTTVTHNPA--------------------------- 77
SEQIDNO:84     SHKTTTHRTTT---------TGTTSHRPTTATHNPTTTSHRNATVHPTSNSTATSQGPSTAT 108
SEQIDNO:85     SHRPTTTS----------HRPTTTSHRPTTTSHRPT-----------------------TTS 85
SEQIDNO:86     AETT--------------------SHAPNTTTHQ---------------------------- 72
SEQIDNO:87     SHRTTTT-------------GTTSDHPTTATHNP---------------------------- 79
SEQIDNO:88     NPHTT----------SHSTATPGTTSHRPTTAT----------------------------- 50
SEQIDNO:89     --RTTTPR----------TTTTGTTSHGPTTVTHNPA------------------------- 47
SEQIDNO:90     SHKTTTHRTTT---------TGTTSHRPTTATHNPNTTSHRNATVHPTSNSTATSQGPSTAT 108
SEQIDNO:91     --TATTYRTS----------TAATTEHS--------------------NSTATS-------- 80
SEQIDNO:92     DHGTTTSHETTTSQGTSTHGTSTPHTTTTGHGTT-TGHQN-----TSH-------------- 91

                             LAMP HOMOLOGY DOMAIN 1

SEQIDNO:80     HSPATTSHGNATVHPT-SNSTATSPG-----------F-T--SSAHPEPPPPSPSPSPTSK 154
SEQIDNO:81     HSPATTSHGNATVHPT-SNSTATSPG-----------F-T--SSAHPEPPPPSPSPSPTSK 154
SEQIDNO:82     ---TTTSHQNTTVHPT-SNITATSPG-----------PST--RSPHPEP-PPSPSPSPGSK 135
SEQIDNO:83     ---TTTSHGNATISHATVSPTT------NG-TATSPRSST--VGPHPGPPPPSP---SPRSK 124
SEQIDNO:84     HRPATTSHGNATVHPT-SNSTATSPG-----------L-T--SSAHPGPPPPSPSPSPASK 154
SEQIDNO:85     HRPTTTSHGNATV------SP-------------TTNSPGFST---VGPHPGPPPPSPSPSPSST 128
SEQIDNO:86     -APTTPGHRNTTIHPTTSNSTSNTTGTTGTGKPHTSTSY--TQPGPGPRPPPPSPGPGPQ 129
SEQIDNO:87     ----TTTSHGNTTVHPTTSNSTVTSPG------------SAS---SSPHPPPPPPSPSPSPGSK 124
SEQIDNO:88     ----PTTGHGNVTVHPTTSNTTSNTTTTTGTS---PGFST---STPHPGPPPPPPSPSPGSR 102
SEQIDNO:89     ----TTTSHGNATVHPT-SSSTATSPG------------SST---RPPHPGPPPPSPSPSPGSQ 91
SEQIDNO:90     HRPATTSHGNATVHPT-SNSTATSPG-----------L-T--SSAHPGPPPPSPSPSPASK 154
SEQIDNO:91     ---YSTTSEGTAVTHGTTTSPRN-----------------TSTT---STSQSVPVPPSPQPTSSPS 123
SEQIDNO:92     --STTTSHGTSTPHNTTTPHPTTSHGTTTSHGTSTGHWTARPTIRPGPPPPPP----SPG 145
                  *  ..  .  .                                 * ** *
```

FIGURE 9 (cont.)

```
                       LAMP HOMOLOGY DOMAIN

                 2
SEQIDNO:80   ETIGDYMWTNGSQPCVHLQAQIQIRVMYTTQGGG----------EAWGISVLNPNK-TKVQ 204
SEQIDNO:81   ETIGDYIWTNGSQPCVHLQAQIQIRVMYTTQGGG----------EAWGISVLNPNK-TKVQ 204
SEQIDNO:82   EAIGDYTWSNGSQPCVRLQAQIQIRVLYPTQGGG----------EAWGISVLNPNR-TKAQ 185
SEQIDNO:83   GALGNYTWANGSQPCVQLQAQIQIRILYPIQGGRKVKLKWGLKRAWGISVLNPNK-TKVQ 183
SEQIDNO:84   ETIGDYMWTNGSQPCVHLQAQIQIRVMYTTQGGG----------EAWGISVLNPNK-TKVQ 204
SEQIDNO:85   GALGNYTWTNGSQPCVQLQAQIQIPILYLTQGGK----------KAWGLSVLNPNK-TKVQ 178
SEQIDNO:86   DAIGDYTWTTGSQPCARLQAPIQIGVVYPTQAGG----------QAWGISVLNPNS-TKPW 179
SEQIDNO:87   EAIGDYIWTNGSQPCVRLQAQIQIRVLYPTLGGG----------KAWGISVLNPNK-TKAQ 174
SEQIDNO:88   EAVGNYIWTNGSQPCVQLQAQIQIRVLYPTQGGG----------QAWGMSVLNPNR-TKAQ 152
SEQIDNO:89   EAIGDYTWTNGSQPCVQLQAQIQIRVLYPTQGGG----------EAWGISVLNPNK-TKAL 141
SEQIDNO:90   ETIGDYMWTNGSQPCVHLQAQIQIRVMYTTQGGG----------EAWGISVLNPNK-TKVQ 204
SEQIDNO:91   GAVGDYIGANGSQLCVHLRAQIQMRVLYQASGGG----------KLWGIPVLNPNR-TMAQ 173
SEQIDNO:92   KAVGNYTVFNGSQPCLRLRAEIPLWVLYQAQEEGEAPPVSG-------AASFPPPRPRPVA 199
              ::*:*    .*** * :*:*.*:: ::*                            : *

                       LAMP HOMOLOGY DOMAIN

              3
SEQIDNO:80   GSCEGAHPHLLLSF----PYGHLSFGFMQDLQQ--RVVYLSYMAVEYNVSFPHAAQWTFS 258
SEQIDNO:81   GSCEGAHPHLLLSF----PYGHLSFGSMQDLQQ--KAVYLSYMAVEYNVSFPHAAQWTFS 258
SEQIDNO:82   GGCEGTHSHLLLSF----PSGQLSFGFKQDPLQ--SAVYLNYMAVEYNVSFPQAVQWTFS 239
SEQIDNO:83   GGCDGTHPHLSLSF----PYGQLTFGFKQDLHQSPSTVYLDYMAVEYNVSFPQAAQWTFM 239
SEQIDNO:84   GSCEGAHPHLLLSF----PYGHLSFGFMQDLQQ--RVVYLSYMAVEYNVSFPHAAQWTFS 258
SEQIDNO:85   GGCDSAHPHLALSF----PYGQLTFGFKQDRHQSHSTVYLNYMAVEYNVSFPQAAQWTFS 234
SEQIDNO:86   GDCDGARPHLLLSF----PFGQLSFGFTQEPQQ--GSVYLDYLALQYNVSFPQAAQWTFS 233
SEQIDNO:87   GGCA--HPHLLLSF----PYGQLSFGFKQEPLQ--STVYLNYIAVEYNVSFPQAAQWTFL 226
SEQIDNO:88   GGCEGPRPHLLLSF----PYGQLSFGFKQDPGQGQSAVYLSYLAVEYNVSFPQAARWTFS 208
SEQIDNO:89   GGCEGAHPHVRLSF----PYGQLTFGFKQQPQE--STVYLNYMAVEYNVSFPRAAQWTFS 195
SEQIDNO:90   GSCEGAHPHLLLSF----PYGHLSFGFMQDLQQ--RVVYLSYMAVEYNVSFPHAAQWTFS 258
SEQIDNO:91   GNCEANHSSLILSF----PNGKLIFGFKQDSIK--KIVYLSHLATEPNVSFPSATRWIFS 227
SEQIDNO:92   GEGDGERSPVTPVASAMTVEGGSPAGFAM------------------------------- 228
             *       :  :              *    **

                       LAMP HOMOLOGY DOMAIN

                            4                                     5
SEQIDNO:80   AQNASLRDLQAPLGQSFSCSNSSIILSPAVHLDLLSLRLQAAQLPHTGVFGQSFSCPSDR 318
SEQIDNO:81   AQNASLRDLQAPLGRSFSCSNSSIILSPAVHLDLLSLRLQAAQLPHTGVFGQSFSCPSDR 318
SEQIDNO:82   VQNSSLPDLQTPLGHSFSCRNASIIVSPALHLDLLSLKLQAAQLSPSGAFGPSFSCPNDK 299
SEQIDNO:83   AQNSSLRELQAPLGQSFCCGNASIVLSPAVHLDLLSLRLQAAQLPDKGHFGPCFSCNRDQ 299
SEQIDNO:84   AQNASLRDLQAPLGQSFSCSNSSIILSPAVHLDLLSLRLQAAQLPHTGVFGQSFSCPSDR 318
SEQIDNO:85   AQNSSLQELQAPLGQSFCCGNTSIVLSPAIHLDLLSLRLQAAQLPDKGHFGPCFSCASDQ 294
SEQIDNO:86   GQNASLRALQAPLGQSFSCRNASILLTPALRLDLLHLKLQAAQLPPSGAFGPSFSCPSEH 293
SEQIDNO:87   VQNSSLRDLQAPLGQRFSCRNASIALSPAFHLDLLSLKLQAAQLTPTGAFGPSFSCPSDQ 286
SEQIDNO:88   AQNASLRDLQAPLGQSFSCRNASIAVSPALHLDLLSLRVQAAQLPRTGIFGPSFSCPADH 268
SEQIDNO:89   VQNSSLRDLQTPVGRSYSCRNASIILSTAFHLDLLSLKLQAAQLPPTGNFGPSFSCPSDQ 255
SEQIDNO:90   AQNASLRDLQAPLGQSFSCSNSSIILSPAVHLDLLSLRLQAAQLPHTGVFGQSFSCPSDR 318
SEQIDNO:91   VENSSLQDLQTPLGHSFSCRNRSIALSPDIHLDLLSLQLQAAQLSSSGAFGAAFSCSADL 287
SEQIDNO:92   -LGAEVRSFAPSLGRAGKTRL--RIHQPVVVLQ--------HTYYV--------------- 263
               .:.::      :*:                 . *:         :
```

FIGURE 9 (cont.)

```
                    Trans. Domain    Cyto Tail

SEQIDNO:80     -SILLPLIIGLILLGLLALVLIAFCIIRRRPSAYQAL 354
SEQIDNO:81     -SILLPLIIGLILLGLLALVLIAFCIIRRRPSAYQAL 354
SEQIDNO:82     -SILLPLIIGLILLGLLTLVLVTFCIIRRRPPTYQPL 335
SEQIDNO:83     -SLLLPLIIGLVLLGLLTLVLIAFCITRRRQSTYQPL 335
SEQIDNO:84     -SILLPLIIGLVLLGLLALVLIAFCIVRRRPSAYQAL 354
SEQIDNO:85     -SLLLPLIIGLVLLGLLTLVLIAFCVTRRRQSTYQPL 330
SEQIDNO:86     -FNLLPLIVGVISLGLLALALVTFCIIRRRPPTYQPL 329
SEQIDNO:87     -SILLPLIIGLILLGLFALVLITFCVIRRRPPTYQAL 322
SEQIDNO:88     PSILVPLIIGLILVGLLALVLVAFCIARRRPSAYQAL 305
SEQIDNO:89     -TILLPLIIGLIFLGLLILVLVTFCIIRRRPPAYQPL 291
SEQIDNO:90     -SILLPLIIGLVLLGLLALVLIAFCIVRRRPSAYQAL 354
SEQIDNO:91     -NILVPLVVGLVLLTLLILVLSAFCISRRRPPAYQPL 323
SEQIDNO:92     ------------------------------------- 263
```

| | Macrosailin | | | | |
|---|---|---|---|---|---|
| Accession No. | *Species* | SEQ ID NO: | Accession No. | *Species* | SEQ ID NO: |
| NP_001242.2 | *H. sapiens* | 80 | XP_849733.1 | *C. lupus familiaris* | 86 |
| XP_003315403.1 | *P. troglodytes* | 81 | NP_001093232.1 | *E. caballus* | 87 |
| NP_001039367.1 | *B. taurus* | 82 | XP_002719034.1 | *O. aries* | 88 |
| BAA23738.1 | *M. musculus* | 83 | XP_003131995.1 | *S. scrofa* | 89 |
| XP_014974003.1 | *M. mulatta* | 84 | XP_003912313.1 | *P. anubis* | 90 |
| NP_001026808.1 | *R. norvegicus* | 85 | XP_001369761.1 | *M. domestica* | 91 |
| | | | XP_001517723.2 | *O. anatinus* | 92 |

FIGURE 10: HUMAN LAMP5 ALIGNMENT WITH ORTHOLOGOUS SEQUENCES
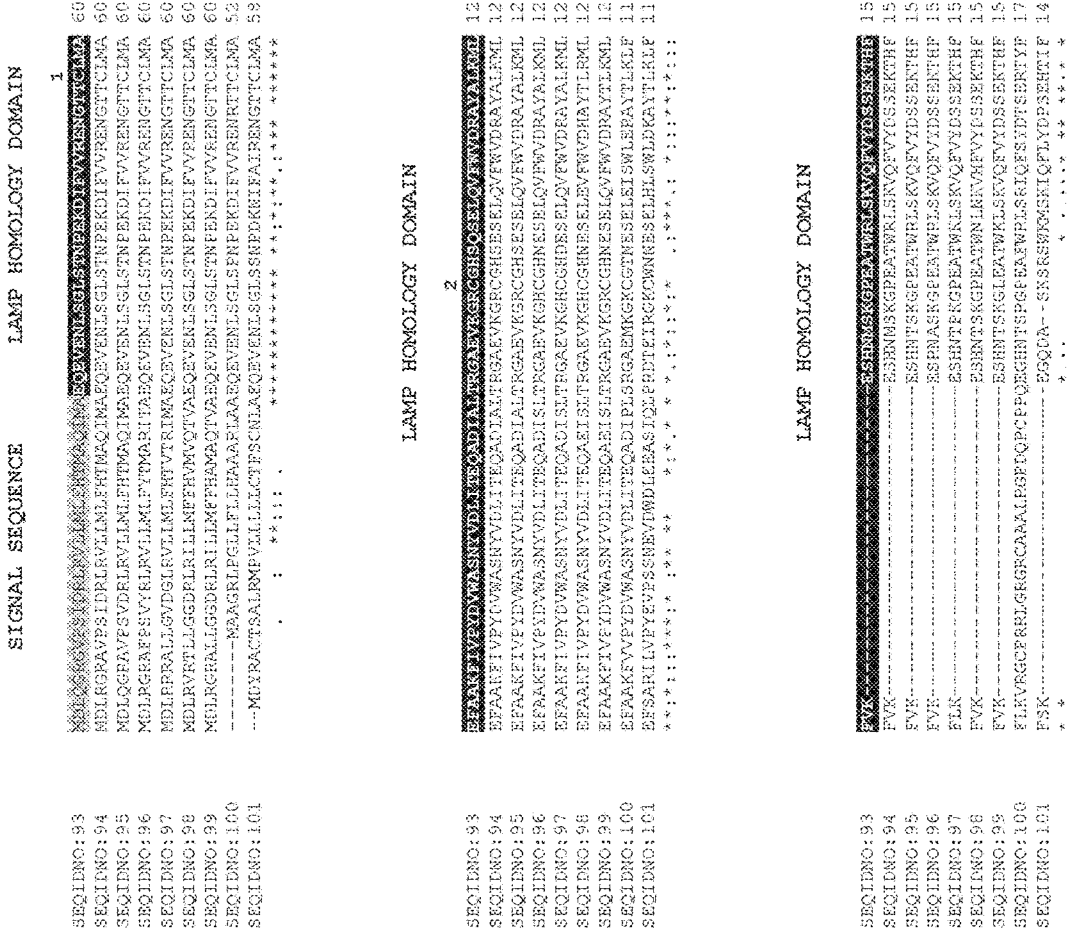

FIGURE 10 (cont.)

```
                              LAMP HOMOLOGY DOMAIN
                                      3
SEQIDNO:93      KDAVSAGKHTANSHHLSALVTPAGKSYECQAQQTISLASSDPQKTVTMILSAVHIQPFDI 213
SEQIDNO:94      KDAVSAGKHTANSHHLSALVTPAGKSYECQAQQTISLASSDLQKTVTMILSAVHIQPFDI 213
SEQIDNO:95      KDAVSAGKHTANSHHLSALVTPAGKSYECQAQQTISLASSDPQKMVTMILSAVHIQPFDI 213
SEQIDNO:96      KDAVSAGKHTANSHHLSALVTPAGKSYECQAQQSISLASSDPQKTVTMILSAVHIQPFDI 213
SEQIDNO:97      KDAVSAGKHTANSHHLSALVTPAGKSYECQAQQTISLASSDPQKTVTMILSAVHIQPFDI 213
SEQIDNO:98      KAPVKVNKYIASSHHLSALVTPAGMSYECQAQQTISLASSDPQKTVTMILSAVHIQPFDI 213
SEQIDNO:99      KDAVSAGKHTANSHHLSALVTPAGMSYECQAQQTISLASSDPQKTVTMILSAVHIQPFDI 213
SEQIDNO:100     KDAVSPGKHTASSHRLSALVTPAGKSYECQAQQTISLISSDHQKSVQLLLSEVRIQPFDI 232
SEQIDNO:101     KSGARPGRHTANSHHLSLMVTPAGMSYECEATQRISLTSTDHQKIVVLYLSEVHLQPFDI 209
                *  .   .:: *.**;** ;***** ****;* * *** *;* ** * ; ** *;;*****

                                  Trans. Domain          Cyto Tail
                     4
SEQIDNO:93      ISDFVFSEEHKCPVDEREQLEETLPLILGLILGLVIMVTLAIYHVHHKMTANQVQIPRDR 273
SEQIDNO:94      ISDFVFSEEHKCPVDEREQLEETLPLILGLILGLVIMVTLAIYHVHHKMTANQVQIPRDR 273
SEQIDNO:95      ISDFVFSEEHKCPVDEREQLEETLPLILGLILGLVIVVTLTIYHVHHKMTANQVQIPRDR 273
SEQIDNO:96      ISDFVFSEEHKCPVDEREQLEETLPLILGLILGLVIVVTLAIYHIHHKMTANQVQIPRDR 273
SEQIDNO:97      ISDFVFSEEHKCPVDEREQLEETLPLILGLILGLVIVVTLVIYHIHHKMTANQVQIPRDR 273
SEQIDNO:98      ISDFVFSEEHKCPVDEQEQLEETLPLILGLILGLVIVITLVIYHIHHKMTANQVQIPRDR 273
SEQIDNO:99      ISDFVFSEEHKCPVDEREQLEETLPLILGLILGLVIVITLVIYHIHHKMTANQVQIPRDR 273
SEQIDNO:100     TADFVFSEEHKCPVDQREQLEETLPLILGLILGLVIVITLCVYHIHHKLTANQVQIPRDR 292
SEQIDNO:101     KSDFVYSEEYKCPTDQRKQLEETLPLILGLTLGVAILIIVAVYHIHHKMTANQVQIPRDR 269
                 :***:***:***.*:::*********** **:.*:: : :**;***:***********

SEQIDNO:93      SQYKHMG     280
SEQIDNO:94      SQYKHMG     280
SEQIDNO:95      SQYKHMG     280
SEQIDNO:96      SQYKHMG     280
SEQIDNO:97      SQYKHMG     280
SEQIDNO:98      SQYKHMG     280
SEQIDNO:99      SQYKHMG     280
SEQIDNO:100     SQYKHMG     299
SEQIDNO:101     SLYKHMG     276
                * *****
```

| LAMP5 | | | | | |
|---|---|---|---|---|---|
| Accession No. | Species | SEQ ID NO: | Accession No. | Species | SEQ ID NO: |
| NP_036393.1 | *H. sapiens* | 93 | NP_001076887.1 | *B. taurus* | 97 |
| XP_514512.3 | *P. troglodytes* | 94 | NP_083806.2 | *M. musculus* | 98 |
| NP_001181627.1 | *M. mulatta* | 95 | NP_001014205.1 | *R. norvegicus* | 99 |
| XP_850634.1 | *C. lupus familiaris* | 96 | XP_004935300.1 | *G. gallus* | 100 |
| | | | NP_001090781.1 | *X. tropicalis* | 101 |

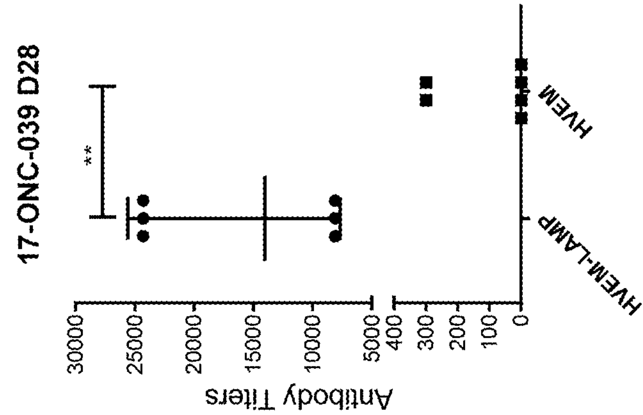
Figure 11 HVEM specific IgG antibody (day 28)

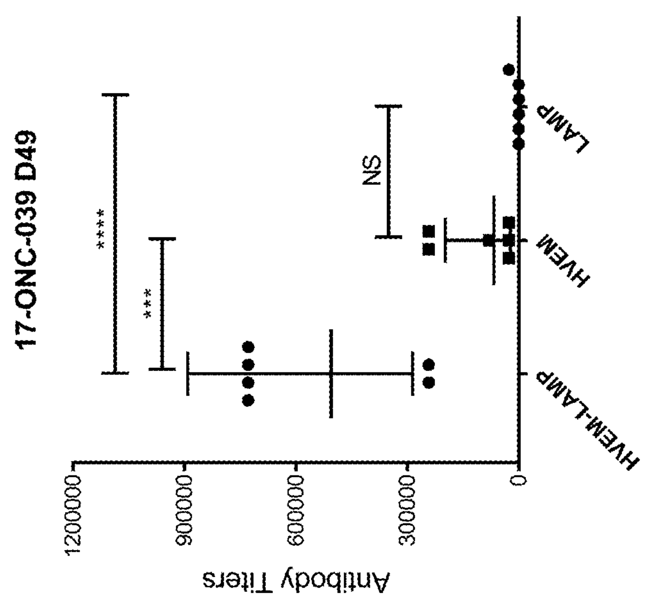
Figure 12 HVEM specific IgG antibody (day 49)

Figure 19

Survivin ~ Example of a Complete LAMP Construct (SEQ ID NO:115)

maprsarrpllllllllllglmhcasaaMFMVKNGNGTACIMANFSAAFSVNYDTKSGPKNMTLDLPSDATVVLNRSSCGKENTSDP
SLVIAFGRGHTLTLNFTRNATRYSVQLMSFVYNLSDTHLFPNASSKEIKTVESITDIRADIDKKYRCVSGTQVHMNNVTVTLH
DATIQAYLSNSSFSRGETRCEQDRPSPTTAPPAPPSPSPSPVPKSPSVDKYNVSGTNGTCLLASMGLQLNLTYERKDNTTVTR
LLNINPNKTSASGSCGAHLVTLELHSEGTTVLLFQFGMNASSSRFFLQGIQLNTILPDARDPAFKAANGSLRALQATVGNSYK
CNAEEHVRVTKAFSVNIFKVWVQAFKVEGGQFGSVEECLLDENSLEMGAPTLPPAWQPFLKDHRISTFKNWPFLEGCAC
TPERMAEAGFIHCPTENEPDLAQCFFCFKELEGWEPDDDPIEEHKKHSSGCAFLSVKKQFEELTLGEFLKLDRERAKNKIA
KETNNKKKEFEETAKKVRRAIEQLAAMDEFTLIPIAVGGALAGLVLIVLIAYLVGRKRSHAGYQTI

Survivin ~ Example of a ILC-1 Construct (SEQ ID NO:116)

maprsarrpllllllllllglmhcasaMGAPTLPPAWQPFLKDHRISTFKNWPFLEGCACTPERMAEAGFIHCPTENEPDLAQCFFC
FKELEGWEPDDDPIEEHKKHSSGCAFLSVKKQFEELTLGEFLKLDRERAKNKIAKETNNKKKEFEETAKKVRRAIEQLAAM
DAMFMVKNGNGTACIMANFSAAFSVNYDTKSGPKNMTLDLPSDATVVLNRSSCGKENTSDPSLVIAFGRGHTLTLNFTRN
ATRYSVQLMSFVYNLSDTHLFPNASSKEIKTVESITDIRADIDKKYRCVSGTQVHMNNVTVTLHDATIQAYLSNSSFSRGETR
CEQDRPSPTTAPPAPPSPSPSPVPKSPSVDKYNVSGTNGTCLLASMGLQLNLTYERKDNTTVTRLLNINPNKTSASGSCGAH
LVTLELHSEGTTVLLFQFGMNASSSRFFLQGIQLNTILPDARDPAFKAANGSLRALQATVGNSYKCNAEEHVRVTKAFSVNIF
KVWVQAFKVEGGQFGSVEECLLDENSMLIPIAVGGALAGLVLIVLIAYLVGRKRSHAGYQTI

Survivin ~ Example of a ILC-2 Construct (SEQ ID NO:117)

maprsarrpllllllllllglmhcasaMGAPTLPPAWQPFLKDHRISTFKNWPFLEGCACTPERMAEAGFIHCPTENEPDLAQCFFCF
KELEGWEPDDDPIEEHKKHSSGCAFLSVKKQFEELTLGEFLKLDRERAKNKIAKETNNKKKEFEETAKKVRRAIEQLAAMDA
MFMVKNGNGTACIMANFSAAFSVNYDTKSGPKNMTLDLPSDATVVLNRSSCGKENTSDPSLVIAFGRGHTLTLNFTRNAT
RYSVQLMSFVYNLSDTHLFPNASSKEIKTVESITDIRADIDKKYRCVSGTQVHMNNVTVTLHDATIQAYLSNSSFSRGETRCE
QDLIPIAVGGALAGLVLIVLIAYLVGRKRSHAGYQTI

Survivin ~ Example of a ILC-3 Construct (SEQ ID NO:118)

maprsarrpllllllllllglmhcasaAMFMVKNGNGTACIMANFSAAFSVNYDTKSGPKNMTLDLPSDATVVLNRSSCGKENTSDP
SLVIAFGRGHTLTLNFTRNATRYSVQLMSFVYNLSDTHLFPNASSKEIKTVESITDIRADIDKKYRCVSGTQVHMNNVTVTLH
DATIQAYLSNSSFSRGETRCEQDLEMGAPTLPPAWQPFLKDHRISTFKNWPFLEGCACTPERMAEAGFIHCPTENEPDLAQ
CFFCFKELEGWEPDDDPIEEHKKHSSGCAFLSVKKQFEELTLGEFLKLDRERAKNKIAKETNNKKKEFEETAKKVRRAIEQLAA
MDEFTLIPIAVGGALAGLVLIVLIAYLVGRKRSHAGYQTI

Survivin – Example of a ILC-4 Construct (SEQ ID NO:119)

maprsarrpllllllllllglmhcasaAMFMVKNGNGTACIMANFSAAFSVNYDTKSGPKNMTLDLPSDATVVLNRSSCGKENTSDP
SLVIAFGRGHTLTLNFTRNATRYSVQLMSFVYNLSDTHLFPNASSKEIKTVESITDIRADIDKKYRCVSGTQVHMNNVTVTLH
DATIQAYLSNSSFSRGETRCEQDLEMGAPTLPPAWQPFLKDHRISTFKNWPFLEGCACTPERMAEAGFIHCPTENEPDLA
QCFFCFKELEGWEPDDDPIEEHKKHSSGCAFLSVKKQFEELTLGEFLKLDRERAKNKIAKETNNKKKEFEETAKKVRRAIEQ
LAAMDEFTCLLASMGLQLNLTYERKDNTTVTRLLNINPNKTSASGSCGAHLVTLELHSEGTTVLLFQFGMNASSSRFFLQG
IQLNTILPDARDPAFKAANGSLRALQATVGNSYKCNAEEHVRVTKAFSVNIFKVWVQAFKVEGGQFGSVEECLLDENSM
LIPIAVGGALAGLVLIVLIAYLVGRKRSHAGYQTI

SEQUENCE LISTING

```
<160> NUMBER OF SEQ ID NOS: 119

<210> SEQ ID NO 1
<211> LENGTH: 417
<212> TYPE: PRT
<213> ORGANISM: Homo sapiens

<400> SEQUENCE: 1

Met Ala Ala Pro Gly Ser Ala Arg Arg Pro Leu Leu Leu Leu Leu Leu
1               5                   10                  15

Leu Leu Leu Leu Gly Leu Met His Cys Ala Ser Ala Ala Met Phe Met
            20                  25                  30

Val Lys Asn Gly Asn Gly Thr Ala Cys Ile Met Ala Asn Phe Ser Ala
        35                  40                  45

Ala Phe Ser Val Asn Tyr Asp Thr Lys Ser Gly Pro Lys Asn Met Thr
    50                  55                  60

Phe Asp Leu Pro Ser Asp Ala Thr Val Val Leu Asn Arg Ser Ser Cys
65                  70                  75                  80

Gly Lys Glu Asn Thr Ser Asp Pro Ser Leu Val Ile Ala Phe Gly Arg
                85                  90                  95

Gly His Thr Leu Thr Leu Asn Phe Thr Arg Asn Ala Thr Arg Tyr Ser
            100                 105                 110

Val Gln Leu Met Ser Phe Val Tyr Asn Leu Ser Asp Thr His Leu Phe
        115                 120                 125

Pro Asn Ala Ser Ser Lys Glu Ile Lys Thr Val Glu Ser Ile Thr Asp
    130                 135                 140

Ile Arg Ala Asp Ile Asp Lys Lys Tyr Arg Cys Val Ser Gly Thr Gln
145                 150                 155                 160

Val His Met Asn Asn Val Thr Val Thr Leu His Asp Ala Thr Ile Gln
                165                 170                 175

Ala Tyr Leu Ser Asn Ser Ser Phe Ser Arg Gly Glu Thr Arg Cys Glu
            180                 185                 190

Gln Asp Arg Pro Ser Pro Thr Thr Ala Pro Pro Ala Pro Pro Ser Pro
        195                 200                 205

Ser Pro Ser Pro Val Pro Lys Ser Pro Ser Val Asp Lys Tyr Asn Val
    210                 215                 220
```

Ser Gly Thr Asn Gly Thr Cys Leu Leu Ala Ser Met Gly Leu Gln Leu
225 230 235 240

Asn Leu Thr Tyr Glu Arg Lys Asp Asn Thr Thr Val Thr Arg Leu Leu
245 250 255

Asn Ile Asn Pro Asn Lys Thr Ser Ala Ser Gly Ser Cys Gly Ala His
260 265 270

Leu Val Thr Leu Glu Leu His Ser Glu Gly Thr Thr Val Leu Leu Phe
275 280 285

Gln Phe Gly Met Asn Ala Ser Ser Ser Arg Phe Phe Leu Gln Gly Ile
290 295 300

Gln Leu Asn Thr Ile Leu Pro Asp Ala Arg Asp Pro Ala Phe Lys Ala
305 310 315 320

Ala Asn Gly Ser Leu Arg Ala Leu Gln Ala Thr Val Gly Asn Ser Tyr
325 330 335

Lys Cys Asn Ala Glu Glu His Val Arg Val Thr Lys Ala Phe Ser Val
340 345 350

Asn Ile Phe Lys Val Trp Val Gln Ala Phe Lys Val Glu Gly Gly Gln
355 360 365

Phe Gly Ser Val Glu Glu Cys Leu Leu Asp Glu Asn Ser Met Leu Ile
370 375 380

Pro Ile Ala Val Gly Gly Ala Leu Ala Gly Leu Val Leu Ile Val Leu
385 390 395 400

Ile Ala Tyr Leu Val Gly Arg Lys Arg Ser His Ala Gly Tyr Gln Thr
405 410 415

Ile

<210> SEQ ID NO 2
<211> LENGTH: 410
<212> TYPE: PRT
<213> ORGANISM: Homo sapiens

<400> SEQUENCE: 2

Met Val Cys Phe Arg Leu Phe Pro Val Pro Gly Ser Gly Leu Val Leu
1 5 10 15

Val Cys Leu Val Leu Gly Ala Val Arg Ser Tyr Ala Leu Glu Leu Asn
20 25 30

Leu Thr Asp Ser Glu Asn Ala Thr Cys Leu Tyr Ala Lys Trp Gln Met
35 40 45

Asn Phe Thr Val Arg Tyr Glu Thr Thr Asn Lys Thr Tyr Lys Thr Val
50 55 60

Thr Ile Ser Asp His Gly Thr Val Thr Tyr Asn Gly Ser Ile Cys Gly
65 70 75 80

Asp Asp Gln Asn Gly Pro Lys Ile Ala Val Gln Phe Gly Pro Gly Phe
85 90 95

Ser Trp Ile Ala Asn Phe Thr Lys Ala Ala Ser Thr Tyr Ser Ile Asp
100 105 110

Ser Val Ser Phe Ser Tyr Asn Thr Gly Asp Asn Thr Thr Phe Pro Asp
115 120 125

Ala Glu Asp Lys Gly Ile Leu Thr Val Asp Glu Leu Leu Ala Ile Arg
130 135 140

Ile Pro Leu Asn Asp Leu Phe Arg Cys Asn Ser Leu Ser Thr Leu Glu
145 150 155 160

Lys Asn Asp Val Val Gln His Tyr Trp Asp Val Leu Val Gln Ala Phe
165 170 175

```
Val Gln Asn Gly Thr Val Ser Thr Asn Glu Phe Leu Cys Asp Lys Asp
            180                 185                 190

Lys Thr Ser Thr Val Ala Pro Thr Ile His Thr Thr Val Pro Ser Pro
        195                 200                 205

Thr Thr Thr Pro Thr Pro Lys Glu Lys Pro Glu Ala Gly Thr Tyr Ser
    210                 215                 220

Val Asn Asn Gly Asn Asp Thr Cys Leu Leu Ala Thr Met Gly Leu Gln
225                 230                 235                 240

Leu Asn Ile Thr Gln Asp Lys Val Ala Ser Val Ile Asn Ile Asn Pro
                245                 250                 255

Asn Thr Thr His Ser Thr Gly Ser Cys Arg Ser His Thr Ala Leu Leu
            260                 265                 270

Arg Leu Asn Ser Ser Thr Ile Lys Tyr Leu Asp Phe Val Phe Ala Val
        275                 280                 285

Lys Asn Glu Asn Arg Phe Tyr Leu Lys Glu Val Asn Ile Ser Met Tyr
    290                 295                 300

Leu Val Asn Gly Ser Val Phe Ser Ile Ala Asn Asn Asn Leu Ser Tyr
305                 310                 315                 320

Trp Asp Ala Pro Leu Gly Ser Ser Tyr Met Cys Asn Lys Glu Gln Thr
                325                 330                 335

Val Ser Val Ser Gly Ala Phe Gln Ile Asn Thr Phe Asp Leu Arg Val
            340                 345                 350

Gln Pro Phe Asn Val Thr Gln Gly Lys Tyr Ser Thr Ala Gln Asp Cys
        355                 360                 365

Ser Ala Asp Asp Asp Asn Phe Leu Val Pro Ile Ala Val Gly Ala Ala
    370                 375                 380

Leu Ala Gly Val Leu Ile Leu Val Leu Leu Ala Tyr Phe Ile Gly Leu
385                 390                 395                 400

Lys His His His Ala Gly Tyr Glu Gln Phe
                405                 410


<210> SEQ ID NO 3
<211> LENGTH: 416
<212> TYPE: PRT
<213> ORGANISM: Homo sapiens

<400> SEQUENCE: 3

Met Pro Arg Gln Leu Ser Ala Ala Ala Ala Leu Phe Ala Ser Leu Ala
1               5                   10                  15

Val Ile Leu His Asp Gly Ser Gln Met Arg Ala Lys Ala Phe Pro Glu
            20                  25                  30

Thr Arg Asp Tyr Ser Gln Pro Thr Ala Ala Ala Thr Val Gln Asp Ile
        35                  40                  45

Lys Lys Pro Val Gln Gln Pro Ala Lys Gln Ala Pro His Gln Thr Leu
    50                  55                  60

Ala Ala Arg Phe Met Asp Gly His Ile Thr Phe Gln Thr Ala Ala Thr
65                  70                  75                  80

Val Lys Ile Pro Thr Thr Thr Pro Ala Thr Thr Lys Asn Thr Ala Thr
                85                  90                  95

Thr Ser Pro Ile Thr Tyr Thr Leu Val Thr Thr Gln Ala Thr Pro Asn
            100                 105                 110

Asn Ser His Thr Ala Pro Pro Val Thr Glu Val Thr Val Gly Pro Ser
        115                 120                 125

Leu Ala Pro Tyr Ser Leu Pro Pro Thr Ile Thr Pro Pro Ala His Thr
    130                 135                 140
```

Thr Gly Thr Ser Ser Ser Thr Val Ser His Thr Thr Gly Asn Thr Thr
145 150 155 160

Gln Pro Ser Asn Gln Thr Thr Leu Pro Ala Thr Leu Ser Ile Ala Leu
165 170 175

His Lys Ser Thr Thr Gly Gln Lys Pro Val Gln Pro Thr His Ala Pro
180 185 190

Gly Thr Thr Ala Ala Ala His Asn Thr Thr Arg Thr Ala Ala Pro Ala
195 200 205

Ser Thr Val Pro Gly Pro Thr Leu Ala Pro Gln Pro Ser Ser Val Lys
210 215 220

Thr Gly Ile Tyr Gln Val Leu Asn Gly Ser Arg Leu Cys Ile Lys Ala
225 230 235 240

Glu Met Gly Ile Gln Leu Ile Val Gln Asp Lys Glu Ser Val Phe Ser
245 250 255

Pro Arg Arg Tyr Phe Asn Ile Asp Pro Asn Ala Thr Gln Ala Ser Gly
260 265 270

Asn Cys Gly Thr Arg Lys Ser Asn Leu Leu Leu Asn Phe Gln Gly Gly
275 280 285

Phe Val Asn Leu Thr Phe Thr Lys Asp Glu Glu Ser Tyr Tyr Ile Ser
290 295 300

Glu Val Gly Ala Tyr Leu Thr Val Ser Asp Pro Glu Thr Ile Tyr Gln
305 310 315 320

Gly Ile Lys His Ala Val Val Met Phe Gln Thr Ala Val Gly His Ser
325 330 335

Phe Lys Cys Val Ser Glu Gln Ser Leu Gln Leu Ser Ala His Leu Gln
340 345 350

Val Lys Thr Thr Asp Val Gln Leu Gln Ala Phe Asp Phe Glu Asp Asp
355 360 365

His Phe Gly Asn Val Asp Glu Cys Ser Ser Asp Tyr Thr Ile Val Leu
370 375 380

Pro Val Ile Gly Ala Ile Val Val Gly Leu Cys Leu Met Gly Met Gly
385 390 395 400

Val Tyr Lys Ile Arg Leu Arg Cys Gln Ser Ser Gly Tyr Gln Arg Ile
405 410 415

<210> SEQ ID NO 4
<211> LENGTH: 478
<212> TYPE: PRT
<213> ORGANISM: Homo sapiens

<400> SEQUENCE: 4

Met Gly Arg Cys Cys Phe Tyr Thr Ala Gly Thr Leu Ser Leu Leu Leu
1 5 10 15

Leu Val Thr Ser Val Thr Leu Leu Val Ala Arg Val Phe Gln Lys Ala
20 25 30

Val Asp Gln Ser Ile Glu Lys Lys Ile Val Leu Arg Asn Gly Thr Glu
35 40 45

Ala Phe Asp Ser Trp Glu Lys Pro Pro Leu Pro Val Tyr Thr Gln Phe
50 55 60

Tyr Phe Phe Asn Val Thr Asn Pro Glu Glu Ile Leu Arg Gly Glu Thr
65 70 75 80

Pro Arg Val Glu Glu Val Gly Pro Tyr Thr Tyr Arg Glu Leu Arg Asn
85 90 95

Lys Ala Asn Ile Gln Phe Gly Asp Asn Gly Thr Thr Ile Ser Ala Val

```
            100                 105                 110

Ser Asn Lys Ala Tyr Val Phe Glu Arg Asp Gln Ser Val Gly Asp Pro
        115                 120                 125

Lys Ile Asp Leu Ile Arg Thr Leu Asn Ile Pro Val Leu Thr Val Ile
    130                 135                 140

Glu Trp Ser Gln Val His Phe Leu Arg Glu Ile Ile Glu Ala Met Leu
145                 150                 155                 160

Lys Ala Tyr Gln Gln Lys Leu Phe Val Thr His Thr Val Asp Glu Leu
                165                 170                 175

Leu Trp Gly Tyr Lys Asp Glu Ile Leu Ser Leu Ile His Val Phe Arg
            180                 185                 190

Pro Asp Ile Ser Pro Tyr Phe Gly Leu Phe Tyr Glu Lys Asn Gly Thr
        195                 200                 205

Asn Asp Gly Asp Tyr Val Phe Leu Thr Gly Glu Asp Ser Tyr Leu Asn
    210                 215                 220

Phe Thr Lys Ile Val Glu Trp Asn Gly Lys Thr Ser Leu Asp Trp Trp
225                 230                 235                 240

Ile Thr Asp Lys Cys Asn Met Ile Asn Gly Thr Asp Gly Asp Ser Phe
                245                 250                 255

His Pro Leu Ile Thr Lys Asp Glu Val Leu Tyr Val Phe Pro Ser Asp
            260                 265                 270

Phe Cys Arg Ser Val Tyr Ile Thr Phe Ser Asp Tyr Glu Ser Val Gln
        275                 280                 285

Gly Leu Pro Ala Phe Arg Tyr Lys Val Pro Ala Glu Ile Leu Ala Asn
    290                 295                 300

Thr Ser Asp Asn Ala Gly Phe Cys Ile Pro Glu Gly Asn Cys Leu Gly
305                 310                 315                 320

Ser Gly Val Leu Asn Val Ser Ile Cys Lys Asn Gly Ala Pro Ile Ile
                325                 330                 335

Met Ser Phe Pro His Phe Tyr Gln Ala Asp Glu Arg Phe Val Ser Ala
            340                 345                 350

Ile Glu Gly Met His Pro Asn Gln Glu Asp His Glu Thr Phe Val Asp
        355                 360                 365

Ile Asn Pro Leu Thr Gly Ile Ile Leu Lys Ala Ala Lys Arg Phe Gln
    370                 375                 380

Ile Asn Ile Tyr Val Lys Lys Leu Asp Asp Phe Val Glu Thr Gly Asp
385                 390                 395                 400

Ile Arg Thr Met Val Phe Pro Val Met Tyr Leu Asn Glu Ser Val His
                405                 410                 415

Ile Asp Lys Glu Thr Ala Ser Arg Leu Lys Ser Met Ile Asn Thr Thr
            420                 425                 430

Leu Ile Ile Thr Asn Ile Pro Tyr Ile Ile Met Ala Leu Gly Val Phe
        435                 440                 445

Phe Gly Leu Val Phe Thr Trp Leu Ala Cys Lys Gly Gln Gly Ser Met
    450                 455                 460

Asp Glu Gly Thr Ala Asp Glu Arg Ala Pro Leu Ile Arg Thr
465                 470                 475


<210> SEQ ID NO 5
<211> LENGTH: 197
<212> TYPE: PRT
<213> ORGANISM: Homo sapiens

<400> SEQUENCE: 5
```

```
Met Ser Arg Leu Ser Arg Ser Leu Leu Trp Ala Ala Thr Cys Leu Gly
1               5                   10                  15

Val Leu Cys Val Leu Ser Ala Asp Lys Asn Thr Thr Gln His Pro Asn
            20                  25                  30

Val Thr Thr Leu Ala Pro Ile Ser Asn Val Thr Ser Ala Pro Val Thr
        35                  40                  45

Ser Leu Pro Leu Val Thr Thr Pro Ala Pro Glu Thr Cys Glu Gly Arg
    50                  55                  60

Asn Ser Cys Val Ser Cys Phe Asn Val Ser Val Val Asn Thr Thr Cys
65                  70                  75                  80

Phe Trp Ile Glu Cys Lys Asp Glu Ser Tyr Cys Ser His Asn Ser Thr
                85                  90                  95

Val Ser Asp Cys Gln Val Gly Asn Thr Thr Asp Phe Cys Ser Val Ser
            100                 105                 110

Thr Ala Thr Pro Val Pro Thr Ala Asn Ser Thr Ala Lys Pro Thr Val
        115                 120                 125

Gln Pro Ser Pro Ser Thr Thr Ser Lys Thr Val Thr Thr Ser Gly Thr
    130                 135                 140

Thr Asn Asn Thr Val Thr Pro Thr Ser Gln Pro Val Arg Lys Ser Thr
145                 150                 155                 160

Phe Asp Ala Ala Ser Phe Ile Gly Gly Ile Val Leu Val Leu Gly Val
                165                 170                 175

Gln Ala Val Ile Phe Phe Leu Tyr Lys Phe Cys Lys Ser Lys Glu Arg
            180                 185                 190

Asn Tyr His Thr Leu
        195


<210> SEQ ID NO 6
<211> LENGTH: 406
<212> TYPE: PRT
<213> ORGANISM: Mus musculus

<400> SEQUENCE: 6

Met Ala Ala Pro Gly Ala Arg Arg Pro Leu Leu Leu Leu Leu Leu Ala
1               5                   10                  15

Gly Leu Ala His Gly Ala Ser Ala Leu Phe Glu Val Lys Asn Asn Gly
            20                  25                  30

Thr Thr Cys Ile Met Ala Ser Phe Ser Ala Ser Phe Leu Thr Thr Tyr
        35                  40                  45

Glu Thr Ala Asn Gly Ser Gln Ile Val Asn Ile Ser Leu Pro Ala Ser
    50                  55                  60

Ala Glu Val Leu Lys Asn Gly Ser Ser Cys Gly Lys Glu Asn Val Ser
65                  70                  75                  80

Asp Pro Ser Leu Thr Ile Thr Phe Gly Arg Gly Tyr Leu Leu Thr Leu
                85                  90                  95

Asn Phe Thr Lys Asn Thr Thr Arg Tyr Ser Val Gln His Met Tyr Phe
            100                 105                 110

Thr Tyr Asn Leu Ser Asp Thr Glu His Phe Pro Asn Ala Ile Ser Lys
        115                 120                 125

Glu Ile Tyr Thr Met Asp Ser Thr Thr Asp Ile Lys Ala Asp Ile Asn
    130                 135                 140

Lys Ala Tyr Arg Cys Val Ser Asp Ile Arg Val Tyr Met Lys Asn Val
145                 150                 155                 160

Thr Val Val Leu Arg Asp Ala Thr Ile Gln Ala Tyr Leu Ser Ser Gly
                165                 170                 175
```

```
Asn Phe Ser Lys Glu Glu Thr His Cys Thr Gln Asp Gly Pro Ser Pro
            180                 185                 190

Thr Thr Gly Pro Pro Ser Pro Ser Pro Pro Leu Val Pro Thr Asn Pro
        195                 200                 205

Thr Val Ser Lys Tyr Asn Val Thr Gly Asn Asn Gly Thr Cys Leu Leu
    210                 215                 220

Ala Ser Met Ala Leu Gln Leu Asn Ile Thr Tyr Leu Lys Lys Asp Asn
225                 230                 235                 240

Lys Thr Val Thr Arg Ala Phe Asn Ile Ser Pro Asn Asp Thr Ser Ser
                245                 250                 255

Gly Ser Cys Gly Ile Asn Leu Val Thr Leu Lys Val Glu Asn Lys Asn
            260                 265                 270

Arg Ala Leu Glu Leu Gln Phe Gly Met Asn Ala Ser Ser Ser Leu Phe
        275                 280                 285

Phe Leu Gln Gly Val Arg Leu Asn Met Thr Leu Pro Asp Ala Leu Val
    290                 295                 300

Pro Thr Phe Ser Ile Ser Asn His Ser Leu Lys Ala Leu Gln Ala Thr
305                 310                 315                 320

Val Gly Asn Ser Tyr Lys Cys Asn Thr Glu Glu His Ile Phe Val Ser
                325                 330                 335

Lys Met Leu Ser Leu Asn Val Phe Ser Val Gln Val Gln Ala Phe Lys
            340                 345                 350

Val Asp Ser Asp Arg Phe Gly Ser Val Glu Glu Cys Val Gln Asp Gly
        355                 360                 365

Asn Asn Met Leu Ile Pro Ile Ala Val Gly Gly Ala Leu Ala Gly Leu
    370                 375                 380

Val Leu Ile Val Leu Ile Ala Tyr Leu Ile Gly Arg Lys Arg Ser His
385                 390                 395                 400

Ala Gly Tyr Gln Thr Ile
                405


<210> SEQ ID NO 7
<211> LENGTH: 411
<212> TYPE: PRT
<213> ORGANISM: Danio rerio

<400> SEQUENCE: 7

Met Ala Arg Ala Ala Gly Val Cys Trp Thr Leu Leu Met Gly Cys Val
1               5                   10                  15

Phe Ala Ala His Ala Val Thr Phe Glu Val Thr Asp Gly Asn Ser Thr
            20                  25                  30

Cys Ile Lys Gly Glu Leu Asn Ala Ser Phe Ser Ile Ser Tyr Asn Thr
        35                  40                  45

Thr Asn Gly Thr Ser Val Ser Val Phe Ala Leu Pro Ala Ser Ala Ser
    50                  55                  60

Val Ser Glu Arg Ser Ser Cys Gly Ser Ala Ala Val Pro Pro Glu Leu
65                  70                  75                  80

Ala Leu Val Phe Gly Asp Thr His Thr His Thr Leu Ser Leu Leu Phe
                85                  90                  95

Ser Arg Asp Gln Arg Leu Tyr Arg Val Ser Asn Ile Ser Leu Gln Tyr
            100                 105                 110

Asn Leu Ser Asp Gly Asp Ile Phe Pro Gln Ser Ser Ser Ala Gly Val
        115                 120                 125

Gln Ser Val Met Ala Ser Val Ser Glu Leu Met Ser Ala Arg Leu Asn
```

```
    130                 135                 140

Ser Thr Tyr Arg Cys Val Ser Ser Ser Ser Ile Ser Leu Ser Ala Ala
145                 150                 155                 160

Val Asn Leu Thr Leu Ser Gly Val Gln Met Glu Ala Tyr Met Ser Ser
                165                 170                 175

Ala Asn Leu Ser Ala Asp Glu Ser Val Cys Ser Ala Asp Gln Pro Ser
            180                 185                 190

Thr Thr Val Ala Pro Pro Pro Ser Thr Thr Thr Ser Pro Pro Pro Ile
        195                 200                 205

Pro Pro Val Pro Glu Arg Gly Asn Tyr Ser Val Thr Asp Gly Asn Gly
    210                 215                 220

Thr Val Cys Val Leu Ala Leu Met Gly Leu Gln Leu Asn Ile Thr His
225                 230                 235                 240

Thr Thr Thr Gln Asn Gln Ser Val Ser Glu Leu Met Asn Leu Gln Pro
                245                 250                 255

Asn Gln Thr Thr Val Ser Gly Ser Cys Gly Val Thr Glu Ser Ser Leu
            260                 265                 270

Arg Leu Ser Asp Glu Thr Thr Asn Leu Thr Phe Ser Phe Thr Met Asn
        275                 280                 285

Ser Thr Thr Gln Lys Tyr Tyr Leu Ser Ala Val Ser Val Ser Ala Leu
    290                 295                 300

Trp Pro Asp Met Ser Val Val Phe Glu Ala Gly Asn Thr Ser Leu Ser
305                 310                 315                 320

Ala Leu Gln Cys Ser Val Gly Arg Ser Tyr Val Cys Ser Ala Gln Gln
                325                 330                 335

Met Leu Ser Val Thr Pro Val Phe Ser Ile Asn Thr Phe Arg Leu Gln
            340                 345                 350

Leu Gln Pro Phe Asn Ile Thr Ala Asn Arg Phe Ser Thr Ala Glu Glu
        355                 360                 365

Cys Arg Val Asp Gln Glu Asn Met Leu Ile Pro Ile Ile Val Gly Ala
    370                 375                 380

Ala Leu Ala Gly Leu Val Leu Ile Val Leu Val Ala Tyr Leu Ile Gly
385                 390                 395                 400

Arg Lys Arg Thr His Ala Gly Tyr Gln Thr Ile
                405                 410


<210> SEQ ID NO 8
<211> LENGTH: 417
<212> TYPE: PRT
<213> ORGANISM: Xenopus laevis

<400> SEQUENCE: 8

Met Ser Trp Arg Gln Val Lys Met Pro Val Tyr Trp Met Ala Val Met
1               5                   10                  15

Leu Leu Ile Gly Val Val Gln Val Ala Thr Ala Val Gln Phe Glu Val
            20                  25                  30

Lys Asp Gly Lys Thr Asn Ile Thr Cys Ile Leu Ala Asp Leu Ser Ile
        35                  40                  45

Asn Phe Ser Val Ser Tyr Asn Val Ser Ser Lys Met Glu Leu Ala Thr
    50                  55                  60

Phe Val Leu Pro Ser Glu Ala Val Thr Asn Ile Asn Lys Ser Ser Cys
65                  70                  75                  80

Gly Val Glu Asn Thr Thr Ala Pro Val Leu Ala Ile Gln Phe Gly Ser
                85                  90                  95
```

```
Asn His Ser Leu Ser Ile His Phe Ala Arg Asn Asn Thr Arg Tyr Glu
            100                 105                 110

Val Ala Glu Leu Val Met Ser Tyr Asn Leu Ser Asp Lys Ile Ile Phe
        115                 120                 125

Pro Asn Ala Ser Glu Asn Gly Thr Lys Thr Val Ser Thr Asn Lys Thr
    130                 135                 140

Ala Val Leu Ala Glu Asn Asp Thr Val Tyr Lys Cys Met Asn Pro His
145                 150                 155                 160

Leu Ile Arg Met Asp Asn Ala Asn Ala Thr Phe His Asp Ile Arg Leu
                165                 170                 175

Glu Ala Tyr Leu Lys Gln Ser Asn Phe Ser Gln Lys Val Ser Thr Cys
            180                 185                 190

Ser Glu Asp Ile Thr Pro Thr Ser Ala Pro Ala Pro Val Thr Thr Thr
        195                 200                 205

Ala Pro Val Pro Ala Pro Val Pro Asp Pro Pro Val Val Gln Tyr Ser
    210                 215                 220

Val Asn Arg Ser Ser Glu Pro Cys Leu Leu Ala Lys Val Gly Leu Gln
225                 230                 235                 240

Met Asn Ile Thr Tyr Thr Thr Lys Asp Gly Lys Asn Gly Ser Tyr Val
                245                 250                 255

Phe Asn Ile Glu Ser Lys Gly Val Thr Val Asp Gly Asn Cys Thr Asn
            260                 265                 270

Thr Thr Ala Tyr Leu Ser Leu Ser Thr Gly Ser Ile Asp Leu Arg Phe
        275                 280                 285

Asn Phe Thr Leu Asn Ser Ser Leu Glu Val Phe Tyr Leu Asp Gly Val
    290                 295                 300

Ser Leu Ser Thr Gly Leu Pro Ala Asp Ala Asn Asp Thr His Phe Glu
305                 310                 315                 320

Ala Ala Asn Ser Ser Leu Asn Tyr Met Gln Thr Asn Val His Lys Ser
                325                 330                 335

Phe Lys Cys Asn Ser Lys Gln Thr Leu Gln Ile Thr Asp Pro Phe Thr
            340                 345                 350

Val Asn Thr Tyr His Leu Gln Val Gln Ala Phe Asn Ser Asp Asn Thr
        355                 360                 365

Phe Ala Ser Ala Val Glu Cys Ser Leu Asp Glu Asn Gly Met Leu Val
    370                 375                 380

Pro Ile Val Val Gly Ala Ala Leu Ala Gly Leu Val Leu Ile Val Leu
385                 390                 395                 400

Ile Ala Tyr Leu Ile Gly Arg Lys Arg Ser His Ala Gly Tyr Gln Thr
                405                 410                 415

Ile


<210> SEQ ID NO 9
<211> LENGTH: 417
<212> TYPE: PRT
<213> ORGANISM: Pan troglodytes

<400> SEQUENCE: 9

Met Ala Ala Pro Gly Ser Ala Arg Arg Pro Leu Leu Leu Leu Leu Leu
1               5                   10                  15

Leu Leu Leu Leu Gly Leu Val His Cys Ala Ser Ala Ala Met Phe Met
            20                  25                  30

Val Lys Asn Gly Asn Gly Thr Ala Cys Ile Met Ala Asn Phe Ser Ala
        35                  40                  45
```

```
Ser Phe Ser Val Asn Tyr Asp Thr Lys Ser Gly Pro Lys Asn Met Thr
    50                  55                  60

Phe Asp Leu Pro Ser Asp Ala Thr Val Val Leu Asn Arg Ser Ser Cys
65                  70                  75                  80

Gly Lys Glu Asn Thr Ser Asp Pro Ser Leu Val Ile Ala Phe Gly Arg
                85                  90                  95

Gly His Thr Leu Thr Leu Asn Phe Thr Arg Asn Ala Thr Arg Tyr Ser
            100                 105                 110

Val Gln Leu Met Ser Phe Val Tyr Asn Leu Ser Asp Thr His Leu Phe
        115                 120                 125

Pro Asn Ala Ser Ser Lys Glu Ile Lys Thr Val Glu Ser Ile Thr Asp
    130                 135                 140

Ile Arg Ala Asp Ile Asp Lys Lys Tyr Arg Cys Val Ser Gly Thr Gln
145                 150                 155                 160

Val His Met Asn Asn Val Thr Val Thr Leu His Asp Ala Thr Ile Gln
                165                 170                 175

Ala Tyr Leu Ser Asn Ser Ser Phe Ser Arg Gly Glu Thr Arg Cys Glu
            180                 185                 190

Gln Asp Arg Pro Ser Pro Thr Thr Ala Pro Pro Ala Pro Pro Ser Pro
        195                 200                 205

Ser Pro Ser Pro Val Pro Glu Ser Pro Ser Val Asp Lys Tyr Asn Val
    210                 215                 220

Ser Gly Thr Asn Gly Thr Cys Leu Leu Ala Ser Met Gly Leu Gln Leu
225                 230                 235                 240

Asn Leu Thr Tyr Glu Arg Lys Asp Asn Thr Thr Val Thr Arg Leu Leu
                245                 250                 255

Asn Ile Asn Pro Asn Lys Thr Ser Ala Ser Gly Ser Cys Gly Ala His
            260                 265                 270

Leu Val Thr Leu Glu Leu His Ser Glu Gly Ser Thr Val Leu Leu Phe
        275                 280                 285

Leu Phe Gly Met Asn Ala Ser Ser Ser Arg Phe Phe Leu Gln Gly Ile
    290                 295                 300

Gln Leu Asn Thr Thr Leu Pro Asp Ala Arg Asp Pro Ala Phe Lys Ala
305                 310                 315                 320

Ala Asn Gly Ser Leu Arg Ala Leu Gln Ala Thr Val Gly Asn Ser Tyr
                325                 330                 335

Lys Cys Asn Ala Glu Glu His Val Arg Val Thr Lys Ala Phe Ser Val
            340                 345                 350

Asn Ile Phe Lys Val Trp Val Gln Ala Phe Lys Val Glu Gly Gly Gln
        355                 360                 365

Phe Gly Ser Val Glu Glu Cys Val Leu Asp Glu Asn Asn Met Leu Ile
    370                 375                 380

Pro Ile Ala Val Gly Gly Ala Leu Ala Gly Leu Val Leu Ile Val Leu
385                 390                 395                 400

Ile Ala Tyr Leu Val Gly Arg Lys Arg Ser His Ala Gly Tyr Gln Thr
                405                 410                 415

Ile
```

<210> SEQ ID NO 10
<211> LENGTH: 415
<212> TYPE: PRT
<213> ORGANISM: Macaca mulatta

<400> SEQUENCE: 10

```
Met Ala Ala Pro Gly Ser Ala Arg Arg Ser Leu Leu Leu Leu Leu Leu
1               5                   10                  15

Leu Leu Leu Gly Leu Thr His Cys Ala Ser Ala Ala Met Phe Ile Val
            20                  25                  30

Lys Asn Gly Asn Gly Thr Ala Cys Ile Met Ala Asn Phe Ser Ala Ala
        35                  40                  45

Phe Ser Val Asn Tyr Asp Thr Lys Ser Gly Pro Lys Asn Met Thr Phe
    50                  55                  60

Asp Leu Pro Ser Asp Ala Lys Val Val Leu Asn Ser Ser Ser Cys Gly
65                  70                  75                  80

Lys Glu Asn Thr Ser Asp Pro Ser Leu Val Ile Ala Phe Gly Arg Gly
                85                  90                  95

Gln Thr Leu Thr Leu Asn Phe Thr Arg Asn Ala Thr Arg Tyr Ser Val
            100                 105                 110

Gln Leu Met Ser Phe Val Tyr Asn Leu Ser Asp Thr His Leu Phe Pro
        115                 120                 125

Asn Ala Ser Ser Lys Glu Ile Lys Thr Val Glu Ser Ile Thr Asp Ile
    130                 135                 140

Arg Ala Asp Ile Asp Lys Lys Tyr Arg Cys Val Ser Gly Thr Gln Val
145                 150                 155                 160

His Met Asn Asn Val Thr Val Thr Leu His Asp Ala Thr Ile Gln Ala
                165                 170                 175

Tyr Leu Ser Asn Ser Ser Phe Ser Arg Glu Glu Thr Arg Cys Glu Gln
            180                 185                 190

Asp Arg Pro Ser Pro Thr Thr Ala Pro Pro Ala Pro Pro Ser Pro Ser
        195                 200                 205

Pro Ser Pro Val Pro Glu Ser Pro Ser Val Asp Lys Tyr Asn Val Ser
    210                 215                 220

Gly Thr Asn Gly Thr Cys Leu Leu Ala Ser Met Gly Leu Gln Leu Asn
225                 230                 235                 240

Leu Thr Tyr Glu Arg Lys Asp Asn Thr Thr Val Thr Arg Leu Leu Asn
                245                 250                 255

Ile Asn Pro Asn Lys Thr Leu Ala Ser Gly Ser Cys Gly Ala His Leu
            260                 265                 270

Val Thr Leu Glu Leu His Ser Glu Gly Ser Thr Val Leu Leu Phe Gln
        275                 280                 285

Phe Gly Met Asn Ala Ser Ser Ser Arg Phe Phe Leu Gln Gly Ile Gln
    290                 295                 300

Leu Asn Thr Thr Leu Pro Asp Ala Arg Asp Pro Ala Phe Lys Ala Ala
305                 310                 315                 320

Asn Ser Ser Leu Arg Ala Leu Gln Ala Thr Val Gly Asn Ser Tyr Lys
                325                 330                 335

Cys Asn Ala Glu Glu His Val Arg Val Thr Lys Ala Phe Ser Val Asn
            340                 345                 350

Ile Phe Lys Val Trp Val Gln Ala Phe Lys Val Glu Gly Gly Gln Phe
        355                 360                 365

Gly Ser Val Glu Glu Cys Leu Leu Asp Glu Asn Asn Met Leu Ile Pro
    370                 375                 380

Ile Ala Val Gly Gly Ala Leu Ala Gly Leu Val Leu Ile Val Leu Ile
385                 390                 395                 400

Ala Tyr Leu Val Gly Arg Lys Arg Ser His Ala Gly Tyr Gln Thr
                405                 410                 415
```

<210> SEQ ID NO 11
<211> LENGTH: 413
<212> TYPE: PRT
<213> ORGANISM: Canis lupus familiaris

<400> SEQUENCE: 11

```
Met Ala Ala Phe Gly Gly Ala Arg Pro Arg Pro Leu Leu Leu Leu Leu
1               5                   10                  15

Leu Ala Gly Leu Val His Gly Ala Ala Ala Val Phe Val Val Lys Asp
            20                  25                  30

Ala Asn Gly Thr Ala Cys Ile Met Ala Asn Phe Ser Ala Ala Phe Leu
        35                  40                  45

Ala Ser Tyr Glu Thr Arg Ser Gly Pro Lys Asn Val Thr Phe Asp Leu
    50                  55                  60

Pro Ser Asp Ala Val Val Leu Asn Ser Ser Ser Cys Gly Lys Glu Asn
65                  70                  75                  80

Thr Ser Asp Pro Ser Leu Met Ile Ala Phe Gly Lys Gly His Gly Leu
                85                  90                  95

Thr Leu Asn Phe Thr Arg Asn Ala Thr Arg Tyr Ser Val Gln Leu Met
            100                 105                 110

Ser Phe Ile Tyr Asn Leu Ser Asp Thr Gln Ile Phe Pro Asn Ala Ser
        115                 120                 125

Ser Lys Glu Thr Lys Thr Val Glu Ser Ala Thr Asp Ile Arg Ala Asp
    130                 135                 140

Ile Asn Lys Lys Tyr Arg Cys Val Ser Asn Thr Gln Ile His Met His
145                 150                 155                 160

Asn Val Thr Val Thr Phe His Asp Val Thr Ile Gln Ala Tyr Leu Ala
                165                 170                 175

Asn Ser Asn Phe Ser Lys Glu Glu Thr Arg Cys Glu Gln Asp Gly Pro
            180                 185                 190

Phe Pro Thr Thr Ala Pro Pro Pro Pro Pro His Pro Ser Pro Ser Pro
        195                 200                 205

Ala Pro Glu Ser Pro Ser Val His Lys Tyr Asn Val Ser Gly Ala Asn
    210                 215                 220

Gly Thr Cys Leu Leu Ala Ser Met Gly Leu Gln Leu Asn Val Thr Tyr
225                 230                 235                 240

Lys Lys Lys Asp Asn Thr Thr Val Val Lys Val Val Ser Ile Asn Pro
                245                 250                 255

Asn Lys Thr Thr Ala Gly Gly Ser Cys Gly Ala Gln Leu Val Thr Leu
            260                 265                 270

Glu Leu Arg Ser Glu Ser Val Thr Leu Leu Ala Phe Gln Phe Gly Met
        275                 280                 285

Asn Ala Ser Thr Ser Arg Phe Phe Leu Gln Gly Ile Gln Leu Asn Met
    290                 295                 300

Thr Leu Pro Asp Ala Arg Asp Pro Thr Phe Lys Ala Gly Asn Asn Ser
305                 310                 315                 320

Leu Arg Ala Leu Gln Ala Thr Ile Gly Asn Ser Tyr Lys Cys Asn Ala
                325                 330                 335

Gly Glu His Val Gln Val Thr Glu Ala Phe Ser Val Asn Ile Ile Lys
            340                 345                 350

Val Trp Val Gln Ala Phe Gln Val Gln Gly Asp Lys Phe Gly Ser Val
        355                 360                 365

Glu Glu Cys Gln Leu Asp Glu Asn Ser Met Leu Ile Pro Ile Ala Val
    370                 375                 380
```

```
Gly Gly Ala Leu Ala Gly Leu Val Leu Ile Val Leu Ile Ala Tyr Leu
385                 390                 395                 400

Ile Gly Arg Lys Arg Ser His Ala Gly Tyr Gln Thr Ile
                405                 410


<210> SEQ ID NO 12
<211> LENGTH: 417
<212> TYPE: PRT
<213> ORGANISM: Oryctolagus cuniculus

<400> SEQUENCE: 12

Met Glu Ala Pro Gly Gly Ala Arg Arg Pro Leu Leu Leu Leu Leu Leu
1               5                   10                  15

Leu Gly Leu Val His Gly Ala Ser Ala Val Phe Val Val Arg Asn Ser
            20                  25                  30

Asn Gly Thr Ala Cys Ile Met Ala Asn Phe Ser Ala Val Phe Ser Val
        35                  40                  45

Ile Tyr Glu Ser Lys Ser Gly Tyr Lys Asn Ala Ser Phe Glu Leu Pro
    50                  55                  60

Ala Thr Ala Glu Val Gln Asn Thr Ser Ser Cys Gly Arg Glu Asn Thr
65                  70                  75                  80

Ser Asn Pro Ser Leu Gln Ile Ala Phe Gly Arg Gly His Val Leu Ala
                85                  90                  95

Leu Asn Phe Thr Arg Asn Ala Thr Leu Tyr Ser Val Pro Leu Leu Ser
            100                 105                 110

Phe Val Tyr Asn Leu Ser Asp Ser Asp Leu Phe Pro Asn Ala Ser Ser
        115                 120                 125

Lys Asp Ile Lys Thr Val Gly Ser Thr Thr Asp Ile Lys Ala Asp Ile
    130                 135                 140

Asp Lys Arg Tyr Arg Cys Val Ser Asp Ser Lys Val Pro Met Gly Asn
145                 150                 155                 160

Val Thr Val Thr Leu Gln Asp Ala Thr Ile Gln Ala Tyr Leu Trp Asn
                165                 170                 175

Asn Ser Phe Ser Gln Ala Glu Ser Arg Cys Arg Gln Asp Met Pro Ser
            180                 185                 190

Pro Thr Thr Ala Pro Pro Ala Pro Pro Val Pro Pro Ser Pro Pro Ser
        195                 200                 205

Pro Ser Pro Pro Pro Lys Pro Glu Ser Pro Ser Val Ser Arg Tyr Asn
    210                 215                 220

Val Ser Asp Gly Asn Ala Thr Cys Leu Leu Ala Ser Met Gly Leu Gln
225                 230                 235                 240

Leu Asn Leu Thr Tyr Val His Arg Asp Asn Ala Thr Val Thr Arg Val
                245                 250                 255

Phe Asn Ile Asn Pro Asn Lys Thr Lys Pro Ser Gly His Cys Gly Ala
            260                 265                 270

Gln Gln Val Thr Leu Glu Leu Gln Ser Glu Arg Ser Thr Val Leu Val
        275                 280                 285

Phe Gln Phe Gly Met Asn Ala Ser Ser Gly Gln Tyr Phe Leu Gln Gly
    290                 295                 300

Val Leu Leu Asn Thr Thr Leu Pro Asp Ala Arg Glu Pro Ala Phe Ser
305                 310                 315                 320

Ala Ser Asn Ser Ser Leu Arg Ala Leu Gln Ala Thr Leu Gly Asn Ser
                325                 330                 335

Tyr Lys Cys Asn Ser Glu Glu His Val Arg Val Thr Pro Ala Phe Ser
            340                 345                 350
```

```
Leu Ser Ile Phe Lys Val Trp Val Gln Ala Phe Gln Val Lys Gly Asp
        355                 360                 365

Lys Phe Gly Ser Val Glu Glu Cys Leu Leu Asp Gln Asp Ser Met Leu
    370                 375                 380

Ile Pro Ile Ala Val Gly Gly Ala Leu Ala Gly Leu Val Leu Val Val
385                 390                 395                 400

Leu Ile Ala Tyr Leu Ile Gly Arg Lys Arg Ser His Ala Gly Tyr Gln
                405                 410                 415

Thr


<210> SEQ ID NO 13
<211> LENGTH: 409
<212> TYPE: PRT
<213> ORGANISM: Bos taurus

<400> SEQUENCE: 13

Met Ala Ala Pro Gly Gly Ala Arg Arg Arg Pro Leu Leu Leu Leu Leu
1               5                   10                  15

Phe Ala Gly Leu Val His Gly Ala Ser Ala Val Phe Val Val Lys Asn
            20                  25                  30

Gly Asn Gly Thr Ala Cys Ile Met Ala Asp Phe Ser Ala Thr Phe Leu
        35                  40                  45

Thr Ser Tyr Asp Thr Arg Ser Gly Pro Gln Asn Lys Ser Phe Glu Leu
    50                  55                  60

Pro Ala Gly Ala Glu Val Ser Asn Ser Ser Ser Cys Gly Lys Glu Asn
65                  70                  75                  80

Ala Ser Asp Ser Ser Leu Val Ile Thr Phe Gly Arg Gly His Thr Leu
                85                  90                  95

Thr Leu Ile Phe Thr Arg Asn Ala Thr Arg Tyr Glu Val Gln Leu Met
            100                 105                 110

Arg Phe Ala Tyr Asn Leu Ser Asp Thr Asp Thr Phe Pro Asn Ser Ser
        115                 120                 125

Ser Thr Gly Val Lys Thr Val Glu Ser Ala Thr Asp Ile Lys Ala Asp
    130                 135                 140

Ile Asn Lys Thr Tyr Arg Cys Val Ser Glu Thr Gln Val Asn Met Asp
145                 150                 155                 160

Asn Val Thr Val Thr Leu Arg Asp Ala Ala Ile Gln Ala Tyr Leu Ser
                165                 170                 175

Ser Ser Asn Phe Ser Arg Glu Glu Thr Arg Cys Glu Gln Asp Leu Pro
            180                 185                 190

Thr Pro Thr Thr Pro Pro Gln Pro Ala Pro Thr Pro Ala Pro Ala Ser
        195                 200                 205

Pro Ala Val Phe Arg Tyr Asn Val Ser Gly Ser Asn Gly Thr Cys Leu
    210                 215                 220

Leu Ala Ser Met Gly Leu Gln Leu Asn Val Thr Tyr Arg Arg Val Asp
225                 230                 235                 240

Asn Lys Thr Val Thr Arg Glu Phe Asn Val Asn Pro Asn Lys Thr Thr
                245                 250                 255

Phe Gly Gly Asn Cys Ser Ala Thr Leu Ala Thr Leu Glu Leu His Ser
            260                 265                 270

Glu Asn Leu Leu Leu Leu Ala Leu Gln Phe Val Met Asn Glu Ser Ser
        275                 280                 285

Ser Arg Val Phe Leu Gln Gly Val Gln Leu Asn Leu Thr Leu Pro Asp
    290                 295                 300
```

```
Ala Lys Glu Gly Ser Phe Thr Ala Thr Asn Ser Ser Leu Arg Ala Leu
305                 310                 315                 320

Gln Ala Thr Ala Gly Asn Ser Tyr Lys Cys Asn Ala Glu Gln Arg Leu
                325                 330                 335

Arg Val Thr Ser Ser Phe Ser Leu Asn Met Phe Arg Val Trp Leu Gln
            340                 345                 350

Ala Phe Arg Val Asp Gly Asp Lys Phe Gly Pro Val Glu Glu Cys Gln
        355                 360                 365

Leu Asp Glu Asn Ser Met Leu Ile Pro Ile Ala Val Gly Gly Ala Leu
    370                 375                 380

Ala Gly Leu Val Leu Ile Val Leu Leu Ala Tyr Leu Ile Gly Arg Lys
385                 390                 395                 400

Arg Ser His Ala Gly Tyr Gln Thr Ile
                405


<210> SEQ ID NO 14
<211> LENGTH: 407
<212> TYPE: PRT
<213> ORGANISM: Rattus norvegicus

<400> SEQUENCE: 14

Met Ala Ala Pro Gly Ala Arg Arg Pro Leu Leu Leu Leu Leu Leu Ala
1               5                   10                  15

Gly Leu Ala His Ser Ala Pro Ala Leu Phe Glu Val Lys Asp Asn Asn
            20                  25                  30

Gly Thr Ala Cys Ile Met Ala Ser Phe Ser Ala Ser Phe Leu Thr Thr
        35                  40                  45

Tyr Asp Ala Gly His Val Ser Lys Val Ser Asn Met Thr Leu Pro Ala
    50                  55                  60

Ser Ala Glu Val Leu Lys Asn Ser Ser Ser Cys Gly Glu Lys Asn Ala
65                  70                  75                  80

Ser Glu Pro Thr Leu Ala Ile Thr Phe Gly Glu Gly Tyr Leu Leu Lys
                85                  90                  95

Leu Thr Phe Thr Lys Asn Thr Thr Arg Tyr Ser Val Gln His Met Tyr
            100                 105                 110

Phe Thr Tyr Asn Leu Ser Asp Thr Gln Phe Phe Pro Asn Ala Ser Ser
        115                 120                 125

Lys Gly Pro Asp Thr Val Asp Ser Thr Thr Asp Ile Lys Ala Asp Ile
    130                 135                 140

Asn Lys Thr Tyr Arg Cys Val Ser Asp Ile Arg Val Tyr Met Lys Asn
145                 150                 155                 160

Val Thr Ile Val Leu Trp Asp Ala Thr Ile Gln Ala Tyr Leu Pro Ser
                165                 170                 175

Ser Asn Phe Ser Lys Glu Glu Thr Arg Cys Pro Gln Asp Gln Pro Ser
            180                 185                 190

Pro Thr Thr Gly Pro Pro Ser Pro Ser Pro Pro Leu Val Pro Thr Asn
        195                 200                 205

Pro Ser Val Ser Lys Tyr Asn Val Thr Gly Asp Asn Gly Thr Cys Leu
    210                 215                 220

Leu Ala Ser Met Ala Leu Gln Leu Asn Ile Thr Tyr Met Lys Lys Asp
225                 230                 235                 240

Asn Thr Thr Val Thr Arg Ala Phe Asn Ile Asn Pro Ser Asp Lys Tyr
                245                 250                 255

Ser Gly Thr Cys Gly Ala Gln Leu Val Thr Leu Lys Val Gly Asn Lys
```

```
            260                 265                 270

Ser Arg Val Leu Glu Leu Gln Phe Gly Met Asn Ala Thr Ser Ser Leu
        275                 280                 285

Phe Phe Leu Gln Gly Val Gln Leu Asn Met Thr Leu Pro Asp Ala Ile
    290                 295                 300

Glu Pro Thr Phe Ser Thr Ser Asn Tyr Ser Leu Lys Ala Leu Gln Ala
305                 310                 315                 320

Ser Val Gly Asn Ser Tyr Lys Cys Asn Ser Glu Glu His Ile Phe Val
                325                 330                 335

Ser Lys Ala Leu Ala Leu Asn Val Phe Ser Val Gln Val Gln Ala Phe
            340                 345                 350

Arg Val Glu Ser Asp Arg Phe Gly Ser Val Glu Glu Cys Val Gln Asp
        355                 360                 365

Gly Asn Asn Met Leu Ile Pro Ile Ala Val Gly Gly Ala Leu Ala Gly
    370                 375                 380

Leu Val Leu Ile Val Leu Ile Ala Tyr Leu Ile Gly Arg Lys Arg Ser
385                 390                 395                 400

His Ala Gly Tyr Gln Thr Ile
                405


<210> SEQ ID NO 15
<211> LENGTH: 414
<212> TYPE: PRT
<213> ORGANISM: Gallus gallus

<400> SEQUENCE: 15

Met Gly Gly Ala Ala Arg Ala Val Leu Leu Gly Phe Leu Gln Ala Ser
1               5                   10                  15

Ser Ser Phe Asp Val Arg Asp Ser Thr Gly Lys Val Cys Ile Ile Ala
            20                  25                  30

Asn Leu Thr Val Ala Phe Ser Val Glu Tyr Lys Ser Ser Gly Gln Lys
        35                  40                  45

Gln Phe Ala His Phe Phe Leu Pro Gln Asn Ala Thr Ser Gln Ser His
    50                  55                  60

Ser Ser Cys Gly Glu Gly Asn Thr Ser His Pro Ile Leu Ala Leu Ser
65                  70                  75                  80

Phe Gly Ala Gly His Leu Ile Ser Leu Asn Phe Ser Lys Thr Leu Asp
                85                  90                  95

Lys Tyr Gln Val Glu Glu Leu Thr Phe His Tyr Asn Leu Ser Asp Glu
            100                 105                 110

Thr Leu Phe Pro Asn Ala Thr Glu Gly Lys Val Met Val Ala Thr Gln
        115                 120                 125

Lys Ser Val Ile Gln Ala Arg Ile Gly Thr Glu Tyr Arg Cys Ile Asn
    130                 135                 140

Ser Lys Tyr Val Arg Met Lys His Val Asn Ile Thr Phe Ser Asn Val
145                 150                 155                 160

Thr Leu Glu Ala Tyr Pro Thr Asn Asp Thr Phe Ser Ala Asn Lys Thr
                165                 170                 175

Glu Cys Arg Glu Asp Met Val Ser Thr Thr Thr Val Ala Pro Thr Thr
            180                 185                 190

Pro Lys His Ala Thr Ser Gln Val Pro Thr Thr Ser Pro Ala Pro Thr
        195                 200                 205

Ala Ala Pro Ser Ser Pro Ala Val Gly Lys Tyr Asn Val Thr Gly Ala
    210                 215                 220
```

```
Asn Gly Thr Cys Val Leu Ala Ser Met Gly Leu Gln Leu Asn Ile Thr
225                 230                 235                 240

Tyr Val Lys Lys Asp Glu Lys Met Gly Leu Asp Leu Leu Asn Phe Ile
                245                 250                 255

Pro His Asn Thr Ser Ala Ser Gly Met Cys Glu Ser Thr Ser Ala Phe
            260                 265                 270

Leu Asn Leu Ala Phe Glu Lys Thr Lys Ile Thr Phe His Phe Val Leu
        275                 280                 285

Asn Ala Ser Ser Glu Lys Phe Phe Leu Gln Gly Val Asn Val Ser Thr
    290                 295                 300

Thr Leu Pro Ser Glu Ala Lys Ala Pro Thr Phe Glu Ala Ser Asn Asp
305                 310                 315                 320

Ser Met Ser Glu Ser Arg Ala Thr Val Gly Asn Ser Tyr Lys Cys Ser
                325                 330                 335

Ala Glu Glu Asn Phe Gln Val Thr Asp Lys Ala Leu Val Asn Val Phe
            340                 345                 350

Asn Val Gln Val Gln Ala Phe Lys Val Asp Gly Asp Lys Phe Gly Ala
        355                 360                 365

Met Glu Glu Cys Gln Leu Asp Glu Asn Asn Met Leu Ile Pro Ile Ile
    370                 375                 380

Val Gly Ala Ala Leu Ala Gly Leu Val Leu Ile Val Leu Ile Ala Tyr
385                 390                 395                 400

Leu Ile Gly Arg Lys Arg Ser His Ala Gly Tyr Gln Thr Ile
                405                 410


<210> SEQ ID NO 16
<211> LENGTH: 413
<212> TYPE: PRT
<213> ORGANISM: Sus scrofa

<400> SEQUENCE: 16

Met Ala Ala Pro Gly Gly Ala Trp Arg Arg Pro Leu Leu Leu Leu Leu
1               5                   10                  15

Leu Leu Leu Gly Leu Ala Arg Gly Ala Ser Ala Val Phe Val Val Ser
            20                  25                  30

Asp Gly Asn Gly Thr Ala Cys Ile Met Ala Asp Phe Ala Ala Ala Phe
        35                  40                  45

Glu Ile Ser Tyr Asp Ser Arg Ser Gly Ala Lys Asn Thr Thr Phe Ser
    50                  55                  60

Leu Pro Ala Ser Ala Gln Val Leu Asn Ser Ser Ser Cys Gly Lys Glu
65                  70                  75                  80

Asn Thr Ser Asp Ser Ser Leu Val Ile Ala Phe Gly Arg Gly His Thr
                85                  90                  95

Leu Thr Leu Ser Phe Thr Arg Asn Ala Thr Arg Tyr Ser Val Gln Leu
            100                 105                 110

Met Thr Leu Val Tyr Asn Leu Ser Asp Ala Glu Phe Phe Pro Ser Ala
        115                 120                 125

Ser Ser Lys Gly Thr Lys Thr Val Ala Ala Ser Thr Asp Ile Arg Ala
    130                 135                 140

Asp Leu Asn Thr Lys Tyr Arg Cys Val Ser Asn Ser Gln Val His Leu
145                 150                 155                 160

Leu Asn Val Thr Val Thr Leu Gly Asn Ala Thr Ile Gln Ala Tyr Leu
                165                 170                 175

Ala Asn Asn Ser Phe Ser Gln Gln Glu Thr Arg Cys Glu Gln Asp Lys
            180                 185                 190
```

```
Pro Ser Pro Pro Thr Pro Thr Ala Pro Pro Thr Pro Thr Pro Thr Pro
        195                 200                 205

Ala Pro Thr Ser Pro Val Val Ser Arg Tyr Asn Val Ser Gly Ala Asn
    210                 215                 220

Gly Thr Cys Leu Leu Ala Ser Met Gly Leu Gln Leu Asn Val Thr Tyr
225                 230                 235                 240

Arg Thr Lys Asp Asn Thr Thr Val Thr Arg Gly Leu Asn Ile Asn Pro
                245                 250                 255

Asn Lys Thr Thr Phe Gly Gly Ser Cys Ser Ala Gln Leu Val Thr Leu
            260                 265                 270

Glu Leu Gln Gly Glu Ser Leu Arg Leu Leu Ala Leu Gln Phe Ala Leu
        275                 280                 285

Asn Thr Ser Ser Ser Arg Val Phe Leu Gln Gly Val Gln Leu Asn Met
    290                 295                 300

Thr Leu Pro Asp Ala Arg Asp Pro Ser Phe Ser Ala Ala Asn Ser Ser
305                 310                 315                 320

Leu Arg Ala Leu Gln Ala Thr Ala Gly Asn Ser Tyr Lys Cys Arg Ser
                325                 330                 335

Glu Gln Arg Leu Gln Val Thr Glu Ala Phe Ala Leu Asn Val Phe Gln
            340                 345                 350

Val Arg Val Gln Ala Phe Arg Val Asp Gly Asp Lys Phe Gly Pro Ala
        355                 360                 365

Glu Glu Cys Gln Leu Asp Glu Asn Ser Met Leu Ile Pro Ile Ala Val
    370                 375                 380

Gly Gly Ala Leu Ala Gly Leu Val Leu Val Val Leu Met Ala Tyr Leu
385                 390                 395                 400

Val Gly Arg Lys Arg Ser His Ala Gly Tyr Gln Thr Ile
                405                 410


<210> SEQ ID NO 17
<211> LENGTH: 422
<212> TYPE: PRT
<213> ORGANISM: Monodelphis domestica

<400> SEQUENCE: 17

Met Ala Glu Pro Gly Gly Ala Arg Thr Pro Gln Arg Leu Leu Leu Leu
1               5                   10                  15

Leu Leu Gly Leu Ile His Val Ala Ser Ser Ile Phe Val Val Lys Asn
            20                  25                  30

Gly Thr Gly Thr Ala Cys Ile Met Ala Asn Phe Ser Ala Thr Phe Ser
        35                  40                  45

Met Asn Tyr Thr Thr Lys Ser Gly Leu Glu Ser Thr Thr Phe Arg Leu
    50                  55                  60

Pro Gln Asn Ala Ser Val Met Asn Ser Ser Ser Cys Gly Lys Glu Asn
65                  70                  75                  80

Thr Ser Asn Pro Ile Leu Glu Ile Gly Phe Gly Gly Gly His Thr Leu
                85                  90                  95

Thr Met Asn Phe Ser Ser Thr Thr Gln Ser Tyr Gln Val Glu Leu Leu
            100                 105                 110

Ser Phe Ser Tyr Asn Leu Ser Asp Ala Thr Leu Phe Pro Asn Ala Ser
        115                 120                 125

Lys Gly Ser Glu Glu Ser Ser Val Lys Ser Lys Thr Asp Ile Gln Ala
    130                 135                 140

Asp Ile His Lys Lys Tyr Arg Cys Val Ser Ser Asn Arg Ile Thr Met
```

```
145                 150                 155                 160

Ser Asn Val Thr Ile Val Leu Ser Asp Val Thr Ile Gln Ala Tyr Leu
                165                 170                 175

Ser Asn Asn Thr Phe Ser Lys Glu Glu Thr Arg Cys Ser Gln Asp Thr
            180                 185                 190

Pro Ser Pro Ser Pro Val Pro Thr Thr His Pro Thr Thr Ile Pro Val
        195                 200                 205

Pro Thr Pro Thr Pro Thr Arg Pro Pro Thr Pro Ala Glu Ile Pro Pro
    210                 215                 220

Ile Phe Lys Tyr Asn Val Ser Asp Ala Asn Gly Thr Cys Leu Leu Ala
225                 230                 235                 240

Ser Met Gly Leu Gln Leu Asn Ile Thr Tyr Ala Lys Lys Asp Asn Ser
                245                 250                 255

Ser Ala Arg Ile Ile Trp Asn Ile Asn Pro Asn Lys Thr Val Ala Gly
            260                 265                 270

Gly Ser Cys Ser Pro Gln Val Ala Ile Leu Glu Leu Gln Thr Glu Asn
        275                 280                 285

Ser Thr Leu Ala Phe Ser Phe Gly Met Asn Ala Thr Thr Ser Lys Phe
    290                 295                 300

Phe Leu Arg Glu Ile Arg Phe His Lys Phe Phe Pro Asp Ala Lys Asp
305                 310                 315                 320

Pro Ala Phe Gly Ala Val Asn Ser Ser Leu Lys Glu Leu Gln Ala Thr
                325                 330                 335

Val Gly Asn Ser Tyr Lys Cys Asn Ala Glu Glu Asn Val His Val Thr
            340                 345                 350

Asp Gly Phe Ser Val Asn Ile Phe Arg Val Arg Val Gln Ala Phe Lys
        355                 360                 365

Val Glu Gly Asp Lys Phe Gly Ser Val Glu Glu Cys Leu Leu Asp Glu
    370                 375                 380

Asn Asn Met Leu Ile Pro Ile Ala Val Gly Gly Ala Leu Ala Gly Leu
385                 390                 395                 400

Val Leu Ile Val Leu Ile Ala Tyr Leu Ile Gly Arg Lys Arg Ser His
                405                 410                 415

Ala Gly Tyr Gln Thr Ile
            420


<210> SEQ ID NO 18
<211> LENGTH: 415
<212> TYPE: PRT
<213> ORGANISM: Meleagris gallopavo

<400> SEQUENCE: 18

Met Ala Arg Ala Leu Leu Ala Ala Val Leu Leu Gly Phe Leu Gln Ala
1               5                   10                  15

Ser Ser Ser Phe Asp Val Arg Asp Ser Thr Gly Lys Val Cys Ile Ile
            20                  25                  30

Ala Asn Leu Thr Val Ala Phe Ser Val Glu Tyr Lys Ser Asn Gly Gln
        35                  40                  45

Lys Gln Phe Ala His Phe Phe Leu Pro Gln Asn Ala Thr Ser Gln Ser
    50                  55                  60

His Ser Ser Cys Gly Glu Gly Asn Thr Ser His Pro Ile Leu Ala Leu
65                  70                  75                  80

Ser Phe Gly Ala Gly His Leu Leu Ser Leu Asn Phe Ser Lys Thr Leu
                85                  90                  95
```

```
Asp Lys Tyr Gln Val Glu Glu Leu Thr Phe His Tyr Asn Leu Ser Asp
            100                 105                 110

Glu Thr Leu Phe Pro Asn Ala Ser Glu Gly Lys Val Met Glu Val Thr
        115                 120                 125

Gln Lys Ser Val Ile Gln Ala Arg Ile Gly Thr Glu Tyr Arg Cys Ile
    130                 135                 140

Asn Ser Lys Tyr Ile Tyr Ile Arg His Val Asn Ile Thr Phe Ser Asn
145                 150                 155                 160

Val Thr Leu Glu Ala Tyr Pro Thr Asn Gly Thr Phe Ser Thr Asn Lys
                165                 170                 175

Thr Glu Cys Ser Glu Asp Met Val Ser Thr Thr Thr Val Ala Pro Thr
            180                 185                 190

Thr Pro Lys His Ile Thr Ser Gln Val Pro Ala Thr Ser Pro Ala Pro
        195                 200                 205

Thr Ala Ala Pro Ser Asn Pro Ala Val Gly Lys Tyr Asn Val Thr Gly
    210                 215                 220

Ala Asn Gly Thr Cys Val Leu Ala Ser Met Gly Leu Gln Leu Asn Ile
225                 230                 235                 240

Thr Tyr Leu Lys Lys Asp Gly Lys Thr Gly Leu Asp Leu Leu Asn Phe
                245                 250                 255

Val Pro His Asn Thr Asn Ala Ser Gly Thr Cys Glu Asn Thr Ser Ala
            260                 265                 270

Phe Leu Asn Leu Ala Phe Glu Lys Thr Lys Ile Thr Phe His Phe Val
        275                 280                 285

Leu Asn Ala Ser Ser Glu Lys Phe Phe Leu Gln Gly Val Asn Val Ser
    290                 295                 300

Thr Thr Leu Pro Ser Glu Ala Lys Ala Pro Met Phe Glu Ala Ser Asn
305                 310                 315                 320

Asp Ser Met Ser Glu Leu Arg Ala Thr Val Gly Asn Ser Tyr Lys Cys
                325                 330                 335

Ser Ala Glu Glu Asn Leu Gln Val Thr Asp Lys Ala Leu Val Asn Val
            340                 345                 350

Phe Asn Val Gln Val Gln Ala Phe Lys Val Asp Gly Asp Lys Phe Gly
        355                 360                 365

Ala Val Glu Glu Cys Gln Leu Asp Glu Asn Asn Met Leu Ile Pro Ile
    370                 375                 380

Ile Val Gly Ala Ala Leu Ala Gly Leu Val Leu Ile Val Leu Ile Ala
385                 390                 395                 400

Tyr Leu Ile Gly Arg Lys Arg Ser His Ala Gly Tyr Gln Thr Ile
                405                 410                 415


<210> SEQ ID NO 19
<211> LENGTH: 415
<212> TYPE: PRT
<213> ORGANISM: Taeniopygia guttata

<400> SEQUENCE: 19

Met Ala Arg Gly Leu Leu Ala Ala Ala Ala Leu Leu Gly Phe Leu Gln
1               5                   10                  15

Ala Ser Ser Ser Phe Glu Val Lys Asp Ser Ser Gly Lys Val Cys Ile
            20                  25                  30

Leu Ala Asp Leu Thr Val Ala Phe Ser Val Glu Tyr Lys Thr Asn Val
        35                  40                  45

Gln Lys Glu Phe Val His Phe Phe Leu Pro Gln Asn Ala Ser Val Asp
    50                  55                  60
```

```
Ser Gln Ser Ser Cys Gly Lys Asp Asn Ala Ser His Pro Ile Leu Val
65                  70                  75                  80

Leu Asp Phe Gly Gly Gly His Ser Leu Ser Leu Asn Phe Ser Glu Ser
                85                  90                  95

Ala Asp Lys Tyr Gln Val Glu Glu Leu Val Phe His Tyr Asn Leu Ser
            100                 105                 110

Asp Ala Thr Leu Phe Pro Asn Ser Ser Thr Gly Gly Met Lys Thr Val
        115                 120                 125

Ser His Lys Ser Ile Ile Gln Ala His Met Gly Thr Gln Tyr Arg Cys
    130                 135                 140

Ile Asn Ser Lys His Ile Asn Met Lys Asn Val Asn Val Thr Phe Ser
145                 150                 155                 160

Asn Val Thr Leu Glu Ala Tyr Leu Thr Asn Gly Thr Leu Ser Val Asn
                165                 170                 175

Lys Thr Glu Cys Ala Glu Asp Arg Val Ser Thr Thr Thr Met Val Pro
            180                 185                 190

Thr Thr Pro Lys Gln Thr Thr Ser Gln Ser Pro Thr Thr Gly Pro Ala
        195                 200                 205

Pro Thr Ser Pro Pro Asn Pro Thr Val Gly Lys Tyr Asn Val Thr Gly
    210                 215                 220

Pro Asn Gly Thr Cys Val Leu Ala Tyr Met Gly Leu Gln Leu Asn Ile
225                 230                 235                 240

Thr Tyr Gln Gln Lys Asp Glu Lys Met Gly Leu Asp Leu Leu Asn Phe
                245                 250                 255

Val Pro His Asn Thr Thr Ser Ser Gly Arg Cys Asp Asn Thr Ser Ala
            260                 265                 270

Leu Leu Asn Leu Thr Phe Glu Lys Thr Arg Val Ile Phe Gln Phe Ala
        275                 280                 285

Leu Asn Ala Thr Ala Glu Lys Phe Phe Leu Gln Gly Val Ser Val Ser
    290                 295                 300

Thr Thr Leu Pro Ser Glu Ala Lys Asn Pro Lys Phe Glu Ala Thr Asn
305                 310                 315                 320

Asn Ser Met Ser Glu Leu Arg Ala Ser Val Gly Asn Ser Tyr Lys Cys
                325                 330                 335

Ser Ser Glu Glu Asn Leu Gln Val Thr Asp Gln Ala Leu Val Asn Val
            340                 345                 350

Phe Asn Val Gln Val Gln Ile Phe Lys Ile Asp Gly Asp Lys Phe Gly
        355                 360                 365

Pro Val Glu Glu Cys Gln Leu Asp Glu Asn Asn Met Leu Ile Pro Ile
    370                 375                 380

Ile Val Gly Ala Ala Leu Ala Gly Leu Val Leu Ile Val Leu Ile Ala
385                 390                 395                 400

Tyr Leu Ile Gly Arg Lys Arg Ser His Ala Gly Tyr Gln Thr Ile
                405                 410                 415


<210> SEQ ID NO 20
<211> LENGTH: 418
<212> TYPE: PRT
<213> ORGANISM: Anolis carolinensis

<400> SEQUENCE: 20

Met Val Ser Ser Ser Ser Cys Arg Arg Gly Leu Leu Leu Ala Ala Val
1               5                   10                  15

Leu Leu Gly Phe Leu Gln Ala Ser Ser Thr Phe Glu Val Arg Asp Lys
```

```
            20                  25                  30

Thr Gly Lys Ile Cys Ile Leu Ala Asn Phe Ser Ala Glu Phe Thr Val
        35                  40                  45

Asp Tyr Ser Thr Lys Ala Lys Val Glu Arg Lys Thr Phe Gln Leu Pro
    50                  55                  60

Ser Ser Ala His Ile Asn Lys Glu Ser Ser Ser Cys Gly Lys Glu Lys
65                  70                  75                  80

Glu Thr Ser Gln Val Leu Val Val Glu Phe Gly Thr Gly Asn Ser Leu
                85                  90                  95

Thr Phe Thr Phe Glu Lys Ser Asn Asp Phe Tyr His Val Ser Asn Leu
            100                 105                 110

Thr Phe Ser Tyr Asn Leu Ser Asp Ser Ser Phe Phe Pro Asn Ser Ser
        115                 120                 125

Gly Gly Gln Arg Glu Val Ser Arg Ala Gly Asp Ile Gln Ala Asn Ile
    130                 135                 140

Asn Thr Thr Tyr Arg Cys Arg Ser Asn His Arg Val Asn Met Thr Asn
145                 150                 155                 160

Val Thr Val Leu Phe Ser Asn Val Thr Leu Glu Ala Tyr Leu Pro Asn
                165                 170                 175

Asn Ala Phe Ser Lys Asn Asp Ser Val Cys Ala Glu Asp Lys Thr Ser
            180                 185                 190

Thr Val Ala Pro Pro Ile Thr Thr His Ile Pro Thr Thr Thr Ser Leu
        195                 200                 205

Ala Pro Pro Thr Pro Pro Pro Thr Asp Thr Pro Lys Ile Gly Arg Tyr
    210                 215                 220

Asn Val Thr Gly Leu His Gly Ile Cys Leu Leu Ala Thr Met Gly Leu
225                 230                 235                 240

Gln Val Asn Val Thr Tyr Ser Thr Lys Asn Lys Thr Ser Lys Ser Glu
                245                 250                 255

Leu Leu Asn Leu Pro Pro Thr Ala Glu Val Ser Gly Thr Cys Glu Asn
            260                 265                 270

Ser Ser Ile Thr Leu Asn Leu Thr Ser Glu Ser Thr Ser Leu Ser Phe
        275                 280                 285

Gln Phe Ser Gln Asn Thr Ser Thr Glu Lys Tyr Phe Leu Gln Gly Ile
    290                 295                 300

Ile Val Thr Ala Asn Leu Pro Pro Glu Ala Thr Glu Lys Asn Ile Ser
305                 310                 315                 320

Tyr Ser Asn His Thr Leu Asn Ala Leu Lys Thr Ser Val Gly Lys Ser
                325                 330                 335

Tyr Lys Cys Ile Ala Glu Glu Ser Ile Trp Ile Ser Gly Lys Ala Ala
            340                 345                 350

Val Asn Ile Phe Asn Ile Gln Leu Gln Ala Phe Lys Ile Pro Gly Asp
        355                 360                 365

Lys Phe Gly Ala Val Glu Glu Cys Gln Leu Asp Glu Asn Asn Met Leu
    370                 375                 380

Ile Pro Ile Ile Val Gly Ala Ala Leu Ala Gly Leu Val Leu Ile Val
385                 390                 395                 400

Leu Ile Ala Tyr Leu Ile Gly Arg Lys Arg Ser His Ala Gly Tyr Gln
                405                 410                 415

Thr Ile
```

<210> SEQ ID NO 21
<211> LENGTH: 418

```
<212> TYPE: PRT
<213> ORGANISM: Oryzias latipes

<400> SEQUENCE: 21

Met Lys Ser Phe Pro Ser Phe Val Ala Leu Phe Ile Val Cys Ser Ala
1               5                   10                  15

Val Leu Ala Asp Thr Gln Ala Val Val Thr Leu Glu Val Lys Glu Gly
            20                  25                  30

Asn Ser Thr Cys Ile Lys Ala Glu Phe Ser Ala Val Phe Ser Ile Thr
        35                  40                  45

Tyr Asn Thr Thr Asn Asp Thr Arg Thr Val Ser Val Phe Leu Pro Asn
    50                  55                  60

Ser Thr Thr Val Asp Ser Ala Asn Ser Ser Cys Gly Ser Asn Gly Ser
65                  70                  75                  80

Thr Pro Gly Leu Met Ala Lys Phe Gly Pro Gly His Tyr Phe Gly Met
                85                  90                  95

Asn Phe Ser Thr Asn Gly Ser Leu Tyr Ser Val Asp Thr Leu Phe Leu
            100                 105                 110

Arg Tyr Asn Leu Ser Asp Ala Ser Leu Phe Pro Glu Ala Asn Ser Ser
        115                 120                 125

Gly Pro Val Asp Phe Glu Leu Ser Ala Ser Val Gly Ile Trp Ala Pro
    130                 135                 140

Thr Asn Thr Thr Tyr Arg Cys Leu Ser Pro Thr Thr Ile Thr Ile Thr
145                 150                 155                 160

Arg Pro Ser Val Thr Phe Ser Glu Met Lys Leu Glu Ala Tyr Met Pro
                165                 170                 175

Gly Asn Asp Phe Ser Pro Ala Glu Arg Val Cys Ala Ala Asp Gln Thr
            180                 185                 190

Thr Thr Gly Ala Pro Thr Thr Thr Thr Ser Ala Ala Thr Pro Thr Thr
        195                 200                 205

Pro Ser Pro Thr Pro Ala Gly Thr Pro Glu Gln Gly Ser Tyr Ser Val
    210                 215                 220

Lys Asn Ala Ser Gly Thr Val Cys Leu Met Ala Lys Met Gly Val Gln
225                 230                 235                 240

Leu Asn Val Ser Tyr Phe Ser Gln Ser Gln Asn Lys Thr Val Gln Glu
                245                 250                 255

Leu Leu Asn Leu Thr Pro Asn Leu Thr Ser Ser Ser Gly Leu Cys Gly
            260                 265                 270

Gly Thr Asn Ala Thr Leu Val Leu Ala Gln Glu Glu Thr Thr Val Leu
        275                 280                 285

Ser Phe Leu Phe Thr Val Asn Ser Thr Ser Asn Lys Tyr His Leu Ser
    290                 295                 300

Gly Ile Thr Leu Gln Ala Asn Trp Thr Asp Met Met Ser Pro Phe Ser
305                 310                 315                 320

Ala Ser Asn Thr Ser Leu Asp Tyr Leu Arg Ser Ser Leu Gly His Ser
                325                 330                 335

Tyr Met Cys Asn Ala Glu Gln Thr Leu Phe Val Val Ser Thr Phe Ser
            340                 345                 350

Ile Asn Met Phe Glu Leu Gln Val Gln Pro Phe Gly Val Thr Ser Thr
        355                 360                 365

Gln Phe Ala Ser Ala Glu Val Cys Gln Ile Asp Gln Asp Gln Met Leu
    370                 375                 380

Ile Pro Ile Ile Val Gly Ala Ala Leu Ala Gly Leu Val Leu Ile Val
385                 390                 395                 400
```

```
Leu Ile Ala Tyr Leu Ile Gly Arg Lys Arg Ser His Ala Gly Tyr Gln
                405                 410                 415

Thr Ile


<210> SEQ ID NO 22
<211> LENGTH: 420
<212> TYPE: PRT
<213> ORGANISM: Takifugu rubripes

<400> SEQUENCE: 22

Met Lys Arg Ser His Ala Leu Val Val Leu Ile Ile Ala Trp Phe Ser
1               5                   10                  15

Leu Ser Gly Cys Ile Gln Ala Val Ser Leu Glu Val Lys Glu Gly Asn
            20                  25                  30

Ser Thr Cys Ile Lys Ala Asn Leu Ser Ala Tyr Phe Ser Ile Thr Tyr
        35                  40                  45

Asn Thr Ser Ser Ser Thr Arg Thr Ala Gln Phe Ile Leu Pro Asp Ser
    50                  55                  60

Ala Thr Val Asp Pro Asp Ser Ser Thr Cys Gly Gly Asn Gly Ser Ser
65                  70                  75                  80

Pro Trp Leu Val Ala Val Phe Gly Ala Gly His Ala Leu Gly Leu Gly
                85                  90                  95

Phe Ser Thr Asn Gly Ser Phe Tyr Ser Val Ala Asn Leu Thr Leu Gln
            100                 105                 110

Tyr Asn Leu Ser Asp Ala Ser Val Phe Pro Asp Ala Asn Ser Ser Gly
        115                 120                 125

Val Val Thr Val Val Ser Ser Ser Val Gly Ile Trp Ala Ala Val Asn
    130                 135                 140

Thr Thr Tyr Arg Cys Leu Ser Ser Val Leu Phe Gln Val Gly Gly Ala
145                 150                 155                 160

Thr Val Thr Phe Ser Asp Met Arg Leu Glu Ala Tyr Met Pro Gly Asn
                165                 170                 175

Asp Leu Ser Pro Arg Glu Ser Phe Cys Ala Ala Asp Gln Thr Thr Thr
            180                 185                 190

Ala Pro Pro Thr Thr Thr Ala Ala Pro Thr Thr Thr Ala Ala Thr Thr
        195                 200                 205

Met Ala Pro Pro Ala Pro Thr Pro Pro Gly Thr Pro Val Arg Gly Thr
    210                 215                 220

Tyr Ser Val Val Asn Gly Asn Asp Thr Thr Cys Leu Leu Ala Gln Met
225                 230                 235                 240

Gly Leu Gln Leu Asn Val Ser Tyr Phe Ser Arg Ser Gln Asn Lys Thr
                245                 250                 255

Val Gln Ser Leu Val Asn Leu Thr Pro Asn Leu Thr Asn Ser Thr Gly
            260                 265                 270

Ser Cys Glu Lys Gly Ser Ala Thr Leu Ile Leu Thr Gln Gln Thr Thr
        275                 280                 285

Ile Leu Ile Phe Thr Phe Ser Leu Asn Ser Thr Ser Ser Lys Tyr His
    290                 295                 300

Leu Ser Gly Leu Ser Leu Gln Ala Asn Trp Ser Asp Met Ala Ala Ala
305                 310                 315                 320

Phe Ser Ala Ser Asn Ala Ser Leu Ser Tyr Leu Arg Ser Thr Phe Gly
                325                 330                 335

His Ser Tyr Met Cys Asn Ala Glu Gln Ile Leu Ala Val Thr Pro Val
            340                 345                 350
```

```
Phe Ser Leu Asn Thr Phe Ser Leu Gln Ile Gln Pro Phe Gly Val Thr
        355                 360                 365

Thr Asn Gln Phe Ala Ala Ala Glu Glu Cys Gln Met Asp Gln Asp Gln
    370                 375                 380

Met Leu Ile Pro Ile Ile Val Gly Ala Ser Leu Ala Gly Leu Val Leu
385                 390                 395                 400

Ile Val Leu Ile Ala Tyr Leu Ile Gly Arg Lys Lys Ser His Ala Gly
                405                 410                 415

Tyr Gln Thr Ile
            420


<210> SEQ ID NO 23
<211> LENGTH: 419
<212> TYPE: PRT
<213> ORGANISM: Salmo salar

<400> SEQUENCE: 23

Met Thr Arg Thr Cys Pro Phe Val Val Gly Ile Ala Cys Phe Ala Ile
1               5                   10                  15

Leu Gly Cys Val Thr Val Val Gln Ser Gln Val Thr Leu Glu Val Thr
            20                  25                  30

Glu Gly Asn Ser Thr Cys Ile Lys Ala Glu Leu Ser Ala Ser Phe Ser
        35                  40                  45

Ile Thr Tyr Asp Thr Ala Asn Gly Thr Arg Thr Val Met Val Pro Leu
    50                  55                  60

Pro Gly Ser Ala Val Val Gly Val Ala Ser Ser Cys Gly Gly Asp Gly
65                  70                  75                  80

Arg Ser Pro Trp Leu Val Ala Leu Phe Gly Asp Gly His Ala Leu Gly
                85                  90                  95

Leu Gly Phe Ser Ser Asn Asp Ser Leu Tyr Ser Val Ala Lys Leu Thr
            100                 105                 110

Leu Gln Tyr Asn Leu Ser Asp Val Ser Asn Phe Pro Glu Ala Asn Ser
        115                 120                 125

Thr Asp Val Val Thr Val Glu Thr Thr Ser Val Gly Met Val Ala Arg
    130                 135                 140

Val Asn Thr Thr Tyr Arg Cys Ile Ser Ala Ser Pro Val Ile Val Gly
145                 150                 155                 160

Gly Ala Thr Val Thr Phe Ser Asn Val Thr Met Glu Ala Phe Met Thr
                165                 170                 175

Gly Glu Asp Leu Ser Pro Asn Glu Ser Val Cys Thr Ala Asp Gln Ser
            180                 185                 190

Phe Thr Thr Ala Pro Pro Pro Pro Pro Ser Thr Thr Thr Ala Ala Pro
        195                 200                 205

Ala Pro Val Pro Thr Pro Pro Gly Thr Pro Ser Gln Gly Ser Tyr Ser
    210                 215                 220

Val Ser Asn Ser Asn Gly Thr Val Cys Leu Leu Ala Arg Met Ala Leu
225                 230                 235                 240

Gln Leu Asn Ile Ser His Phe Ser Ala Ser Gln Asn Lys Thr Ile Gln
                245                 250                 255

Glu Val Val Asn Leu Leu Pro Asn Gln Thr Thr Ser Ser Gly Ser Cys
            260                 265                 270

Asp Pro Thr Ser Ala Thr Leu Val Leu Thr Gln Ala Asn Ala Thr Asn
        275                 280                 285

Leu Ser Phe Leu Phe Thr Leu Asn Ser Thr Ser Asn Arg Tyr His Leu
```

```
    290                 295                 300

Thr Gly Leu Ser Val Val Ala Ala Trp Ser Asp Met Thr Ala Pro Phe
305                 310                 315                 320

Asn Thr Ser Asn Ser Ser Leu Asp Tyr Gln Arg Gly Ser Leu Gly Arg
                325                 330                 335

Ser Tyr Met Cys Ile Ser Glu Gln Thr Leu Val Val Asp Gln Asn Phe
            340                 345                 350

Ser Leu Asn Thr Phe Gln Leu Gln Val Gln Pro Phe Gly Ile Thr Arg
        355                 360                 365

Gly Gln Phe Ala Gln Ala Glu Glu Cys Gln Leu Asp Gln Asp Asn Met
    370                 375                 380

Leu Ile Pro Ile Val Val Gly Ala Ala Leu Ala Gly Leu Val Leu Ile
385                 390                 395                 400

Val Leu Ile Ala Tyr Leu Ile Gly Arg Lys Arg Ser His Ala Gly Tyr
                405                 410                 415

Gln Thr Ile


<210> SEQ ID NO 24
<211> LENGTH: 247
<212> TYPE: PRT
<213> ORGANISM: Oreochromis niloticus

<400> SEQUENCE: 24

Met Val Gln Ile Cys Arg Val Gln Ser Trp Phe Val Gly Val Thr Pro
1               5                   10                  15

Leu Leu Ile Phe Ala Thr Val Leu His Gln Gly Phe Ala Thr Val Ala
            20                  25                  30

Pro Pro Thr Pro Ala Pro His Lys Glu Pro Gly Arg Pro Glu Arg Gly
        35                  40                  45

Tyr Tyr Asn Val Thr Asn His Asn Gly Thr Ile Cys Leu Met Ala Tyr
    50                  55                  60

Met Gly Leu Gln Leu Asn Ile Ser Tyr Asn Ser Thr Ser Gln Lys Lys
65                  70                  75                  80

Val Val Gln Asp Val Met Asn Leu Gln Pro Asn Leu Thr Lys His Ser
                85                  90                  95

Gly Leu Cys Asp Ser Asp Ile Ala Ser Leu Asn Leu Thr Val Asp Ala
            100                 105                 110

Val Lys Thr Asn Leu Thr Phe Val Phe Thr Met Asn Ser Thr Ser Asn
        115                 120                 125

Lys Tyr His Leu Ser Glu Val Thr Val Ser Ala Ala Trp Pro Glu Met
    130                 135                 140

Lys Glu Pro Val Ser Val His Asn Ser Ser Leu Asp Tyr Leu Arg Gly
145                 150                 155                 160

Thr Val Gly Tyr Ser Tyr Phe Cys Arg Asp Glu Gln Thr Leu Asn Val
                165                 170                 175

Ala Gln Asn Leu Ser Ile Asn Thr Phe Gln Leu Gln Val Gln Pro Phe
            180                 185                 190

Ala Val Lys Gly Asp Gln Phe Gly Ala Ala Glu Glu Cys Gln Leu Asp
        195                 200                 205

Glu Asp Asp Met Leu Ile Pro Ile Val Val Gly Ala Ala Leu Ala Gly
    210                 215                 220

Leu Val Val Ile Val Leu Leu Ala Tyr Leu Ile Gly Arg Lys Arg Ser
225                 230                 235                 240

His Ala Gly Tyr Gln Ser Ile
```

245

<210> SEQ ID NO 25
<211> LENGTH: 415
<212> TYPE: PRT
<213> ORGANISM: Mus musculus

<400> SEQUENCE: 25

Met Cys Leu Ser Pro Val Lys Gly Ala Lys Leu Ile Leu Ile Phe Leu
1 5 10 15

Phe Leu Gly Ala Val Gln Ser Asn Ala Leu Ile Val Asn Leu Thr Asp
20 25 30

Ser Lys Gly Thr Cys Leu Tyr Ala Glu Trp Glu Met Asn Phe Thr Ile
35 40 45

Thr Tyr Glu Thr Thr Asn Gln Thr Asn Lys Thr Ile Thr Ile Ala Val
50 55 60

Pro Asp Lys Ala Thr His Asp Gly Ser Ser Cys Gly Asp Asp Arg Asn
65 70 75 80

Ser Ala Lys Ile Met Ile Gln Phe Gly Phe Ala Val Ser Trp Ala Val
85 90 95

Asn Phe Thr Lys Glu Ala Ser His Tyr Ser Ile His Asp Ile Val Leu
100 105 110

Ser Tyr Asn Thr Ser Asp Ser Thr Val Phe Pro Gly Ala Val Ala Lys
115 120 125

Gly Val His Thr Val Lys Asn Pro Glu Asn Phe Lys Val Pro Leu Asp
130 135 140

Val Ile Phe Lys Cys Asn Ser Val Leu Thr Tyr Asn Leu Thr Pro Val
145 150 155 160

Val Gln Lys Tyr Trp Gly Ile His Leu Gln Ala Phe Val Gln Asn Gly
165 170 175

Thr Val Ser Lys Asn Glu Gln Val Cys Glu Glu Asp Gln Thr Pro Thr
180 185 190

Thr Val Ala Pro Ile Ile His Thr Thr Ala Pro Ser Thr Thr Thr Thr
195 200 205

Leu Thr Pro Thr Ser Thr Pro Thr Pro Thr Pro Thr Pro Thr Pro Thr
210 215 220

Val Gly Asn Tyr Ser Ile Arg Asn Gly Asn Thr Thr Cys Leu Leu Ala
225 230 235 240

Thr Met Gly Leu Gln Leu Asn Ile Thr Glu Glu Lys Val Pro Phe Ile
245 250 255

Phe Asn Ile Asn Pro Ala Thr Thr Asn Phe Thr Gly Ser Cys Gln Pro
260 265 270

Gln Ser Ala Gln Leu Arg Leu Asn Asn Ser Gln Ile Lys Tyr Leu Asp
275 280 285

Phe Ile Phe Ala Val Lys Asn Glu Lys Arg Phe Tyr Leu Lys Glu Val
290 295 300

Asn Val Tyr Met Tyr Leu Ala Asn Gly Ser Ala Phe Asn Ile Ser Asn
305 310 315 320

Lys Asn Leu Ser Phe Trp Asp Ala Pro Leu Gly Ser Ser Tyr Met Cys
325 330 335

Asn Lys Glu Gln Val Leu Ser Val Ser Arg Ala Phe Gln Ile Asn Thr
340 345 350

Phe Asn Leu Lys Val Gln Pro Phe Asn Val Thr Lys Gly Gln Tyr Ser
355 360 365

```
Thr Ala Gln Glu Cys Ser Leu Asp Asp Asp Thr Ile Leu Ile Pro Ile
    370                 375                 380

Ile Val Gly Ala Gly Leu Ser Gly Leu Ile Ile Val Ile Val Ile Ala
385                 390                 395                 400

Tyr Leu Ile Gly Arg Arg Lys Thr Tyr Ala Gly Tyr Gln Thr Leu
                405                 410                 415


<210> SEQ ID NO 26
<211> LENGTH: 415
<212> TYPE: PRT
<213> ORGANISM: Xenopus laevis

<400> SEQUENCE: 26

Met Gly Asp Thr Gly Ala Met Glu Arg Cys Ala Cys Pro Ala Ala Val
1               5                   10                  15

Leu Leu Leu Ser Leu Val Leu Met Gly Ala Thr Ala Phe Glu Val Glu
            20                  25                  30

Ile Lys Asp Asp Lys Asn Ala Thr Cys Ile Tyr Ala Lys Leu Ser Val
        35                  40                  45

Asn Ile Thr Val Gln Tyr Glu Thr Asp Thr Ser Ser Ser Lys Asn Ile
    50                  55                  60

Thr Phe Pro Val Pro Ser Asp Val Thr Thr Asn Gly Ser Ser Cys Gly
65                  70                  75                  80

Ser Asp Gly Lys Ala Pro Leu Leu Val Ile Asn Phe Gly Asn Ser Gln
                85                  90                  95

Ser Trp Ser Leu Asn Phe Thr Arg Asn Asn Ser Thr Tyr Ser Gly Ser
            100                 105                 110

Ala Leu Ile Phe Thr Tyr Asn Thr Asn Asp Thr Ile Leu Phe Pro Asp
        115                 120                 125

Ala Leu Arg Lys Gly Leu Ile Ser Ser Thr Ala Met Phe Leu Gly Pro
    130                 135                 140

Val Pro Leu Asn Ser Thr Tyr Lys Cys Ile Ser Arg Glu Val Val Val
145                 150                 155                 160

Ser Glu Asn Val Thr Gln Ile Ile Tyr Asp Val Lys Leu Glu Ala Phe
                165                 170                 175

Met Ala Asn Gly Thr Leu Gly Lys Glu Ile Ile Cys Asp Ala Asp Lys
            180                 185                 190

Pro Ser Pro Val Pro Ser Pro Thr Gln Pro Ser Thr Thr Ala Ser Thr
        195                 200                 205

Ala Ile Pro Ala Pro Thr Ser Lys Pro Leu Asp Lys Pro Thr Met Gly
    210                 215                 220

Asn Tyr Thr Val Ser Asp Ala Ser Gly Ile Cys Leu Leu Ala Ser Met
225                 230                 235                 240

Gly Leu Gln Ile Asn Thr Ser Leu Leu Ser Glu Gly Lys Asn Ile Trp
                245                 250                 255

Arg Pro Phe Asn Ile Asp Pro Leu Gly Ile Lys Thr Asn Gly Thr Cys
            260                 265                 270

Thr Asn Gln Thr Gly Thr Leu Ile Leu Thr Glu Asn Arg Thr Ile Ile
        275                 280                 285

Glu Phe Thr Phe Ala Leu Lys Asn Lys Asn His Phe Tyr Leu Glu Glu
    290                 295                 300

Val Asn Ile Thr Leu Ile Asn Gly Ser Ala Phe Ser Ser Arg Gln Asn
305                 310                 315                 320

Gln Asn Leu Ser Thr Trp Glu Ala Ser Val Asp Ser Ser Tyr Met Cys
                325                 330                 335
```

```
His Lys Glu Gln Gln Ile Lys Val Ser Glu Asp Leu Phe Ile Asn Ala
            340                 345                 350

Phe Asp Val Arg Val Gln Pro Phe Gly Val Asn Asn Gly Thr Phe Ala
        355                 360                 365

Thr Ala Glu Asp Cys Phe Ala Asp Gln Asn Phe Ile Val Pro Ile Val
    370                 375                 380

Val Gly Ala Ala Leu Gly Val Leu Val Val Leu Val Met Val Ala Tyr
385                 390                 395                 400

Phe Ile Gly Arg Arg Lys Gln Ser Ser Ala Gly Tyr Glu Gln Met
                405                 410                 415


<210> SEQ ID NO 27
<211> LENGTH: 355
<212> TYPE: PRT
<213> ORGANISM: Danio rerio

<400> SEQUENCE: 27

Met Ala Val Arg Gly Phe Leu Pro Leu Leu Phe Ile Leu Leu Ser Gly
1               5                   10                  15

Ile Val His Ala Asp Asp Met Met Thr Ser Pro Leu Pro Ser Thr Ala
            20                  25                  30

Glu Leu Lys Thr Ala Asn Leu Pro Leu Val Ile Gln Thr Thr Ser Ser
        35                  40                  45

Thr Thr Ser Thr Thr Thr Thr Ser Arg Pro Ser Ser Thr Ser Thr His
    50                  55                  60

Ser Thr Leu Thr Thr Glu Pro Ala Ala Lys Thr Thr Thr Ala Arg Thr
65                  70                  75                  80

Thr Val Thr Thr Ser Ala Pro Thr Ser Thr Gln Ser Thr Ser Ser Ser
                85                  90                  95

Ser Thr Ser Ala Thr Val Thr Thr Leu Ala Pro Thr Thr Thr Gly His
            100                 105                 110

Asn Thr Thr Asn Ser Thr Thr Glu Pro Pro Thr Thr Thr Gly His Asn
        115                 120                 125

Thr Thr Asn Ser Thr Thr Asp Ala Pro Thr Thr Thr His Thr Asn Ala
    130                 135                 140

Thr Val Ala Pro Thr Pro Pro Pro Thr Thr Pro Ser Val Pro Lys Pro
145                 150                 155                 160

Thr Val Gly Asn Tyr Ser Val Lys Thr Asp Asn Val Ser Asp Cys Leu
                165                 170                 175

Leu Ala Lys Met Gly Leu Gln Phe Ser Phe Lys Ile Ser Gly Asn Ala
            180                 185                 190

Ser Leu Gln Thr Val Asn Leu Asp Pro Asn Val Thr Lys Val Asn Gly
        195                 200                 205

Thr Cys Gly Ser Gly Gly Ser Asp Ser Ser Leu Phe Leu Thr Ser Lys
    210                 215                 220

Asp Ile Thr Val His Phe Val Phe Thr Asn Asp Ser Gln Lys Phe Arg
225                 230                 235                 240

Leu His Ala Leu Thr Leu Thr Val Asp Leu Gly Asn Gly Asn Ile Phe
                245                 250                 255

Asn Asp Ser Asn Thr Asn Leu Ser Leu Trp Glu Ala Ser Val Gly Ser
            260                 265                 270

Ser Tyr Met Cys Arg Lys Glu Gln Ser Tyr Asn Ile Ser Asp Lys Leu
        275                 280                 285

Thr Leu Asn Thr Phe Glu Leu Gln Val Gln Pro Phe Asp Val Lys Lys
```

```
    290                 295                 300

Asn Ser Phe Ser Thr Ala His Glu Cys Ser Leu Asp Asp Thr Ser Leu
305                 310                 315                 320

Leu Ile Pro Ile Ile Val Gly Ala Ala Leu Ala Gly Leu Ile Phe Ile
                325                 330                 335

Val Val Ile Ala Tyr Val Ile Gly Arg Arg Arg Thr Tyr Val Gly Tyr
            340                 345                 350

Gln Thr Leu
        355


<210> SEQ ID NO 28
<211> LENGTH: 411
<212> TYPE: PRT
<213> ORGANISM: Papio anubis

<400> SEQUENCE: 28

Met Val Cys Phe Arg Leu Phe Pro Val Pro Gly Ser Gly Leu Val Leu
1               5                   10                  15

Val Cys Leu Val Leu Gly Ala Val Gln Ser Tyr Ala Leu Glu Leu Asn
            20                  25                  30

Leu Thr Asp Ser Gly Lys Ala Thr Cys Leu Tyr Ala Lys Trp Gln Met
        35                  40                  45

Asn Phe Thr Val Arg Tyr Glu Thr Thr Asn Lys Thr Tyr Lys Thr Val
    50                  55                  60

Thr Ile Ser Asp Arg Gly Thr Val Thr Tyr Asn Gly Ser Ile Cys Gly
65                  70                  75                  80

Asp Asp Gln Asn Gly Pro Lys Ile Ala Val Gln Phe Gly Pro Gly Phe
                85                  90                  95

Ser Trp Ile Ala Asn Phe Ser Lys Ala Ala Ser Thr Tyr Ser Ile Asp
            100                 105                 110

Ser Ile Ser Phe Ser Tyr Asn Thr Gly Asp Asn Thr Thr Phe Pro Asp
        115                 120                 125

Ala Glu Asp Lys Gly Ile Ile Thr Val Asp Glu Leu Leu Ala Ile Lys
    130                 135                 140

Ile Pro Leu Asn Asp Leu Phe Arg Cys Asn Ser Leu Ser Thr Leu Glu
145                 150                 155                 160

Lys Asn Asp Val Val Gln Asn Tyr Trp Asp Val Leu Val Gln Ala Phe
                165                 170                 175

Val Gln Asn Gly Thr Val Ser Thr Asn Glu Phe Leu Cys Asp Glu Asp
            180                 185                 190

Lys Thr Ser Thr Val Ala Pro Thr Ile His Thr Thr Val Pro Ser Pro
        195                 200                 205

Thr Thr Thr Pro Thr Pro Lys Glu Lys Pro Glu Ala Gly Thr Tyr Ser
    210                 215                 220

Val Asn Asn Gly Asn Asp Thr Cys Leu Leu Ala Thr Met Gly Leu Gln
225                 230                 235                 240

Leu Asn Ile Thr Gln Asp Lys Val Ala Ser Val Ile Asn Ile Asn Pro
                245                 250                 255

Asn Thr Thr His Ser Thr Gly Ser Cys Arg Ser His Thr Ala Leu Leu
            260                 265                 270

Arg Leu Asn Ser Ser Thr Ile Lys Tyr Leu Asp Phe Val Phe Ala Val
        275                 280                 285

Lys Asn Glu Asn Arg Phe Tyr Leu Lys Glu Val Asn Val Ser Met Tyr
    290                 295                 300
```

```
Leu Val Asn Gly Ser Val Phe Ser Ile Ala Asn Asn Asn Leu Ser Tyr
305                 310                 315                 320

Trp Asp Ala Pro Leu Gly Ser Ser Tyr Met Cys Asn Lys Glu Gln Thr
                325                 330                 335

Val Ser Val Ser Gly Ala Phe Gln Ile Asn Thr Phe Asp Leu Arg Val
            340                 345                 350

Gln Pro Phe Asn Val Thr Gln Gly Lys Tyr Ser Thr Ala Glu Glu Cys
        355                 360                 365

Ser Ala Asp Ser Asp Leu Asn Phe Leu Ile Pro Val Ala Val Gly Val
    370                 375                 380

Ala Leu Gly Phe Leu Ile Ile Val Val Phe Ile Ser Tyr Met Ile Gly
385                 390                 395                 400

Arg Arg Lys Ser Arg Thr Gly Tyr Gln Ser Val
                405                 410


<210> SEQ ID NO 29
<211> LENGTH: 410
<212> TYPE: PRT
<213> ORGANISM: Macaca mulatta

<400> SEQUENCE: 29

Met Val Cys Phe Arg Leu Phe Pro Val Pro Gly Ser Gly Leu Val Leu
1               5                   10                  15

Val Cys Leu Val Leu Gly Ala Val Gln Ser Tyr Ala Leu Glu Leu Asn
            20                  25                  30

Leu Thr Asp Ser Gly Lys Ala Thr Cys Leu Tyr Ala Lys Trp Gln Met
        35                  40                  45

Asn Phe Thr Val Arg Tyr Glu Thr Thr Asn Lys Thr Tyr Lys Thr Val
    50                  55                  60

Thr Ile Ser Asp Arg Gly Thr Val Thr Tyr Asn Gly Ser Ile Cys Gly
65                  70                  75                  80

Asp Asp Gln Asn Gly Pro Lys Ile Ala Val Gln Phe Gly Pro Gly Phe
                85                  90                  95

Ser Trp Ile Ala Asn Phe Ser Lys Ala Ala Ser Thr Tyr Ser Ile Asp
            100                 105                 110

Ser Ile Ser Phe Ser Tyr Asn Thr Gly Asp Asn Thr Thr Phe Pro Asp
        115                 120                 125

Ala Glu Asp Lys Gly Ile Ile Thr Val Asp Glu Leu Leu Ala Ile Lys
    130                 135                 140

Ile Pro Leu Asn Asp Leu Phe Arg Cys Asn Ser Leu Ser Thr Leu Glu
145                 150                 155                 160

Lys Asn Asp Val Val Gln Asn Tyr Trp Asp Val Leu Val Gln Ala Phe
                165                 170                 175

Val Gln Asn Gly Thr Val Ser Thr Asn Glu Phe Leu Cys Asp Glu Asp
            180                 185                 190

Lys Thr Ser Thr Val Ala Pro Thr Ile His Thr Thr Val Pro Ser Pro
        195                 200                 205

Thr Thr Thr Pro Thr Pro Lys Glu Lys Pro Glu Ala Gly Thr Tyr Ser
    210                 215                 220

Val Asn Asn Gly Asn Glu Thr Cys Leu Leu Ala Thr Met Gly Leu Gln
225                 230                 235                 240

Leu Asn Ile Thr Gln Asp Lys Val Ala Ser Val Ile Asn Ile Asn Pro
                245                 250                 255

Asn Thr Thr His Ser Thr Gly Ser Cys Arg Ser His Thr Ala Leu Leu
            260                 265                 270
```

```
Arg Leu Asn Ser Ser Thr Ile Lys Tyr Leu Asp Phe Val Phe Ala Val
        275                 280                 285

Lys Asn Glu Asn Arg Phe Tyr Leu Lys Glu Val Asn Val Ser Met Tyr
    290                 295                 300

Leu Val Asn Gly Ser Val Phe Ser Ile Ala Asn Asn Asn Leu Ser Tyr
305                 310                 315                 320

Trp Asp Ala Pro Leu Gly Ser Ser Tyr Met Cys Asn Lys Glu Gln Thr
                325                 330                 335

Val Ser Val Ser Gly Ala Phe Gln Ile Asn Thr Phe Asp Leu Arg Val
            340                 345                 350

Gln Pro Phe Asn Val Thr Gln Gly Lys Tyr Ser Thr Ala Gln Asp Cys
        355                 360                 365

Ser Ala Asp Asp Asp Asn Phe Leu Val Pro Ile Ala Val Gly Ala Ala
    370                 375                 380

Leu Ala Gly Val Leu Ile Leu Val Leu Leu Ala Tyr Phe Ile Gly Leu
385                 390                 395                 400

Lys Arg His His Ala Gly Tyr Glu Gln Phe
                405                 410


<210> SEQ ID NO 30
<211> LENGTH: 364
<212> TYPE: PRT
<213> ORGANISM: Pan troglodytes
<220> FEATURE:
<221> NAME/KEY: SITE
<222> LOCATION: (200)..(200)
<223> OTHER INFORMATION: Xaa can be any naturally occurring amino acid

<400> SEQUENCE: 30

Met Val Cys Phe Arg Leu Phe Pro Val Pro Gly Ser Gly Leu Val Leu
1               5                   10                  15

Val Cys Leu Val Leu Gly Ala Val Arg Ser His Ala Leu Glu Leu Asn
            20                  25                  30

Glu Ala Asp Ser Ala Ile Asn Cys Ser Lys Cys Lys Thr Val Thr Ile
        35                  40                  45

Ser Asp His Gly Thr Val Thr Tyr Asn Gly Ser Ile Cys Gly Asp Asp
    50                  55                  60

Gln Asn Gly Pro Lys Ile Ala Val Gln Phe Gly Pro Gly Phe Ser Trp
65                  70                  75                  80

Ile Ala Asn Phe Thr Lys Ala Ala Ser Thr Tyr Ser Ile Asp Ser Ile
                85                  90                  95

Ser Phe Ser Tyr Asn Thr Gly Asp Asn Thr Thr Phe Pro Asp Ala Glu
            100                 105                 110

Asp Lys Gly Ile Leu Thr Val Asp Glu Leu Leu Ala Ile Lys Ile Pro
        115                 120                 125

Leu Asn Asp Leu Phe Arg Cys Asn Ser Leu Ser Thr Leu Glu Lys Asn
    130                 135                 140

Asp Val Val Gln His Tyr Trp Asp Val Leu Val Gln Ala Phe Val Gln
145                 150                 155                 160

Asn Gly Thr Val Ser Thr Asn Glu Phe Leu Cys Asp Lys Asp Lys Thr
                165                 170                 175

Ser Thr Val Ala Pro Thr Val His Thr Thr Val Pro Ser Pro Thr Thr
            180                 185                 190

Thr Pro Thr Arg Ile Pro Pro Xaa Val Ala Ser Val Ile Asn Ile Asn
        195                 200                 205
```

```
Pro Asn Thr Thr His Ser Thr Gly Ser Cys Arg Ser His Thr Ala Leu
    210                 215                 220

Leu Arg Leu Asn Ser Ser Thr Ile Lys Tyr Leu Asp Phe Val Phe Ala
225                 230                 235                 240

Val Lys Asn Glu Asn Arg Phe Tyr Leu Lys Glu Val Asn Ile Ser Met
                245                 250                 255

Tyr Leu Val Asn Gly Ser Val Phe Ser Ile Ala Asn Asn Asn Leu Ser
            260                 265                 270

Tyr Trp Asp Ala Pro Leu Gly Ser Ser Tyr Met Cys Asn Lys Glu Gln
        275                 280                 285

Thr Val Ser Val Ser Gly Ala Phe Gln Ile Asn Thr Phe Asp Leu Arg
    290                 295                 300

Val Gln Pro Phe Asn Val Thr Gln Gly Lys Tyr Ser Thr Ala Glu Glu
305                 310                 315                 320

Cys Ser Ala Asp Ser Asp Leu Asn Phe Leu Ile Pro Val Ala Val Gly
                325                 330                 335

Val Ala Leu Gly Phe Leu Ile Ile Val Val Phe Ile Ser Tyr Met Ile
            340                 345                 350

Gly Arg Arg Lys Ser Arg Thr Gly Tyr Gln Ser Val
        355                 360


<210> SEQ ID NO 31
<211> LENGTH: 411
<212> TYPE: PRT
<213> ORGANISM: Canis lupus familiaris

<400> SEQUENCE: 31

Met Val Cys Phe Arg Leu Ser Pro Ala Pro Gly Ser Gly Leu Val Leu
1               5                   10                  15

Leu Cys Leu Val Leu Gly Ala Val Ser Ser Tyr Ala Leu Glu Val Asn
            20                  25                  30

Val Thr Asp Ser Glu Lys Ala Thr Cys Leu Tyr Ala Lys Trp Gln Met
        35                  40                  45

Asn Phe Thr Ile Gln Tyr Asn Thr Thr Ser Lys Asn Phe Lys Thr Ala
    50                  55                  60

Thr Ile Ser Asp Phe Ser Thr Ala Thr Tyr Asn Gly Ser Val Cys Gly
65                  70                  75                  80

Asn Asp Gln Asn Asn Pro Lys Ile Val Val Gln Phe Gly Ser Gly Phe
                85                  90                  95

Ser Trp Ile Val Asn Phe Thr Lys Lys Glu Ser Ala Tyr Leu Ile Asp
            100                 105                 110

Ser Ile Ser Phe Ser Tyr Asn Leu Ser Asp Asn Ala Thr Phe Pro Asp
        115                 120                 125

Ala Lys Glu Lys Gly Ile Leu Thr Val His Asp Leu Val Gly Phe Arg
    130                 135                 140

Ile Pro Leu Asn Asn Ile Phe Arg Cys Asn Ser Leu Ser Thr Leu Glu
145                 150                 155                 160

Lys Asn Gly Val Val Gln Tyr Tyr Trp Asp Val His Val Gln Ala Phe
                165                 170                 175

Val Gln Asn Gly Thr Val Ser Thr Lys Glu Phe Leu Cys Glu Lys Asp
            180                 185                 190

Lys Thr Ser Thr Thr Val Val Pro Thr Ile Ser Thr Thr Thr Pro Ser
        195                 200                 205

Pro Thr Thr Thr Pro Thr Pro Lys Glu Lys Pro Glu Val Gly Ser Tyr
    210                 215                 220
```

```
Ser Val Asn Asn Ser Asn Gly Thr Cys Leu Leu Ala Thr Met Gly Leu
225                 230                 235                 240

Gln Leu Asn Ile Thr His Asn Lys Val Ala Ser Val Ile Asn Ile Asn
                245                 250                 255

Pro Asn Thr Thr Asp Phe Thr Gly Ser Cys Gln Pro Gln Thr Ala Leu
            260                 265                 270

Leu Arg Leu Asn Ser Ser Asn Ile Lys Tyr Leu Asp Phe Val Phe Ala
        275                 280                 285

Val Lys Asn Glu Asn Arg Phe Tyr Leu Lys Glu Val Asn Val Ser Met
    290                 295                 300

Tyr Leu Val Asn Gly Ser Val Phe Ser Ile Ala Asn Asn Asn Leu Ser
305                 310                 315                 320

Tyr Trp Asp Ala Pro Leu Gly Ser Ser Tyr Met Cys Asn Lys Glu Gln
                325                 330                 335

Thr Val Ser Val Ser Gly Ala Phe Gln Ile Asn Thr Phe Asp Leu Arg
            340                 345                 350

Val Gln Pro Phe Asn Val Met Glu Gly Lys Tyr Ser Thr Ala Gln Glu
        355                 360                 365

Cys Ser Leu Asp Asp Asp Thr Ile Leu Ile Pro Ile Ile Val Gly Ala
    370                 375                 380

Gly Leu Ser Gly Leu Ile Ile Val Ile Val Ile Ala Tyr Leu Ile Gly
385                 390                 395                 400

Arg Arg Lys Ser Tyr Ala Gly Tyr Gln Thr Leu
                405                 410
```

<210> SEQ ID NO 32
<211> LENGTH: 417
<212> TYPE: PRT
<213> ORGANISM: Equus caballus

<400> SEQUENCE: 32

```
Met Val Cys Phe Arg Leu Ser Pro Val Pro Gly Ser Gly Leu Val Leu
1               5                   10                  15

Leu Cys Leu Val Leu Gly Ala Val Ser Ser Tyr Ala Leu Glu Leu Asn
            20                  25                  30

Leu Thr Asp Ser Glu Lys Ala Leu Cys Leu Tyr Ala Lys Trp Gln Met
        35                  40                  45

Asn Phe Thr Ile Pro Tyr Glu Thr Thr Ser Lys Ser Tyr Lys Thr Val
    50                  55                  60

Thr Ile Ser Asn Phe Gly Thr Pro Thr Tyr Asn Gly Ser Ile Cys Gly
65                  70                  75                  80

Asp Asn Gln Asn Gly Ser Arg Ile Ala Val Gln Phe Gly Ser Gly Phe
                85                  90                  95

Ser Trp Ile Val Asn Phe Thr Lys Ser Val Ser Val Tyr Ser Ile Asp
            100                 105                 110

Ser Ile Ser Phe Ser Tyr Asn Thr Gly Asp Asn Thr Thr Phe Pro Asp
        115                 120                 125

Ala Lys Asp Lys Gly Ile Leu Thr Val Asn Glu Ser Val Ala Phe Lys
    130                 135                 140

Ile Pro Leu Asn Asp Ile Phe Arg Cys Asn Ser Leu Ser Ser Leu Val
145                 150                 155                 160

Lys Asn Gly Val Val Gln Asn Tyr Trp Asp Val His Val Gln Ala Phe
                165                 170                 175

Val Gln Asn Gly Thr Val Ser Thr Asn Glu Tyr Leu Cys Glu Lys Asp
```

```
            180                 185                 190

Asn Thr Thr Thr Thr Val Ala Pro Ile Val Pro Thr Thr Val Pro Ser
        195                 200                 205

Pro Thr Thr Thr Ser Ser Pro Thr Thr Thr Pro Ser Pro Lys Glu Lys
    210                 215                 220

Pro Asp Val Gly Ser Tyr Leu Val Lys Asn Gly Ser Asp Thr Cys Leu
225                 230                 235                 240

Leu Ala Thr Met Gly Leu Gln Leu Asn Val Thr His Asp Lys Val Ala
                245                 250                 255

Ser Val Ile Asn Ile Asn Pro Asn Val Thr Gly Tyr Ser Gly Ser Cys
            260                 265                 270

His Pro Gln Thr Ala Leu Leu Arg Leu Asn Ser Ser Asn Ile Lys Tyr
        275                 280                 285

Leu Asp Phe Val Phe Ala Val Lys Asn Glu Asn Arg Phe Tyr Leu Lys
    290                 295                 300

Glu Val Asn Val Ser Met Tyr Leu Ala Asn Gly Ser Val Phe Ser Phe
305                 310                 315                 320

Ala Asn Asn Asn Leu Ser Tyr Trp Asp Ala Pro Leu Gly Ser Ser Tyr
                325                 330                 335

Met Cys Asn Lys Glu Gln Thr Val Ser Val Ser Gly Glu Phe Gln Ile
            340                 345                 350

Asn Thr Phe Asp Leu Arg Val Gln Pro Phe Asn Val Lys Asp Gly Lys
        355                 360                 365

Tyr Ser Thr Ala Gln Asp Cys Arg Ala Asp Asp Asp Asn Phe Leu Val
    370                 375                 380

Pro Ile Ala Val Gly Ala Ala Leu Ala Gly Val Leu Ile Leu Val Leu
385                 390                 395                 400

Leu Ala Tyr Phe Ile Gly Leu Lys Arg His His Ala Gly Tyr Glu Gln
                405                 410                 415

Phe
```

<210> SEQ ID NO 33
<211> LENGTH: 407
<212> TYPE: PRT
<213> ORGANISM: Bos taurus

<400> SEQUENCE: 33

```
Met Val Cys Phe Arg Leu Ala Pro Val Pro Gly Ser Gly Phe Leu Leu
1               5                   10                  15

Leu Cys Leu Val Leu Gly Ala Val Ser Ser Tyr Ala Leu Glu Leu Asn
            20                  25                  30

Leu Thr Asp Ser Ser Asn Ala Thr Cys Leu Tyr Ala Lys Trp Gln Met
        35                  40                  45

Asn Phe Thr Ile Arg Tyr Glu Thr Thr Asp Lys His Asn Lys Thr Val
    50                  55                  60

Pro Ile Ser Asp Leu Gly Ala Ala Thr Tyr Asn Gly Ser Phe Cys Gly
65                  70                  75                  80

Asp Asp Gln Asn Gly Pro Lys Ile Ala Val Gln Phe Gly Ser Gly Phe
                85                  90                  95

Ser Trp Ile Val Asn Phe Thr Lys Glu Ala Ala Ser Pro Ser Thr Tyr
            100                 105                 110

Leu Val Asp Thr Ile Ser Phe Ser Tyr Asn Thr Asn Asp Asn Lys Thr
        115                 120                 125

Phe Pro Asp Ala Lys Glu Lys Glu Val Phe Thr Val Asn Asn Arg Val
```

```
    130                 135                 140

Ala Leu Lys Ile Pro Leu Asn Asp Ile Phe Arg Cys Asn Ser Leu Ser
145                 150                 155                 160

Thr Leu Glu Asn Arg Asp Val Val Gln His Tyr Trp Asp Val His Val
                165                 170                 175

Gln Ala Phe Val Gln Asn Gly Thr Val Ser Thr Thr Glu Phe Leu Cys
            180                 185                 190

Asp Lys Asp Lys Thr Val Thr Thr Ala Val Pro Ile Val Pro Thr Thr
        195                 200                 205

Leu Pro Ser Pro Thr Lys Pro Val Val Gly Ser Tyr Ser Val Val Asn
    210                 215                 220

Ser Asn Gly Thr Cys Leu Leu Ala Thr Met Gly Leu Gln Leu Asn Ile
225                 230                 235                 240

Thr His Asp Lys Val Ala Ser Val Phe Asn Ile Asn Pro Asn Thr Thr
                245                 250                 255

Asn Ala Thr Gly Ser Cys Gln Pro Gln Thr Ala Leu Leu Arg Leu Ser
            260                 265                 270

Ser Ser Asn Ile Lys Tyr Leu Asp Phe Val Phe Ala Val Lys Asn Glu
        275                 280                 285

Asn Arg Phe Tyr Leu Lys Glu Val Asn Val Ser Met Ile Leu Val Asn
    290                 295                 300

Gly Ser Val Tyr Ser Ile Ser Asn Thr Asn Leu Ser Tyr Trp Asp Ala
305                 310                 315                 320

Pro Leu Gly Ser Ser Tyr Met Cys Asn Lys Glu Gln Thr Val Ser Val
                325                 330                 335

Ser Gly Ala Phe Gln Ile Asn Thr Phe Asp Leu Arg Val Gln Pro Phe
            340                 345                 350

Ser Val Thr Glu Gly Lys Tyr Ser Thr Ala Gln Glu Cys Ser Leu Asp
        355                 360                 365

Asp Asp Thr Ile Leu Ile Pro Ile Ile Val Gly Ala Gly Leu Ser Gly
    370                 375                 380

Leu Ile Ile Val Ile Val Ile Ala Tyr Leu Ile Gly Arg Arg Lys Ser
385                 390                 395                 400

Tyr Ala Gly Tyr Gln Thr Leu
                405


<210> SEQ ID NO 34
<211> LENGTH: 411
<212> TYPE: PRT
<213> ORGANISM: Sus scrofa

<400> SEQUENCE: 34

Met Val Cys Phe Arg Leu Ser Pro Val Pro Gly Ser Gly Leu Leu Met
1               5                   10                  15

Leu Cys Leu Val Leu Gly Ala Val Ser Ser Tyr Ala Leu Glu Leu Asn
            20                  25                  30

Leu Thr Asn Ser Glu Lys Ala Thr Cys Leu Tyr Ala Lys Trp Gln Met
        35                  40                  45

Asn Phe Thr Ile Arg Tyr Glu Thr Thr Asn Asn Ser His Lys Thr Val
    50                  55                  60

Ser Ile Ser Asp Phe Gly Ala Ala Thr Tyr Asn Gly Ser Phe Cys Gly
65                  70                  75                  80

Asp Asp His Asn Asp Pro Gln Ile Val Met Gln Phe Gly Ser Gly Phe
                85                  90                  95
```

```
Ser Trp Ile Val Asn Phe Ala Lys Glu Ser Ser Ser Tyr Leu Ile Asn
            100                 105                 110

Ser Ile Ser Phe Ser Tyr Asn Thr Ser Asp Thr Thr Thr Phe Pro Asp
        115                 120                 125

Ala Lys Lys Lys Gly Val Leu Thr Val Asn Asp Ser Val Gly Phe Gln
    130                 135                 140

Val Pro Leu Asn Asp Ile Phe Arg Cys Asn Ser Leu Ser Thr Leu Glu
145                 150                 155                 160

Lys Asp Asn Val Val Gln His Tyr Trp Asp Val His Val Gln Ala Phe
                165                 170                 175

Val Gln Asn Gly Thr Val Ser Thr Lys Glu Phe Leu Cys Asp Lys Asp
            180                 185                 190

Lys Thr Leu Thr Thr Thr Val Pro Val Ile Pro Thr Ser Val Pro Ser
        195                 200                 205

Pro Thr Thr Thr Pro Thr Pro Lys Glu Lys Pro Glu Thr Gly Ser Tyr
    210                 215                 220

Ser Val Thr Ser Ser Asn Gly Thr Cys Leu Leu Ala Asn Met Gly Leu
225                 230                 235                 240

Gln Leu Asn Ile Thr Gln Asp Lys Val Ala Ser Val Ile Asn Ile Asn
                245                 250                 255

Pro Asn Thr Thr Asn Ala Thr Gly Asn Cys His Ser Lys Thr Ala Leu
            260                 265                 270

Leu Arg Leu Ser Gly Ser Asn Ile Lys Tyr Leu Asp Phe Val Phe Ala
        275                 280                 285

Val Lys Asn Asp Asn Arg Phe Tyr Leu Lys Glu Val Asn Val Ser Val
    290                 295                 300

Tyr Leu Val Asn Gly Ser Val Phe Ser Ile Ala Asn Asn Asn Leu Ser
305                 310                 315                 320

Tyr Trp Asp Ala Pro Leu Gly Ser Ser Tyr Met Cys Asn Lys Glu Gln
                325                 330                 335

Thr Val Ser Val Ser Gly Ala Phe Gln Ile Asn Thr Phe Asn Leu Arg
            340                 345                 350

Val Gln Pro Phe Ser Val Met Glu Gly Lys Tyr Ser Thr Ala Gln Asp
        355                 360                 365

Cys Ser Ala Asp Asp Asp Asn Phe Ile Val Pro Ile Ala Val Gly Ala
    370                 375                 380

Ala Leu Ala Gly Val Leu Ile Leu Val Leu Leu Ala Tyr Phe Ile Gly
385                 390                 395                 400

Leu Lys Arg His His Ala Gly Tyr Glu Gln Phe
                405                 410


<210> SEQ ID NO 35
<211> LENGTH: 408
<212> TYPE: PRT
<213> ORGANISM: Ovis aries

<400> SEQUENCE: 35

Met Val Cys Phe Arg Leu Ala Pro Val Pro Gly Cys Gly Phe Leu Leu
1               5                   10                  15

Phe Cys Leu Val Leu Gly Thr Val Ser Ser Tyr Ala Leu Glu Leu Asn
            20                  25                  30

Leu Thr Asp Ser Ser Lys Ala Thr Cys Leu Tyr Ala Lys Trp Gln Met
        35                  40                  45

Asn Phe Thr Ile Arg Tyr Glu Thr Thr Asp Lys His Asn Lys Thr Val
    50                  55                  60
```

```
Thr Ile Ser Asp Phe Asp Ala Ala Ala Tyr Asn Gly Ser Val Cys Gly
65                  70                  75                  80

Asp Asp Gln Asn Gly Pro Lys Ile Ala Val Gln Phe Gly Ser Gly Phe
                85                  90                  95

Ser Trp Ile Val Asn Phe Thr Lys Glu Ala Ser Ser Thr Ser Thr Tyr
            100                 105                 110

Leu Val Asp Ser Ile Ser Phe Ser Tyr Asn Thr Asn Asp Asn Ala Thr
        115                 120                 125

Phe Pro Asp Ala Lys Glu Lys Gly Val Phe Thr Val Asn Asn Arg Val
    130                 135                 140

Ala Leu Lys Ile Pro Leu Asn Asp Ile Phe Arg Cys Asn Ser Leu Ser
145                 150                 155                 160

Thr Leu Glu Lys Ser Asp Val Val Gln His Tyr Trp Asp Val His Val
                165                 170                 175

Gln Ala Phe Val Gln Asn Gly Thr Val Ser Thr Thr Glu Phe Leu Cys
            180                 185                 190

Asp Lys Asp Lys Thr Val Thr Thr Ala Met Pro Ile Val Pro Thr Thr
        195                 200                 205

Ala Pro Ser Pro Thr Lys Pro Val Val Gly Ser Tyr Ser Val Val Asn
    210                 215                 220

Ser Asn Gly Thr Cys Leu Leu Ala Thr Met Gly Leu Gln Leu Asn Ile
225                 230                 235                 240

Thr His Asp Lys Val Ala Ser Val Phe Asn Ile Asn Pro Asn Thr Thr
                245                 250                 255

Asn Ala Thr Gly Ser Cys Gln Pro Gln Thr Ala Leu Leu Arg Leu Ser
            260                 265                 270

Ser Ser Asn Ile Lys Tyr Leu Asp Phe Val Phe Ala Val Lys Asn Glu
        275                 280                 285

Asn Arg Phe Tyr Leu Lys Glu Val Asn Val Ser Met Ile Leu Val Asn
    290                 295                 300

Gly Ser Val Tyr Ser Ile Ser Asn Thr Asn Leu Ser Tyr Trp Asp Ala
305                 310                 315                 320

Pro Leu Gly Ser Ser Tyr Met Cys Asn Lys Glu Gln Thr Val Ser Val
                325                 330                 335

Ser Gly Ala Leu Gln Ile Asn Thr Phe Asp Leu Arg Val Gln Pro Phe
            340                 345                 350

Ser Val Thr Glu Gly Lys Tyr Ser Thr Ala Glu Glu Cys Ser Ala Asp
        355                 360                 365

Ser Asp Leu Asn Phe Leu Ile Pro Val Ala Val Gly Val Ala Leu Gly
    370                 375                 380

Phe Leu Ile Ile Val Val Phe Ile Ser Tyr Met Ile Gly Arg Arg Lys
385                 390                 395                 400

Ser Arg Thr Gly Tyr Gln Ser Val
                405


<210> SEQ ID NO 36
<211> LENGTH: 411
<212> TYPE: PRT
<213> ORGANISM: Rattus norvegicus

<400> SEQUENCE: 36

Met Arg Leu Leu Ser Pro Val Thr Gly Ser Lys Leu Val Leu Leu Phe
1               5                   10                  15

Leu Phe Leu Gly Ala Val Arg Ser Asp Ala Leu Lys Leu Asn Leu Thr
```

```
            20                  25                  30

Asp Ser Lys Gly Thr Cys Leu Tyr Ala Glu Trp Glu Met Asn Phe Thr
        35                  40                  45

Ile Thr Tyr Glu Ala Leu Lys Val Asn Glu Thr Val Thr Ile Thr Val
    50                  55                  60

Pro Asp Lys Val Thr Tyr Asn Gly Ser Ser Cys Gly Asp Asp Lys Asn
65                  70                  75                  80

Gly Ala Lys Ile Met Ile Gln Tyr Gly Ser Thr Leu Ser Trp Ala Val
                85                  90                  95

Asn Phe Thr Lys Glu Ala Ser Gln Tyr Phe Ile Asn Asn Ile Thr Leu
            100                 105                 110

Ser Tyr Asn Thr Asn Asp Thr Lys Thr Phe Pro Gly Ala Val Pro Lys
        115                 120                 125

Gly Ile Leu Thr Val Ile Ile Pro Val Gly Ser Gln Leu Pro Leu Gly
    130                 135                 140

Val Ile Phe Lys Cys Ser Ser Val Leu Thr Phe Asn Leu Ser Pro Val
145                 150                 155                 160

Val Gln His Tyr Trp Gly Ile His Leu Gln Ala Phe Val Gln Asn Gly
                165                 170                 175

Thr Val Ser Lys His Glu Gln Val Cys Lys Glu Asp Lys Thr Ala Thr
            180                 185                 190

Thr Val Ala Pro Ile Ile His Thr Thr Val Pro Ser Pro Thr Thr Thr
        195                 200                 205

Leu Thr Pro Thr Ser Ile Pro Val Pro Thr Pro Thr Val Gly Asn Tyr
    210                 215                 220

Thr Ile Ser Asn Gly Asn Ala Thr Cys Leu Leu Ala Thr Met Gly Leu
225                 230                 235                 240

Gln Leu Asn Ile Thr Glu Glu Lys Val Pro Phe Ile Phe Asn Ile Asn
                245                 250                 255

Pro Ala Thr Thr Asn Phe Thr Gly Ser Cys Gln Pro Gln Thr Ala Gln
            260                 265                 270

Leu Arg Leu Asn Asn Ser Gln Ile Lys Tyr Leu Asp Phe Ile Phe Ala
        275                 280                 285

Val Lys Asn Glu Lys Arg Phe Tyr Leu Lys Glu Val Asn Val Asn Met
    290                 295                 300

Tyr Leu Ala Asn Gly Ser Ala Phe His Val Ser Asn Asn Asn Leu Ser
305                 310                 315                 320

Phe Trp Asp Ala Pro Leu Gly Ser Ser Tyr Met Cys Asn Lys Glu Gln
                325                 330                 335

Val Val Ser Val Ser Arg Thr Phe Gln Ile Asn Thr Phe Asn Leu Lys
            340                 345                 350

Val Gln Pro Phe Asn Val Thr Lys Gly Glu Tyr Ser Thr Ala Gln Asp
        355                 360                 365

Cys Ser Ala Asp Glu Asp Asn Phe Leu Val Pro Ile Ala Val Gly Ala
    370                 375                 380

Ala Leu Gly Gly Val Leu Ile Leu Val Leu Leu Ala Tyr Phe Ile Gly
385                 390                 395                 400

Leu Lys Arg His His Thr Gly Tyr Glu Gln Phe
                405                 410
```

<210> SEQ ID NO 37
<211> LENGTH: 570
<212> TYPE: PRT
<213> ORGANISM: Ornithorhynchus anatinus

<400> SEQUENCE: 37

```
Met Ala Met Lys Asn Phe Thr Leu Gln Gln Glu Arg Asp Thr Ser Val
1               5                   10                  15

Ala Leu Ile Ile Arg Thr Tyr Val Arg Ala Phe Leu Lys Val Tyr Thr
            20                  25                  30

Lys Val Pro Lys Pro Gln Arg Cys His Asn Gln Trp Gln Ser Leu Asn
        35                  40                  45

Ile Glu Gly Ile Glu Gly Ile Glu Ile Val Lys Gly Ser Lys Trp Arg
    50                  55                  60

Ser Ala Leu Glu Thr Ile Ile Thr Ile Gln Val Lys Arg Lys Ser Gln
65                  70                  75                  80

Val Gln Lys Tyr His Pro Phe Ser Leu His Ser Glu Cys Gln Lys Thr
                85                  90                  95

Asn Gln Glu Gly Thr Gly Gly Val Ala Thr Val Ile Ala Asp Glu Cys
            100                 105                 110

Leu Leu Trp Pro Ser Ile Pro Phe Ser Thr Leu Ala Gln Lys Val Asn
        115                 120                 125

Leu Gly Ser Cys Glu Ala Phe Ser Ile Ile Gly Tyr Ser Val Phe Ala
    130                 135                 140

Leu Phe Ile Tyr Leu Lys Pro Asn Met Leu Asp Phe Ile Glu Leu Ala
145                 150                 155                 160

Glu Leu Met Leu Ser Thr Glu Thr Gln Leu Leu Glu Pro Thr Arg Val
                165                 170                 175

Cys Cys Gly Ile Cys Gln Ser Tyr Ala Leu Glu Ile Asn Leu Thr Asp
            180                 185                 190

Ser Lys Asn Ala Thr Cys Leu Tyr Ser Lys Trp Gln Met Thr Phe Thr
        195                 200                 205

Ile Asn Tyr Glu Thr Thr Gly Asn Glu Thr Lys Asn Val Thr Val Thr
    210                 215                 220

Val Pro Glu Asn Val Thr Tyr Asp Gly Ser Ser Cys Gly Asp Asn Gln
225                 230                 235                 240

Thr Val Pro Gln Ile Ala Val Gln Phe Gly Leu Gly Tyr Ser Trp His
                245                 250                 255

Leu Asn Phe Thr Lys Lys Glu Asn Asn Ser Tyr Ser Phe Asp Thr Ile
            260                 265                 270

Val Phe Thr Tyr Asn Thr Ser Asp Asn Glu Thr Phe Pro Glu Ala Lys
        275                 280                 285

Glu Lys Gly Gln Val Leu Ser Val Phe Glu Phe Arg Tyr Ala Arg Ile
    290                 295                 300

Pro Leu Asn Lys Ile Phe Arg Cys His Ser Glu Glu Ser Leu Ile Gly
305                 310                 315                 320

Asp Lys Ala Thr His His Tyr Trp Glu Thr Val Val Gln Ala Phe Ile
                325                 330                 335

Gln Asn Gly Thr Ile Ser Lys Glu Glu Phe Ile Cys Ser Lys Asp Arg
            340                 345                 350

Ala Ser Thr Thr Val Ala Pro Val Thr Thr Gln Val Val Pro Ser Thr
        355                 360                 365

Thr Ala Thr Pro Val Pro Gln Asp Lys Pro Tyr Pro Gly Lys Tyr Ala
    370                 375                 380

Val Lys Asn Gly Asn Asp Thr Cys Leu Leu Ala Thr Met Gly Leu Gln
385                 390                 395                 400

Leu Asn Val Thr Gln Asn Lys Val Asn Ser Val Ile Asn Ile Asn Pro
```

```
                405                 410                 415

Asn Val Thr Asp Phe Thr Gly Ser Cys Ser Asn Glu Thr Ala Glu Leu
            420                 425                 430

Arg Leu Ser Gly Ser Asn Val Lys Tyr Ile Asp Phe Ile Phe Ala Val
        435                 440                 445

Lys Asn Gly Asn Arg Phe Tyr Leu Lys Glu Val Asn Val Ser Ile Ser
    450                 455                 460

Phe Val Asn Ala Ser Asp Leu Asn Val Ala Asn Asn Asn Leu Ser Tyr
465                 470                 475                 480

Trp Asp Ala Pro Leu Gly Ser Ser Tyr Met Cys Asn Lys Glu Gln Thr
                485                 490                 495

Leu Ala Leu Ala Asp Ser Leu Gln Ile Asn Thr Phe Asn Leu Arg Val
            500                 505                 510

Gln Pro Phe Ser Val Val Ala Gly Lys Tyr Ser Thr Ala Glu Asp Cys
        515                 520                 525

Ser Ala Asp Asp Asp Asn Phe Ile Val Pro Ile Ala Val Gly Ala Ala
    530                 535                 540

Leu Gly Gly Leu Val Ile Leu Val Leu Met Ala Tyr Phe Val Gly Arg
545                 550                 555                 560

Lys Arg Arg Ala Thr Gly Tyr Glu Gln Phe
                565                 570


<210> SEQ ID NO 38
<211> LENGTH: 425
<212> TYPE: PRT
<213> ORGANISM: Gallus gallus

<400> SEQUENCE: 38

Met Ala Pro Pro Arg Cys Pro Ala Gly Leu Ala Leu Leu Leu Leu Leu
1               5                   10                  15

Leu Gly Ala Cys Gly Phe Phe Gln Ser Tyr Ala Val Glu Val Asp Val
            20                  25                  30

Lys Asp Ala Ser Asn Phe Thr Cys Leu Tyr Ala Gln Trp Met Met Lys
        35                  40                  45

Phe Leu Ile Lys Tyr Glu Thr Asn Ser Ser Asp Tyr Lys Asn Ala Ser
    50                  55                  60

Leu Asp Leu Thr Ser Thr Val Thr His Asn Gly Ser Ile Cys Gly Ser
65                  70                  75                  80

Asp Thr Gln Ala Ala Leu Leu Ala Val Gln Phe Gly Asp Gly His Ser
                85                  90                  95

Trp Ser Ile Asn Phe Thr Lys Asn Asn Glu Thr Tyr Arg Ala Glu Phe
            100                 105                 110

Ile Thr Phe Thr Tyr Asn Thr Asn Asp Thr Ala Val Phe Pro Asp Ala
        115                 120                 125

Arg Arg Gln Gly Pro Val Thr Ile Val Val Lys Asp Ala Met His Pro
    130                 135                 140

Ile Gln Leu Asn Asn Val Phe Val Cys His His Thr Thr Ser Leu Glu
145                 150                 155                 160

Ala Glu Asn Val Thr Gln Ile Phe Trp Asn Val Thr Met Gln Pro Phe
                165                 170                 175

Val Gln Asn Gly Thr Ile Ser Lys Lys Glu Ser Arg Cys Tyr Ala Asp
            180                 185                 190

Thr Pro Thr Ala Ala Pro Thr Val Leu Pro Thr Val Ala Asn Val Thr
        195                 200                 205
```

```
Thr Ala Ser Thr Thr Ile Ser Pro Ala Pro Thr Thr Ala Pro Lys Pro
    210                 215                 220

Ala Glu Asn Pro Val Thr Gly Asn Tyr Ser Leu Lys Thr Gly Asn Lys
225                 230                 235                 240

Thr Cys Leu Leu Ala Thr Val Gly Leu Gln Leu Asn Ile Ser Gln Asp
                245                 250                 255

Lys Pro Leu Leu Ile Asn Ile Asp Pro Lys Thr Thr His Ala Asp Gly
            260                 265                 270

Thr Cys Gly Asn Thr Ser Ala Thr Leu Lys Leu Asn Asp Gly Asn Arg
        275                 280                 285

Thr Leu Ile Asp Phe Thr Phe Ile Val Asn Ala Ser Ala Ser Val Gln
    290                 295                 300

Lys Phe Tyr Leu Arg Glu Val Asn Val Thr Leu Leu Asn Tyr Gln Asn
305                 310                 315                 320

Gly Ser Val Ile Leu Ser Ala Asp Asn Asn Asn Leu Ser Lys Trp Asp
                325                 330                 335

Ala Ser Leu Gly Asn Ser Tyr Met Cys Arg Lys Glu Gln Thr Leu Glu
            340                 345                 350

Ile Asn Glu Asn Leu Gln Val His Thr Phe Asn Leu Trp Val Gln Pro
        355                 360                 365

Phe Leu Val Lys Glu Asn Lys Phe Ser Ile Ala Glu Glu Cys Phe Ala
    370                 375                 380

Asp Ser Asp Leu Asn Phe Leu Ile Pro Val Ala Val Gly Met Ala Leu
385                 390                 395                 400

Gly Phe Leu Ile Ile Leu Val Phe Ile Ser Tyr Ile Ile Gly Arg Arg
                405                 410                 415

Lys Ser Arg Thr Gly Tyr Gln Ser Val
            420                 425


<210> SEQ ID NO 39
<211> LENGTH: 556
<212> TYPE: PRT
<213> ORGANISM: Taeniopygia guttata

<400> SEQUENCE: 39

Met Glu Cys Arg Glu Gly Glu Val Thr Arg Cys Lys Gln Lys Asn Asn
1               5                   10                  15

Leu Phe Ser Gly Ile Asn Asp Asp Ile Ser Gly Ala Lys Gln Ala Lys
            20                  25                  30

Gln Arg Gln Cys Thr Pro Gln Lys Pro Pro Lys Arg Ala Thr Ala Thr
        35                  40                  45

Leu Pro Leu Gln Arg Pro Pro Arg Gly Ile Pro Gly Pro Ala Pro Ala
    50                  55                  60

Ala Val Ala Ala Ala Val Ala Ala Asp Arg Ile Thr Pro Ser Gly Ser
65                  70                  75                  80

His Gln Thr Arg Pro Pro Glu Ala Ala Arg Asp Glu Arg Pro Val Arg
                85                  90                  95

Asp Pro Arg Asn Arg Ala Ala Ala Pro Ser Gly His Trp Arg Arg Ala
            100                 105                 110

Gly Gly Pro Gln Arg His Arg His His Arg His Arg Arg His Gly Pro
        115                 120                 125

Ala Pro Leu Arg Arg Leu Leu Leu Arg Pro Pro Pro Pro Ala Ala Ala
    130                 135                 140

Ala Ala Arg Phe Leu Gly Phe Phe Gln Ser Tyr Ala Val Glu Val Asp
145                 150                 155                 160
```

```
Ile Lys Asp Ala Ser Asn Ala Thr Cys Leu Tyr Ala Asp Trp Met Met
                165                 170                 175

Arg Phe Leu Ile Lys Tyr Glu Ser Asn Ser Gly Asp Tyr Lys Thr Thr
            180                 185                 190

Thr Leu Asn Leu Ser Ser Ser Val Thr His Asn Gly Ser Val Cys Gly
        195                 200                 205

Asn Asp Thr Gln Ala Ala Leu Val Ala Val Gln Phe Gly Glu Gly His
    210                 215                 220

Ser Trp Ser Ile Asn Ile Thr Lys Asn Asn Glu Thr Tyr Gln Gly Asp
225                 230                 235                 240

Phe Ile Thr Leu Thr Tyr Asn Thr Asn Asp Thr Ala Val Phe Pro Asp
                245                 250                 255

Ala Lys Arg Lys Gly Pro Ile Thr Val Leu Val Arg Asp Pro Ser Arg
            260                 265                 270

Pro Ile Gln Leu Asn Thr Val Phe Val Cys His Asn Ser Phe Val Ile
        275                 280                 285

Glu Ala Glu Asn Thr Thr Gln Ile Phe Trp Asn Val Thr Met Gln Ala
    290                 295                 300

Phe Val Gln Asn Gly Thr Val Ser Lys Lys Glu Ser Arg Cys Pro Ala
305                 310                 315                 320

Asp Thr Pro Thr Ser Glu Pro Thr Val Pro Pro Thr Ile Ala Asn Val
                325                 330                 335

Thr Thr Ala Ser Thr Thr Thr Leu Ser Pro Ala Pro Thr Thr Ala Pro
            340                 345                 350

Lys Pro Val Glu Asn Pro Val Thr Gly Asn Tyr Ser Leu Lys Ser Gly
        355                 360                 365

Asn Lys Thr Cys Phe Leu Ala Thr Val Gly Leu Gln Leu Asn Val Ser
    370                 375                 380

Gln Glu Lys Pro Leu Leu Ile Asn Ile Asn Pro Lys Thr Thr Val Ala
385                 390                 395                 400

Asp Gly Ala Cys Gly Asn Thr Thr Ala Thr Leu Lys Leu Asn Asp Gly
                405                 410                 415

Asn Ser Thr Leu Ile Gly Phe Thr Phe Ala Val Lys Asn Thr Ser Ala
            420                 425                 430

Ser Val Gln Lys Phe Tyr Leu Arg Glu Val Asn Val Thr Leu Leu Asn
        435                 440                 445

Arg Leu Asn Gly Ser Val Ile Ser Ser Ala Asp Asn Ser Asn Leu Ser
    450                 455                 460

Lys Trp Asp Ala Phe Leu Gly Ser Ser Tyr Met Cys Arg Lys Glu Gln
465                 470                 475                 480

Thr Leu Gln Ile Asn Glu Asn Val Gln Val His Thr Phe Asn Leu Trp
                485                 490                 495

Ile Gln Pro Phe Leu Val Glu Ala Asn Lys Phe Ala Thr Ala Glu Glu
            500                 505                 510

Cys Ile Ala Asp Ser Asp Leu Asn Phe Leu Ile Pro Ile Ala Val Gly
        515                 520                 525

Val Ala Leu Gly Phe Leu Ile Ile Leu Val Phe Ile Ser Tyr Ile Ile
    530                 535                 540

Gly Arg Arg Lys Ser Arg Thr Gly Tyr Gln Ser Val
545                 550                 555
```

<210> SEQ ID NO 40
<211> LENGTH: 408

```
<212> TYPE: PRT
<213> ORGANISM: Xenopus tropicalis

<400> SEQUENCE: 40

Met Glu Arg Cys Ala Cys Pro Ala Ala Leu Leu Leu Leu Ser Leu Val
1               5                   10                  15

Leu Met Gly Ala Met Ala Phe Asp Val Glu Ile Lys Asp Asp Lys Asn
            20                  25                  30

Ala Thr Cys Ile Tyr Ala Lys Leu Ser Val Asn Val Thr Val Gln Tyr
        35                  40                  45

Glu Thr Asn Thr Ser Ser Thr Lys Asn Val Thr Phe Ser Val Pro Ser
    50                  55                  60

Glu Val Thr Thr Asn Gly Ser Ser Cys Gly Ser Asn Gly Lys Ala Pro
65                  70                  75                  80

Ile Leu Val Ile Asn Phe Gly Asn Gly His Ser Trp Ser Leu Asn Phe
                85                  90                  95

Thr Arg Asn Asp Ser Met Tyr Ser Gly Gly Ala Leu Ile Phe Thr Tyr
            100                 105                 110

Asn Thr Asn Asp Ser Thr Leu Phe Pro Asp Ala Leu Lys Glu Gly Leu
        115                 120                 125

Ile Ser Ser Thr Ala Ala Phe Leu Gly Pro Ile Pro Leu Asn Ser Thr
    130                 135                 140

Tyr Lys Cys Ile Ser Ser Glu Val Val Val Ser Glu Asn Val Thr Gln
145                 150                 155                 160

Ile Ile Ser Asp Val Lys Leu Glu Ala Phe Met Gln Asn Gly Thr Leu
                165                 170                 175

Gly Lys Glu Val Ser Cys Asp Ala Asp Lys Pro Ser Pro Thr Pro Thr
            180                 185                 190

Thr Asn Pro Ser Thr Thr Ala Ser Thr Thr Thr Pro Thr Pro Thr Ser
        195                 200                 205

Lys Pro Leu Asp Asn Pro Thr Thr Gly Asn Tyr Ser Val Ser Asp Val
    210                 215                 220

Asn Gly Thr Cys Leu Leu Ala Ser Met Gly Leu Gln Ile Asn Thr Ser
225                 230                 235                 240

Leu Leu Ser Glu Gly Lys Asn Ile Trp Thr Ala Phe Asn Ile Asp Pro
                245                 250                 255

Thr Ala Met Ser Lys Asn Gly Thr Cys Ser Asn Gln Thr Gly Thr Leu
            260                 265                 270

Ile Leu Thr Asp Asn Ser Thr Val Ile Glu Phe Thr Leu Ala Leu Lys
        275                 280                 285

Asn Lys Asn His Phe Tyr Leu Lys Glu Val Asn Val Ala Leu Ile Asn
    290                 295                 300

Gly Ser Ala Ser Ser Thr Arg Gln Asn Gln Asn Leu Ser Ala Trp Glu
305                 310                 315                 320

Ala Ser Val Gly Ser Ser Tyr Met Cys His Lys Glu Gln Gln Ile Lys
                325                 330                 335

Val Ser Glu Asp Leu Val Ile Asn Ser Phe Asp Val Arg Val Gln Leu
            340                 345                 350

Phe Gly Val Lys Asn Glu Thr Phe Ala Thr Ala Gln Gln Cys Ser Leu
        355                 360                 365

Asp Asp Asp Ser Ile Val Ile Pro Ile Val Val Gly Ala Ala Leu Ala
    370                 375                 380

Gly Leu Ile Val Ile Ile Val Ile Ala Tyr Leu Ile Gly Arg Arg Lys
385                 390                 395                 400
```

```
Gly Tyr Ser Gly Tyr Gln Thr Leu
                405


<210> SEQ ID NO 41
<211> LENGTH: 404
<212> TYPE: PRT
<213> ORGANISM: Salmo salar

<400> SEQUENCE: 41

Met Phe Arg Cys Ala Phe Leu Ile Leu Phe Leu Ala Leu Gly Asn Glu
1               5                   10                  15

Leu His Leu Ser His Gly Thr Glu Val Ser Val Asn Asn Thr Glu Asn
            20                  25                  30

Lys Leu Cys Leu Tyr Ala Asn Leu Met Val Asn Phe Ser Val Thr Tyr
        35                  40                  45

Glu Val Gly Val Asn Lys Asn Glu Thr Val Ile Phe Val Leu Pro Glu
    50                  55                  60

Asn Val Thr Thr Glu Gly Ser Thr Cys Asp Asn Thr Thr Ser Thr Leu
65                  70                  75                  80

Lys Leu Ser Phe Gly His Gly His Ser Trp Thr Val Glu Phe Thr Lys
                85                  90                  95

Lys Asn Lys Thr Tyr Gln Val Asp Thr Ile Val Phe Ser Tyr Asn Leu
            100                 105                 110

Asn Asp Ser Ser Val Phe Pro Asn Ser Thr Ser Lys Glu Thr Lys Phe
        115                 120                 125

Val Thr Val Lys Ser Ile Ile Thr Asn Val Ser Val Asp Thr Tyr Tyr
    130                 135                 140

Ser Cys Lys Ser Glu Asn Val Leu Thr Val Glu Ser Val Ile Gln Thr
145                 150                 155                 160

Leu Tyr Asp Val Ala Leu Gln Ala Phe Val Ile Asn Gly Ser Lys Ser
                165                 170                 175

Asp Thr Asp Thr Val Cys Ser Ala Asp Met Thr Ser Thr Thr Val Ala
            180                 185                 190

Pro Thr Thr Thr Val Thr Ser Thr Ala Ala Pro Thr Ser Thr Pro Thr
        195                 200                 205

Leu Pro Thr Pro Thr Thr Gly Lys Tyr Ser Ile Ala Pro Asp Val Asn
    210                 215                 220

Ser Thr Ala Cys Leu Met Ala Thr Phe Gly Leu Gln Ile Gly Tyr Lys
225                 230                 235                 240

Gln Gly Asp Lys Glu Glu Thr Ile Asn Leu Val Pro Asn Ile Thr Glu
                245                 250                 255

Val Gly Gly Ala Cys Gly Ala Asn Ser Ser Asp Leu Ile Leu Thr Ser
            260                 265                 270

Asp Thr Ile Thr Ile Met Phe Thr Phe Ser Asn Asp Gly Lys Lys Phe
        275                 280                 285

His Leu His Ala Leu Lys Val Thr Val Lys Pro Ala Thr Gly Asp Pro
    290                 295                 300

Val Ile Ala Val Asn Asn Asn Met Ser Ile Trp Ala Ala Ala Val Gly
305                 310                 315                 320

Ser Ser Tyr Met Cys Asn Lys Glu Gln Thr Leu Asn Val Thr Asp Thr
                325                 330                 335

Leu Thr Leu Tyr Thr Phe Glu Leu Arg Val Gln Pro Phe Glu Val Asn
            340                 345                 350

Lys Gly Glu Phe Ala Thr Ala His Glu Cys Ser Leu Asp Asp Thr Ser
```

```
        355                 360                 365

Ile Leu Ile Pro Ile Ile Val Gly Ala Ala Leu Ala Gly Leu Ile Leu
    370                 375                 380

Ile Val Val Ile Ala Tyr Val Ile Gly Arg Arg Lys Thr Tyr Val Gly
385                 390                 395                 400

Tyr Gln Thr Leu


<210> SEQ ID NO 42
<211> LENGTH: 410
<212> TYPE: PRT
<213> ORGANISM: Oreochromis niloticus

<400> SEQUENCE: 42

Met Lys Val Ser His Ala Thr Ala Gly Leu Val Val Trp Phe Val Val
1               5                   10                  15

Leu Gly Cys Ile Asp Ala Val Thr Leu Glu Val Lys Glu Ser Asn Thr
            20                  25                  30

Thr Cys Ile Lys Ala Asp Leu Ser Ala Ser Phe Ser Ile Ile Tyr Asn
        35                  40                  45

Thr Thr His Ala Glu Arg Thr Val Gln Val Leu Leu Pro Asn Ser Thr
    50                  55                  60

Thr Val Asp Thr Ala Asn Ser Thr Cys Gly Lys Asp Gly Ser Ser Pro
65                  70                  75                  80

Arg Leu Val Ala Val Phe Gly Ser Gly Tyr Thr Leu Gly Leu Asn Phe
                85                  90                  95

Ser Thr Asn Gly Thr Leu Tyr Gln Val Ser Ser Leu Thr Leu Gln Tyr
            100                 105                 110

Asn Leu Ser Asp Thr Ser Val Phe Pro Asn Ala Thr Ile Ser Gly Val
        115                 120                 125

Val Thr Leu Val Ser Ala Ser Val Gly Ile Glu Ala Asn Val Asn Thr
    130                 135                 140

Thr Tyr Lys Cys Ala Ser Pro Thr Val Ile Asp Val Ala Thr Ala Lys
145                 150                 155                 160

Val Asn Phe Thr Asp Met Arg Leu Glu Ala Tyr Met Pro Gly Asn Glu
                165                 170                 175

Leu Ser Pro Asn Glu Thr Val Cys Phe Ala Asp Gln Thr Ser Thr Thr
            180                 185                 190

Pro Ser Pro Thr Thr Val Ser Thr Thr Ala Val Pro Thr Gln Thr Pro
        195                 200                 205

Pro Gly Thr Pro Gln Gln Gly Asn Tyr Thr Val Lys Asp Ala Asn Asp
    210                 215                 220

Thr Ile Cys Leu Leu Ala Lys Met Gly Leu Gln Leu Asn Val Ser Tyr
225                 230                 235                 240

Thr Ser Gln Asn Lys Thr Val Gln Asp Val Leu Asn Leu Asn Pro Asn
                245                 250                 255

Val Thr Asn Ser Thr Gly Ser Cys Gly Ala Ser Ser Ala Thr Leu Val
            260                 265                 270

Leu Thr Gln Thr Gln Ser Thr Ile Leu Thr Phe Asn Phe Thr Leu Asn
        275                 280                 285

Ser Thr Thr Asn Lys Tyr His Leu Ser Gly Val Thr Leu Ile Ala Asn
    290                 295                 300

Trp Phe Asp Ser Ala His Phe Ser Met Ser Asn Asn Ser Leu Asn Tyr
305                 310                 315                 320

Leu Arg Ser Thr Leu Gly Tyr Ser Tyr Met Cys Asn Ala Glu Gln Thr
```

```
                325                 330                 335

Leu Phe Val Thr Pro Ser Phe Ser Leu Asn Thr Phe Asp Leu Gln Val
            340                 345                 350

Gln Pro Phe Gly Val Lys Ser Gly Arg Phe Ala Thr Ala Glu Glu Cys
        355                 360                 365

Gln Met Asp Gln Asn Gln Met Ile Ile Pro Ile Ile Val Gly Ala Ala
    370                 375                 380

Leu Ala Gly Leu Val Leu Ile Thr Leu Ile Ala Tyr Leu Ile Gly Lys
385                 390                 395                 400

Arg Arg Ser His Ala Gly Tyr Gln Ala Ile
                405                 410


<210> SEQ ID NO 43
<211> LENGTH: 249
<212> TYPE: PRT
<213> ORGANISM: Takifugu rubripes

<400> SEQUENCE: 43

Met Thr Gln Ile Gly Gly Val Gln Pro Val Phe Leu Ala Val Thr Val
1               5                   10                  15

His Leu Ile Leu Ala Thr Val Leu His Gln Thr Phe Ala Thr Val Thr
            20                  25                  30

Pro Pro Val Thr Thr Ala Val Pro His Lys Glu Pro Gly Arg Pro Asp
        35                  40                  45

Gln Gly Asp Tyr Gln Val Thr Ser Ser Asn Gly Thr Val Cys Phe Leu
    50                  55                  60

Ala Ser Met Gly Leu Gln Leu Asn Ile Thr Phe Asn Ser Thr Ser Gln
65                  70                  75                  80

Asn Lys Thr Leu Gln Glu Val Ile Asn Ile Gln Pro Asn Arg Thr Lys
                85                  90                  95

Ser Ser Gly Ser Cys Asp Thr Ser Ser Ala Leu Leu Thr Leu Thr Thr
            100                 105                 110

Asp Ala Glu Lys Thr Asn Leu Thr Phe Val Phe Ala Leu Asn Thr Thr
        115                 120                 125

Ser Asn Lys Tyr His Leu Ser Glu Val Ser Leu Ser Ala Ala Leu Ser
    130                 135                 140

Asp Met Lys Glu Thr Phe Val Ala Gln Asn His Ser Leu Asp Tyr Leu
145                 150                 155                 160

Arg Gly Thr Leu Gly Phe Ser Tyr Met Cys Arg Glu Arg Gln Thr Leu
                165                 170                 175

Gly Val Thr Pro Asp Phe Ala Ile Asn Thr Phe Gln Val Gln Val Gln
            180                 185                 190

Pro Phe Gly Val Thr Gly Lys Gln Phe Ala Ala Ala Glu Glu Cys Gln
        195                 200                 205

Leu Asp Lys Asp Asp Met Leu Ile Pro Ile Ile Val Gly Ala Ala Leu
    210                 215                 220

Ala Ala Leu Val Leu Ile Val Leu Ser Ala Tyr Leu Ile Gly Arg Lys
225                 230                 235                 240

Arg Ser His Ala Gly Tyr Gln Ser Ile
                245


<210> SEQ ID NO 44
<211> LENGTH: 418
<212> TYPE: PRT
<213> ORGANISM: Pan troglodytes
```

<400> SEQUENCE: 44

```
Met Pro Arg Gln Leu Ser Ala Ala Ala Ala Leu Phe Ala Ser Leu Ala
1               5                   10                  15

Val Ile Leu His Asp Gly Ser Gln Met Arg Ala Lys Ala Phe Pro Glu
            20                  25                  30

Thr Arg Asp Tyr Ser Gln Pro Ser Ala Ala Ala Thr Val Gln Asp Ile
        35                  40                  45

Lys Lys Pro Val Gln Gln Pro Ala Lys Gln Ala Pro His Gln Thr Leu
    50                  55                  60

Ala Ala Arg Phe Met Asp Gly His Ile Thr Phe Gln Thr Ala Ala Thr
65                  70                  75                  80

Val Lys Thr Pro Thr Thr Thr Pro Ala Thr Thr Lys Asn Thr Ala Thr
                85                  90                  95

Thr Ser Pro Ile Thr Tyr Thr Leu Val Thr Thr Gln Ala Thr Pro Asn
            100                 105                 110

Asn Ser His Thr Ala Pro Pro Val Thr Glu Val Thr Val Gly Pro Ser
        115                 120                 125

Leu Val Pro Tyr Ser Leu Pro Pro Thr Ile Thr Pro Pro Ala His Thr
    130                 135                 140

Thr Gly Thr Ser Ser Ser Thr Val Ser His Thr Thr Gly Asn Thr Thr
145                 150                 155                 160

Gln Pro Ser Asn Gln Thr Thr Leu Pro Ala Thr Leu Ser Ile Ala Leu
                165                 170                 175

His Lys Ser Thr Thr Gly Gln Lys Pro Val Gln Pro Thr His Ala Pro
            180                 185                 190

Gly Thr Thr Ala Ala Ala His Asn Thr Thr Arg Thr Ala Ala Pro Ala
        195                 200                 205

Ser Thr Val Pro Gly Pro Thr Leu Ala Pro Gln Pro Ser Ser Val Lys
    210                 215                 220

Thr Gly Ile Tyr Gln Val Leu Asn Gly Ser Arg Leu Cys Ile Lys Ala
225                 230                 235                 240

Glu Met Gly Ile Gln Leu Ile Val Gln Asp Lys Glu Ser Val Ser Trp
                245                 250                 255

Gly His Arg Thr Ile Thr Leu Ser Ser Lys Ser Leu Ser Gly Gly Cys
            260                 265                 270

Leu Ala Arg Asn Glu His Ser Pro His Pro Leu Phe Leu Phe Phe Glu
        275                 280                 285

Lys Gly Pro Pro Ser Val Thr Gln Ala Glu Asp Glu Glu Ser Tyr Tyr
    290                 295                 300

Ile Ser Glu Val Gly Ala Tyr Leu Thr Val Ser Asp Pro Glu Thr Ile
305                 310                 315                 320

Tyr Gln Gly Ile Lys His Ala Val Val Met Phe Gln Thr Ala Val Gly
                325                 330                 335

His Ser Phe Lys Cys Val Ser Glu Gln Ser Leu Gln Leu Ser Ala His
            340                 345                 350

Leu Gln Leu Lys Thr Thr Asp Val Gln Leu Gln Ala Phe Asp Phe Glu
        355                 360                 365

Asp Asp His Phe Gly Asn Val Asp Glu Cys Ser Ser Asp Tyr Thr Ile
    370                 375                 380

Val Leu Pro Val Ile Gly Ala Ile Val Val Gly Leu Cys Leu Met Gly
385                 390                 395                 400

Met Gly Val Tyr Lys Ile Arg Leu Arg Cys Gln Ser Ser Gly Tyr Gln
                405                 410                 415
```

```
Arg Ile

<210> SEQ ID NO 45
<211> LENGTH: 416
<212> TYPE: PRT
<213> ORGANISM: Papio anubis

<400> SEQUENCE: 45

Met Pro Arg Gln Leu Ser Ala Ala Ala Val Leu Phe Ala Ser Leu Ala
1               5                   10                  15

Val Ile Leu His Asp Gly Ser Gln Met Arg Ala Lys Ala Phe Pro Lys
            20                  25                  30

Thr Arg Asp Tyr Ser Gln Pro Thr Ala Ala Ala Thr Gly Gln Asp Ile
        35                  40                  45

Ala Lys Pro Val Gln Gln Pro Ala Asn Gln Ala Pro His Gln Thr Leu
    50                  55                  60

Ala Ala Arg Leu Met Asp Gly His Ile Thr Phe Gln Thr Ala Ala Thr
65                  70                  75                  80

Ile Lys Thr Pro Thr Thr Thr Pro Val Thr Thr Lys Asn Thr Pro Thr
                85                  90                  95

Thr Ser Pro Ile Ile Tyr Thr Leu Val Thr Thr Gln Ala Thr Ser Asn
            100                 105                 110

Asn Ser His Thr Ala Pro Pro Leu Thr Lys Val Thr Val Gly Pro Ser
        115                 120                 125

Leu Ala Pro Tyr Ser Leu Pro Pro Thr Ile Thr Pro Pro Ala His Thr
    130                 135                 140

Thr Gly Thr Ser Ser Ser Thr Val Asn His Thr Thr Gly Asn Ala Thr
145                 150                 155                 160

Gln Pro Ser Asn Gln Thr Thr Leu Pro Ala Thr Leu Ser Ile Ala Leu
                165                 170                 175

His Lys Ser Thr Thr Gly Gln Lys Pro Val Gln Pro Thr His Ala Pro
            180                 185                 190

Gly Thr Thr Ala Ala Ala His Asn Thr Thr Arg Thr Ala Ala Pro Ala
        195                 200                 205

Ser Thr Val Pro Gly Ser Thr Leu Ala Pro Gln Pro Ser Ser Val Lys
    210                 215                 220

Thr Gly Ile Tyr Gln Val Leu Asn Gly Ser Arg Leu Cys Ile Lys Ala
225                 230                 235                 240

Glu Met Gly Ile Gln Leu Ile Val Gln Asp Lys Glu Ser Val Phe Ser
                245                 250                 255

Pro Arg Arg Tyr Phe Asn Leu Asp Pro Asn Ala Thr Gln Ala Ser Gly
            260                 265                 270

Asn Cys Gly Thr Arg Asn Ser Asn Leu Leu Leu Asn Phe Gln Gly Gly
        275                 280                 285

Phe Val Asn Leu Thr Phe Thr Lys Asp Glu Gly Ser Tyr Tyr Ile Ser
    290                 295                 300

Glu Val Gly Ala Cys Leu Thr Val Ser Asp Pro Glu Thr Ile Tyr Gln
305                 310                 315                 320

Gly Met Lys His Ala Val Val Met Phe Gln Thr Ala Val Gly His Ser
                325                 330                 335

Phe Lys Cys Val Ser Glu Gln Ser Leu Gln Leu Ser Ala His Leu Gln
            340                 345                 350

Leu Lys Thr Thr Asn Val Gln Leu Gln Ala Phe Asp Phe Glu Asp Asp
        355                 360                 365
```

```
His Phe Gly Asn Val Asp Glu Cys Ser Ser Asp Tyr Thr Ile Val Leu
    370                 375                 380

Pro Val Ile Gly Ala Ile Val Val Gly Leu Cys Leu Val Gly Ile Gly
385                 390                 395                 400

Val Tyr Lys Ile Arg Leu Arg Cys Gln Ser Ser Gly Tyr Gln Arg Ile
                405                 410                 415
```

```
<210> SEQ ID NO 46
<211> LENGTH: 416
<212> TYPE: PRT
<213> ORGANISM: Macaca mulatta

<400> SEQUENCE: 46

Met Pro Arg Gln Leu Ser Ala Ala Ala Val Leu Phe Ala Ser Leu Ala
1               5                   10                  15

Val Ile Leu His Asp Gly Ser Gln Met Arg Ala Lys Ala Phe Pro Lys
            20                  25                  30

Thr Arg Asp Tyr Ser Gln Pro Thr Ala Ala Ala Thr Gly Gln Asp Ile
        35                  40                  45

Ala Lys Pro Val Gln Gln Pro Ala Asn Gln Ala Pro His Gln Thr Leu
    50                  55                  60

Ala Ala Arg Leu Met Asp Gly His Ile Thr Phe Gln Thr Ala Ala Thr
65                  70                  75                  80

Ile Lys Thr Pro Thr Thr Thr Pro Val Thr Thr Lys Asn Thr Pro Thr
                85                  90                  95

Thr Ser Pro Ile Ile Tyr Thr Leu Val Thr Thr Gln Ala Thr Ser Asn
            100                 105                 110

Asn Ser His Thr Ala Pro Pro Leu Thr Lys Val Thr Val Gly Pro Ser
        115                 120                 125

Leu Ala Pro Tyr Ser Leu Pro Pro Thr Ile Thr Pro Pro Ala His Thr
    130                 135                 140

Thr Gly Thr Ser Ser Ser Thr Val Asn His Thr Thr Gly Asn Ala Thr
145                 150                 155                 160

Gln Pro Ser Asn Gln Thr Thr Leu Pro Ala Thr Leu Ser Ile Ala Pro
                165                 170                 175

His Lys Ser Thr Thr Gly Gln Lys Pro Val Gln Pro Thr His Ala Pro
            180                 185                 190

Gly Thr Thr Ala Ala Ala His Asn Thr Thr Arg Thr Ala Ala Pro Ala
        195                 200                 205

Ser Thr Val Pro Gly Ser Thr Leu Ala Pro Gln Pro Ser Ser Ile Lys
    210                 215                 220

Thr Gly Ile Tyr Gln Val Leu Asn Gly Ser Arg Leu Cys Ile Lys Ala
225                 230                 235                 240

Glu Met Gly Ile Gln Leu Ile Val Gln Asp Lys Glu Ser Val Phe Ser
                245                 250                 255

Pro Arg Arg Tyr Phe Asn Leu Asp Pro Asn Ala Thr Gln Ala Ser Gly
            260                 265                 270

Asn Cys Gly Thr Arg Asn Ser Asn Leu Leu Leu Asn Phe Gln Gly Gly
        275                 280                 285

Phe Val Asn Leu Thr Phe Thr Lys Asp Glu Gly Ser Tyr Tyr Ile Ser
    290                 295                 300

Glu Val Gly Ala Cys Leu Thr Val Ser Asp Pro Glu Thr Ile Tyr Gln
305                 310                 315                 320

Gly Met Lys His Ala Val Val Met Phe Gln Thr Val Val Gly His Ser
```

```
                325                 330                 335

Phe Lys Cys Val Ser Glu Gln Ser Leu Gln Leu Ser Ala His Leu Gln
            340                 345                 350

Leu Lys Thr Thr Asn Val Gln Leu Gln Ala Phe Asp Phe Glu Asp Asp
        355                 360                 365

His Phe Gly Asn Val Asp Glu Cys Ser Ser Asp Tyr Thr Ile Val Leu
    370                 375                 380

Pro Val Ile Gly Ala Ile Val Val Gly Leu Cys Leu Val Gly Met Gly
385                 390                 395                 400

Val Tyr Lys Ile Arg Leu Arg Cys Gln Ser Ser Gly Tyr Gln Arg Ile
                405                 410                 415


<210> SEQ ID NO 47
<211> LENGTH: 428
<212> TYPE: PRT
<213> ORGANISM: Canis lupus familiaris

<400> SEQUENCE: 47

Met Ser Trp Gln Leu Ser Ala Ala Val Ala Leu Phe Val Ser Leu Ala
1               5                   10                  15

Leu Ile Leu His Tyr Gly Ser Gln Ile Arg Ala Lys Met Phe Pro Glu
            20                  25                  30

Thr Val Asp Phe Gln Pro Thr Thr Ala Ala Thr Val Arg Ala Thr Ala
        35                  40                  45

Lys Pro Phe Leu His Leu Thr Asn Gln Val Pro Ser Gln Thr Leu Ala
    50                  55                  60

Ala Arg Ser Met Asp Gly His Ile Ala Ser Gln Arg Ala Ala Thr Thr
65                  70                  75                  80

Ser Ser Ser Glu Pro Pro Thr Thr His Thr Thr Val Lys Thr Leu Val
                85                  90                  95

Thr Thr Ser Leu Val Thr Ala Asn Ser Thr Pro Ser Ser Ser Pro Ile
            100                 105                 110

Ile Tyr Thr Leu Val Thr Thr Ile Val Thr Pro Asn Asn Ser Asn Thr
        115                 120                 125

Ala Ala Pro Val Thr Glu Ala Thr Ile Gly Pro Ser Ala Asp Pro Gly
    130                 135                 140

Ser Leu Pro Thr Thr Ser Thr Pro Leu Ala His Thr Thr Arg Thr Asn
145                 150                 155                 160

Pro Ser Thr Leu Ser His Lys Thr Arg Lys Thr Thr His Phe Gly Asn
                165                 170                 175

Gln Thr Thr Leu Pro Ala Thr Leu Ser Thr Ser Thr His Lys Ser Thr
            180                 185                 190

Ser Ser His Lys Ser Ala Gln Ser Thr His Ala Pro Gly Pro Thr Thr
        195                 200                 205

Ala Ala His Asn Thr Thr Gln Thr Ala Ser Pro Ala Thr Pro Ala Ser
    210                 215                 220

Gly Pro Thr Leu Ala Pro Gln Pro Ser Ser Pro Lys Thr Gly Ile Tyr
225                 230                 235                 240

Gln Val Leu Asn Gly Ser Arg Leu Cys Ile Lys Ala Glu Met Gly Ile
                245                 250                 255

Glu Leu Met Val Gln Asp Thr Lys Ser Val Phe Ser Pro Gln Arg Tyr
            260                 265                 270

Phe Asn Ile Asp Pro Asn Ala Thr Gln Thr Ser Gly Asn Cys Gly Ser
        275                 280                 285
```

```
Gln Lys Ser Asn Leu Leu Leu Asn Phe Gln Gly Gly Phe Val Asn Leu
    290                 295                 300

Thr Phe Leu Lys Asp Glu Asn Ser Tyr Tyr Ile Asn Glu Val Gly Ala
305                 310                 315                 320

Tyr Leu Ala Val Ser Asn Pro Glu Lys Ile Tyr Gln Gly Met Lys Ser
                325                 330                 335

Ser Val Val Met Phe Glu Thr Gly Val Gly His Ser Phe Lys Cys Val
            340                 345                 350

Ser Glu Gln Ser Ile Gln Leu Ser Thr His Leu Gln Leu Lys Thr Met
        355                 360                 365

Asn Val Gln Phe Gln Ala Phe Asp Phe Glu Asp Asp His Phe Gly Asn
    370                 375                 380

Val Asp Glu Cys Ser Ser Asp Tyr Thr Val Val Leu Pro Val Ile Gly
385                 390                 395                 400

Ala Ile Val Leu Gly Leu Cys Ala Val Gly Leu Ile Val Tyr Gly Ile
                405                 410                 415

His Leu Arg Arg Glu Ser Ser Gly Tyr Gln Arg Ile
            420                 425


<210> SEQ ID NO 48
<211> LENGTH: 430
<212> TYPE: PRT
<213> ORGANISM: Sus scrofa

<400> SEQUENCE: 48

Met Ser Trp Arg Leu Ser Ala Val Leu Val Ser Phe Val Ser Leu Ala
1               5                   10                  15

Val Phe Leu His Tyr Gly His His Met Lys Ala Lys Val Phe Pro Glu
            20                  25                  30

Ile Thr Asp Ser Ser Ser Pro Thr Thr Ala Ala Thr Val Gln Ala Thr
        35                  40                  45

Ala Glu Pro Ser Leu Trp Lys Pro Thr Asn His Thr Pro His Lys Thr
    50                  55                  60

Leu Ala Ala Lys Ser Thr Asp Gly His Val Thr Ser Gln Ile Ala Thr
65                  70                  75                  80

Thr Val Thr Asp Ser Glu Thr Leu Thr Thr His Thr Thr Ile Thr Thr
                85                  90                  95

Leu Ala Ala Thr Ser Leu Ala Ala Thr Asn Ser Thr Pro Ser Thr Ser
            100                 105                 110

Pro Thr Thr His Thr Leu Phe Thr Thr Leu Ala Thr Pro Asn Thr Ser
        115                 120                 125

His Met Ala Ala Pro Val Thr Glu Ala Ala Ile Ser Pro Ser Ala Gly
    130                 135                 140

Leu Ser Ser Leu Leu Pro Thr Ile Ile Pro Pro Ala His Thr Thr Gly
145                 150                 155                 160

Thr Arg Ser Ser Thr Leu Ser Pro Thr Ala Gly Lys Thr Thr Gln Pro
                165                 170                 175

Ser Asn Gln Thr Thr Leu Pro Ala Thr Leu Ser Thr Ser Pro His Asn
            180                 185                 190

Ser Thr Ala Ser Gln Lys Pro Thr His Pro Asn His Thr Pro Gly Pro
        195                 200                 205

Thr Thr Gly Ala His Asn Thr Thr Gln Thr Ala Ser Pro Ala Thr Ile
    210                 215                 220

Ala Pro Gly Pro Thr Leu Ala Pro Gln Pro Ser Ser Ala Lys Thr Gly
225                 230                 235                 240
```

```
Ile Tyr Gln Val Leu Asn Gly Ser Lys Leu Cys Ile Lys Ala Glu Met
            245                 250                 255

Gly Ile Glu Leu Thr Val Gln Asp Thr Gln Ser Val Phe Ser Pro Gln
        260                 265                 270

Arg Tyr Phe Asn Ile Asp Pro Asn Thr Thr Gln Ala Ser Gly Asn Cys
    275                 280                 285

Gly Ser Arg Lys Ser Lys Leu Leu Leu Asn Phe Gln Gly Gly Phe Val
    290                 295                 300

Asn Leu Thr Phe Thr Lys Asp Glu Asn Ser Tyr Tyr Val Ser Gly Val
305                 310                 315                 320

Gly Ala Tyr Leu Thr Val Ser Asn Pro Glu Lys Val Tyr Gln Gly Met
            325                 330                 335

Lys Asn Ala Val Val Met Phe Glu Thr Met Ile Gly His Ser Phe Lys
        340                 345                 350

Cys Val Ser Glu Gln Ser Ile Gln Leu Ser Pro His Leu Gln Leu Asn
    355                 360                 365

Thr Met Asn Val Gln Leu Gln Ala Phe Asp Phe Glu Asp Asp His Phe
    370                 375                 380

Gly Asn Val Asp Glu Cys Ser Ser Asp Tyr Thr Ile Val Leu Pro Val
385                 390                 395                 400

Ile Gly Ala Ile Val Leu Gly Leu Cys Ala Val Gly Leu Ile Val Tyr
            405                 410                 415

Gly Ile Arg Leu Lys Arg Glu Ser Ser Glu Tyr Gln Arg Ile
        420                 425                 430
```

<210> SEQ ID NO 49
<211> LENGTH: 259
<212> TYPE: PRT
<213> ORGANISM: Danio rerio

<400> SEQUENCE: 49

```
Met Thr Gln Ser Ser Arg Ser Val Leu Leu Leu Met Leu Ser Ser Leu
1               5                   10                  15

His Cys Leu Gly Ser Ser Leu Glu Ser Asn Pro Lys Asp Pro Ser Val
            20                  25                  30

Leu Ala Glu Ala Pro Gly Gln Asn Lys Arg Asp Ser Asp Ile Ser Leu
        35                  40                  45

Val Pro Gln Met Pro Val Leu Gln Pro Lys Glu Thr Ala Pro Pro Leu
    50                  55                  60

Val Thr Tyr Thr Ile Arg Asn Pro Gln Gly Lys Val Cys Val Arg Ala
65                  70                  75                  80

Ser Phe Gly Val Glu Phe Val Val Arg Glu Asn Lys Lys Lys Tyr Tyr
                85                  90                  95

Phe Asn Leu Thr Pro Asn Ser Ala Arg Ala Thr Gly Tyr Cys Ala Asn
            100                 105                 110

Gln Lys Thr Val Leu Ser Leu Glu Phe Ser Gly Gly Asn Leu Glu Phe
        115                 120                 125

Thr Phe Ile Lys Asp Gly Asp Gln Ser Tyr Val Lys Thr Val Lys Gly
    130                 135                 140

Ser Leu Arg Ala Ala Pro Pro Cys Lys Asn Cys Pro Ser Lys Ile Tyr
145                 150                 155                 160

Val Gly Leu Val Asp Asn Glu Lys Leu Phe Lys Ala Lys Asn Gly Leu
                165                 170                 175

Ser Phe Asn Cys Lys Ser Glu Thr Met Leu Ile Leu Ala Asp Tyr Phe
```

```
            180                 185                 190

Arg Leu Lys Leu Val Pro Leu Gln Ile Gln Ala Phe Asp Leu Val Asn
        195                 200                 205

Gly Ala Phe Gly Lys Glu Val Glu Cys Trp Ala Asp Tyr Asn Lys Arg
    210                 215                 220

Met Ile Pro Ile Ile Leu Gly Ala Val Ala Ala Ala Ile Cys Leu Ile
225                 230                 235                 240

Ala Ile Leu Thr Tyr Val Leu Val Arg Glu His Arg Asn Gln Gly Tyr
                245                 250                 255

Glu Gln Leu


<210> SEQ ID NO 50
<211> LENGTH: 432
<212> TYPE: PRT
<213> ORGANISM: Equus caballus

<400> SEQUENCE: 50

Met Ala Trp Gln Leu Ser Ala Val Val Val Leu Phe Val Ser Leu Ala
1               5                   10                  15

Val Ile Leu Tyr Tyr Gly Ser His Val Arg Ala Asn Val Phe Pro Glu
            20                  25                  30

Ile Thr Asp Tyr Ser Gln Pro Thr Thr Ala Ala Thr Ile Gln Thr Arg
        35                  40                  45

Ala Gln Pro Ser Leu Ser Gln Pro Thr Asn Gln Val Pro His Lys Thr
    50                  55                  60

Leu Ala Thr Arg Ser Met Asp Gly Gln Val Thr Ser Gln Thr Ala Ala
65                  70                  75                  80

Thr Thr Val Asn Pro Glu Thr Pro Val Thr His Thr Thr Ile Lys Thr
                85                  90                  95

Ala Ala Ala Thr Ser Leu Val Thr Thr Asn Ser Thr Leu Ser Thr Ser
            100                 105                 110

Pro Ile Thr Asn Thr Leu Leu Thr Thr Leu Ala Thr Pro Asp Asn Thr
        115                 120                 125

His Thr Thr Thr Pro Val Thr Glu Ala Thr Ile Gly Pro Ser Ala Gly
    130                 135                 140

Pro Gly Ser Pro Pro Thr Thr Ile Thr Thr Thr Ser Ser Ala Tyr Thr
145                 150                 155                 160

Thr Gly Thr Arg Ser Ser Thr Val Ser His Thr Thr Gly Lys Thr Thr
                165                 170                 175

Gln Leu Ser Asn Gln Thr Thr Leu Pro Ala Thr Leu Ser Thr Ser Pro
            180                 185                 190

His Asn Ser Thr Thr Ser Gln Asn Pro Ala His Ser Thr His Thr Pro
        195                 200                 205

Gly Pro Thr Thr Gly Thr Cys Asn Thr Thr Gln Thr Ala Ser Pro Thr
    210                 215                 220

Thr Thr Ala Pro Gly Pro Thr Leu Ala Pro Gln Pro Ser Ser Ala Lys
225                 230                 235                 240

Thr Gly Met Tyr Gln Ile Leu Asn Gly Ser Lys Leu Cys Ile Lys Ala
                245                 250                 255

Glu Met Gly Ile Gln Leu Thr Val Gln Asp Thr Lys Ser Ala Ser Pro
            260                 265                 270

Pro Gln Gly Tyr Phe Asn Ile Asp Pro Asn Thr Thr Gln Val Ser Gly
        275                 280                 285

Ile Cys Gly Ser Arg Lys Ser Asn Leu Leu Leu Asn Phe Trp Gly Gly
```

```
    290                 295                 300

Phe Val Asn Leu Thr Phe Thr Lys Asp Glu Asn Ser Tyr Tyr Ile Ser
305                 310                 315                 320

Glu Val Gly Ala Tyr Leu Thr Val Ser Asn Pro Glu Lys Thr Tyr Gln
                325                 330                 335

Gly Met Lys Ser Pro Val Val Met Phe Glu Thr Val Ile Gly His Ser
            340                 345                 350

Phe Lys Cys Val Ser Glu Gln Ser Leu Glu Leu Ser Thr Gln Leu His
        355                 360                 365

Leu Lys Thr Thr Asn Val Gln Leu Gln Ala Phe Asp Phe Glu Asp Asp
    370                 375                 380

Asn Phe Gly Asn Val Asp Glu Cys Ser Ser Asp Tyr Thr Val Val Leu
385                 390                 395                 400

Pro Val Ile Gly Ala Ile Val Leu Gly Leu Phe Ala Val Gly Leu Ile
                405                 410                 415

Val Tyr Gly Val Arg Val Arg Arg Glu Ala Ser Gly Tyr Gln Arg Ile
            420                 425                 430


<210> SEQ ID NO 51
<211> LENGTH: 433
<212> TYPE: PRT
<213> ORGANISM: Bos taurus

<400> SEQUENCE: 51

Met Ser Trp Gln Ile Pro Ala Val Val Met Ser Phe Met Ala Leu Val
1               5                   10                  15

Ala Ile Trp Tyr Tyr Asp Ser His Tyr Asn Ser His Met Gln Ala Lys
            20                  25                  30

Val Phe Pro Glu Ile Thr Gly Tyr Ser Ser Pro Thr Thr Gly Gln Ala
        35                  40                  45

Thr Val Lys Pro Ser Leu Leu Gln Pro Thr Asn Tyr Val Pro His Lys
    50                  55                  60

Thr Ala Ala Ala Arg Ser Thr Asp Gly His Val Thr Ser Gln Thr Val
65                  70                  75                  80

Ala Lys Thr Ser Ser Ser Glu Thr Leu Thr Thr Asn Thr Thr Ile Asp
                85                  90                  95

Val Leu Ala Thr Thr Ser Pro Val Thr Thr Lys Ser Thr Leu Pro Thr
            100                 105                 110

Thr Pro Thr Thr His Thr Leu Val Thr Thr Leu Ala Thr Pro Asn Lys
        115                 120                 125

Ser His Val Thr Phe Pro Val Thr Glu Ala Lys Val Gly Leu Ser Val
    130                 135                 140

Gly Pro Ser Ser Pro Pro Val Thr Val Asn Pro Thr Ala His Thr Thr
145                 150                 155                 160

Gly Asn Arg Pro Ser Thr Ala Ser His Thr Thr Gly Lys Thr Thr Gln
                165                 170                 175

Leu Ser Asn Gln Thr Thr Leu Pro Ala Thr Leu Ser Thr Ser Pro His
            180                 185                 190

Asn Ile Thr Thr Ser Gln Lys Pro Thr Gln Pro Thr His Thr Pro Gly
        195                 200                 205

Pro Thr Thr Ala Thr Tyr Asn Thr Thr Gln Thr Ala Ser Pro Ala Thr
    210                 215                 220

Ile Ala Pro Arg Pro Thr Leu Ala Pro Gln Pro Leu Ser Pro Lys Thr
225                 230                 235                 240
```

Gly Ile Tyr Gln Val His Asn Gly Ser Lys Leu Cys Ile Lys Ala Glu
245 250 255

Met Gly Ile Gln Leu Thr Val Gln Asp Ser Val Ser Val Phe Ser Pro
260 265 270

Gln Lys Tyr Phe Asn Ile Asp Pro Asn Ala Thr Gln Ala Ser Gly Asn
275 280 285

Cys Gly Ser Arg Lys Ser Asn Leu Leu Leu Asn Phe Gln Gly Gly Phe
290 295 300

Val Asn Leu Thr Phe Thr Lys Gly Glu Lys Ser Tyr Tyr Ile Ser Glu
305 310 315 320

Val Glu Ala Tyr Leu Thr Val Ser Asn Pro Ala Lys Val Tyr Gln Gly
325 330 335

Leu Lys His Ala Met Met Met Phe Glu Thr Val Val Gly His Ser Phe
340 345 350

Lys Cys Val Ser Glu Gln Ser Ile Gln Leu Ser Thr Tyr Leu Gln Leu
355 360 365

Lys Thr Met Asn Val Gln Leu Gln Ala Phe Asp Phe Glu Asp Asp His
370 375 380

Phe Gly Asn Ala Asp Glu Cys Ile Ser Asp Arg Asn Arg Arg Glu Ile
385 390 395 400

Pro Val Ala Val Gly Leu Ser Ile Ala Val Leu Leu Ala Val Leu Leu
405 410 415

Thr Ala Cys Leu Val Thr Arg Lys Arg Pro Ser Arg Gly Tyr Glu Arg
420 425 430

Met

<210> SEQ ID NO 52
<211> LENGTH: 429
<212> TYPE: PRT
<213> ORGANISM: Ovis aries

<400> SEQUENCE: 52

Met Ser Trp Gln Ile Ser Ala Val Val Leu Phe Phe Val Ser Leu Ala
1 5 10 15

Val Ile Trp Tyr Tyr Asp Ser His Met Lys Ala Asn Val Phe Pro Glu
20 25 30

Ile Thr Gly Tyr Ser Ser Pro Thr Thr Gly Gln Ala Thr Val Lys Pro
35 40 45

Ser Leu Leu Gln Pro Thr Asn His Val Pro Cys Asn Thr Ala Ala Ala
50 55 60

Lys Ser Thr Asp Gly His Val Thr Ser Gln Thr Val Ala Lys Thr Ser
65 70 75 80

Ser Pro Glu Thr Leu Thr Thr Asn Thr Thr Ile Glu Val Leu Val Thr
85 90 95

Thr Ser Pro Val Thr Thr Gln Ser Thr Leu Pro Thr Thr Pro Thr Thr
100 105 110

His Thr Leu Val Thr Thr Leu Ala Thr Pro Ser Lys Ser His Val Thr
115 120 125

Phe Pro Val Thr Glu Ala Lys Ala Gly Leu Ser Ile Gly Pro Ser Ser
130 135 140

Pro Pro Val Thr Ile Asn Pro Ala Ala His Thr Thr Gly Asn Arg Pro
145 150 155 160

Ser Thr Ala Ser His Thr Thr Gly Lys Thr Thr Gln Leu Ser Asn Gln
165 170 175

```
Thr Thr Leu Pro Ala Thr Leu Ser Thr Ser Pro His Asn Ile Thr Thr
            180                 185                 190

Ser Gln Lys Pro Thr Gln Pro Thr His Thr Pro Gly Pro Thr Thr Ala
        195                 200                 205

Ala Asn Asn Thr Thr His Thr Ala Ser Pro Ala Thr Ile Ala Pro Arg
    210                 215                 220

Pro Thr Leu Ala Pro Gln Pro Leu Ser Pro Lys Thr Gly Leu Tyr Gln
225                 230                 235                 240

Val Leu Asn Gly Ser Lys Leu Cys Ile Lys Ala Glu Met Gly Ile Gln
                245                 250                 255

Leu Thr Val Gln Asp Ser Val Ser Val Phe Ser Pro Gln Lys Tyr Phe
            260                 265                 270

Asn Ile Asp Pro Asn Ala Thr Gln Ala Ser Gly Asn Cys Gly Ser Arg
        275                 280                 285

Lys Ser Asn Leu Leu Leu Asn Phe Gln Gly Gly Phe Val Asn Leu Thr
    290                 295                 300

Phe Ile Lys Asp Glu Asn Ser Tyr Tyr Ile Ser Glu Val Glu Ala Tyr
305                 310                 315                 320

Leu Thr Val Ser Asn Pro Ala Lys Val Tyr Gln Gly Met Lys Tyr Ala
                325                 330                 335

Met Met Met Phe Glu Thr Val Val Gly His Ser Phe Lys Cys Val Ser
            340                 345                 350

Glu Gln Ser Ile Gln Leu Ser Asn His Leu Gln Leu Lys Thr Val Asn
        355                 360                 365

Val Gln Leu Gln Ala Phe Asp Phe Glu Asp Asp Arg Phe Gly Asn Ala
    370                 375                 380

Asp Glu Cys Ile Ser Asp Arg Asn Arg Arg Glu Ile Pro Val Ala Val
385                 390                 395                 400

Gly Leu Ser Ile Ala Val Leu Leu Ala Val Leu Leu Thr Ala Cys Leu
                405                 410                 415

Val Thr Arg Lys Arg Pro Ser Arg Gly Tyr Glu Arg Met
            420                 425


<210> SEQ ID NO 53
<211> LENGTH: 408
<212> TYPE: PRT
<213> ORGANISM: Rattus norvegicus

<400> SEQUENCE: 53

Met Pro Gly Gln Thr Ser Ala Val Ala Val Leu Leu Cys Leu Ala Val
1               5                   10                  15

Ile Leu His Gly Tyr Gln Ile Arg Glu Lys Glu Phe Pro Glu Ala Arg
            20                  25                  30

Gly Tyr Leu Gln Tyr Thr Ala Thr Thr Thr Glu Gln Ile Thr Ala Lys
        35                  40                  45

Pro Pro Leu Pro Leu Thr Asn Gln Thr Ser His Ala Thr Leu Ala Ser
    50                  55                  60

Arg Ser Lys Asp Asp Tyr Ile Gln Thr Ala Ala Glu Thr Ser Thr Phe
65                  70                  75                  80

Glu Asp Thr Ala His Ile Thr Met Lys Thr Ala Ile Pro Val Thr Thr
                85                  90                  95

Lys Ser Leu Leu Pro Ile Ser Ser Thr Ser Tyr Thr Phe Val Arg Thr
            100                 105                 110

Asn Asn Ser His Met Thr Ala Ser Ser Thr Glu Asp Thr Ile Gly Ser
        115                 120                 125
```

```
Gly Ser Ile Thr His Leu Pro Phe Pro Thr Thr Arg Ala Ser Leu Ala
    130                 135                 140

Ala Val Asn His Ile Thr Gly Arg Ser Thr Gln Leu Gly Gly Gln Thr
145                 150                 155                 160

Thr Leu Pro Lys Ala Leu Phe Thr Pro Ser His Glu Ser Thr Thr Thr
                165                 170                 175

Gln Arg Pro Thr Leu Ser Thr Ile Val Ser Glu Leu Thr Pro Thr Gly
            180                 185                 190

Lys Asp Arg Ser Thr Thr Ser Ser Val Pro Leu Val Pro Arg Pro Thr
        195                 200                 205

Phe Val Thr Trp Ser Ser Pro Ala Lys Ile Gly Thr Tyr Glu Val Leu
    210                 215                 220

Asn Gly Ser Arg Leu Cys Ile Lys Ala Glu Met Gly Ile Ala Leu Ile
225                 230                 235                 240

Val Gln Glu Lys Gly Leu Asp Ser Ala Thr Gln Arg His Phe Asn Ile
                245                 250                 255

Asp Pro Ser Leu Thr His Ala Ser Gly Lys Cys Gly Ser Gln Asn Ser
            260                 265                 270

Asn Leu Phe Leu Asn Phe Gln Gly Gly Ser Val Asn Val Thr Phe Thr
        275                 280                 285

Lys Glu Glu Asn Leu Tyr Tyr Val Ser Glu Val Gly Ala Tyr Leu Thr
    290                 295                 300

Ile Ser Asn Thr Glu Lys Thr Tyr Gln Gly Lys Ser Thr Met Met Met
305                 310                 315                 320

Phe Glu Thr Val Val Gly His Ser Phe Lys Cys Val Ser Glu Gln Ser
                325                 330                 335

Ile Gln Leu Ser Ala Gln Leu Gln Met Lys Thr Met Asn Ile His Leu
            340                 345                 350

Gln Ala Phe Asp Phe Glu Gly Asp Ser Phe Gly Ile Val Asp Glu Cys
        355                 360                 365

Leu Ser Asp Tyr Thr Val Val Leu Pro Val Val Gly Ile Ile Val Val
    370                 375                 380

Val Leu Cys Val Val Gly Leu Gly Ile Tyr Lys Ile Arg Gln Arg Arg
385                 390                 395                 400

Gln Ser Ser Ala Tyr Gln Arg Ile
                405


<210> SEQ ID NO 54
<211> LENGTH: 411
<212> TYPE: PRT
<213> ORGANISM: Mus musculus

<400> SEQUENCE: 54

Met Pro Gly Gln Ile Ser Ala Val Ala Val Leu Phe Leu Ser Leu Thr
1               5                   10                  15

Val Ile Leu His Gly Tyr Gln Ile Arg Glu Lys Glu Phe Pro Lys Ala
            20                  25                  30

Arg Gly Tyr Leu Gln Tyr Thr Ala Thr Ser Ala Glu Gln Ile Thr Thr
        35                  40                  45

Lys Pro Leu Leu Gln Leu Ile Asn Gln Arg Ser His Ile Thr Leu Ala
    50                  55                  60

Ser Arg Phe Lys Asp Asp Tyr Ile Gln Met Ala Ala Glu Thr Ser Ala
65                  70                  75                  80

Ile Glu Asn Thr Ala His Ile Thr Met Lys Thr Val Thr Pro Val Thr
```

```
                85                  90                  95

Thr Lys Ser Leu Pro Pro Ile Ser Ser Ala Ser Tyr Thr Phe Val Arg
            100                 105                 110

Ser Asn Asn Ala His Met Thr Ala Ser Ser Thr Asp Asp Thr Ile Gly
        115                 120                 125

Ser Gly Ser Ile Ala His Leu Pro Val Pro Thr Thr Arg Ala Ser Leu
    130                 135                 140

Ala Ile Val Asn Tyr Ile Thr Gly Arg Ala Thr Gln Leu Gly Gly Gln
145                 150                 155                 160

Thr Thr Leu Pro Lys Thr Phe Phe Thr Ala Ser His Lys Ser Thr Thr
                165                 170                 175

Asn Gln Arg Pro Thr Leu Ser Thr Asn Val Leu Gly Thr Ser Thr Pro
            180                 185                 190

Thr His Lys Asp Arg Ser Thr Thr Ser Pro Val Pro Leu Val Pro Arg
        195                 200                 205

Pro Thr Leu Val Thr Trp Ser Ser Pro Ala Lys Ile Gly Thr Tyr Glu
    210                 215                 220

Val Leu Asn Gly Ser Arg Leu Cys Ile Lys Ala Glu Met Gly Leu Ala
225                 230                 235                 240

Leu Ile Val Gln Glu Lys Asp Leu Asp Ser Ala Thr Gln Arg Tyr Phe
                245                 250                 255

Asn Ile Asp Pro Ser Leu Thr His Ala Ser Gly Lys Cys Asp Ser Gln
            260                 265                 270

Lys Ser Asn Leu Phe Leu Asn Phe Gln Gly Gly Ser Val Asn Ile Thr
        275                 280                 285

Phe Thr Lys Glu Glu Asn Leu Tyr Tyr Ile Ser Glu Val Gly Ala Tyr
    290                 295                 300

Leu Thr Ile Ser Asn Thr Glu Lys Thr Tyr Gln Gly Lys Lys Asn Thr
305                 310                 315                 320

Leu Met Met Phe Glu Thr Val Val Gly His Ser Phe Lys Cys Val Ser
                325                 330                 335

Glu Gln Ser Ile Gln Leu Ser Ala Gln Leu Gln Met Lys Thr Met Asn
            340                 345                 350

Ile His Leu Gln Ala Phe Asp Phe Glu Gly Asp Ser Phe Gly Asn Val
        355                 360                 365

Asn Glu Cys Leu Ser Asp Tyr Thr Val Val Leu Pro Met Val Ala Ile
    370                 375                 380

Ile Val Val Val Ile Cys Val Val Gly Leu Ser Val Tyr Lys Ile Arg
385                 390                 395                 400

Gln Arg His Gln Ser Ser Ala Tyr Gln Arg Ile
                405                 410


<210> SEQ ID NO 55
<211> LENGTH: 314
<212> TYPE: PRT
<213> ORGANISM: Xenopus tropicalis

<400> SEQUENCE: 55

Met Asp Arg Val Ser Leu Leu Ser Thr Ile Leu Leu Leu Tyr Gly Leu
1               5                   10                  15

Leu Tyr Ile Asn Asp Ala Tyr Ser Glu Asn Thr Phe Ala Gln Pro Ser
            20                  25                  30

Asn Thr Thr Thr Pro Ala Pro Asn Thr Thr Thr Thr His Val Thr Ser
        35                  40                  45
```

```
Asn Thr Thr Thr Leu Ala Pro Asn Thr Thr Thr Thr His Val Thr Ser
    50                  55                  60

Asn Thr Thr Thr Leu Ala Pro Asn Thr Thr Thr Thr His Ile Thr Ser
65                  70                  75                  80

Asn Thr Thr Thr Leu Ala Pro Asn Thr Thr Thr Thr Leu Ala Pro Asn
                85                  90                  95

Thr Thr Thr Thr His Ser Val Thr Thr Thr Lys Thr Ala Ser Thr Thr
            100                 105                 110

Thr Pro Thr Pro Thr Leu Glu Pro Lys Pro Ser Pro Pro Glu Thr Gly
        115                 120                 125

Asn Tyr Thr Val Lys Ile Lys Asn Glu Phe Cys Ile Glu Ala Leu Met
    130                 135                 140

Gly Leu Glu Leu Glu Leu Thr Asn Ser Thr Lys Thr Gln Gln Tyr Phe
145                 150                 155                 160

Asn Ile Val Pro Ser Gln Ile Asn Ser Asn Gly Thr Cys Glu Lys Ser
                165                 170                 175

Lys Ala Asn Leu Asn Leu Thr Phe Ala Asn Ser Tyr Ile Asn Phe Val
            180                 185                 190

Phe Ala Gln Asp Asp Asn Ser Tyr Tyr Leu Asp Asn Val Thr Val Tyr
        195                 200                 205

Phe Asn Leu Thr Arg Ser Glu Ser Trp Tyr Gly Asn Ala Thr Asn Gln
    210                 215                 220

Lys Leu Leu Lys Thr Glu Asn Gly Tyr Ser Val Lys Cys Lys Asn Thr
225                 230                 235                 240

Pro Lys Ile Gln Leu Gly Asp Thr Met Asn Leu Val Met Thr Asn Val
                245                 250                 255

Lys Leu Gln Val Phe Asn Phe Lys Asp Asn Ser Phe Gly Lys Glu Thr
            260                 265                 270

Thr Cys Lys Tyr Asp His Asn Phe Gly Leu Met Ile Ala Gly Ile Val
        275                 280                 285

Ile Val Val Ile Val Val Leu Gly Val Ile Ile Tyr Phe Ile Trp His
    290                 295                 300

Lys Arg Lys Ser Ser Gly Tyr Gln Arg Ile
305                 310


<210> SEQ ID NO 56
<211> LENGTH: 478
<212> TYPE: PRT
<213> ORGANISM: Pan troglodytes

<400> SEQUENCE: 56

Met Gly Arg Cys Cys Phe Tyr Thr Ala Gly Thr Leu Ser Leu Leu Leu
1               5                   10                  15

Leu Val Thr Ser Val Thr Leu Leu Val Ala Arg Val Phe Gln Lys Ala
            20                  25                  30

Val Asp Gln Ser Ile Glu Lys Lys Ile Val Leu Arg Asn Gly Thr Glu
        35                  40                  45

Ala Phe Asp Ser Trp Glu Lys Pro Pro Leu Pro Val Tyr Thr Gln Phe
    50                  55                  60

Tyr Phe Phe Asn Val Thr Asn Pro Glu Glu Ile Leu Arg Gly Glu Thr
65                  70                  75                  80

Pro Arg Val Glu Glu Val Gly Pro Tyr Thr Tyr Arg Glu Leu Arg Asn
                85                  90                  95

Lys Ala Asn Ile Gln Phe Gly Asp Asn Gly Thr Thr Ile Ser Ala Val
            100                 105                 110
```

```
Ser Asn Lys Ala Tyr Val Phe Glu Arg Asp Gln Ser Val Gly Asp Pro
        115                 120                 125

Lys Ile Asp Leu Ile Arg Thr Leu Asn Ile Pro Val Leu Thr Val Ile
    130                 135                 140

Glu Trp Ser Gln Val Arg Phe Leu Arg Glu Ile Ile Glu Ala Met Leu
145                 150                 155                 160

Lys Ala Tyr Gln Gln Lys Leu Phe Val Thr His Thr Val Asp Glu Leu
                165                 170                 175

Leu Trp Gly Tyr Lys Asp Glu Ile Leu Ser Leu Ile His Val Phe Arg
            180                 185                 190

Pro Asp Ile Ser Pro Tyr Phe Gly Leu Phe Tyr Glu Lys Asn Gly Thr
        195                 200                 205

Asn Asp Gly Asp Tyr Val Phe Leu Thr Gly Glu Asp Ser Tyr Leu Asn
    210                 215                 220

Phe Thr Lys Ile Val Glu Trp Asn Gly Lys Thr Ser Leu Asp Trp Trp
225                 230                 235                 240

Ile Thr Asp Lys Cys Asn Met Ile Asn Gly Thr Asp Gly Asp Ser Phe
                245                 250                 255

His Pro Leu Ile Thr Lys Asp Glu Val Leu Tyr Val Phe Pro Ser Asp
            260                 265                 270

Phe Cys Arg Ser Val Tyr Ile Thr Phe Ser Asp Tyr Glu Ser Val Gln
        275                 280                 285

Gly Leu Pro Ala Phe Arg Tyr Lys Val Pro Ala Glu Ile Leu Ala Asn
    290                 295                 300

Thr Ser Asp Asn Ala Gly Phe Cys Ile Pro Glu Gly Asn Cys Leu Gly
305                 310                 315                 320

Ser Gly Val Leu Asn Val Ser Ile Cys Lys Asn Gly Ala Pro Ile Ile
                325                 330                 335

Met Ser Phe Pro His Phe Tyr Gln Ala Asp Glu Arg Phe Val Ser Ala
            340                 345                 350

Ile Glu Gly Met His Pro Asn Lys Glu Asp His Glu Thr Phe Val Asp
        355                 360                 365

Ile Asn Pro Leu Thr Gly Ile Ile Leu Lys Ala Ala Lys Arg Phe Gln
    370                 375                 380

Ile Asn Ile Tyr Val Lys Lys Leu Asp Asp Phe Val Glu Thr Gly Asp
385                 390                 395                 400

Ile Arg Thr Met Val Phe Pro Val Met Tyr Leu Asn Glu Ser Val His
                405                 410                 415

Ile Asp Lys Glu Thr Ala Ser Arg Leu Lys Ser Met Ile Asn Thr Thr
            420                 425                 430

Leu Ile Ile Thr Asn Ile Pro Tyr Ile Ile Met Ala Leu Gly Val Phe
        435                 440                 445

Phe Gly Leu Val Phe Thr Trp Leu Ala Cys Lys Gly Gln Gly Ser Met
    450                 455                 460

Asp Glu Gly Thr Ala Asp Glu Arg Ala Pro Leu Ile Arg Thr
465                 470                 475


<210> SEQ ID NO 57
<211> LENGTH: 478
<212> TYPE: PRT
<213> ORGANISM: Macaca mulatta

<400> SEQUENCE: 57

Met Gly Arg Cys Cys Phe Tyr Thr Ala Gly Thr Leu Ser Leu Leu Leu
```

```
1               5                   10                  15

Leu Val Thr Ser Val Thr Leu Leu Val Ala Arg Val Phe Gln Lys Ala
            20                  25                  30

Val Asp Gln Ser Ile Glu Lys Lys Ile Val Leu Arg Asn Gly Thr Glu
        35                  40                  45

Ala Phe Asp Ser Trp Glu Lys Pro Pro Leu Pro Val Tyr Thr Gln Phe
    50                  55                  60

Tyr Phe Phe Asn Val Thr Asn Pro Glu Glu Ile Leu Arg Gly Glu Thr
65                  70                  75                  80

Pro Arg Val Glu Glu Val Gly Pro Tyr Thr Tyr Arg Glu Leu Arg Asn
                85                  90                  95

Lys Ala Asn Val Gln Phe Gly Asp Asn Gly Thr Thr Ile Ser Ala Val
            100                 105                 110

Ser Asn Lys Ala Tyr Val Phe Glu Arg Asp Gln Ser Val Gly Asp Pro
        115                 120                 125

Lys Ile Asp Leu Ile Arg Thr Leu Asn Ile Pro Val Leu Thr Val Ile
    130                 135                 140

Glu Trp Ser Gln Val His Phe Leu Arg Glu Ile Ile Glu Ala Met Leu
145                 150                 155                 160

Lys Ala Tyr Gln Gln Lys Leu Phe Val Thr His Thr Val Asp Glu Leu
                165                 170                 175

Leu Trp Gly Tyr Lys Asp Glu Ile Leu Ser Leu Ile His Val Phe Arg
            180                 185                 190

Pro Asp Ile Ser Pro Tyr Phe Gly Leu Phe Tyr Glu Lys Asn Gly Thr
        195                 200                 205

Asn Asp Gly Asp Tyr Val Phe Leu Thr Gly Glu Asp Asn Tyr Leu Asn
    210                 215                 220

Phe Thr Lys Ile Val Glu Trp Asn Gly Lys Thr Ser Leu Asp Trp Trp
225                 230                 235                 240

Ile Thr Asp Lys Cys Asn Met Ile Asn Gly Thr Asp Gly Asp Ser Phe
                245                 250                 255

His Pro Leu Ile Thr Lys Asp Glu Val Leu Tyr Val Phe Pro Ser Asp
            260                 265                 270

Phe Cys Arg Ser Val Tyr Ile Thr Phe Ser Asp Tyr Glu Ser Val Gln
        275                 280                 285

Gly Leu Pro Ala Phe Arg Tyr Lys Val Pro Ala Glu Ile Leu Ala Asn
    290                 295                 300

Thr Ser Asp Asn Ala Gly Phe Cys Ile Pro Glu Gly Asn Cys Leu Gly
305                 310                 315                 320

Ser Gly Val Leu Asn Val Ser Ile Cys Lys Asn Gly Ala Pro Ile Ile
                325                 330                 335

Met Ser Phe Pro His Phe Tyr Gln Ala Asp Glu Arg Phe Val Ser Ala
            340                 345                 350

Ile Glu Gly Met His Pro Asn Lys Glu Asp His Glu Thr Phe Val Asp
        355                 360                 365

Ile Asn Pro Leu Thr Gly Ile Ile Leu Lys Ala Ala Lys Arg Phe Gln
    370                 375                 380

Ile Asn Ile Tyr Val Lys Lys Leu Asp Asp Phe Val Glu Thr Gly Asp
385                 390                 395                 400

Ile Arg Thr Met Val Phe Pro Val Met Tyr Leu Asn Glu Ser Val Leu
                405                 410                 415

Ile Asp Lys Glu Thr Ala Ser Arg Leu Lys Ser Val Ile Asn Thr Thr
            420                 425                 430
```

```
Leu Ile Ile Thr Asn Ile Pro Tyr Ile Ile Met Ala Leu Gly Val Phe
        435                 440                 445

Phe Gly Phe Val Phe Thr Trp Leu Ala Cys Lys Gly Gln Gly Ser Met
    450                 455                 460

Asp Glu Gly Thr Ala Asp Glu Arg Ala Pro Leu Ile Arg Thr
465                 470                 475


<210> SEQ ID NO 58
<211> LENGTH: 478
<212> TYPE: PRT
<213> ORGANISM: Canis lupus familiaris

<400> SEQUENCE: 58

Met Gly Arg Cys Cys Phe Tyr Thr Val Gly Thr Leu Ser Leu Leu Leu
1               5                   10                  15

Leu Val Thr Ser Ile Ala Leu Leu Val Ala Arg Val Phe Gln Lys Ala
            20                  25                  30

Val Asp Gln Thr Ile Glu Lys Asn Ile Val Leu Arg Asn Gly Ser Glu
        35                  40                  45

Thr Phe Asp Ser Trp Lys Lys Pro Pro Leu Pro Val Tyr Ala Gln Phe
    50                  55                  60

Tyr Phe Phe Asn Val Thr Asn Pro Glu Glu Ile Leu Arg Gly Glu Ile
65                  70                  75                  80

Pro Arg Leu Glu Glu Val Gly Pro Tyr Thr Tyr Arg Glu Leu Arg Asp
                85                  90                  95

Lys Ala Asp Ile Gln Phe Gly Asp Asn Gly Thr Thr Ile Ser Ala Val
            100                 105                 110

Ser Asn Lys Ala Tyr Val Phe Glu Arg Asn Gln Ser Val Gly Asp Pro
        115                 120                 125

Lys Thr Asp Leu Ile Arg Thr Leu Asn Ile Pro Ala Val Thr Ala Met
    130                 135                 140

Glu Trp Ala His Leu His Phe Phe Arg Glu Leu Ile Glu Ala Leu Leu
145                 150                 155                 160

Lys Ala Tyr Gln Gln Thr Leu Phe Val Thr His Thr Val Asp Glu Leu
                165                 170                 175

Leu Trp Gly Tyr Lys Asp Glu Ile Leu Ser Leu Ile Asn Val Phe Lys
            180                 185                 190

Pro Glu Ile Ser Pro Tyr Phe Gly Leu Tyr Tyr Gly Lys Asn Gly Thr
        195                 200                 205

Asn Asp Gly Asp Tyr Val Phe Leu Thr Gly Glu Asp Asn Tyr Leu Asn
    210                 215                 220

Phe Ser Lys Ile Val Glu Trp Asn Gly Lys Thr Ser Leu Asp Trp Trp
225                 230                 235                 240

Thr Thr Asp Lys Cys Asn Met Ile Asn Gly Thr Asp Gly Asp Ser Phe
                245                 250                 255

His Pro Leu Ile Asp Lys Asp Glu Ile Leu Tyr Val Phe Pro Ser Glu
            260                 265                 270

Phe Cys Arg Ser Val Tyr Ile Thr Phe Ser Asp Phe Lys Ser Val Gln
        275                 280                 285

Gly Leu Pro Ala Phe Arg Tyr Lys Val Pro Gly Glu Val Leu Ala Asn
    290                 295                 300

Thr Ser Asp Asn Ala Gly Phe Cys Val Pro Lys Gly Asn Cys Leu Gly
305                 310                 315                 320

Ser Gly Val Leu Asn Ile Ser Ile Cys Lys Asn Gly Ala Pro Ile Ile
```

```
                325                 330                 335

Ile Ser Phe Pro His Phe Tyr Glu Ala Asp Lys Lys Phe Val Ser Ala
            340                 345                 350

Ile Asp Gly Met Arg Pro Asn Lys Asp Tyr His Glu Thr Phe Val Asp
        355                 360                 365

Ile Asn Pro Leu Thr Gly Ile Ile Leu Arg Ala Ala Lys Arg Phe Gln
    370                 375                 380

Ile Asn Val Tyr Val Lys Lys Leu Asp Asp Phe Ile Glu Thr Gly Asn
385                 390                 395                 400

Ile Arg Thr Met Val Phe Pro Val Met Tyr Ile Asn Glu Ser Val Leu
                405                 410                 415

Ile Asp Lys Asp Thr Ala Ser Arg Leu Lys Ser Val Ile Asn Thr Thr
            420                 425                 430

Leu Ile Ile Thr Asn Ile Pro Tyr Ile Val Met Ala Leu Gly Val Phe
        435                 440                 445

Phe Gly Leu Ile Phe Thr Trp Leu Ala Cys Arg Gly Gln Gly Ser Met
    450                 455                 460

Asp Glu Gly Thr Pro Asp Glu Arg Ala Pro Leu Ile Arg Thr
465                 470                 475


<210> SEQ ID NO 59
<211> LENGTH: 478
<212> TYPE: PRT
<213> ORGANISM: Bos taurus

<400> SEQUENCE: 59

Met Gly Arg Cys Cys Phe Tyr Ala Val Gly Thr Leu Ser Leu Leu Leu
1               5                   10                  15

Leu Val Thr Ser Ile Thr Leu Leu Val Ala Arg Val Phe Gln Lys Ala
            20                  25                  30

Val Asp Gln Thr Ile Glu Lys Asn Ile Val Leu Arg Asn Gly Ser Glu
        35                  40                  45

Thr Phe Asp Ser Trp Lys Lys Pro Pro Leu Pro Val Tyr Thr Gln Phe
    50                  55                  60

Tyr Phe Phe Asn Val Thr Asn Pro Glu Glu Ile Leu Asn Gly Glu Thr
65                  70                  75                  80

Pro Arg Leu Glu Glu Val Gly Pro Tyr Thr Tyr Arg Glu Leu Arg Asn
                85                  90                  95

Lys Asp Asp Ile Gln Phe Gly Asp Asn Gly Thr Thr Ile Ser Ala Val
            100                 105                 110

Ser Asn Lys Ala Tyr Val Phe Glu Arg Asp Lys Ser Val Gly Asp Pro
        115                 120                 125

Lys Ile Asp Leu Leu Arg Thr Leu Asn Ile Pro Ala Leu Thr Ala Met
    130                 135                 140

Glu Trp Thr Gln Leu Pro Leu Leu Arg Asp Ile Ile Glu Ala Leu Leu
145                 150                 155                 160

Lys Ala Tyr Arg Gln Lys Leu Phe Val Thr His Thr Val Asp Glu Leu
                165                 170                 175

Leu Trp Gly Tyr Lys Asp Glu Ile Leu Ser Leu Ile Asn Thr Phe Lys
            180                 185                 190

His Asp Val Ser Pro Tyr Phe Gly Leu Phe Tyr Gly Lys Asn Gly Thr
        195                 200                 205

Asn Asp Gly Asp Tyr Val Phe Leu Thr Gly Glu Asp Asn Tyr Leu Asn
    210                 215                 220
```

```
Phe Ser Lys Ile Val Glu Trp Asn Gly Lys Thr Ser Leu Asp Trp Trp
225                 230                 235                 240

Thr Ala Asp Glu Cys Asn Met Ile Asn Gly Thr Asp Gly Asp Thr Phe
                245                 250                 255

His Pro Leu Ile Thr Arg Asp Glu Val Leu Tyr Val Phe Pro Ser Asp
            260                 265                 270

Phe Cys Arg Ser Val Tyr Ile Thr Phe Ser Asp Phe Glu Ser Val Gln
        275                 280                 285

Gly Leu Pro Ala Leu Arg Tyr Lys Val Pro Ala Glu Ile Leu Ala Asn
    290                 295                 300

Thr Ser Asp Asn Ala Gly Phe Cys Ile Pro Lys Gly Asn Cys Leu Gly
305                 310                 315                 320

Ser Gly Val Leu Asn Val Ser Val Cys Lys Asn Gly Ala Pro Ile Ile
                325                 330                 335

Met Ser Phe Pro His Phe Tyr Gln Ala Asp Glu Lys Phe Val Ser Ala
            340                 345                 350

Ile Gly Gly Met His Pro Asn Lys Glu Tyr His Glu Thr Phe Val Asp
        355                 360                 365

Ile Asn Pro Leu Thr Gly Ile Ile Leu Arg Ala Ala Lys Arg Phe Gln
    370                 375                 380

Ile Asn Val Tyr Val Arg Lys Leu Asp Asp Phe Val Glu Thr Gly Asn
385                 390                 395                 400

Ile Gln Thr Leu Val Phe Pro Val Met Tyr Ile Asn Glu Ser Val Leu
                405                 410                 415

Ile Asp Lys Glu Thr Ala Ser Arg Leu Lys Ser Val Ile Asn Thr Thr
            420                 425                 430

Leu Ile Val Thr Asn Ile Pro Tyr Ile Ile Met Ala Leu Gly Val Phe
        435                 440                 445

Phe Gly Leu Ile Phe Thr Trp Leu Ala Cys Arg Gly Gln Gly Ser Thr
    450                 455                 460

Asp Glu Gly Thr Ala Asp Glu Arg Ala Pro Leu Ile Arg Thr
465                 470                 475


<210> SEQ ID NO 60
<211> LENGTH: 478
<212> TYPE: PRT
<213> ORGANISM: Mus musculus

<400> SEQUENCE: 60

Met Gly Arg Cys Cys Phe Tyr Thr Ala Gly Thr Leu Ser Leu Leu Leu
1               5                   10                  15

Leu Val Thr Ser Val Thr Leu Leu Val Ala Arg Val Phe Gln Lys Ala
            20                  25                  30

Val Asp Gln Thr Ile Glu Lys Asn Met Val Leu Gln Asn Gly Thr Lys
        35                  40                  45

Val Phe Asn Ser Trp Glu Lys Pro Pro Leu Pro Val Tyr Ile Gln Phe
    50                  55                  60

Tyr Phe Phe Asn Val Thr Asn Pro Glu Glu Ile Leu Gln Gly Glu Ile
65                  70                  75                  80

Pro Leu Leu Glu Glu Val Gly Pro Tyr Thr Tyr Arg Glu Leu Arg Asn
                85                  90                  95

Lys Ala Asn Ile Gln Phe Gly Glu Asn Gly Thr Thr Ile Ser Ala Val
            100                 105                 110

Thr Asn Lys Ala Tyr Val Phe Glu Arg Asn Gln Ser Val Gly Asp Pro
        115                 120                 125
```

```
Asn Val Asp Leu Ile Arg Thr Ile Asn Ile Pro Leu Leu Thr Val Val
    130                 135                 140

Asp Leu Ala Gln Leu Thr Leu Leu Arg Glu Leu Ile Glu Ala Met Leu
145                 150                 155                 160

Lys Ala Tyr Gln Gln Lys Leu Phe Val Ile His Thr Val His Glu Leu
                165                 170                 175

Leu Trp Gly Tyr Lys Asp Glu Ile Leu Ser Leu Val His Ile Phe Lys
            180                 185                 190

Pro Asp Val Ser Pro Asn Phe Gly Leu Phe Tyr Glu Arg Asn Gly Thr
        195                 200                 205

Asn Asp Gly Glu Tyr Val Phe Leu Thr Gly Glu Asp Asn Tyr Leu Asn
    210                 215                 220

Phe Ser Lys Ile Val Glu Trp Asn Gly Lys Thr Ser Leu Asp Trp Trp
225                 230                 235                 240

Thr Thr Asp Thr Cys Asn Met Ile Asn Gly Thr Asp Gly Asp Ser Phe
                245                 250                 255

His Pro Leu Ile Ser Lys Asp Glu Val Leu Tyr Leu Phe Pro Ser Asp
            260                 265                 270

Leu Cys Arg Ser Val His Ile Thr Phe Ser Ser Phe Glu Asn Val Glu
        275                 280                 285

Gly Leu Pro Ala Phe Arg Tyr Lys Val Pro Ala Glu Ile Leu Ala Asn
    290                 295                 300

Thr Ser Glu Asn Ala Gly Phe Cys Ile Pro Glu Gly Asn Cys Met Asp
305                 310                 315                 320

Ser Gly Val Leu Asn Ile Ser Ile Cys Lys Asn Gly Ala Pro Ile Ile
                325                 330                 335

Met Ser Phe Pro His Phe Tyr Gln Ala Asp Glu Lys Phe Val Ser Ala
            340                 345                 350

Ile Lys Gly Met His Pro Asn Lys Glu Glu His Glu Ser Phe Val Asp
        355                 360                 365

Ile Asn Pro Leu Thr Gly Ile Ile Leu Arg Gly Ala Lys Arg Phe Gln
    370                 375                 380

Ile Asn Thr Tyr Val Arg Lys Leu Asp Asp Phe Val Glu Thr Gly Asp
385                 390                 395                 400

Ile Arg Thr Met Val Phe Pro Val Met Tyr Leu Asn Glu Ser Val Leu
                405                 410                 415

Ile Asp Lys Glu Thr Ala Asn Gln Leu Lys Ser Val Ile Asn Thr Thr
            420                 425                 430

Leu Val Val Thr Asn Ile Pro Tyr Ile Ile Met Ala Leu Gly Val Phe
        435                 440                 445

Phe Gly Leu Val Phe Thr Trp Leu Ala Cys Arg Gly Gln Gly Ser Met
    450                 455                 460

Asp Glu Gly Thr Ala Asp Glu Arg Ala Pro Leu Ile Arg Thr
465                 470                 475


<210> SEQ ID NO 61
<211> LENGTH: 531
<212> TYPE: PRT
<213> ORGANISM: Danio rerio

<400> SEQUENCE: 61

Met Thr Arg Arg Ser Cys Thr Ile Tyr Ala Thr Gly Ile Val Cys Ala
1               5                   10                  15

His Leu Leu Ile Leu Gly Ile Ala Leu Leu Leu Ala Gln Val Phe Gln
```

```
            20                  25                  30

Thr Met Ile Gln Glu Arg Ile Lys Lys Glu Ile Thr Leu Ala Glu Asn
        35                  40                  45

Ser Arg Val Leu Asp Gly Trp Ile Asn Pro Pro Pro Pro Val Tyr Met
    50                  55                  60

Gln Tyr Phe Phe Phe Asn Val Thr Asn Pro Asp Glu Phe Leu Ala Gly
65                  70                  75                  80

Lys Glu Lys Ala Lys Val Thr Gln Met Gly Pro Tyr Thr Tyr Arg Glu
                85                  90                  95

Tyr Arg Pro Arg Glu Asn Val Thr Tyr Leu Glu Asn Gly Thr Lys Ile
            100                 105                 110

Phe Ala Thr Asn Pro Lys Ser Phe Val Phe Leu Arg Asn Met Ser Ala
        115                 120                 125

Gly Asp Pro Glu Val Asp Arg Val Thr Thr Val Asn Ile Pro Met Ile
    130                 135                 140

Ala Val Met Asn Glu Leu Asn Ser Tyr Ser Phe Phe Val Arg Thr Ala
145                 150                 155                 160

Val Ser Met Tyr Met Gly Ser Met Gly Met Gly Leu Phe Met Asn Arg
                165                 170                 175

Thr Val His Glu Ile Leu Trp Gly Phe Lys Asp Pro Leu Leu Thr Lys
            180                 185                 190

Leu His Ala Met Arg Pro Glu Val Asp Glu His Phe Gly Leu Met Tyr
        195                 200                 205

Asn Lys Asn Gly Thr His Glu Gly Glu Phe Val Phe His Thr Gly Glu
    210                 215                 220

Lys Asn Tyr Met Asn Tyr Gly Lys Ile Asp Thr Trp Asn Gly Ile Ser
225                 230                 235                 240

Gln Met Asn Trp Trp Ser Ser Asn Gln Ser Asn Met Ile Asn Gly Thr
                245                 250                 255

Asp Gly Ser Val Phe His Thr Phe Leu Ser Arg Lys Glu Leu Leu Tyr
            260                 265                 270

Ile Phe Ala Ala Asp Leu Cys Arg Ser Ile His Leu Gly Tyr Val Arg
        275                 280                 285

Asp Met Glu Val Lys Gly Ile Pro Ala Phe Arg Phe Ala Pro Pro Ser
    290                 295                 300

Asp Val Leu Ala Pro Pro Asp Glu Asn Pro Ala Asn Ala Gly Phe Cys
305                 310                 315                 320

Val Pro Ala Gly Asp Cys Leu Gly Lys Gly Val Leu Lys Val Ser Val
                325                 330                 335

Cys Arg Gln Gly Ala Pro Ile Val Val Ser Phe Pro His Phe Tyr Gln
            340                 345                 350

Ala Asp Glu Arg Tyr Ile Asn Ala Ile Glu Gly Met Asn Pro Asn Glu
        355                 360                 365

Glu Glu His Glu Thr Tyr Leu Asp Ile Asn Pro Thr Thr Gly Val Pro
    370                 375                 380

Ile Arg Ala Cys Lys Arg Ala Gln Leu Asn Ile Ile Leu Lys Arg Val
385                 390                 395                 400

Arg Gly Phe Pro Asn Thr Lys Phe Leu Asn Glu Thr Ile Phe Pro Ile
                405                 410                 415

Met Tyr Val Asn Glu Thr Ala Thr Ile Asp Asp Glu Ser Ala Ala Gln
            420                 425                 430

Met Arg Met Leu Leu Leu Ile Val Thr Val Val Ser Asn Phe Pro Val
        435                 440                 445
```

```
Ile Ile Leu Ala Leu Gly Val Ile Leu Leu Val Val Leu Ile Phe Leu
    450                 455                 460

Val Cys Arg Asn Arg Gln Arg Lys Asn Glu Val Lys Arg Ile Asp Phe
465                 470                 475                 480

Thr Glu Ala Phe His Ser Phe Ala Thr Thr Lys Asp Glu Thr Ala Tyr
                485                 490                 495

Thr Gln Val Ser Asn Gln Ala Glu Asp Ser Pro Glu Asn Arg Asn Asn
            500                 505                 510

Gln Pro Leu Arg Asn Gly Ser Tyr Ile Ala Met Ser Pro Val Glu Ala
        515                 520                 525

Gln Lys Cys
    530


<210> SEQ ID NO 62
<211> LENGTH: 478
<212> TYPE: PRT
<213> ORGANISM: Rattus norvegicus

<400> SEQUENCE: 62

Met Ala Arg Cys Cys Phe Tyr Thr Ala Gly Thr Leu Ser Leu Leu Leu
1               5                   10                  15

Leu Val Thr Ser Val Thr Leu Leu Val Ala Arg Val Phe Gln Lys Ala
            20                  25                  30

Val Asp Gln Thr Ile Glu Lys Asn Met Val Leu Gln Asn Gly Thr Lys
        35                  40                  45

Val Phe Asp Ser Trp Glu Lys Pro Pro Leu Pro Val Tyr Ile Gln Phe
    50                  55                  60

Tyr Phe Phe Asn Val Thr Asn Pro Glu Glu Ile Leu Gln Gly Glu Ile
65                  70                  75                  80

Pro Leu Leu Glu Glu Val Gly Pro Tyr Thr Tyr Arg Glu Leu Arg Asn
                85                  90                  95

Lys Ala Asn Val Gln Phe Gly Glu Asn Gly Thr Thr Ile Ser Ala Val
            100                 105                 110

Thr Asn Lys Ala Tyr Ile Phe Glu Arg Asn Gln Ser Val Gly Asp Pro
        115                 120                 125

Thr Val Asp Leu Ile Arg Thr Ile Asn Ile Pro Leu Leu Thr Val Val
    130                 135                 140

Glu Met Ala Gln Gln Pro Phe Leu Arg Glu Ile Ile Glu Ala Met Leu
145                 150                 155                 160

Lys Ala Tyr Gln Gln Thr Leu Phe Val Thr His Thr Val His Glu Leu
                165                 170                 175

Leu Trp Gly Tyr Lys Asp Glu Val Leu Ser Leu Val His Ile Phe Arg
            180                 185                 190

Pro Asp Val Ser Pro Asn Phe Gly Leu Phe Tyr Glu Arg Asn Gly Thr
        195                 200                 205

Asn Asp Gly Glu Tyr Val Phe Leu Thr Gly Glu Asp Asn Tyr Leu Asn
    210                 215                 220

Phe Thr Lys Ile Val Glu Trp Asn Gly Lys Thr Ser Leu Asp Trp Trp
225                 230                 235                 240

Thr Thr Asp Thr Cys Asn Met Ile Asn Gly Thr Asp Gly Asp Ser Phe
                245                 250                 255

His Pro Leu Ile Ser Lys Asp Glu Thr Leu Tyr Ile Phe Pro Ser Asp
            260                 265                 270

Phe Cys Arg Ser Val Tyr Ile Thr Phe Ser Ser Phe Glu Asn Val Glu
```

```
        275                 280                 285

Gly Leu Pro Ala Phe Arg Tyr Lys Val Pro Ala Glu Ile Leu Ala Asn
    290                 295                 300

Ser Ser Glu Asn Ala Gly Phe Cys Ile Pro Glu Gly Asn Cys Met Asp
305                 310                 315                 320

Ala Gly Val Leu Asn Val Ser Ile Cys Lys Asn Gly Ala Pro Ile Ile
                325                 330                 335

Met Ser Phe Pro His Phe Tyr Gln Ala Asp Glu Lys Phe Val Ser Ala
            340                 345                 350

Ile Lys Gly Met Arg Pro Asn Lys Glu Glu His Glu Ser Phe Val Asp
        355                 360                 365

Ile Asn Pro Leu Thr Gly Ile Ile Leu Arg Gly Ala Lys Arg Phe Gln
    370                 375                 380

Ile Asn Thr Tyr Val Lys Lys Leu Asp Asp Phe Val Glu Thr Gly Asn
385                 390                 395                 400

Ile Arg Thr Met Val Phe Pro Val Met Tyr Leu Asn Glu Ser Val Leu
                405                 410                 415

Ile Asp Lys Glu Thr Ala Ser Gln Leu Lys Ser Val Ile Asn Thr Thr
            420                 425                 430

Leu Ile Val Thr Asn Ile Pro Tyr Ile Ile Met Ala Leu Gly Val Phe
        435                 440                 445

Phe Gly Leu Ile Phe Thr Trp Leu Ala Cys Arg Gly Gln Gly Ser Thr
    450                 455                 460

Asp Glu Gly Thr Ala Asp Glu Arg Ala Pro Leu Ile Arg Thr
465                 470                 475


<210> SEQ ID NO 63
<211> LENGTH: 481
<212> TYPE: PRT
<213> ORGANISM: Gallus gallus

<400> SEQUENCE: 63

Met Arg Ser Leu Cys Leu Val Thr Val Gly Val Leu Ala Leu Thr Leu
1               5                   10                  15

Leu Ile Ala Ser Ile Ser Leu Leu Val Ala His Val Phe Gln Thr Val
            20                  25                  30

Val Asp Leu Gln Val Lys Gln Gly Thr Val Leu Lys Asn Gly Thr Glu
        35                  40                  45

Thr Phe Glu Ala Trp Glu Asp Pro Pro Pro Pro Val Tyr Met Gln Phe
    50                  55                  60

Tyr Phe Phe Asn Val Thr Asn Pro Leu Glu Val Leu Gln Gly Ala Thr
65                  70                  75                  80

Pro Leu Val Glu Glu Lys Gly Pro Tyr Thr Tyr Arg Glu Tyr Arg Pro
                85                  90                  95

Arg Val His Val Gln Phe Leu Asp Asn Gly Thr Lys Val Ser Ala Leu
            100                 105                 110

Asn Pro Lys Thr Tyr Val Phe Glu Pro Glu Lys Ser Val Gly Asn Pro
        115                 120                 125

Glu Val Asp Leu Ile Arg Thr Ile Asn Val Pro Ala Val Thr Ala Met
    130                 135                 140

Glu Trp Thr Arg Ala Thr Ser Leu Gln Phe Ala Thr Glu Val Leu Leu
145                 150                 155                 160

Leu Leu Tyr Gln Glu Ser Leu Phe Thr Val Arg Thr Val His Glu Leu
                165                 170                 175
```

```
Leu Trp Gly Tyr Lys Asp Lys Leu Leu Ser Thr Ile His Val Leu His
            180                 185                 190

Pro Glu Ile Asp Pro Val Phe Gly Phe Phe Asn Lys Met Asn Gly Thr
        195                 200                 205

Asp Asp Gly Glu Tyr Val Phe Leu Ser Gly Glu Met Asn Tyr Leu Asn
    210                 215                 220

Phe Ser Arg Ile Val Glu Trp Lys Gly Lys Glu Ser Leu Asn Trp Trp
225                 230                 235                 240

Thr Thr Lys Thr Cys Asn Met Ile Asn Gly Thr Asp Gly Thr Ser Phe
                245                 250                 255

His Pro Leu Ile Ser Lys Asp Glu Asn Ile Tyr Ile Phe Ser Ser Asp
            260                 265                 270

Phe Cys Arg Ser Leu Tyr Leu Val Tyr Asp Ser Ser Gly Ser Val Ala
        275                 280                 285

Gly Val Pro Thr Tyr Arg Phe Val Pro Ser Pro Met Val Phe Ala Asn
    290                 295                 300

Thr Thr Val Asn Pro Asp Asn Ala Gly Phe Cys Val Pro Pro Gly Asn
305                 310                 315                 320

Cys Pro Gly Ala Gly Val Leu Asn Val Ser Ile Cys Lys Gln Gly Ala
                325                 330                 335

Pro Ile Phe Leu Ser Ala Pro His Phe Tyr Gln Ala Asp Gln Lys Phe
            340                 345                 350

Val Ser Asp Ile Glu Gly Met His Pro Thr Lys Glu Tyr His Glu Thr
        355                 360                 365

Phe Val Asp Ile Asn Pro Leu Thr Gly Leu Val Leu Gln Ala Ala Lys
    370                 375                 380

Arg Met Gln Ile Asn Ile His Val Arg Lys Leu Pro Glu Phe Phe Glu
385                 390                 395                 400

Thr Gly Asn Ile Arg Thr Leu Ile Phe Pro Val Met Tyr Ile Asn Glu
                405                 410                 415

Ser Val Leu Ile Asp Glu Ala Ser Ala Asn Lys Leu Lys His Val Leu
            420                 425                 430

Leu Glu Ala Ser Val Val Thr Gly Ile Pro Phe Val Ile Met Ala Ile
        435                 440                 445

Gly Ile Val Phe Gly Ile Val Phe Ser Val Leu Val Cys Arg Ala Gln
    450                 455                 460

Gly Ala Arg Glu Glu Ser Thr Glu Glu Glu Arg Ser Pro Leu Ile Arg
465                 470                 475                 480

Thr


<210> SEQ ID NO 64
<211> LENGTH: 483
<212> TYPE: PRT
<213> ORGANISM: Xenopus tropicalis

<400> SEQUENCE: 64

Met Val Lys Trp Ala Val Phe Gly Thr Ala Ala Val Ser Val Thr Leu
1               5                   10                  15

Leu Ile Val Ser Ile Val Leu Leu Leu Thr His Thr Phe Met Asp Ile
            20                  25                  30

Val Glu Gly Gln Val Lys Gln Ala Ile Val Leu Lys Asn Glu Ser Glu
        35                  40                  45

Val Phe Glu Asp Trp Ala Asn Pro Pro Pro Pro Val Tyr Met Gln Phe
    50                  55                  60
```

```
Tyr Phe Phe Asn Val Thr Asn Pro Leu Glu Val Leu Ser Gly Glu Lys
65                  70                  75                  80

Pro Phe Val Asp Glu Ile Gly Pro Tyr Thr Tyr Arg Glu Tyr Arg Pro
                85                  90                  95

Arg Glu Asn Ile Thr Phe Ser Val Asn Gly Thr Glu Val Ser Ala Val
            100                 105                 110

Thr Pro Lys Thr Tyr Val Phe Glu Pro Glu Lys Ser Ile Gly Asp Pro
        115                 120                 125

Lys Val Asp Leu Ile Arg Thr Val Asn Ile Pro Leu Val Thr Ile Leu
    130                 135                 140

Glu Met Thr Lys Asp Ser Ser Leu Leu Arg Pro Phe Ile Ile Ala Ala
145                 150                 155                 160

Leu Lys Thr Tyr Lys Glu Gly Met Phe Val Thr Arg Thr Val Asp Glu
                165                 170                 175

Leu Leu Trp Gly Tyr Lys Asp Ala Val Leu Ser Ile Leu His Pro Phe
            180                 185                 190

Lys Lys Asn Ile Ser Asp Thr Phe Gly Leu Phe Tyr Lys Met Asn Thr
        195                 200                 205

Thr Asp Asp Gly Glu Tyr Ile Phe Leu Ser Gly Glu Lys Asp Tyr Leu
    210                 215                 220

Glu Phe Thr Gln Ile Ala Glu Trp Lys Gly Gln Lys Ala Leu Asn Trp
225                 230                 235                 240

Trp Thr Thr Glu Thr Cys Asn Met Ile Asn Gly Thr Asp Gly Thr Ser
                245                 250                 255

Phe His Pro Leu Leu Asn Lys Asp Asp Thr Ile Tyr Met Phe Ser Ser
            260                 265                 270

Asp Leu Cys Arg Ser Ile Tyr Ala Val Tyr Glu Ser Ser Glu Asn Ile
        275                 280                 285

Lys Asp Ile Ser Val Phe Arg Phe Ser Pro Pro Ala Ser Val Phe Ala
    290                 295                 300

Asn Val Ser Val Asn Pro Gln Asn Lys Gly Phe Cys Val Pro Glu Gly
305                 310                 315                 320

Asn Cys Leu Pro Ser Gly Leu Leu Asn Val Ser Ile Cys Lys Glu Gly
                325                 330                 335

Ala Pro Ile Val Leu Ser Ser Pro His Phe Tyr Gln Ala Asp Glu Asn
            340                 345                 350

Val Ile Asn Ser Ile Arg Gly Met Lys Pro Val Lys Glu His His Met
        355                 360                 365

Thr Phe Leu Asp Leu Asn Pro Leu Thr Gly Thr Leu Ile Gln Ala Ala
    370                 375                 380

Lys Arg Ile Gln Val Asn Val Tyr Val Arg Lys Ile Asn Val Tyr Leu
385                 390                 395                 400

Ile Thr Gln Asp Ile Gln Thr Leu Phe Phe Pro Val Met His Leu Asn
                405                 410                 415

Glu Ser Val Leu Ile Asp Asp Lys Ser Ala Gly Arg Leu Arg Ser Ile
            420                 425                 430

Leu Phe Gln Gly Arg Val Val Ala Asn Ile Pro Phe Ile Ile Met Gly
        435                 440                 445

Leu Gly Ile Ile Leu Ala Phe Leu Phe Thr Thr Leu Ser Cys Leu Gln
    450                 455                 460

Lys Arg Ser Arg Asp Glu Gly Thr Glu Glu Glu Arg Gly Pro Leu Ile
465                 470                 475                 480

Arg Ala Ser
```

<210> SEQ ID NO 65
<211> LENGTH: 551
<212> TYPE: PRT
<213> ORGANISM: Drosophila melanogaster

<400> SEQUENCE: 65

```
Met Gln Leu Asp Asp Ile Leu His Ile Asn Asn Cys Lys Ala Asp Cys
1               5                   10                  15

Ser Ser Leu Ser Thr Thr Pro Asn Pro Lys Thr Asp Leu Val Asn Met
            20                  25                  30

Asn Gly Pro Lys His Lys Phe Cys Thr Lys Leu Ser Ser Thr Tyr Leu
        35                  40                  45

Arg Lys Trp Trp Ile Thr Ile Val Val Ala Ala Ala Leu Ile Ile Gly
    50                  55                  60

Gly Ile Val Val Ala Cys Glu Phe Thr Val Leu Ile Asp Ala Val Val
65                  70                  75                  80

Asp Arg Met Val Ala Leu Arg Pro Gly Ala Lys Thr Phe Gly Trp Trp
                85                  90                  95

Ala Lys Pro Pro Val Glu Pro Arg Ile Ser Leu Tyr Ile Tyr Asn Val
            100                 105                 110

Thr Asn Ala Asp Asp Phe Leu Ser Asn Gly Ser Lys Ala Ile Val Asp
        115                 120                 125

Glu Val Gly Pro Tyr Val Tyr Ser Glu Thr Trp Glu Lys Val Asn Ile
    130                 135                 140

Val Glu Asn Asp Asn Gly Thr Leu Ser Tyr Asn Leu Arg Lys Ile Tyr
145                 150                 155                 160

Ser Phe Arg Glu Asp Leu Ser Val Gly Pro Glu Asp Asp Val Val Ile
                165                 170                 175

Val Pro Asn Ile Pro Met Leu Ser Ala Thr Ser Gln Ser Lys His Ala
            180                 185                 190

Ala Arg Phe Leu Arg Leu Ala Met Ala Ser Ile Met Asp Ile Leu Lys
        195                 200                 205

Ile Lys Pro Phe Val Gln Val Ser Val Gly Gln Leu Leu Trp Gly Tyr
    210                 215                 220

Glu Asp Pro Leu Leu Lys Leu Ala Lys Asp Val Val Pro Lys Glu Gln
225                 230                 235                 240

Lys Leu Pro Tyr Glu Glu Phe Gly Leu Leu Tyr Gly Lys Asn Gly Thr
                245                 250                 255

Ser Ser Asp Arg Val Thr Val Asn Thr Gly Val Asp Asp Ile Arg Arg
            260                 265                 270

Tyr Gly Ile Ile Asp Asn Phe Asn Gly Arg Thr His Leu Pro His Trp
        275                 280                 285

Thr Thr Asp Ala Cys Asn Thr Leu Ala Gly Thr Asp Gly Ser Ile Phe
    290                 295                 300

Pro Pro His Ile Asp His Asp Arg Ile Leu His Val Tyr Asp Lys Asp
305                 310                 315                 320

Leu Cys Arg Leu Leu Pro Leu Val Phe Glu Lys Glu Val Met Thr Ser
                325                 330                 335

Asn Glu Val Pro Gly Tyr Arg Phe Thr Pro Pro Glu Trp Val Phe Ala
            340                 345                 350

Asp Val Asp Ser His Pro Asp Asn Met Cys Phe Cys Pro Ala Gly Lys
        355                 360                 365

Pro Ser Cys Ser Pro Asn Gly Leu Phe Asn Val Ser Leu Cys Gln Tyr
```

```
    370                 375                 380

Asp Ser Pro Ile Met Leu Ser Phe Pro His Phe Tyr Leu Ala Asp Glu
385                 390                 395                 400

Ser Leu Arg Thr Gln Val Glu Gly Ile Ser Pro Pro Met Lys Glu Lys
                405                 410                 415

His Gln Phe Phe Phe Asp Val Gln Pro Lys Met Gly Thr Thr Leu Arg
            420                 425                 430

Val Arg Ala Arg Ile Gln Ile Asn Leu Ala Val Ser Gln Val Phe Asp
        435                 440                 445

Ile Lys Gln Val Ala Asn Phe Pro Asp Ile Ile Phe Pro Ile Leu Trp
    450                 455                 460

Phe Glu Glu Gly Ile Asp Asn Leu Pro Asp Glu Val Thr Asp Leu Met
465                 470                 475                 480

Arg Phe Ala Glu Gln Val Pro Pro Lys Ile Arg Val Ala Leu Ile Val
                485                 490                 495

Gly Leu Cys Ala Leu Gly Val Ile Leu Leu Leu Leu Ser Thr Phe Cys
            500                 505                 510

Leu Ile Arg Asn Ser His Arg Gln Ser Thr Leu His Leu Glu Gly Ser
        515                 520                 525

Asn Tyr Leu Ala Thr Ala Gln Val Asp Met Asn Lys Lys Gln Asn Lys
    530                 535                 540

Asp Asn Gln Pro Ala Arg Tyr
545                 550


<210> SEQ ID NO 66
<211> LENGTH: 522
<212> TYPE: PRT
<213> ORGANISM: Anopheles gambiae
<220> FEATURE:
<223> OTHER INFORMATION: str. PEST

<400> SEQUENCE: 66

Met Tyr Gly Arg Ser Asn Arg Leu Cys Ala Lys Leu Ser Ser Ala Phe
1               5                   10                  15

Leu Arg Lys Trp Trp Phe Val Ile Ala Phe Ala Leu Ser Leu Leu Val
            20                  25                  30

Leu Gly Ala Leu Val Thr Phe Gly Phe Thr Ala Phe Ile Arg Thr Ile
        35                  40                  45

Ile Asp His Gln Val Ala Leu Arg Val Gly Gly Gln Ser Phe Gly Trp
    50                  55                  60

Trp Ser Arg Pro Pro Val Glu Pro Ile Ile Arg Ile Phe Val Tyr Asn
65                  70                  75                  80

Val Thr Asn Ala Asp Glu Phe Leu Asn Asn Gly Thr Lys Pro Ile Leu
                85                  90                  95

Asp Glu Leu Gly Pro Tyr Val Tyr Val Gln Thr Trp Glu Lys Val Asn
            100                 105                 110

Ile Lys Glu Asn Pro Asn Gly Thr Ile Ser Tyr Asn Gln Lys Arg Val
        115                 120                 125

Tyr Ile Phe Asn Glu Asp Leu Ser Gly Gly Leu Glu Asp Asp Val Val
    130                 135                 140

Ile Val Pro Asn Ile Pro Met Leu Ser Ala Thr Ser Gln Ser Lys His
145                 150                 155                 160

Ala Ala Arg Phe Leu Arg Leu Ala Met Ala Ser Ile Met Asp Ile Leu
                165                 170                 175

Lys Ile Lys Pro Phe Val Glu Val Ser Val Gly Gln Leu Leu Trp Gly
```

```
            180                 185                 190

Tyr Glu Asp Pro Leu Leu Lys Leu Ala Lys Asp Val Val Pro Lys Glu
        195                 200                 205

Gln Lys Leu Pro Tyr Glu Glu Phe Gly Leu Met Tyr Gly Lys Asn Ser
    210                 215                 220

Thr Ser Lys Asp Thr Val Thr Val Trp Thr Gly Val Asp Asp Ile Thr
225                 230                 235                 240

Gln Tyr Gly Ile Ile Asp Lys Tyr Asn Gly Arg Ser His Gln Thr His
                245                 250                 255

Trp Leu Ser Glu Gln Cys Asn Arg Leu Asn Gly Thr Asp Gly Ser Ile
            260                 265                 270

Phe Pro Pro Arg Ile Thr Lys Asn Ser Thr Leu His Val Tyr Glu Lys
        275                 280                 285

Asp Leu Cys Arg Leu Leu Pro Leu Ser Phe Glu Lys Glu Val Thr Val
    290                 295                 300

Arg Gly Gly Val Lys Gly Tyr Arg Phe Thr Pro Ser Pro Asp Val Phe
305                 310                 315                 320

Ala Ser Val Asp Lys Asn Pro Asn Asn Met Cys Tyr Cys Pro Ala Gly
                325                 330                 335

Pro Pro Cys Ala Pro His Gly Leu Phe Asn Val Ser Leu Cys Gln Tyr
            340                 345                 350

Asp Ser Pro Ile Leu Leu Ser Phe Pro His Phe Tyr Met Ala Asp Gln
        355                 360                 365

Thr Leu Arg Thr Ala Val Glu Gly Ile Ser Pro Pro Glu Lys Asp Lys
    370                 375                 380

His Gln Leu Phe Ile Asp Val Gln Pro Asp Met Gly Thr Ala Leu Arg
385                 390                 395                 400

Ala Arg Ala Arg Ile Gln Ile Asn Leu Ala Val Ser Gln Val Val Asp
                405                 410                 415

Ile Lys Gln Val Ala Asn Phe Pro Asp Ile Val Phe Pro Ile Leu Trp
            420                 425                 430

Phe Glu Glu Gly Ile Asp Ser Leu Pro Asp Glu Ile Leu Asp Leu Met
        435                 440                 445

Lys Val Ala Thr Asn Ile Pro Pro Arg Ala Lys Phe Ile Leu Thr Ile
    450                 455                 460

Ala Leu Phe Gly Leu Gly Gly Phe Leu Phe Val Val Ala Val Ile Cys
465                 470                 475                 480

Leu Val Arg Lys Ser His Arg Gln Ser Thr Leu His Leu Glu Gly Ser
                485                 490                 495

Asn Tyr Leu Ala Thr Ala Ser Val Asp Gln Ala Lys Lys Lys Ala Lys
            500                 505                 510

Met Asp Asn Gly Met Ser Ser Lys Ser Asn
        515                 520


<210> SEQ ID NO 67
<211> LENGTH: 338
<212> TYPE: PRT
<213> ORGANISM: Homo sapiens

<400> SEQUENCE: 67

Met Val Arg Arg Val Gln Pro Asp Arg Lys Gln Leu Pro Leu Val Leu
1               5                   10                  15

Leu Arg Leu Leu Cys Leu Leu Pro Thr Gly Leu Pro Val Arg Ser Val
            20                  25                  30
```

```
Asp Phe Asn Arg Gly Thr Asp Asn Ile Thr Val Arg Gln Gly Asp Thr
        35                  40                  45

Ala Ile Leu Arg Cys Val Val Glu Asp Lys Asn Ser Lys Val Ala Trp
    50                  55                  60

Leu Asn Arg Ser Gly Ile Ile Phe Ala Gly His Asp Lys Trp Ser Leu
65                  70                  75                  80

Asp Pro Arg Val Glu Leu Glu Lys Arg His Ser Leu Glu Tyr Ser Leu
                85                  90                  95

Arg Ile Gln Lys Val Asp Val Tyr Asp Glu Gly Ser Tyr Thr Cys Ser
            100                 105                 110

Val Gln Thr Gln His Glu Pro Lys Thr Ser Gln Val Tyr Leu Ile Val
        115                 120                 125

Gln Val Pro Pro Lys Ile Ser Asn Ile Ser Ser Asp Val Thr Val Asn
    130                 135                 140

Glu Gly Ser Asn Val Thr Leu Val Cys Met Ala Asn Gly Arg Pro Glu
145                 150                 155                 160

Pro Val Ile Thr Trp Arg His Leu Thr Pro Thr Gly Arg Glu Phe Glu
                165                 170                 175

Gly Glu Glu Glu Tyr Leu Glu Ile Leu Gly Ile Thr Arg Glu Gln Ser
            180                 185                 190

Gly Lys Tyr Glu Cys Lys Ala Ala Asn Glu Val Ser Ser Ala Asp Val
        195                 200                 205

Lys Gln Val Lys Val Thr Val Asn Tyr Pro Pro Thr Ile Thr Glu Ser
    210                 215                 220

Lys Ser Asn Glu Ala Thr Thr Gly Arg Gln Ala Ser Leu Lys Cys Glu
225                 230                 235                 240

Ala Ser Ala Val Pro Ala Pro Asp Phe Glu Trp Tyr Arg Asp Asp Thr
                245                 250                 255

Arg Ile Asn Ser Ala Asn Gly Leu Glu Ile Lys Ser Thr Glu Gly Gln
            260                 265                 270

Ser Ser Leu Thr Val Thr Asn Val Thr Glu Glu His Tyr Gly Asn Tyr
        275                 280                 285

Thr Cys Val Ala Ala Asn Lys Leu Gly Val Thr Asn Ala Ser Leu Val
    290                 295                 300

Leu Phe Arg Pro Gly Ser Val Arg Gly Ile Asn Gly Ser Ile Ser Leu
305                 310                 315                 320

Ala Val Pro Leu Trp Leu Leu Ala Ala Ser Leu Leu Cys Leu Leu Ser
                325                 330                 335

Lys Cys


<210> SEQ ID NO 68
<211> LENGTH: 338
<212> TYPE: PRT
<213> ORGANISM: Pan troglodytes

<400> SEQUENCE: 68

Met Val Arg Arg Val Gln Pro Asp Arg Lys Gln Leu Pro Leu Val Leu
1               5                   10                  15

Leu Arg Leu Leu Cys Leu Leu Pro Thr Gly Leu Pro Val Arg Ser Val
            20                  25                  30

Asp Phe Asn Arg Gly Thr Asp Asn Ile Thr Val Arg Gln Gly Asp Thr
        35                  40                  45

Ala Ile Leu Arg Cys Val Val Glu Asp Lys Asn Ser Lys Val Ala Trp
    50                  55                  60
```

```
Leu Asn Arg Ser Gly Ile Ile Phe Ala Gly His Asp Lys Trp Ser Leu
65                  70                  75                  80

Asp Pro Arg Val Glu Leu Glu Lys Arg His Ser Leu Glu Tyr Ser Leu
                85                  90                  95

Arg Ile Gln Lys Val Asp Val Tyr Asp Glu Gly Ser Tyr Thr Cys Ser
            100                 105                 110

Val Gln Thr Gln His Glu Pro Lys Thr Ser Gln Val Tyr Leu Ile Val
        115                 120                 125

Gln Val Pro Pro Lys Ile Ser Asn Ile Ser Ser Asp Val Thr Val Asn
    130                 135                 140

Glu Gly Ser Asn Val Thr Leu Val Cys Met Ala Asn Gly Arg Pro Glu
145                 150                 155                 160

Pro Val Ile Thr Trp Arg His Leu Thr Pro Thr Gly Arg Glu Phe Glu
                165                 170                 175

Gly Glu Glu Glu Tyr Leu Glu Ile Leu Gly Ile Thr Arg Glu Gln Ser
            180                 185                 190

Gly Lys Tyr Glu Cys Lys Ala Ala Asn Glu Val Ser Ser Ala Asp Val
        195                 200                 205

Lys Gln Val Lys Val Thr Val Asn Tyr Pro Pro Thr Ile Thr Glu Ser
    210                 215                 220

Lys Ser Asn Glu Ala Thr Thr Gly Arg Gln Ala Ser Leu Lys Cys Glu
225                 230                 235                 240

Ala Ser Ala Val Pro Ala Pro Asp Phe Glu Trp Tyr Arg Asp Asp Thr
                245                 250                 255

Arg Ile Asn Ser Ala Asn Gly Leu Glu Ile Lys Ser Thr Glu Gly Gln
            260                 265                 270

Ser Ser Leu Thr Val Thr Asn Val Thr Glu Glu His Tyr Gly Asn Tyr
        275                 280                 285

Thr Cys Val Ala Ala Asn Lys Leu Gly Val Thr Asn Ala Ser Leu Val
    290                 295                 300

Leu Phe Arg Pro Gly Ser Val Arg Gly Ile Asn Gly Ser Ile Ser Leu
305                 310                 315                 320

Ala Val Pro Leu Trp Leu Leu Ala Ala Ser Leu Leu Cys Leu Leu Ser
                325                 330                 335

Lys Cys


<210> SEQ ID NO 69
<211> LENGTH: 338
<212> TYPE: PRT
<213> ORGANISM: Oryctolagus cuniculus

<400> SEQUENCE: 69

Met Gly Ala Arg Val Gln Pro Asp Arg Lys Gln Leu Pro Leu Val Leu
1               5                   10                  15

Leu Arg Leu Leu Cys Leu Leu Pro Thr Gly Leu Pro Val Arg Ser Val
            20                  25                  30

Asp Phe Asn Arg Gly Thr Asp Asn Ile Thr Val Arg Gln Gly Asp Thr
        35                  40                  45

Ala Ile Leu Arg Cys Val Val Glu Asp Lys Asn Ser Lys Val Ala Trp
    50                  55                  60

Leu Asn Arg Ser Gly Ile Ile Phe Ala Gly His Asp Lys Trp Ser Leu
65                  70                  75                  80

Asp Pro Arg Val Glu Leu Glu Lys Arg His Ser Leu Glu Tyr Ser Leu
                85                  90                  95
```

```
Arg Ile Gln Lys Val Asp Val Tyr Asp Glu Gly Ser Tyr Thr Cys Ser
            100                 105                 110

Val Gln Thr Gln His Glu Pro Lys Thr Ser Gln Val Tyr Leu Ile Val
        115                 120                 125

Gln Val Pro Pro Lys Ile Ser Asn Ile Ser Ser Asp Val Thr Val Asn
    130                 135                 140

Glu Gly Ser Asn Val Thr Leu Val Cys Met Ala Asn Gly Arg Pro Glu
145                 150                 155                 160

Pro Val Ile Thr Trp Arg His Leu Thr Pro Thr Gly Arg Glu Phe Glu
                165                 170                 175

Gly Glu Glu Glu Tyr Leu Glu Ile Leu Gly Ile Thr Arg Glu Gln Ser
            180                 185                 190

Gly Lys Tyr Glu Cys Lys Ala Ala Asn Glu Val Ser Ser Ala Asp Val
        195                 200                 205

Lys Gln Val Lys Val Thr Val Asn Tyr Pro Pro Thr Ile Thr Glu Ser
    210                 215                 220

Lys Ser Asn Glu Ala Thr Thr Gly Arg Gln Ala Ser Leu Lys Cys Glu
225                 230                 235                 240

Ala Ser Ala Val Pro Ala Pro Asp Phe Glu Trp Tyr Arg Asp Asp Thr
                245                 250                 255

Arg Ile Asn Ser Ala Asn Gly Leu Glu Ile Lys Ser Thr Glu Gly Gln
            260                 265                 270

Ser Ser Leu Thr Val Thr Asn Val Thr Glu Glu His Tyr Gly Asn Tyr
        275                 280                 285

Thr Cys Val Ala Ala Asn Lys Leu Gly Val Thr Asn Ala Ser Leu Val
    290                 295                 300

Leu Phe Arg Pro Gly Ser Val Arg Gly Ile Asn Gly Ser Ile Ser Leu
305                 310                 315                 320

Ala Val Pro Leu Trp Leu Leu Ala Ala Ser Leu Leu Cys Leu Leu Ser
                325                 330                 335

Lys Cys


<210> SEQ ID NO 70
<211> LENGTH: 341
<212> TYPE: PRT
<213> ORGANISM: Mus musculus

<400> SEQUENCE: 70

Met Val Gly Arg Val Gln Pro Asp Arg Lys Gln Leu Pro Leu Val Leu
1               5                   10                  15

Leu Arg Leu Leu Cys Leu Leu Pro Thr Gly Leu Pro Val Arg Ser Val
            20                  25                  30

Asp Phe Asn Arg Gly Thr Asp Asn Ile Thr Val Arg Gln Gly Asp Thr
        35                  40                  45

Ala Ile Leu Arg Cys Val Val Glu Asp Lys Asn Ser Lys Val Ala Trp
    50                  55                  60

Leu Asn Arg Ser Gly Ile Ile Phe Ala Gly His Asp Lys Trp Ser Leu
65                  70                  75                  80

Asp Pro Arg Val Glu Leu Glu Lys Arg His Ala Leu Glu Tyr Ser Leu
                85                  90                  95

Arg Ile Gln Lys Val Asp Val Tyr Asp Glu Gly Ser Tyr Thr Cys Ser
            100                 105                 110

Val Gln Thr Gln His Glu Pro Lys Thr Ser Gln Val Tyr Leu Ile Val
        115                 120                 125
```

```
Gln Val Pro Pro Lys Ile Ser Asn Ile Ser Ser Asp Val Thr Val Asn
    130                 135                 140

Glu Gly Ser Asn Val Thr Leu Val Cys Met Ala Asn Gly Arg Pro Glu
145                 150                 155                 160

Pro Val Ile Thr Trp Arg His Leu Thr Pro Leu Gly Arg Glu Phe Glu
                165                 170                 175

Gly Glu Glu Glu Tyr Leu Glu Ile Leu Gly Ile Thr Arg Glu Gln Ser
            180                 185                 190

Gly Lys Tyr Glu Cys Lys Ala Ala Asn Glu Val Ser Ser Ala Asp Val
        195                 200                 205

Lys Gln Val Lys Val Thr Val Asn Tyr Pro Pro Thr Ile Thr Glu Ser
    210                 215                 220

Lys Ser Asn Glu Ala Thr Thr Gly Arg Gln Ala Ser Leu Lys Cys Glu
225                 230                 235                 240

Ala Ser Ala Val Pro Ala Pro Asp Phe Glu Trp Tyr Arg Asp Asp Thr
                245                 250                 255

Arg Ile Asn Ser Ala Asn Gly Leu Glu Ile Lys Ser Thr Glu Gly Gln
            260                 265                 270

Ser Ser Leu Thr Val Thr Asn Val Thr Glu Glu His Tyr Gly Asn Tyr
        275                 280                 285

Thr Cys Val Ala Ala Asn Lys Leu Gly Val Thr Asn Ala Ser Leu Val
    290                 295                 300

Leu Phe Ser Lys Tyr Ala Lys Thr Glu Pro Asp Ser Met Gln Val Ile
305                 310                 315                 320

Glu Phe Leu His Ile Asp Leu Lys Ser Ile Arg His Pro Leu Lys Val
                325                 330                 335

Asn Pro Ile Gln Lys
            340
```

<210> SEQ ID NO 71
<211> LENGTH: 337
<212> TYPE: PRT
<213> ORGANISM: Xenopus laevis

<400> SEQUENCE: 71

```
Met Val Gly Arg Ser Gln Ser Asp Arg Asn Gln Leu Pro Leu Phe Leu
1               5                   10                  15

Leu Arg Leu Leu Cys Leu Leu Pro Thr Gly Leu Pro Val Arg Ser Gly
            20                  25                  30

Asp Phe Asn Arg Ser Thr Asp Asn Met Thr Val Arg Gln Gly Asp Thr
        35                  40                  45

Ala Ile Leu Arg Cys Phe Val Glu Asp Lys Ser Ser Lys Val Ala Trp
    50                  55                  60

Leu Asn Arg Ser Gly Ile Ile Phe Ala Val Asp Asp Lys Trp Ser Leu
65                  70                  75                  80

Asp Pro Arg Val Glu Leu Glu Lys Arg Ser Pro Phe Glu Tyr Ser Leu
                85                  90                  95

Arg Ile Gln Lys Val Asp Val Ser Asp Glu Gly Pro Tyr Ile Cys Ser
            100                 105                 110

Val Gln Thr Asn Gln His Thr Lys Thr Met Gln Val Tyr Leu Ile Val
        115                 120                 125

Gln Val Pro Pro Lys Ile Ser Asn Ile Ser Ala Asp Ile Thr Val Asn
    130                 135                 140

Glu Gly Ser Asn Val Thr Leu Met Cys Ile Ala Tyr Gly Arg Pro Glu
145                 150                 155                 160
```

```
Pro Met Ile Thr Trp Arg His Leu Thr Pro Thr Ala Arg Asp Phe Glu
                165                 170                 175

Gly Glu Glu Glu Phe Leu Glu Ile Gln Gly Ile Thr Arg Glu Gln Ser
            180                 185                 190

Gly Arg Tyr Glu Cys Lys Ala Ala Asn Glu Val Ala Ser Ala Asp Val
        195                 200                 205

Lys Gln Val Arg Val Thr Val Asn Tyr Pro Pro Ile Ile Thr Glu Ser
    210                 215                 220

Asn Ser Asn Glu Ala Thr Thr Gly Lys Gln Ala Ile Leu Arg Cys Glu
225                 230                 235                 240

Ala Ser Ala Val Pro Ala Pro Asp Phe Glu Trp Tyr Lys Asp Asp Thr
                245                 250                 255

Arg Ile Asn Ser Ala Gln Gly Leu Glu Ile Arg Asn Thr Gly Ser Arg
            260                 265                 270

Ser Val Leu Met Val Ala Asn Val Thr Glu Glu His Tyr Gly Asn Tyr
        275                 280                 285

Thr Cys Val Ala Ala Asn Lys Leu Gly Ile Thr Asn Thr Ser Leu Tyr
    290                 295                 300

Leu Tyr Ile Gly Pro Gly Thr Pro Ile Asp Asn Ala Thr Ser Leu Ala
305                 310                 315                 320

Ala Ser Leu Trp Leu Met Ala Asn Ile Leu Leu Cys Leu Phe Cys Thr
                325                 330                 335

Cys


<210> SEQ ID NO 72
<211> LENGTH: 333
<212> TYPE: PRT
<213> ORGANISM: Danio rerio

<400> SEQUENCE: 72

Met Ser Cys Leu Trp Ile His Ser Val Phe Ile Pro Gly Phe Phe Leu
1               5                   10                  15

Leu Phe Gly Phe Glu Gly Phe Pro Val Ile Ser Val Glu Ser Gln Arg
            20                  25                  30

Ser Thr Asp Asn Ile Thr Ile Arg Gln Gly Asp Thr Thr Val Ile Arg
        35                  40                  45

Cys Tyr Val Asp Asp Lys Val Ser Lys Val Ala Trp Leu Asn Arg Ser
    50                  55                  60

Asn Ile Ile Phe Ala Gly Glu Asp Lys Trp Ser Leu Asp Pro Arg Val
65                  70                  75                  80

Glu Leu Val Thr Gln Gly Gln Leu Glu Tyr Ser Leu Arg Ile Gln Lys
                85                  90                  95

Val Asp Val Phe Asp Glu Gly Pro Tyr Thr Cys Ser Ile Gln Thr Lys
            100                 105                 110

Gln Gln Ser Lys Thr Ser Gln Val Tyr Leu Ile Val Gln Val Pro Ala
        115                 120                 125

Ile Ile Tyr Lys Val Ser Glu Asp Ile Thr Val Asn Glu Gly Ser Asn
    130                 135                 140

Val Ala Leu Thr Cys Leu Ala Asn Gly Arg Pro Asp Pro Ala Ile Thr
145                 150                 155                 160

Trp Arg Leu Leu Asn Pro Ser Ala Glu Ala Leu Asp Val Gly Glu Tyr
                165                 170                 175

Leu Glu Ile Ser Gly Val Val Arg Ser Gln Ala Gly Arg Tyr Glu Cys
            180                 185                 190
```

```
Lys Ala Ser Asn Asp Val Ser Thr Pro Asp Val Lys Tyr Val Asn Val
        195                 200                 205

Val Val Asn Tyr Pro Pro Tyr Ile Lys Asp Val Arg Ser Ser Glu Thr
    210                 215                 220

Ala Val Gly Gln Ala Gly Val Leu His Cys Glu Ala Ser Ala Val Pro
225                 230                 235                 240

Gln Pro Glu Phe Glu Trp Tyr Arg Asp Glu Arg Arg Leu Ser Ser Ser
                245                 250                 255

Gln Ser Leu Thr Ile Gln Val Ser Gly Ser Arg Thr Val Leu Val Val
            260                 265                 270

Ala Asn Val Thr Glu Glu Asp Tyr Gly Asn Tyr Thr Cys Val Ala Thr
        275                 280                 285

Asn Arg Leu Gly Val His Asn Ala Ser Val Phe Leu Tyr Lys Pro Gly
    290                 295                 300

Met Gly Arg Asp Ile Asn Ser Ala Gly Cys Ile Cys Gln Ser Leu Trp
305                 310                 315                 320

Leu Leu Leu Leu Cys Val Ser Ser Ala Leu Leu Gln Cys
                325                 330


<210> SEQ ID NO 73
<211> LENGTH: 197
<212> TYPE: PRT
<213> ORGANISM: Mus musculus

<400> SEQUENCE: 73

Met Ser Gly Ser Ser Arg Arg Leu Leu Trp Ala Ala Thr Cys Leu Ala
1               5                   10                  15

Val Leu Cys Val Ser Ala Ala Gln Pro Asn Ile Thr Thr Leu Ala Pro
            20                  25                  30

Asn Val Thr Glu Val Pro Thr Thr Thr Thr Lys Val Val Pro Thr Thr
        35                  40                  45

Gln Met Pro Thr Val Leu Pro Glu Thr Cys Ala Ser Phe Asn Ser Cys
    50                  55                  60

Val Ser Cys Val Asn Ala Thr Phe Thr Asn Asn Ile Thr Cys Phe Trp
65                  70                  75                  80

Leu His Cys Gln Glu Ala Asn Lys Thr Tyr Cys Ala Asn Glu Pro Leu
                85                  90                  95

Ser Asn Cys Ser Gln Val Asn Arg Thr Asp Leu Cys Ser Val Ile Pro
            100                 105                 110

Pro Thr Thr Pro Val Pro Thr Asn Ser Thr Ala Lys Pro Thr Thr Arg
        115                 120                 125

Pro Ser Ser Pro Thr Pro Thr Pro Ser Val Val Thr Ser Ala Gly Thr
    130                 135                 140

Thr Asn Thr Thr Leu Thr Pro Thr Ser Gln Pro Glu Arg Lys Ser Thr
145                 150                 155                 160

Phe Asp Ala Ala Ser Phe Ile Gly Gly Ile Val Leu Val Leu Gly Val
                165                 170                 175

Gln Ala Val Ile Phe Phe Leu Tyr Lys Phe Cys Lys Ser Lys Glu Arg
            180                 185                 190

Asn Tyr His Thr Leu
        195


<210> SEQ ID NO 74
<211> LENGTH: 197
<212> TYPE: PRT
```

<213> ORGANISM: Macaca mulatta

<400> SEQUENCE: 74

```
Met Ser Arg Leu Ser Arg Ser Leu Leu Trp Ala Val Thr Cys Leu Ala
1               5                   10                  15

Val Leu Cys Val Leu Ser Ala Glu Glu Asn Pro Thr Pro His Thr Asn
            20                  25                  30

Val Thr Ser Leu Ala Pro Thr Ser Asn Ile Thr Ser Ala Pro Val Thr
        35                  40                  45

Ser Leu Pro Leu Val Thr Thr Pro Ala Pro Glu Thr Cys Glu Gly Arg
    50                  55                  60

Asn Ser Cys Val Ser Cys Phe Asn Ala Ser Thr Val Asn Thr Thr Cys
65                  70                  75                  80

Phe Trp Ile Glu Cys Lys Asp Glu Ser Tyr Cys Ser His Asn Ser Thr
                85                  90                  95

Val Ser Asp Cys Gln Val Gly Asn Thr Thr Asp Phe Cys Ser Val Pro
            100                 105                 110

Thr Ala Thr Leu Val Pro Thr Ala Asn Ser Thr Ala Lys Pro Thr Val
        115                 120                 125

Gln Pro Ser Pro Ser Thr Thr Ser Lys Thr Val Thr Thr Ser Gly Thr
    130                 135                 140

Thr Asn Thr Thr Val Thr Pro Thr Ser Gln Pro Val Arg Lys Ser Thr
145                 150                 155                 160

Phe Asp Ala Ala Ser Phe Ile Gly Gly Ile Val Leu Val Leu Gly Val
                165                 170                 175

Gln Ala Val Ile Phe Phe Leu Tyr Lys Phe Cys Lys Ser Lys Glu Arg
            180                 185                 190

Asn Tyr His Thr Leu
        195
```

<210> SEQ ID NO 75
<211> LENGTH: 194
<212> TYPE: PRT
<213> ORGANISM: Sus scrofa

<400> SEQUENCE: 75

```
Met Leu Gly Leu Ser Arg Gln Leu Leu Trp Ala Val Gly Cys Leu Ala
1               5                   10                  15

Ala Leu Cys Val Leu Thr Ala Ala Lys Asn Ser Thr Ile Leu Pro Pro
            20                  25                  30

Ser Thr Thr Thr Pro Trp Leu Ser Pro Pro Thr Thr Gln Thr Thr Ser
        35                  40                  45

Ala Pro Pro Lys Thr Leu Pro Thr Pro Ala Pro Glu Ile Cys Glu Asn
    50                  55                  60

Arg Asn Ser Cys Ile Ser Cys Phe Asp Ala Asn Asn Thr Cys Phe Trp
65                  70                  75                  80

Ile Glu Cys Lys Gly Lys Ser Tyr Cys Ser Asp Asn Ser Thr Val Ser
                85                  90                  95

Asp Cys His Val Val Asn Gly Thr Asp Phe Cys Ser Gly Pro Thr Val
            100                 105                 110

Thr Pro Leu Pro Thr Asn Ser Thr Ala Lys Thr Thr Thr Leu Pro Ser
        115                 120                 125

Pro Ser Ser Ala Ser Thr Thr Ala Thr Thr Ser Gly Thr Thr Asn Thr
    130                 135                 140

Thr Leu Ala Pro Thr Thr Gln Pro Met Arg Lys Ser Thr Phe Asp Ala
```

```
145                 150                 155                 160

Ala Ser Phe Ile Gly Gly Ile Val Leu Val Leu Gly Val Gln Ala Val
                165                 170                 175

Ile Phe Phe Leu Tyr Lys Phe Cys Lys Ser Lys Glu Arg Asn Tyr His
            180                 185                 190

Thr Leu


<210> SEQ ID NO 76
<211> LENGTH: 198
<212> TYPE: PRT
<213> ORGANISM: Bos taurus

<400> SEQUENCE: 76

Met Ser Gly Leu Ser Arg Pro Leu Leu Leu Ala Val Gly Cys Leu Ala
1               5                   10                  15

Ala Leu Cys Val Ile Thr Ala Ala Gly Asn Thr Thr Leu Ala Pro Asn
            20                  25                  30

Val Thr Thr Ala Ser Ser Pro Pro Pro Thr Thr Thr Thr Val Pro Val
        35                  40                  45

Ser Pro Thr Thr Leu Ser Pro Leu Pro Val Thr Thr Pro Ala Pro Asp
    50                  55                  60

Ile Cys Gly Ser Arg Asn Ser Cys Val Ser Cys Val Asp Gly Asn Ala
65                  70                  75                  80

Thr Cys Phe Trp Ile Glu Cys Lys Gly Lys Ser Tyr Cys Ser Asp Asn
                85                  90                  95

Ser Thr Ala Gly Asp Cys Lys Val Val Asn Thr Thr Gly Phe Cys Ser
            100                 105                 110

Val Pro Thr Thr Thr Pro Thr Pro Thr Asn Ser Thr Ala Lys Thr Thr
        115                 120                 125

Thr Leu Pro Ser Thr Thr Thr Thr Ser Thr Thr Ala Thr Thr Ser Gly
    130                 135                 140

Thr Thr Asn Thr Thr Leu Ser Pro Thr Ile Gln Pro Thr Arg Lys Ser
145                 150                 155                 160

Thr Phe Asp Ala Ala Ser Phe Ile Gly Gly Ile Val Leu Val Leu Gly
                165                 170                 175

Val Gln Ala Val Ile Phe Phe Leu Tyr Lys Phe Cys Lys Ser Lys Glu
            180                 185                 190

Arg Asn Tyr His Thr Leu
        195


<210> SEQ ID NO 77
<211> LENGTH: 198
<212> TYPE: PRT
<213> ORGANISM: Ovis aries

<400> SEQUENCE: 77

Met Ser Gly Leu Ser Arg Pro Leu Leu Leu Ala Val Gly Tyr Leu Ala
1               5                   10                  15

Ala Leu Cys Val Ile Thr Ala Ala Arg Asn Thr Thr Val Thr Pro Asn
            20                  25                  30

Val Thr Thr Pro Ser Ser Pro Pro Pro Thr Thr Ala Thr Val Pro Val
        35                  40                  45

Ser Pro Thr Thr Leu Thr Pro Pro Pro Val Thr Thr Pro Ala Pro Asp
    50                  55                  60

Ile Cys Gly Ser Arg Asn Ser Cys Ile Ser Cys Val Asp Gly Asn Ala
65                  70                  75                  80
```

```
Thr Cys Phe Trp Ile Glu Cys Lys Gly Lys Ser Tyr Cys Ser Asp Asn
                85                  90                  95

Ser Thr Val Ser Asp Cys Lys Val Val Asn Thr Thr Gly Phe Cys Ala
            100                 105                 110

Val Pro Thr Thr Thr Pro Thr Pro Thr Asn Ser Thr Ala Lys Thr Thr
        115                 120                 125

Thr Leu Pro Ser Thr Thr Thr Thr Ser Thr Thr Ala Thr Thr Ser Gly
    130                 135                 140

Thr Ala Asn Thr Thr Leu Thr Pro Thr Ile Gln Pro Met Arg Lys Ser
145                 150                 155                 160

Thr Phe Asp Ala Ala Ser Phe Ile Gly Gly Ile Val Leu Val Leu Gly
                165                 170                 175

Val Gln Ala Val Ile Phe Phe Leu Tyr Lys Phe Cys Lys Ser Lys Glu
            180                 185                 190

Arg Asn Tyr His Thr Leu
        195


<210> SEQ ID NO 78
<211> LENGTH: 198
<212> TYPE: PRT
<213> ORGANISM: Canis lupus familiaris

<400> SEQUENCE: 78

Met Ser Gly Leu Ser Arg Gln Leu Cys Trp Ala Ala Ala Cys Leu Ala
1               5                   10                  15

Ala Leu Cys Ala Leu Thr Ala Ala Gln Ser Phe Ser Ser Asp Pro Asn
            20                  25                  30

Gly Thr Thr Thr Thr Thr Gln Ala Thr Thr Asp Ala Ala Thr Thr Arg
        35                  40                  45

Val Thr Thr Ala Ala Pro Ala Thr Thr Pro Ala Pro Asp Pro Cys Asp
    50                  55                  60

Asn Arg Asn Ser Cys Val Ser Cys Val Asn Thr Ser Val Asp Ala Thr
65                  70                  75                  80

Ala Cys Ser Trp Ile Glu Cys Lys Glu Lys Ser Tyr Cys Ser His Asn
                85                  90                  95

Thr Thr Val Ser Asp Cys Gln Val Val Asn Ser Thr Gln Leu Cys Ser
            100                 105                 110

Ala Pro Glu Pro Thr Met Met Pro Thr Asn Ser Thr Ala Lys Thr Thr
        115                 120                 125

Thr Gln Pro Ser Ser Ser Thr Ala Thr Thr Thr Ala Thr Thr Ser Gly
    130                 135                 140

Thr Thr Asn Ile Thr Leu Ser Pro Thr Ser Gln Pro Gly Arg Lys Ser
145                 150                 155                 160

Thr Phe Asp Ala Ala Ser Phe Ile Gly Gly Ile Val Leu Ile Leu Gly
                165                 170                 175

Val Gln Ala Val Ile Phe Phe Leu Tyr Lys Phe Cys Lys Ser Lys Glu
            180                 185                 190

Arg Asn Tyr His Thr Leu
        195


<210> SEQ ID NO 79
<211> LENGTH: 195
<212> TYPE: PRT
<213> ORGANISM: Rattus norvegicus

<400> SEQUENCE: 79
```

```
Met Ser Gly Ala Ser Arg Gly Leu Phe Trp Ala Ala Thr Cys Leu Ala
1               5                   10                  15

Ala Leu Cys Leu Ser Ala Ala Gln Ser Asn Ser Ser Ala Ser Pro Asn
            20                  25                  30

Val Thr Asp Pro Pro Thr Thr Thr Ser Lys Val Val Pro Thr Thr Leu
        35                  40                  45

Thr Thr Thr Lys Pro Pro Glu Thr Cys Glu Ser Phe Asn Ser Cys Val
    50                  55                  60

Ser Cys Val Asn Ala Thr Leu Thr Asn Asn Ile Thr Cys Val Trp Leu
65                  70                  75                  80

Asp Cys His Glu Ala Asn Lys Thr Tyr Cys Ser Ser Glu Leu Val Ser
                85                  90                  95

Asn Cys Thr Gln Lys Thr Ser Thr Asp Ser Cys Ser Val Ile Pro Thr
            100                 105                 110

Thr Pro Val Pro Thr Asn Ser Thr Ala Lys Pro Thr Thr Arg Pro Ser
        115                 120                 125

Ser Pro Thr Pro Thr Pro Ser Val Val Thr Ser Ala Gly Ala Thr Asn
    130                 135                 140

Thr Thr Val Thr Pro Thr Ser Gln Pro Glu Arg Lys Ser Thr Phe Asp
145                 150                 155                 160

Ala Ala Ser Phe Ile Gly Gly Ile Val Leu Val Leu Gly Val Gln Ala
                165                 170                 175

Val Ile Phe Phe Leu Tyr Lys Phe Cys Lys Ser Lys Glu Arg Asn Tyr
            180                 185                 190

His Thr Leu
        195


<210> SEQ ID NO 80
<211> LENGTH: 354
<212> TYPE: PRT
<213> ORGANISM: Homo sapiens

<400> SEQUENCE: 80

Met Arg Leu Ala Val Leu Phe Ser Gly Ala Leu Leu Gly Leu Leu Ala
1               5                   10                  15

Ala Gln Gly Thr Gly Asn Asp Cys Pro His Lys Lys Ser Ala Thr Leu
            20                  25                  30

Leu Pro Ser Phe Thr Val Thr Pro Thr Val Thr Glu Ser Thr Gly Thr
        35                  40                  45

Thr Ser His Arg Thr Thr Lys Ser His Lys Thr Thr Thr His Arg Thr
    50                  55                  60

Thr Thr Thr Gly Thr Thr Ser His Gly Pro Thr Thr Ala Thr His Asn
65                  70                  75                  80

Pro Thr Thr Thr Ser His Gly Asn Val Thr Val His Pro Thr Ser Asn
                85                  90                  95

Ser Thr Ala Thr Ser Gln Gly Pro Ser Thr Ala Thr His Ser Pro Ala
            100                 105                 110

Thr Thr Ser His Gly Asn Ala Thr Val His Pro Thr Ser Asn Ser Thr
        115                 120                 125

Ala Thr Ser Pro Gly Phe Thr Ser Ser Ala His Pro Glu Pro Pro Pro
    130                 135                 140

Pro Ser Pro Ser Pro Ser Pro Thr Ser Lys Glu Thr Ile Gly Asp Tyr
145                 150                 155                 160

Thr Trp Thr Asn Gly Ser Gln Pro Cys Val His Leu Gln Ala Gln Ile
```

```
                165                 170                 175

Gln Ile Arg Val Met Tyr Thr Thr Gln Gly Gly Gly Glu Ala Trp Gly
            180                 185                 190

Ile Ser Val Leu Asn Pro Asn Lys Thr Lys Val Gln Gly Ser Cys Glu
        195                 200                 205

Gly Ala His Pro His Leu Leu Leu Ser Phe Pro Tyr Gly His Leu Ser
    210                 215                 220

Phe Gly Phe Met Gln Asp Leu Gln Gln Lys Val Val Tyr Leu Ser Tyr
225                 230                 235                 240

Met Ala Val Glu Tyr Asn Val Ser Phe Pro His Ala Ala Gln Trp Thr
                245                 250                 255

Phe Ser Ala Gln Asn Ala Ser Leu Arg Asp Leu Gln Ala Pro Leu Gly
            260                 265                 270

Gln Ser Phe Ser Cys Ser Asn Ser Ser Ile Ile Leu Ser Pro Ala Val
        275                 280                 285

His Leu Asp Leu Leu Ser Leu Arg Leu Gln Ala Ala Gln Leu Pro His
    290                 295                 300

Thr Gly Val Phe Gly Gln Ser Phe Ser Cys Pro Ser Asp Arg Ser Ile
305                 310                 315                 320

Leu Leu Pro Leu Ile Ile Gly Leu Ile Leu Leu Gly Leu Leu Ala Leu
                325                 330                 335

Val Leu Ile Ala Phe Cys Ile Ile Arg Arg Arg Pro Ser Ala Tyr Gln
            340                 345                 350

Ala Leu


<210> SEQ ID NO 81
<211> LENGTH: 354
<212> TYPE: PRT
<213> ORGANISM: Pan troglodytes

<400> SEQUENCE: 81

Met Arg Leu Ala Val Leu Phe Ser Gly Ala Leu Leu Gly Leu Leu Ala
1               5                   10                  15

Ala Gln Gly Thr Gly Asn Asp Cys Pro His Lys Lys Ser Ala Thr Leu
            20                  25                  30

Leu Pro Ser Phe Thr Val Thr Pro Thr Val Thr Glu Ser Thr Gly Thr
        35                  40                  45

Thr Ser His Arg Thr Thr Lys Ser His Lys Thr Thr Thr His Arg Thr
    50                  55                  60

Thr Thr Thr Gly Thr Ala Ser His Gly Pro Thr Thr Ala Thr His Asn
65                  70                  75                  80

Pro Thr Thr Thr Ser His Gly Asn Val Thr Val His Pro Thr Ser Asn
                85                  90                  95

Ser Thr Ala Thr Ser Gln Gly Pro Ser Thr Ala Thr His Ser Pro Ala
            100                 105                 110

Thr Thr Ser His Gly Asn Ala Thr Val His Pro Thr Ser Asn Ser Thr
        115                 120                 125

Ala Thr Ser Pro Gly Phe Thr Ser Ser Ala His Pro Glu Pro Pro Pro
    130                 135                 140

Pro Ser Pro Ser Pro Ser Pro Thr Ser Lys Glu Thr Ile Gly Asp Tyr
145                 150                 155                 160

Thr Trp Thr Asn Gly Ser Gln Pro Cys Val His Leu Gln Ala Gln Ile
                165                 170                 175

Gln Ile Arg Val Met Tyr Thr Thr Gln Gly Gly Gly Glu Ala Trp Gly
```

```
            180                 185                 190

Ile Ser Val Leu Asn Pro Asn Lys Thr Lys Val Gln Gly Ser Cys Glu
        195                 200                 205

Gly Ala His Pro His Leu Leu Leu Ser Phe Pro Tyr Gly His Leu Ser
    210                 215                 220

Phe Gly Phe Met Gln Asp Leu Gln Gln Lys Ala Val Tyr Leu Ser Tyr
225                 230                 235                 240

Met Ala Val Glu Tyr Asn Val Ser Phe Pro His Ala Ala Gln Trp Thr
                245                 250                 255

Phe Ser Ala Gln Asn Ala Ser Leu Arg Asp Leu Gln Ala Pro Leu Gly
            260                 265                 270

Arg Ser Phe Ser Cys Ser Asn Ser Ser Ile Ile Leu Ser Pro Ala Val
        275                 280                 285

His Leu Asp Leu Leu Ser Leu Arg Leu Gln Ala Ala Gln Leu Pro His
    290                 295                 300

Thr Gly Val Phe Gly Gln Ser Phe Ser Cys Pro Ser Asp Arg Ser Ile
305                 310                 315                 320

Leu Leu Pro Leu Ile Ile Gly Leu Ile Leu Leu Gly Leu Leu Ala Leu
                325                 330                 335

Val Leu Ile Ala Phe Cys Ile Ile Arg Arg Arg Pro Ser Ala Tyr Gln
            340                 345                 350

Ala Leu


<210> SEQ ID NO 82
<211> LENGTH: 335
<212> TYPE: PRT
<213> ORGANISM: Bos taurus

<400> SEQUENCE: 82

Met Arg Leu Ala Val Phe Phe Ser Gly Ala Leu Leu Gly Leu Leu Ala
1               5                   10                  15

Ala Gln Gly Thr Gly Asn Asp Cys Pro His Lys Lys Ser Ala Thr Leu
            20                  25                  30

Leu Pro Ser Phe Thr Val Thr Pro Thr Ala Thr Glu Ser Thr Pro Ser
        35                  40                  45

Pro Gly Thr Thr Ser His Arg Thr Thr Lys Ser His Arg Thr Thr Thr
    50                  55                  60

Trp Arg Ile Ser Thr Thr Thr His Thr Thr Asn Thr Thr Gly Thr Thr
65                  70                  75                  80

Ser Ser Glu Ser Pro Thr Ala Thr His Ser Pro Ala Thr Thr Thr Ser
                85                  90                  95

His Gln Asn Thr Thr Val His Pro Thr Ser Asn Ile Thr Ala Thr Ser
            100                 105                 110

Pro Gly Pro Ser Thr Arg Ser Pro His Pro Glu Pro Pro Pro Ser Pro
        115                 120                 125

Ser Pro Ser Pro Gly Ser Lys Glu Ala Ile Gly Asp Tyr Thr Trp Ser
    130                 135                 140

Asn Gly Ser Gln Pro Cys Val Arg Leu Gln Ala Gln Ile Gln Ile Arg
145                 150                 155                 160

Val Leu Tyr Pro Thr Gln Gly Gly Gly Glu Ala Trp Gly Ile Ser Val
                165                 170                 175

Leu Asn Pro Asn Arg Thr Lys Ala Gln Gly Gly Cys Glu Gly Thr His
            180                 185                 190

Ser His Leu Leu Leu Ser Phe Pro Ser Gly Gln Leu Ser Phe Gly Phe
```

```
        195                 200                 205

Lys Gln Asp Pro Leu Gln Ser Ala Val Tyr Leu Asn Tyr Met Ala Val
    210                 215                 220

Glu Tyr Asn Val Ser Phe Pro Gln Ala Val Gln Trp Thr Phe Ser Val
225                 230                 235                 240

Gln Asn Ser Ser Leu Arg Asp Leu Gln Thr Pro Leu Gly His Ser Phe
                245                 250                 255

Ser Cys Arg Asn Ala Ser Ile Ile Val Ser Pro Ala Leu His Leu Asp
            260                 265                 270

Leu Leu Ser Leu Lys Leu Gln Ala Ala Gln Leu Ser Pro Ser Gly Ala
        275                 280                 285

Phe Gly Pro Ser Phe Ser Cys Pro Asn Asp Lys Ser Ile Leu Leu Pro
    290                 295                 300

Leu Ile Ile Gly Leu Ile Leu Leu Gly Leu Leu Thr Leu Val Leu Val
305                 310                 315                 320

Thr Phe Cys Ile Ile Arg Arg Arg Pro Pro Thr Tyr Gln Pro Leu
                325                 330                 335


<210> SEQ ID NO 83
<211> LENGTH: 335
<212> TYPE: PRT
<213> ORGANISM: Mus musculus

<400> SEQUENCE: 83

Met Arg Leu Pro Val Cys Leu Ile Leu Leu Gly Pro Leu Ile Ala Gln
1               5                   10                  15

Gly Thr Glu Glu Asp Cys Pro His Lys Lys Ala Val Thr Leu Leu Pro
            20                  25                  30

Ser Phe Thr Met Thr Pro Thr Ala Thr Glu Ser Thr Ala Ser Pro Thr
        35                  40                  45

Thr Ser His Arg Pro Thr Thr Thr Ser His Gly Asn Val Thr Val His
    50                  55                  60

Thr Ser Ser Gly Pro Thr Thr Val Thr His Asn Pro Ala Thr Thr Thr
65                  70                  75                  80

Ser His Gly Asn Ala Thr Ile Ser His Ala Thr Val Ser Pro Thr Thr
                85                  90                  95

Asn Gly Thr Ala Thr Ser Pro Arg Ser Ser Thr Val Gly Pro His Pro
            100                 105                 110

Gly Pro Pro Pro Pro Ser Pro Ser Pro Arg Ser Lys Gly Ala Leu Gly
        115                 120                 125

Asn Tyr Thr Trp Ala Asn Gly Ser Gln Pro Cys Val Gln Leu Gln Ala
    130                 135                 140

Gln Ile Gln Ile Arg Ile Leu Tyr Pro Ile Gln Gly Gly Arg Lys Val
145                 150                 155                 160

Lys Leu Lys Trp Gly Leu Lys Arg Ala Trp Gly Ile Ser Val Leu Asn
                165                 170                 175

Pro Asn Lys Thr Lys Val Gln Gly Gly Cys Asp Gly Thr His Pro His
            180                 185                 190

Leu Ser Leu Ser Phe Pro Tyr Gly Gln Leu Thr Phe Gly Phe Lys Gln
        195                 200                 205

Asp Leu His Gln Ser Pro Ser Thr Val Tyr Leu Asp Tyr Met Ala Val
    210                 215                 220

Glu Tyr Asn Val Ser Phe Pro Gln Ala Ala Gln Trp Thr Phe Met Ala
225                 230                 235                 240
```

```
Gln Asn Ser Ser Leu Arg Glu Leu Gln Ala Pro Leu Gly Gln Ser Phe
                245                 250                 255

Cys Cys Gly Asn Ala Ser Ile Val Leu Ser Pro Ala Val His Leu Asp
            260                 265                 270

Leu Leu Ser Leu Arg Leu Gln Ala Ala Gln Leu Pro Asp Lys Gly His
        275                 280                 285

Phe Gly Pro Cys Phe Ser Cys Asn Arg Asp Gln Ser Leu Leu Leu Pro
    290                 295                 300

Leu Ile Ile Gly Leu Val Leu Leu Gly Leu Leu Thr Leu Val Leu Ile
305                 310                 315                 320

Ala Phe Cys Ile Thr Arg Arg Arg Gln Ser Thr Tyr Gln Pro Leu
                325                 330                 335


<210> SEQ ID NO 84
<211> LENGTH: 354
<212> TYPE: PRT
<213> ORGANISM: Macaca mulatta

<400> SEQUENCE: 84

Met Arg Leu Ala Val Leu Phe Leu Gly Ala Leu Leu Gly Leu Leu Ala
1               5                   10                  15

Ala Gln Gly Thr Gly Asn Asp Cys Pro His Lys Lys Ser Ala Thr Leu
            20                  25                  30

Leu Pro Ser Phe Thr Val Thr Pro Thr Ala Thr Glu Ser Thr Gly Thr
        35                  40                  45

Thr Ser His Arg Thr Thr Lys Ser His Lys Thr Thr Thr His Arg Thr
    50                  55                  60

Thr Thr Thr Gly Thr Thr Ser His Arg Pro Thr Thr Ala Thr His Asn
65                  70                  75                  80

Pro Thr Thr Thr Ser His Arg Asn Ala Thr Val His Pro Thr Ser Asn
                85                  90                  95

Ser Thr Ala Thr Ser Gln Gly Pro Ser Thr Ala Thr His Arg Pro Ala
            100                 105                 110

Thr Thr Ser His Gly Asn Ala Thr Val His Pro Thr Ser Asn Ser Thr
        115                 120                 125

Ala Thr Ser Pro Gly Leu Thr Ser Ser Ala His Pro Gly Pro Pro Pro
    130                 135                 140

Pro Ser Pro Ser Pro Ser Pro Ala Ser Lys Glu Thr Ile Gly Asp Tyr
145                 150                 155                 160

Met Trp Thr Asn Gly Ser Gln Pro Cys Val His Leu Gln Ala Gln Ile
                165                 170                 175

Gln Ile Arg Val Met Tyr Thr Thr Gln Gly Gly Gly Glu Ala Trp Gly
            180                 185                 190

Ile Ser Val Leu Asn Pro Asn Lys Thr Lys Val Gln Gly Ser Cys Glu
        195                 200                 205

Gly Ala His Pro His Leu Leu Leu Ser Phe Pro Tyr Gly His Leu Ser
    210                 215                 220

Phe Gly Phe Met Gln Asp Leu Gln Gln Arg Val Val Tyr Leu Ser Tyr
225                 230                 235                 240

Met Ala Val Glu Tyr Asn Val Ser Phe Pro His Ala Ala Gln Trp Thr
                245                 250                 255

Phe Ser Ala Gln Asn Ala Ser Leu Arg Asp Leu Gln Ala Pro Leu Gly
            260                 265                 270

Gln Ser Phe Ser Cys Ser Asn Ser Ser Ile Ile Leu Ser Pro Ala Val
        275                 280                 285
```

```
His Leu Asp Leu Leu Ser Leu Arg Leu Gln Ala Ala Gln Leu Pro His
    290                 295                 300

Thr Gly Val Phe Gly Gln Ser Phe Ser Cys Pro Ser Asp Arg Ser Ile
305                 310                 315                 320

Leu Leu Pro Leu Ile Ile Gly Leu Val Leu Leu Gly Leu Leu Ala Leu
                325                 330                 335

Val Leu Ile Ala Phe Cys Ile Val Arg Arg Arg Pro Ser Ala Tyr Gln
            340                 345                 350

Ala Leu


<210> SEQ ID NO 85
<211> LENGTH: 330
<212> TYPE: PRT
<213> ORGANISM: Rattus norvegicus

<400> SEQUENCE: 85

Met Arg Phe Pro Val Cys Leu Thr Leu Leu Val Leu Leu Val Ala Gln
1               5                   10                  15

Gly Thr Gly Lys Asp Cys Pro His Lys Lys Ala Ala Thr Leu Leu Pro
            20                  25                  30

Ser Phe Thr Glu Thr Pro Thr Thr Thr Gly Ser Thr Ala Ser Pro Thr
        35                  40                  45

Thr Thr His Arg Pro Thr Thr Thr Ser His Arg Pro Thr Thr Thr Ser
    50                  55                  60

His Arg Pro Thr Thr Thr Ser His Arg Pro Thr Thr Thr Ser His Arg
65                  70                  75                  80

Pro Thr Thr Thr Ser His Arg Pro Thr Thr Thr Ser His Gly Asn Ala
                85                  90                  95

Thr Val Ser Pro Thr Thr Asn Ser Pro Gly Phe Ser Thr Val Gly Pro
            100                 105                 110

His Pro Gly Pro Pro Pro Pro Ser Pro Ser Pro Ser Pro Ser Ser Thr
        115                 120                 125

Gly Ala Leu Gly Asn Tyr Thr Trp Thr Asn Gly Ser Gln Pro Cys Val
    130                 135                 140

Gln Leu Gln Ala Gln Ile Gln Ile Arg Ile Leu Tyr Leu Thr Gln Gly
145                 150                 155                 160

Gly Lys Lys Ala Trp Gly Leu Ser Val Leu Asn Pro Asn Lys Thr Lys
                165                 170                 175

Val Gln Gly Gly Cys Asp Ser Ala His Pro His Leu Ala Leu Ser Phe
            180                 185                 190

Pro Tyr Gly Gln Leu Thr Phe Gly Phe Lys Gln Asp Arg His Gln Ser
        195                 200                 205

His Ser Thr Val Tyr Leu Asn Tyr Met Ala Val Glu Tyr Asn Val Ser
    210                 215                 220

Phe Pro Gln Ala Ala Gln Trp Thr Phe Ser Ala Gln Asn Ser Ser Leu
225                 230                 235                 240

Gln Glu Leu Gln Ala Pro Leu Gly Gln Ser Phe Cys Cys Gly Asn Thr
                245                 250                 255

Ser Ile Val Leu Ser Pro Ala Ile His Leu Asp Leu Leu Ser Leu Arg
            260                 265                 270

Leu Gln Ala Ala Gln Leu Pro Asp Lys Gly His Phe Gly Pro Cys Phe
        275                 280                 285

Ser Cys Ala Ser Asp Gln Ser Leu Leu Leu Pro Leu Ile Ile Gly Leu
    290                 295                 300
```

```
Val Leu Leu Gly Leu Leu Thr Leu Val Leu Ile Ala Phe Cys Val Thr
305                 310                 315                 320

Arg Arg Arg Gln Ser Thr Tyr Gln Pro Leu
                325                 330


<210> SEQ ID NO 86
<211> LENGTH: 329
<212> TYPE: PRT
<213> ORGANISM: Canis lupus familiaris

<400> SEQUENCE: 86

Met Arg Pro Ala Val Phe Phe Leu Gly Ala Leu Val Gly Leu Leu Ala
1               5                   10                  15

Ala Gln Gly Thr Arg Ser Asp Cys Pro His Lys Lys Ser Ala Thr Leu
            20                  25                  30

Leu Pro Ser Phe Thr Val Thr Pro Thr Ala Thr Glu Ser Thr Gly Ser
        35                  40                  45

Pro Gly Thr Thr Ser His Ser Thr Thr Thr Ala Glu Thr Thr Ser His
    50                  55                  60

Ala Pro Asn Thr Thr Thr His Gln Ala Pro Thr Thr Pro Gly His Arg
65                  70                  75                  80

Asn Thr Thr Ile His Pro Thr Thr Ser Asn Ser Thr Ser Asn Thr Thr
                85                  90                  95

Gly Thr Thr Gly Thr Gly Lys Pro His Thr Ser Thr Ser Tyr Thr Gln
            100                 105                 110

Pro Gly Pro Gly Pro Arg Pro Pro Pro Pro Ser Pro Gly Pro Gly Pro
        115                 120                 125

Gln Asp Ala Ile Gly Asp Tyr Thr Trp Thr Thr Gly Ser Gln Pro Cys
    130                 135                 140

Ala Arg Leu Gln Ala Arg Ile Gln Ile Gly Val Val Tyr Pro Thr Gln
145                 150                 155                 160

Ala Gly Gly Gln Ala Trp Gly Ile Ser Val Leu Asn Pro Asn Ser Thr
                165                 170                 175

Lys Pro Trp Gly Asp Cys Asp Gly Ala Arg Pro His Leu Leu Leu Ser
            180                 185                 190

Phe Pro Phe Gly Gln Leu Ser Phe Gly Phe Thr Gln Glu Pro Gln Gln
        195                 200                 205

Gly Ser Val Tyr Leu Asp Tyr Leu Ala Leu Gln Tyr Asn Val Ser Phe
    210                 215                 220

Pro Gln Ala Ala Gln Trp Thr Phe Ser Gly Gln Asn Ala Ser Leu Arg
225                 230                 235                 240

Ala Leu Gln Ala Pro Leu Gly Gln Ser Phe Ser Cys Arg Asn Ala Ser
                245                 250                 255

Ile Leu Leu Thr Pro Ala Leu Arg Leu Asp Leu Leu His Leu Lys Leu
            260                 265                 270

Gln Ala Ala Gln Leu Pro Pro Ser Gly Ala Phe Gly Pro Ser Phe Ser
        275                 280                 285

Cys Pro Ser Glu His Phe Asn Leu Leu Pro Leu Ile Val Gly Val Ile
    290                 295                 300

Ser Leu Gly Leu Leu Ala Leu Ala Leu Val Thr Phe Cys Ile Ile Arg
305                 310                 315                 320

Arg Arg Pro Pro Thr Tyr Gln Pro Leu
                325
```

<210> SEQ ID NO 87
<211> LENGTH: 322
<212> TYPE: PRT
<213> ORGANISM: Equus caballus

<400> SEQUENCE: 87

```
Met Arg Leu Ala Val Leu Phe Ser Gly Ala Leu Leu Gly Leu Leu Ala
1               5                   10                  15

Ala Gln Glu Thr Gly Asn Asp Cys Pro His Lys Lys Ser Ala Thr Leu
            20                  25                  30

Leu Pro Ser Phe Thr Val Thr Pro Thr Ala Thr Glu Ser Thr Ala Ser
        35                  40                  45

Pro Gly Thr Thr Ser His Gln Thr Thr Gln Ser His Arg Thr Thr Thr
    50                  55                  60

Thr Gly Thr Thr Ser Asp His Pro Thr Thr Ala Thr His Asn Pro Thr
65                  70                  75                  80

Thr Thr Ser His Gly Asn Thr Thr Val His Pro Thr Thr Ser Asn Ser
                85                  90                  95

Thr Val Thr Ser Pro Gly Ser Ala Ser Ser Ser Pro His Pro Arg Pro
            100                 105                 110

Pro Pro Pro Ser Pro Ser Pro Ser Pro Gly Ser Lys Glu Ala Ile Gly
        115                 120                 125

Asp Tyr Ile Trp Thr Asn Gly Ser Gln Pro Cys Val Arg Leu Gln Ala
    130                 135                 140

Gln Ile Gln Ile Arg Val Leu Tyr Pro Thr Leu Gly Gly Gly Lys Ala
145                 150                 155                 160

Trp Gly Ile Ser Val Leu Asn Pro Asn Lys Thr Lys Ala Gln Gly Gly
                165                 170                 175

Cys Ala His Pro His Leu Leu Leu Ser Phe Pro Tyr Gly Gln Leu Ser
            180                 185                 190

Phe Gly Phe Lys Gln Glu Pro Leu Gln Ser Thr Val Tyr Leu Asn Tyr
        195                 200                 205

Ile Ala Val Glu Tyr Asn Val Ser Phe Pro Gln Ala Ala Gln Trp Thr
    210                 215                 220

Phe Leu Val Gln Asn Ser Ser Leu Arg Asp Leu Gln Ala Pro Leu Gly
225                 230                 235                 240

Gln Arg Phe Ser Cys Arg Asn Ala Ser Ile Ala Leu Ser Pro Ala Phe
                245                 250                 255

His Leu Asp Leu Leu Ser Leu Lys Leu Gln Ala Ala Gln Leu Thr Pro
            260                 265                 270

Thr Gly Ala Phe Gly Pro Ser Phe Ser Cys Pro Ser Asp Gln Ser Ile
        275                 280                 285

Leu Leu Pro Leu Ile Ile Gly Leu Ile Leu Leu Gly Leu Phe Ala Leu
    290                 295                 300

Val Leu Ile Thr Phe Cys Val Ile Arg Arg Arg Pro Pro Thr Tyr Gln
305                 310                 315                 320

Ala Leu
```

<210> SEQ ID NO 88
<211> LENGTH: 305
<212> TYPE: PRT
<213> ORGANISM: Oryctolagus cuniculus

<400> SEQUENCE: 88

```
Met Arg Leu Pro Val Leu Phe Leu Ala Leu Leu Gly Leu His Ala Ala
1               5                   10                  15
```

```
Ser Ser Gly Thr Thr Ser His Arg Thr Thr Lys Asn Pro His Thr Thr
            20                  25                  30

Ser His Ser Thr Ala Thr Pro Gly Thr Thr Ser His Arg Pro Thr Thr
        35                  40                  45

Ala Thr Pro Thr Thr Gly His Gly Asn Val Thr Val His Pro Thr Thr
    50                  55                  60

Ser Asn Thr Thr Ser Asn Thr Thr Thr Thr Thr Gly Thr Ser Pro Gly
65                  70                  75                  80

Phe Ser Thr Ser Thr Pro His Pro Gly Pro Pro Pro Pro Pro Pro Ser
                85                  90                  95

Pro Ser Pro Gly Ser Arg Glu Ala Val Gly Asn Tyr Thr Trp Thr Asn
            100                 105                 110

Gly Ser Gln Pro Cys Val Gln Leu Gln Ala Gln Ile Gln Ile Arg Val
        115                 120                 125

Leu Tyr Pro Thr Gln Gly Gly Gly Gln Ala Trp Gly Met Ser Val Leu
    130                 135                 140

Asn Pro Asn Arg Thr Lys Ala Gln Gly Gly Cys Glu Gly Pro Arg Pro
145                 150                 155                 160

His Leu Leu Leu Ser Phe Pro Tyr Gly Gln Leu Ser Phe Gly Phe Lys
                165                 170                 175

Gln Asp Pro Gly Gln Gly Gln Ser Ala Val Tyr Leu Ser Tyr Leu Ala
            180                 185                 190

Val Glu Tyr Asn Val Ser Phe Pro Gln Ala Ala Arg Trp Thr Phe Ser
        195                 200                 205

Ala Gln Asn Ala Ser Leu Arg Asp Leu Gln Ala Pro Leu Gly Gln Ser
    210                 215                 220

Phe Ser Cys Arg Asn Ala Ser Ile Ala Val Ser Pro Ala Leu His Leu
225                 230                 235                 240

Asp Leu Leu Ser Leu Arg Val Gln Ala Ala Gln Leu Pro Arg Thr Gly
                245                 250                 255

Ile Phe Gly Pro Ser Phe Ser Cys Pro Ala Asp His Pro Ser Ile Leu
            260                 265                 270

Val Pro Leu Ile Ile Gly Leu Ile Leu Val Gly Leu Leu Ala Leu Val
        275                 280                 285

Leu Val Ala Phe Cys Ile Ala Arg Arg Arg Pro Ser Ala Tyr Gln Ala
    290                 295                 300

Leu
305


<210> SEQ ID NO 89
<211> LENGTH: 291
<212> TYPE: PRT
<213> ORGANISM: Sus scrofa

<400> SEQUENCE: 89

Met Thr Leu Ala Val Leu Phe Leu Gly Ala Leu Leu Gly Leu Leu Ala
1               5                   10                  15

Glu Ser Thr Thr Ser His Arg Thr Thr Thr Pro Arg Thr Thr Thr Thr
            20                  25                  30

Gly Thr Thr Ser His Gly Pro Thr Thr Val Thr His Asn Pro Ala Thr
        35                  40                  45

Thr Thr Ser His Gly Asn Ala Thr Val His Pro Thr Ser Ser Ser Thr
    50                  55                  60

Ala Thr Ser Pro Gly Ser Ser Thr Arg Pro Pro His Pro Gly Pro Pro
```

```
65                  70                  75                  80

Pro Pro Ser Pro Ser Pro Ser Pro Gly Ser Gln Glu Ala Ile Gly Asp
                85                  90                  95

Tyr Thr Trp Thr Asn Gly Ser Gln Pro Cys Val Gln Leu Gln Ala Gln
            100                 105                 110

Ile Gln Ile Arg Val Leu Tyr Pro Thr Gln Gly Gly Gly Glu Ala Trp
        115                 120                 125

Gly Ile Ser Val Leu Asn Pro Asn Lys Thr Lys Ala Leu Gly Gly Cys
    130                 135                 140

Glu Gly Ala His Pro His Val Arg Leu Ser Phe Pro Tyr Gly Gln Leu
145                 150                 155                 160

Thr Phe Gly Phe Lys Gln Gln Pro Gln Glu Ser Thr Val Tyr Leu Asn
                165                 170                 175

Tyr Met Ala Val Glu Tyr Asn Val Ser Phe Pro Arg Ala Ala Gln Trp
            180                 185                 190

Thr Phe Ser Val Gln Asn Ser Ser Leu Arg Asp Leu Gln Thr Pro Val
        195                 200                 205

Gly Arg Ser Tyr Ser Cys Arg Asn Ala Ser Ile Ile Leu Ser Thr Ala
    210                 215                 220

Phe His Leu Asp Leu Leu Ser Leu Lys Leu Gln Ala Ala Gln Leu Pro
225                 230                 235                 240

Pro Thr Gly Asn Phe Gly Pro Ser Phe Ser Cys Pro Ser Asp Gln Thr
                245                 250                 255

Ile Leu Leu Pro Leu Ile Ile Gly Leu Ile Phe Leu Gly Leu Leu Ile
            260                 265                 270

Leu Val Leu Val Thr Phe Cys Ile Ile Arg Arg Arg Pro Pro Ala Tyr
        275                 280                 285

Gln Pro Leu
    290


<210> SEQ ID NO 90
<211> LENGTH: 354
<212> TYPE: PRT
<213> ORGANISM: Papio anubis

<400> SEQUENCE: 90

Met Arg Leu Ala Val Leu Phe Ser Gly Ala Leu Leu Gly Leu Leu Ala
1               5                   10                  15

Ala Gln Gly Thr Gly Asn Asp Cys Pro His Lys Lys Ser Ala Thr Leu
            20                  25                  30

Leu Pro Ser Phe Thr Val Thr Pro Thr Ala Thr Glu Ser Thr Gly Thr
        35                  40                  45

Thr Ser His Arg Thr Thr Lys Ser His Lys Thr Thr Thr His Arg Thr
    50                  55                  60

Thr Thr Thr Gly Thr Thr Ser His Arg Pro Thr Thr Ala Thr His Asn
65                  70                  75                  80

Pro Asn Thr Thr Ser His Arg Asn Ala Thr Val His Pro Thr Ser Asn
                85                  90                  95

Ser Thr Ala Thr Ser Gln Gly Pro Ser Thr Ala Thr His Arg Pro Ala
            100                 105                 110

Thr Thr Ser His Gly Asn Ala Thr Val His Pro Thr Ser Asn Ser Thr
        115                 120                 125

Ala Thr Ser Pro Gly Leu Thr Ser Ser Ala His Pro Gly Pro Pro Pro
    130                 135                 140
```

```
Pro Ser Pro Ser Pro Ser Pro Ala Ser Lys Glu Thr Ile Gly Asp Tyr
145                 150                 155                 160

Met Trp Thr Asn Gly Ser Gln Pro Cys Val His Leu Gln Ala Gln Ile
                165                 170                 175

Gln Ile Arg Val Met Tyr Thr Thr Gln Gly Gly Gly Glu Ala Trp Gly
            180                 185                 190

Ile Ser Val Leu Asn Pro Asn Lys Thr Lys Val Gln Gly Ser Cys Glu
        195                 200                 205

Gly Ala His Pro His Leu Leu Leu Ser Phe Pro Tyr Gly His Leu Ser
    210                 215                 220

Phe Gly Phe Met Gln Asp Leu Gln Gln Arg Val Val Tyr Leu Ser Tyr
225                 230                 235                 240

Met Ala Val Glu Tyr Asn Val Ser Phe Pro His Ala Ala Gln Trp Thr
                245                 250                 255

Phe Ser Ala Gln Asn Ala Ser Leu Arg Asp Leu Gln Ala Pro Leu Gly
            260                 265                 270

Gln Ser Phe Ser Cys Ser Asn Ser Ser Ile Ile Leu Ser Pro Ala Val
        275                 280                 285

His Leu Asp Leu Leu Ser Leu Arg Leu Gln Ala Ala Gln Leu Pro His
    290                 295                 300

Thr Gly Val Phe Gly Gln Ser Phe Ser Cys Pro Ser Asp Arg Ser Ile
305                 310                 315                 320

Leu Leu Pro Leu Ile Ile Gly Leu Val Leu Leu Gly Leu Leu Ala Leu
                325                 330                 335

Val Leu Ile Ala Phe Cys Ile Val Arg Arg Arg Pro Ser Ala Tyr Gln
            340                 345                 350

Ala Leu


<210> SEQ ID NO 91
<211> LENGTH: 323
<212> TYPE: PRT
<213> ORGANISM: Monodelphis domestica

<400> SEQUENCE: 91

Met Arg Leu Ser Leu Leu Leu Ser Gly Ile Leu Leu Gly Leu Leu Ala
1               5                   10                  15

Glu Gln Gly Ala Gly Asp Lys Cys Pro Gln Glu Lys Ser Val Thr Leu
            20                  25                  30

Val Pro Ser Phe Thr Val Thr Thr Ile Ala Thr Glu Arg Ser Thr Thr
        35                  40                  45

Ser Pro Glu Thr Thr Thr Ser Ser Gly Ser Thr Ala Thr Thr Tyr Arg
    50                  55                  60

Thr Ser Thr Ala Ala Thr Thr Pro His Ser Asn Ser Thr Ala Thr Ser
65                  70                  75                  80

Tyr Ser Thr Thr Ser Glu Gly Thr Ala Val Thr His Gly Thr Thr Thr
                85                  90                  95

Ser Pro Arg Asn Thr Ser Thr Thr Ser Thr Ser Gln Ser Val Pro Val
            100                 105                 110

Pro Pro Ser Pro Gln Pro Thr Ser Ser Pro Ser Gly Ala Val Gly Asp
        115                 120                 125

Tyr Ile Gly Ala Asn Gly Ser Gln Leu Cys Val His Leu Arg Ala Gln
    130                 135                 140

Ile Gln Met Arg Val Leu Tyr Gln Ala Ser Gly Gly Gly Lys Leu Trp
145                 150                 155                 160
```

```
Gly Ile Phe Val Leu Asn Pro Asn Arg Thr Met Ala Gln Gly Asn Cys
                165                 170                 175

Glu Ala Asn His Ser Ser Leu Ile Leu Ser Phe Pro Asn Gly Lys Leu
            180                 185                 190

Ile Phe Gly Phe Lys Gln Asp Ser Ile Lys Lys Ile Val Tyr Leu Ser
        195                 200                 205

His Leu Ala Thr Glu Phe Asn Val Ser Phe Pro Ser Ala Thr Arg Trp
    210                 215                 220

Ile Phe Ser Val Glu Asn Ser Ser Leu Gln Asp Leu Gln Thr Pro Leu
225                 230                 235                 240

Gly His Ser Phe Ser Cys Arg Asn Arg Ser Ile Ala Leu Ser Pro Asp
                245                 250                 255

Ile His Leu Asp Leu Leu Ser Leu Gln Leu Gln Ala Ala Gln Leu Ser
            260                 265                 270

Ser Ser Gly Ala Phe Gly Ala Ala Phe Ser Cys Ser Ala Asp Leu Asn
        275                 280                 285

Ile Leu Val Pro Leu Val Val Gly Leu Val Leu Leu Thr Leu Leu Ile
    290                 295                 300

Leu Val Leu Ser Ala Phe Cys Ile Ser Arg Arg Arg Pro Pro Ala Tyr
305                 310                 315                 320

Gln Pro Leu


<210> SEQ ID NO 92
<211> LENGTH: 263
<212> TYPE: PRT
<213> ORGANISM: Ornithorhynchus anatinus

<400> SEQUENCE: 92

Met Gly Leu Thr Leu Pro Leu Pro Ala Gln Gly Ser Gln Cys Arg Ala
1               5                   10                  15

Asn Cys Pro His Lys Lys Ser Ala Thr Leu Val Pro Ser Phe Thr Val
            20                  25                  30

Thr Pro Thr Ala Thr Ser Gly Pro Thr Thr Thr Ala His Gln Thr Thr
        35                  40                  45

Thr Asp His Gly Thr Thr Thr Ser His Glu Thr Thr Thr Ser Gln Gly
    50                  55                  60

Thr Ser Thr His Gly Thr Ser Thr Pro His Thr Thr Thr Thr Gly His
65                  70                  75                  80

Gly Thr Thr Thr Gly His Gln Asn Thr Ser His Ser Thr Thr Thr Ser
                85                  90                  95

His Gly Thr Ser Thr Pro His Lys Thr Thr Thr Arg His Pro Thr Thr
            100                 105                 110

Ser His Gly Thr Thr Thr Ser His Gly Thr Ser Thr Gly His Trp Thr
        115                 120                 125

Ala Arg Pro Thr Ile Arg Pro Gly Pro Pro Pro Pro Pro Pro Ser Pro
    130                 135                 140

Gly Lys Ala Val Gly Asn Tyr Thr Val Phe Asn Gly Ser Gln Pro Cys
145                 150                 155                 160

Leu Arg Leu Arg Ala Glu Ile Arg Leu Trp Val Leu Tyr Gln Ala Gln
                165                 170                 175

Glu Glu Gly Glu Ala Pro Pro Val Ser Gly Ala Ala Ser Phe Pro Pro
            180                 185                 190

Pro Arg Pro Arg Pro Val Ala Gly Glu Gly Asp Gly Glu Arg Ser Arg
        195                 200                 205
```

```
Val Thr Pro Val Ala Ser Ala Met Thr Val Glu Gly Gly Ser Arg Ala
    210                 215                 220

Gly Phe Ala Met Leu Gly Ala Glu Val Arg Ser Arg Ala Pro Ser Leu
225                 230                 235                 240

Gly Arg Ala Gly Lys Thr Arg Leu Arg Ile His Gln Pro Val Val Val
                245                 250                 255

Leu Gln His Thr Tyr Tyr Val
            260
```

<210> SEQ ID NO 93
<211> LENGTH: 280
<212> TYPE: PRT
<213> ORGANISM: Homo sapiens

<400> SEQUENCE: 93

```
Met Asp Leu Gln Gly Arg Gly Val Pro Ser Ile Asp Arg Leu Arg Val
1               5                   10                  15

Leu Leu Met Leu Phe His Thr Met Ala Gln Ile Met Ala Glu Gln Glu
            20                  25                  30

Val Glu Asn Leu Ser Gly Leu Ser Thr Asn Pro Glu Lys Asp Ile Phe
        35                  40                  45

Val Val Arg Glu Asn Gly Thr Thr Cys Leu Met Ala Glu Phe Ala Ala
    50                  55                  60

Lys Phe Ile Val Pro Tyr Asp Val Trp Ala Ser Asn Tyr Val Asp Leu
65                  70                  75                  80

Ile Thr Glu Gln Ala Asp Ile Ala Leu Thr Arg Gly Ala Glu Val Lys
                85                  90                  95

Gly Arg Cys Gly His Ser Gln Ser Glu Leu Gln Val Phe Trp Val Asp
            100                 105                 110

Arg Ala Tyr Ala Leu Lys Met Leu Phe Val Lys Glu Ser His Asn Met
        115                 120                 125

Ser Lys Gly Pro Glu Ala Thr Trp Arg Leu Ser Lys Val Gln Phe Val
    130                 135                 140

Tyr Asp Ser Ser Glu Lys Thr His Phe Lys Asp Ala Val Ser Ala Gly
145                 150                 155                 160

Lys His Thr Ala Asn Ser His His Leu Ser Ala Leu Val Thr Pro Ala
                165                 170                 175

Gly Lys Ser Tyr Glu Cys Gln Ala Gln Gln Thr Ile Ser Leu Ala Ser
            180                 185                 190

Ser Asp Pro Gln Lys Thr Val Thr Met Ile Leu Ser Ala Val His Ile
        195                 200                 205

Gln Pro Phe Asp Ile Ile Ser Asp Phe Val Phe Ser Glu Glu His Lys
    210                 215                 220

Cys Pro Val Asp Glu Arg Glu Gln Leu Glu Glu Thr Leu Pro Leu Ile
225                 230                 235                 240

Leu Gly Leu Ile Leu Gly Leu Val Ile Met Val Thr Leu Ala Ile Tyr
                245                 250                 255

His Val His His Lys Met Thr Ala Asn Gln Val Gln Ile Pro Arg Asp
            260                 265                 270

Arg Ser Gln Tyr Lys His Met Gly
        275                 280
```

<210> SEQ ID NO 94
<211> LENGTH: 280
<212> TYPE: PRT
<213> ORGANISM: Pan troglodytes

<400> SEQUENCE: 94

```
Met Asp Leu Arg Gly Arg Ala Val Pro Ser Ile Asp Arg Leu Arg Val
1               5                   10                  15

Leu Leu Met Leu Phe His Thr Met Ala Gln Ile Met Ala Glu Gln Glu
            20                  25                  30

Val Glu Asn Leu Ser Gly Leu Ser Thr Asn Pro Glu Lys Asp Ile Phe
        35                  40                  45

Val Val Arg Glu Asn Gly Thr Thr Cys Leu Met Ala Glu Phe Ala Ala
    50                  55                  60

Lys Phe Ile Val Pro Tyr Asp Val Trp Ala Ser Asn Tyr Val Asp Leu
65                  70                  75                  80

Ile Thr Glu Gln Ala Asp Ile Ala Leu Thr Arg Gly Ala Glu Val Lys
                85                  90                  95

Gly Arg Cys Gly His Ser Glu Ser Glu Leu Gln Val Phe Trp Val Asp
            100                 105                 110

Arg Ala Tyr Ala Leu Lys Met Leu Phe Val Lys Glu Ser His Asn Met
        115                 120                 125

Ser Lys Gly Pro Glu Ala Thr Trp Arg Leu Ser Lys Val Gln Phe Val
    130                 135                 140

Tyr Asp Ser Ser Glu Lys Thr His Phe Lys Asp Ala Val Ser Ala Gly
145                 150                 155                 160

Lys His Thr Ala Asn Ser His His Leu Ser Ala Leu Val Thr Pro Ala
                165                 170                 175

Gly Lys Ser Tyr Glu Cys Gln Ala Gln Gln Thr Ile Ser Leu Ala Ser
            180                 185                 190

Ser Asp Leu Gln Lys Thr Val Thr Met Ile Leu Ser Ala Val His Ile
        195                 200                 205

Gln Pro Phe Asp Ile Ile Ser Asp Phe Val Phe Ser Glu Glu His Lys
    210                 215                 220

Cys Pro Val Asp Glu Arg Glu Gln Leu Glu Glu Thr Leu Pro Leu Ile
225                 230                 235                 240

Leu Gly Leu Ile Leu Gly Leu Val Ile Met Val Thr Leu Ala Ile Tyr
                245                 250                 255

His Val His His Lys Met Thr Ala Asn Gln Val Gln Ile Pro Arg Asp
            260                 265                 270

Arg Ser Gln Tyr Lys His Met Gly
        275                 280
```

<210> SEQ ID NO 95
<211> LENGTH: 280
<212> TYPE: PRT
<213> ORGANISM: Macaca mulatta

<400> SEQUENCE: 95

```
Met Asp Leu Gln Gly Arg Ala Val Pro Ser Val Asp Arg Leu Arg Val
1               5                   10                  15

Leu Leu Met Leu Phe His Thr Met Ala Gln Ile Met Ala Glu Gln Glu
            20                  25                  30

Val Glu Asn Leu Ser Gly Leu Ser Thr Asn Pro Glu Lys Asp Ile Phe
        35                  40                  45

Val Val Arg Glu Asn Gly Thr Thr Cys Leu Met Ala Glu Phe Ala Ala
    50                  55                  60

Lys Phe Ile Val Pro Tyr Asp Val Trp Ala Ser Asn Tyr Val Asp Leu
65                  70                  75                  80
```

```
Ile Thr Glu Gln Ala Asp Ile Ala Leu Thr Arg Gly Ala Glu Val Lys
                85                  90                  95

Gly Arg Cys Gly His Ser Glu Ser Glu Leu Gln Val Phe Trp Val Asp
            100                 105                 110

Arg Ala Tyr Ala Leu Lys Met Leu Phe Val Lys Glu Ser His Asn Thr
        115                 120                 125

Ser Lys Gly Pro Glu Ala Thr Trp Arg Leu Ser Lys Val Gln Phe Val
    130                 135                 140

Tyr Asp Ser Ser Glu Lys Thr His Phe Lys Asp Ala Val Ser Ala Gly
145                 150                 155                 160

Lys His Thr Ala Asn Ser His His Leu Ser Ala Leu Val Thr Pro Ala
                165                 170                 175

Gly Lys Ser Tyr Glu Cys Gln Ala Gln Gln Thr Ile Ser Leu Ala Ser
            180                 185                 190

Ser Asp Pro Gln Lys Met Val Thr Met Ile Leu Ser Ala Val His Ile
        195                 200                 205

Gln Pro Phe Asp Ile Ile Ser Asp Phe Val Phe Ser Glu Glu His Lys
    210                 215                 220

Cys Pro Val Asp Glu Arg Glu Gln Leu Glu Glu Thr Leu Pro Leu Ile
225                 230                 235                 240

Leu Gly Leu Ile Leu Gly Leu Val Ile Val Val Thr Leu Thr Ile Tyr
                245                 250                 255

His Val His His Lys Met Thr Ala Asn Gln Val Gln Ile Pro Arg Asp
            260                 265                 270

Arg Ser Gln Tyr Lys His Met Gly
        275                 280


<210> SEQ ID NO 96
<211> LENGTH: 280
<212> TYPE: PRT
<213> ORGANISM: Canis lupus familiaris

<400> SEQUENCE: 96

Met Asp Leu Arg Gly Arg Ala Phe Pro Ser Val Tyr Arg Leu Arg Val
1               5                   10                  15

Leu Leu Met Leu Phe Tyr Thr Met Ala Arg Ile Thr Ala Glu Gln Glu
            20                  25                  30

Val Glu Asn Leu Ser Gly Leu Ser Thr Asn Pro Glu Lys Asp Ile Phe
        35                  40                  45

Val Val Arg Glu Asn Gly Thr Thr Cys Leu Met Ala Glu Phe Ala Ala
    50                  55                  60

Lys Phe Ile Val Pro Tyr Asp Val Trp Ala Ser Asn Tyr Val Asp Leu
65                  70                  75                  80

Ile Thr Glu Gln Ala Asp Ile Ser Leu Thr Arg Gly Ala Glu Val Lys
                85                  90                  95

Gly His Cys Gly His Asn Glu Ser Glu Leu Gln Val Phe Trp Val Asp
            100                 105                 110

Arg Ala Tyr Ala Leu Lys Met Leu Phe Val Lys Glu Ser Arg Asn Ala
        115                 120                 125

Ser Lys Gly Pro Glu Ala Thr Trp Arg Leu Ser Lys Val Gln Phe Val
    130                 135                 140

Tyr Asp Ser Ser Glu Lys Thr His Phe Lys Asp Ala Val Ser Ala Gly
145                 150                 155                 160

Lys His Thr Ala Asn Ser His Arg Leu Ser Ala Leu Val Thr Pro Ala
```

```
                165                 170                 175

Gly Lys Ser Tyr Glu Cys Gln Ala Gln Gln Ser Ile Ser Leu Ala Ser
            180                 185                 190

Ser Asp Pro Gln Lys Thr Val Thr Met Ile Leu Ser Ala Val His Ile
        195                 200                 205

Gln Pro Phe Asp Ile Ile Ser Asp Phe Val Phe Ser Glu Glu His Lys
    210                 215                 220

Cys Pro Val Asp Glu Arg Glu Gln Leu Glu Glu Thr Leu Pro Leu Ile
225                 230                 235                 240

Leu Gly Leu Ile Leu Gly Leu Val Ile Val Val Thr Leu Ala Ile Tyr
                245                 250                 255

His Ile His His Lys Met Thr Ala Asn Gln Val Gln Ile Pro Arg Asp
            260                 265                 270

Arg Ser Gln Tyr Lys His Met Gly
        275                 280


<210> SEQ ID NO 97
<211> LENGTH: 280
<212> TYPE: PRT
<213> ORGANISM: Bos taurus

<400> SEQUENCE: 97

Met Asp Leu Arg Arg Arg Ala Leu Leu Gly Val Asp Gly Leu Arg Val
1               5                   10                  15

Leu Leu Met Leu Phe His Thr Val Thr Arg Ile Met Ala Glu Gln Glu
            20                  25                  30

Val Glu Asn Leu Ser Gly Leu Ser Thr Asn Pro Glu Lys Asp Ile Phe
        35                  40                  45

Val Val Arg Glu Asn Gly Thr Thr Cys Leu Met Ala Glu Phe Ala Ala
    50                  55                  60

Lys Phe Ile Val Pro Tyr Asp Val Trp Ala Ser Asn Tyr Val Asp Leu
65                  70                  75                  80

Ile Thr Glu Gln Ala Asp Ile Ser Leu Thr Arg Gly Ala Glu Val Lys
                85                  90                  95

Gly His Cys Gly His Asp Glu Ser Glu Leu Gln Val Phe Trp Val Asp
            100                 105                 110

Arg Ala Tyr Ala Leu Lys Met Leu Phe Leu Lys Glu Ser His Asn Thr
        115                 120                 125

Pro Lys Gly Pro Glu Ala Thr Trp Lys Leu Ser Lys Val Gln Phe Val
    130                 135                 140

Tyr Asp Ser Ser Glu Lys Thr His Phe Lys Asp Ala Val Ser Ala Gly
145                 150                 155                 160

Lys His Thr Ala Asn Ser His His Leu Ser Ala Leu Val Thr Pro Ala
                165                 170                 175

Gly Lys Ser Tyr Glu Cys Gln Ala Gln Gln Thr Ile Ser Leu Ala Ser
            180                 185                 190

Ser Asp Pro Gln Lys Thr Val Thr Met Ile Leu Ser Ala Val His Ile
        195                 200                 205

Gln Pro Phe Asp Ile Ile Ser Asp Phe Val Phe Ser Glu Glu His Lys
    210                 215                 220

Cys Pro Val Asp Glu Arg Glu Gln Leu Glu Glu Thr Leu Pro Leu Ile
225                 230                 235                 240

Leu Gly Leu Ile Leu Gly Leu Val Ile Val Val Thr Leu Val Ile Tyr
                245                 250                 255
```

```
His Ile His His Lys Met Thr Ala Asn Gln Val Gln Ile Pro Arg Asp
            260                 265                 270

Arg Ser Gln Tyr Lys His Met Gly
        275                 280


<210> SEQ ID NO 98
<211> LENGTH: 280
<212> TYPE: PRT
<213> ORGANISM: Mus musculus

<400> SEQUENCE: 98

Met Asp Leu Arg Val Arg Thr Leu Leu Gly Gly Asp Arg Leu Arg Ile
1               5                   10                  15

Leu Leu Met Phe Phe His Val Met Val Gln Thr Val Ala Glu Gln Glu
            20                  25                  30

Val Glu Asn Leu Ser Gly Leu Ser Thr Asn Pro Glu Lys Asp Ile Phe
        35                  40                  45

Val Val Arg Glu Asn Gly Thr Thr Cys Leu Met Ala Glu Phe Ala Ala
    50                  55                  60

Lys Phe Ile Val Pro Tyr Asp Val Trp Ala Ser Asn Tyr Val Asp Leu
65                  70                  75                  80

Ile Thr Glu Gln Ala Glu Ile Ser Leu Thr Arg Gly Ala Glu Val Lys
                85                  90                  95

Gly His Cys Gly His Asn Glu Ser Glu Leu Glu Val Phe Trp Val Asp
            100                 105                 110

His Ala Tyr Thr Leu Arg Met Leu Phe Val Lys Glu Ser His Asn Thr
        115                 120                 125

Ser Lys Gly Pro Glu Ala Thr Trp Asn Leu Asn Lys Val His Phe Val
    130                 135                 140

Tyr Asp Ser Ser Glu Lys Thr His Phe Lys Ala Pro Val Lys Val Asn
145                 150                 155                 160

Lys Tyr Ile Ala Ser Ser His His Leu Ser Ala Leu Val Thr Pro Ala
                165                 170                 175

Gly Met Ser Tyr Glu Cys Gln Ala Gln Gln Thr Ile Ser Leu Ala Ser
            180                 185                 190

Ser Asp Pro Gln Lys Thr Val Thr Met Ile Leu Ser Ala Val His Ile
        195                 200                 205

Gln Pro Phe Asp Ile Ile Ser Asp Phe Val Phe Ser Glu Glu His Lys
    210                 215                 220

Cys Pro Val Asp Glu Gln Glu Gln Leu Glu Glu Thr Leu Pro Leu Ile
225                 230                 235                 240

Leu Gly Leu Ile Leu Gly Leu Val Ile Val Ile Thr Leu Val Ile Tyr
                245                 250                 255

His Ile His His Lys Met Thr Ala Asn Gln Val Gln Ile Pro Arg Asp
            260                 265                 270

Arg Ser Gln Tyr Lys His Met Gly
        275                 280


<210> SEQ ID NO 99
<211> LENGTH: 280
<212> TYPE: PRT
<213> ORGANISM: Rattus norvegicus

<400> SEQUENCE: 99

Met Asp Leu Arg Gly Arg Ala Leu Leu Gly Gly Asp Arg Leu Arg Ile
1               5                   10                  15
```

```
Leu Leu Met Phe Phe His Ala Met Ala Gln Thr Val Ala Glu Gln Glu
            20                  25                  30

Val Glu Asn Leu Ser Gly Leu Ser Thr Asn Pro Glu Lys Asp Ile Phe
        35                  40                  45

Val Val Arg Glu Asn Gly Thr Thr Cys Leu Met Ala Glu Phe Ala Ala
    50                  55                  60

Lys Phe Ile Val Pro Tyr Asp Val Trp Ala Ser Asn Tyr Val Asp Leu
65                  70                  75                  80

Ile Thr Glu Gln Ala Glu Ile Ser Leu Thr Arg Gly Ala Glu Val Lys
                85                  90                  95

Gly Arg Cys Gly His Asn Glu Ser Glu Leu Gln Val Phe Trp Val Asp
            100                 105                 110

Arg Ala Tyr Thr Leu Lys Met Leu Phe Val Lys Glu Ser His Asn Thr
        115                 120                 125

Ser Lys Gly Leu Glu Ala Thr Trp Lys Leu Ser Lys Val Gln Phe Val
    130                 135                 140

Tyr Asp Ser Ser Glu Lys Thr His Phe Lys Asp Ala Val Ser Ala Gly
145                 150                 155                 160

Lys His Thr Ala Asn Ser His His Leu Ser Ala Leu Val Thr Pro Ala
                165                 170                 175

Gly Met Ser Tyr Glu Cys Gln Ala Gln Gln Thr Ile Ser Leu Ala Ser
            180                 185                 190

Ser Asp Pro Gln Lys Thr Val Thr Met Ile Leu Ser Ala Val His Ile
        195                 200                 205

Gln Pro Phe Asp Ile Ile Ser Asp Phe Val Phe Ser Glu Glu His Lys
    210                 215                 220

Cys Pro Val Asp Glu Arg Glu Gln Leu Glu Glu Thr Leu Pro Leu Ile
225                 230                 235                 240

Leu Gly Leu Ile Leu Gly Leu Val Ile Val Ile Thr Leu Val Ile Tyr
                245                 250                 255

His Ile His His Lys Met Thr Ala Asn Gln Val Gln Ile Pro Arg Asp
            260                 265                 270

Arg Ser Gln Tyr Lys His Met Gly
        275                 280


<210> SEQ ID NO 100
<211> LENGTH: 299
<212> TYPE: PRT
<213> ORGANISM: Gallus gallus

<400> SEQUENCE: 100

Met Ala Ala Gly Arg Leu Pro Gly Leu Leu Phe Leu Leu His Ala Ala
1               5                   10                  15

Ala Arg Leu Ala Ala Glu Gln Glu Val Glu Asn Leu Ser Gly Leu Ser
            20                  25                  30

Pro Asn Pro Glu Lys Asp Ile Phe Val Val Arg Glu Asn Arg Thr Thr
        35                  40                  45

Cys Leu Met Ala Glu Phe Ala Ala Lys Phe Val Val Pro Tyr Asp Val
    50                  55                  60

Trp Ala Ser Asn Tyr Val Asp Leu Ile Thr Glu Gln Ala Asp Ile Pro
65                  70                  75                  80

Leu Ser Arg Gly Ala Glu Met Lys Gly Lys Cys Gly Thr Asn Glu Ser
                85                  90                  95

Glu Leu Glu Ile Ser Trp Leu Glu Arg Ala Tyr Thr Leu Lys Leu Phe
            100                 105                 110
```

```
Phe Leu Lys Val Arg Gly Cys Pro Arg Arg Leu Gly Arg Gly Arg Cys
        115                 120                 125

Ala Ala Ala Leu Arg Gly Pro Asp Gln Pro Cys Pro Pro Gln Glu Gly
    130                 135                 140

His Asn Thr Ser Arg Gly Pro Glu Ala Phe Trp Arg Leu Ser Arg Ile
145                 150                 155                 160

Gln Phe Ser Tyr Asp Thr Ser Glu Arg Thr Tyr Phe Lys Asp Ala Val
                165                 170                 175

Ser Pro Gly Lys His Thr Ala Ser Ser His Arg Leu Ser Ala Leu Val
            180                 185                 190

Thr Pro Ala Gly Lys Ser Tyr Glu Cys Gln Ala Gln Gln Thr Ile Ser
        195                 200                 205

Leu Ile Ser Ser Asp His Gln Lys Ser Val Gln Leu Leu Leu Ser Glu
    210                 215                 220

Val Arg Ile Gln Pro Phe Asp Ile Thr Ala Asp Phe Val Phe Ser Glu
225                 230                 235                 240

Glu His Lys Cys Pro Val Asp Gln Arg Glu Gln Leu Glu Glu Thr Leu
                245                 250                 255

Pro Leu Ile Leu Gly Leu Ile Leu Gly Leu Val Ile Val Ile Thr Leu
            260                 265                 270

Cys Val Tyr His Ile His His Lys Leu Thr Ala Asn Gln Val Gln Ile
        275                 280                 285

Pro Arg Asp Arg Ser Gln Tyr Lys His Met Gly
    290                 295


<210> SEQ ID NO 101
<211> LENGTH: 276
<212> TYPE: PRT
<213> ORGANISM: Xenopus tropicalis

<400> SEQUENCE: 101

Met Asp Tyr Arg Ala Cys Thr Ser Ala Leu Arg Met Pro Val Leu Leu
1               5                   10                  15

Leu Leu Leu Cys Thr Phe Ser Cys Asn Leu Ala Glu Gln Glu Val Glu
            20                  25                  30

Asn Leu Ser Gly Leu Ser Ser Asn Pro Asp Lys Asn Ile Phe Ala Ile
        35                  40                  45

Arg Glu Asn Gly Thr Thr Cys Leu Met Ala Glu Phe Ser Ala Arg Ile
    50                  55                  60

Leu Val Pro Tyr Glu Val Pro Ser Ser Asn Glu Val Asp Trp Asp Leu
65                  70                  75                  80

Glu Glu Ala Ser Ile Gln Leu Pro Arg Asp Thr Glu Ile Arg Gly Lys
                85                  90                  95

Cys Trp Asn Asn Glu Ser Glu Leu His Leu Ser Trp Leu Asp Lys Ala
            100                 105                 110

Tyr Thr Leu Lys Leu Phe Phe Ser Lys Glu Gly Gln Asp Ala Ser Lys
        115                 120                 125

Ser Arg Ser Trp Lys Met Ser Lys Ile Gln Phe Leu Tyr Asp Pro Ser
    130                 135                 140

Glu His Thr Ile Phe Lys Ser Gly Ala Arg Pro Gly Arg His Thr Ala
145                 150                 155                 160

Asn Ser His His Leu Ser Leu Met Val Thr Pro Ala Gly Met Ser Tyr
                165                 170                 175

Glu Cys Glu Ala Thr Gln Arg Ile Ser Leu Thr Ser Thr Asp His Gln
```

```
            180                 185                 190

Lys Ile Val Val Leu Tyr Leu Ser Glu Val His Leu Gln Pro Phe Asp
        195                 200                 205

Ile Lys Ser Asp Phe Val Tyr Ser Glu Glu Tyr Lys Cys Pro Thr Asp
    210                 215                 220

Gln Arg Lys Gln Leu Glu Glu Thr Leu Pro Leu Ile Leu Gly Leu Thr
225                 230                 235                 240

Leu Gly Val Ala Ile Leu Ile Ile Val Ala Val Tyr His Ile His His
                245                 250                 255

Lys Met Thr Ala Asn Gln Val Gln Ile Pro Arg Asp Arg Ser Leu Tyr
            260                 265                 270

Lys His Met Gly
        275


<210> SEQ ID NO 102
<211> LENGTH: 338
<212> TYPE: PRT
<213> ORGANISM: Rattus norvegicus

<400> SEQUENCE: 102

Met Val Gly Arg Val Gln Pro Asp Arg Lys Gln Leu Pro Leu Val Leu
1               5                   10                  15

Leu Arg Leu Leu Cys Leu Leu Pro Thr Gly Leu Pro Val Arg Ser Val
            20                  25                  30

Asp Phe Asn Arg Gly Thr Asp Asn Ile Thr Val Arg Gln Gly Asp Thr
        35                  40                  45

Ala Ile Leu Arg Cys Val Val Glu Asp Lys Asn Ser Lys Val Ala Trp
    50                  55                  60

Leu Asn Arg Ser Gly Ile Ile Phe Ala Gly His Asp Lys Trp Ser Leu
65                  70                  75                  80

Asp Pro Arg Val Glu Leu Glu Lys Arg His Ala Leu Glu Tyr Ser Leu
                85                  90                  95

Arg Ile Gln Lys Val Asp Val Tyr Asp Glu Gly Ser Tyr Thr Cys Ser
            100                 105                 110

Val Gln Thr Gln His Glu Pro Lys Thr Ser Gln Val Tyr Leu Ile Val
        115                 120                 125

Gln Val Pro Pro Lys Ile Ser Asn Ile Ser Ser Asp Val Thr Val Asn
    130                 135                 140

Glu Gly Ser Asn Val Thr Leu Val Cys Met Ala Asn Gly Arg Pro Glu
145                 150                 155                 160

Pro Val Ile Thr Trp Arg His Leu Thr Pro Leu Gly Arg Glu Phe Glu
                165                 170                 175

Gly Glu Glu Glu Tyr Leu Glu Ile Leu Gly Ile Thr Arg Glu Gln Ser
            180                 185                 190

Gly Lys Tyr Glu Cys Lys Ala Ala Asn Glu Val Ser Ser Ala Asp Val
        195                 200                 205

Lys Gln Val Lys Val Thr Val Asn Tyr Pro Pro Thr Ile Thr Glu Ser
    210                 215                 220

Lys Ser Asn Glu Ala Thr Thr Gly Arg Gln Ala Ser Leu Lys Cys Glu
225                 230                 235                 240

Ala Ser Ala Val Pro Ala Pro Asp Phe Glu Trp Tyr Arg Asp Asp Thr
                245                 250                 255

Arg Ile Asn Ser Ala Asn Gly Leu Glu Ile Lys Ser Thr Glu Gly Gln
            260                 265                 270
```

```
Ser Ser Leu Thr Val Thr Asn Val Thr Glu Glu His Tyr Gly Asn Tyr
        275                 280                 285

Thr Cys Val Ala Ala Asn Lys Leu Gly Val Thr Asn Ala Ser Leu Val
    290                 295                 300

Leu Phe Arg Pro Gly Ser Val Arg Gly Ile Asn Gly Ser Ile Ser Leu
305                 310                 315                 320

Ala Val Pro Leu Trp Leu Leu Ala Ala Ser Leu Phe Cys Leu Leu Ser
                325                 330                 335

Lys Cys


<210> SEQ ID NO 103
<211> LENGTH: 338
<212> TYPE: PRT
<213> ORGANISM: Equus caballus

<400> SEQUENCE: 103

Met Val Gly Arg Val Gln Pro Asp Arg Lys Gln Leu Pro Leu Val Leu
1               5                   10                  15

Leu Arg Leu Leu Cys Leu Leu Pro Thr Gly Leu Pro Val Arg Ser Val
            20                  25                  30

Asp Phe Asn Arg Gly Thr Asp Asn Ile Thr Val Arg Gln Gly Asp Thr
        35                  40                  45

Ala Ile Leu Arg Cys Val Val Glu Asp Lys Asn Ser Lys Val Ala Trp
    50                  55                  60

Leu Asn Arg Ser Gly Ile Ile Phe Ala Gly His Asp Lys Trp Ser Leu
65                  70                  75                  80

Asp Pro Arg Val Glu Leu Glu Lys Arg His Ser Leu Glu Tyr Ser Leu
                85                  90                  95

Arg Ile Gln Lys Val Asp Val Tyr Asp Glu Gly Ser Tyr Thr Cys Ser
            100                 105                 110

Val Gln Thr Gln His Glu Pro Lys Thr Ser Gln Val Tyr Leu Ile Val
        115                 120                 125

Gln Val Pro Pro Lys Ile Ser Asn Ile Ser Ser Asp Val Thr Val Asn
    130                 135                 140

Glu Gly Ser Asn Val Thr Leu Val Cys Met Ala Asn Gly Arg Pro Glu
145                 150                 155                 160

Pro Val Ile Thr Trp Arg His Leu Thr Pro Thr Gly Arg Glu Phe Glu
                165                 170                 175

Gly Glu Glu Glu Tyr Leu Glu Ile Leu Gly Ile Thr Arg Glu Gln Ser
            180                 185                 190

Gly Lys Tyr Glu Cys Lys Ala Ala Asn Glu Val Ser Ser Ala Asp Val
        195                 200                 205

Lys Gln Val Lys Val Thr Val Asn Tyr Pro Pro Thr Ile Thr Glu Ser
    210                 215                 220

Lys Ser Asn Glu Ala Thr Thr Gly Arg Gln Ala Ser Leu Lys Cys Glu
225                 230                 235                 240

Ala Ser Ala Val Pro Ala Pro Asp Phe Glu Trp Tyr Arg Asp Asp Thr
                245                 250                 255

Arg Ile Thr Ser Ala Asn Gly Leu Glu Ile Lys Ser Thr Glu Gly Gln
            260                 265                 270

Ser Ser Leu Thr Val Ala Asn Val Thr Glu Glu His Tyr Gly Asn Tyr
        275                 280                 285

Thr Cys Val Ala Ala Asn Asn Leu Gly Val Thr Asn Ala Ser Leu Val
    290                 295                 300
```

-continued

```
Leu Phe Arg Pro Gly Ser Val Arg Gly Ile Asn Gly Ser Ile Ser Leu
305                 310                 315                 320

Ala Val Pro Leu Trp Leu Leu Ala Ala Ser Leu Leu Cys Leu Leu Ser
                325                 330                 335

Lys Cys


<210> SEQ ID NO 104
<211> LENGTH: 338
<212> TYPE: PRT
<213> ORGANISM: Sus scrofa

<400> SEQUENCE: 104

Met Val Ala Arg Val Gln Pro Asp Arg Lys Gln Leu Pro Leu Val Leu
1               5                   10                  15

Leu Arg Leu Leu Cys Leu Leu Pro Thr Gly Leu Pro Val Arg Ser Val
            20                  25                  30

Asp Phe Asn Arg Gly Thr Asp Asn Ile Thr Val Arg Gln Gly Asp Thr
        35                  40                  45

Ala Ile Leu Arg Cys Val Val Glu Asp Lys Asn Ser Lys Val Ala Trp
    50                  55                  60

Leu Asn Arg Ser Gly Ile Ile Phe Ala Gly His Asp Lys Trp Ser Leu
65                  70                  75                  80

Asp Pro Arg Val Glu Leu Glu Lys Arg His Ser Leu Glu Tyr Ser Leu
                85                  90                  95

Arg Ile Gln Lys Val Asp Val Tyr Asp Glu Gly Ser Tyr Thr Cys Ser
            100                 105                 110

Val Gln Thr Gln His Glu Pro Lys Thr Ser Gln Val Tyr Leu Ile Val
        115                 120                 125

Gln Val Pro Pro Lys Ile Ser Asn Ile Ser Ser Asp Val Thr Val Asn
    130                 135                 140

Glu Gly Ser Asn Val Thr Leu Val Cys Met Ala Asn Gly Arg Pro Glu
145                 150                 155                 160

Pro Val Ile Thr Trp Arg His Leu Thr Pro Thr Gly Arg Glu Leu Glu
                165                 170                 175

Gly Glu Glu Glu Tyr Leu Glu Ile Leu Gly Ile Thr Arg Glu Gln Ser
            180                 185                 190

Gly Lys Tyr Glu Cys Lys Ala Ala Asn Glu Val Ser Ser Ala Asp Val
        195                 200                 205

Lys Gln Val Lys Val Thr Val Asn Tyr Pro Pro Thr Ile Thr Glu Ser
    210                 215                 220

Lys Ser Asn Glu Ala Thr Thr Gly Arg Lys Ala Ser Leu Lys Cys Glu
225                 230                 235                 240

Ala Ser Ala Val Pro Ala Pro Asp Phe Glu Trp Tyr Arg Asp Asp Thr
                245                 250                 255

Arg Ile Asn Ser Ala Asn Gly Leu Glu Ile Lys Ser Thr Glu Gly Gln
            260                 265                 270

Ser Ser Leu Thr Val Thr Asn Val Thr Glu Glu His Tyr Gly Asn Tyr
        275                 280                 285

Thr Cys Val Ala Ala Asn Asn Leu Gly Val Thr Asn Ala Ser Leu Val
    290                 295                 300

Leu Phe Arg Pro Gly Ser Val Arg Gly Ile Asn Gly Ser Ile Ser Leu
305                 310                 315                 320

Ala Val Pro Leu Trp Leu Leu Ala Ala Ser Leu Leu Cys Leu Leu Ser
                325                 330                 335
```

Lys Cys

<210> SEQ ID NO 105
<211> LENGTH: 338
<212> TYPE: PRT
<213> ORGANISM: Bos taurus

<400> SEQUENCE: 105

```
Met Val Ala Arg Val Gln Pro Asp Arg Lys Gln Leu Pro Leu Val Leu
1               5                   10                  15

Leu Arg Leu Leu Cys Leu Leu Pro Thr Gly Leu Pro Val Arg Ser Val
            20                  25                  30

Asp Phe Asn Arg Gly Thr Asp Asn Ile Thr Val Arg Gln Gly Asp Thr
        35                  40                  45

Ala Ile Leu Arg Cys Val Val Glu Asp Lys Asn Ser Lys Val Ala Trp
    50                  55                  60

Leu Asn Arg Ser Gly Ile Ile Phe Ala Gly His Asp Lys Trp Ser Leu
65                  70                  75                  80

Asp Pro Arg Val Glu Leu Glu Lys Arg His Ser Leu Glu Tyr Ser Leu
                85                  90                  95

Arg Ile Gln Lys Val Asp Val Tyr Asp Glu Gly Ser Tyr Thr Cys Ser
            100                 105                 110

Val Gln Thr Gln His Glu Pro Lys Thr Ser Gln Val Tyr Leu Ile Val
        115                 120                 125

Gln Val Pro Pro Lys Ile Ser Asn Ile Ser Ser Asp Val Thr Val Asn
    130                 135                 140

Glu Gly Ser Asn Val Thr Leu Val Cys Met Ala Asn Gly Arg Pro Glu
145                 150                 155                 160

Pro Val Ile Thr Trp Arg His Leu Thr Pro Thr Gly Arg Glu Phe Glu
                165                 170                 175

Gly Glu Glu Glu Tyr Leu Glu Ile Leu Gly Ile Thr Arg Glu Gln Ser
            180                 185                 190

Gly Lys Tyr Glu Cys Lys Ala Ala Asn Glu Val Ser Ser Ala Asp Val
        195                 200                 205

Lys Gln Val Lys Val Thr Val Asn Tyr Pro Pro Thr Ile Thr Glu Ser
    210                 215                 220

Lys Ser Asn Glu Ala Thr Thr Gly Arg Lys Ala Ser Leu Lys Cys Glu
225                 230                 235                 240

Ala Ser Ala Val Pro Ala Pro Asp Phe Glu Trp Tyr Arg Asp Asp Thr
                245                 250                 255

Arg Ile Asn Ser Ala Asn Gly Leu Glu Ile Lys Ser Thr Glu Gly Gln
            260                 265                 270

Ser Ser Leu Thr Val Thr Asn Val Thr Glu Glu His Tyr Gly Asn Tyr
        275                 280                 285

Thr Cys Val Ala Ala Asn Asn Leu Gly Met Thr Asn Ala Ser Leu Val
    290                 295                 300

Leu Phe Arg Pro Gly Ser Val Arg Gly Ile Asn Gly Ser Ile Ser Leu
305                 310                 315                 320

Ala Val Pro Leu Trp Leu Leu Ala Ala Ser Leu Leu Cys Leu Leu Ser
                325                 330                 335

Lys Cys
```

<210> SEQ ID NO 106
<211> LENGTH: 417
<212> TYPE: PRT

```
<213> ORGANISM: Anopheles gambiae
<220> FEATURE:
<223> OTHER INFORMATION: str. PEST

<400> SEQUENCE: 106

Met Ser Phe Ala Gly Glu Ala Ala Ser Gln Ile Leu Asn Lys Ala Glu
1               5                   10                  15

Pro Leu Phe Ile Ser Arg Ser Glu Ala Phe Lys Phe Ala Val Gly Asp
            20                  25                  30

Thr Ile Thr Leu Pro Cys Glu Val Ala Ser Pro Gly Thr Tyr Val Leu
        35                  40                  45

Ala Trp Lys Arg Gly Ile Ala Ile Leu Thr Ala Gly Ser Val Lys Val
    50                  55                  60

Thr Pro Asp Pro Arg Val Arg Leu Val Asn Gly Tyr Ser Leu Gln Ile
65                  70                  75                  80

Arg Asp Ala Val Pro Gln Asp Ala Gly Asp Tyr Ile Cys Gln Ile Ala
                85                  90                  95

Met Leu Asp Pro Arg Glu Ile Thr His Ser Val Glu Ile Leu Val Pro
            100                 105                 110

Pro Lys Ile Thr His Val Thr Ser Gly Gly His Leu Gln Val Arg Lys
        115                 120                 125

Gly Ser Pro Val Arg Leu Glu Cys Ser Ala Thr Gly Asn Pro Met Pro
    130                 135                 140

Asn Ile Thr Trp Thr Arg Lys Asn Asn Leu Leu Pro Asn Gly Glu Glu
145                 150                 155                 160

Gln Phe Thr Asn Pro Val Tyr Val Ile Glu Asn Met Asp Arg His Lys
                165                 170                 175

Gly Gly Thr Tyr Ile Cys Thr Ala Asn Asn Gly Val Gly Gln Val Ala
            180                 185                 190

Thr Ser Gln Ile Ile Leu His Val Leu Tyr Pro Pro Glu Ile Ser Val
        195                 200                 205

Glu Asn Pro Thr Val Tyr Ser Gly Glu Gly Gln Glu Ala Met Leu Val
    210                 215                 220

Cys Ile Val His Gly Glu Ser Gln Pro Glu Val Leu Trp His Lys Asp
225                 230                 235                 240

Thr Met Gln Ile Asp Gln Thr Glu Arg His Val Ile Glu Asn Arg Gly
                245                 250                 255

Ala Arg His Thr Leu Ile Ile Arg Lys Val His Pro Gln Asp Phe Gly
            260                 265                 270

Asn Tyr Ser Cys Ile Ala Asp Asn Gln Leu Gly Lys Thr Arg Lys Thr
        275                 280                 285

Val Thr Leu Thr Gly Lys Pro Lys Thr Ala Val Phe Arg Ser Val Pro
    290                 295                 300

Asn Ser Gln Trp Lys Asp Lys Tyr Asn Ile Ser Trp Ile Val Asp Ser
305                 310                 315                 320

His Ser Pro Ile Glu Glu Phe Lys Leu Tyr Tyr Arg Gln Met Thr Phe
                325                 330                 335

Ser Ile Gly Gln Leu Gln Pro Leu Gln Thr Asp Trp Arg Asp Ile Val
            340                 345                 350

Leu Pro Ala Phe Pro Tyr Ser His His Tyr Thr Gln Gly Met Ser Tyr
        355                 360                 365

Leu Ile Arg Gly Leu Glu Pro Asp Gln Gln Tyr Glu Ala Arg Val Gln
    370                 375                 380

Ser Arg Asn Arg Tyr Gly Trp Ser Asp Phe Ser Glu Ser Phe Leu Phe
```

```
385                 390                 395                 400

Thr Thr Ser Asn Thr Gly Lys Trp Met Gly Gln Cys Cys Thr Asn Pro
                405                 410                 415

Gly


<210> SEQ ID NO 107
<211> LENGTH: 334
<212> TYPE: PRT
<213> ORGANISM: Xenopus tropicalis

<400> SEQUENCE: 107

Met Arg Pro Cys Leu Leu His Ser Ile Trp Met Leu Gly Phe Val Leu
1               5                   10                  15

Cys Leu Leu Ser Leu Gln Gly Leu Pro Val Arg Ser Gly Asp Phe Asn
            20                  25                  30

Arg Ser Thr Asp Asn Ile Thr Val Arg Gln Gly Asp Thr Ala Ile Leu
        35                  40                  45

Arg Cys Phe Val Glu Asp Arg Ser Ser Arg Val Ala Trp Leu Asn Arg
    50                  55                  60

Ser Gly Ile Ile Phe Ala Gly Asp Asp Lys Trp Ser Leu Asp Pro Arg
65                  70                  75                  80

Val Glu Leu Glu Lys Arg Ser Leu Leu Glu Tyr Ser Leu Arg Ile Gln
                85                  90                  95

Lys Val Asp Val Ser Asp Glu Gly Pro Tyr Thr Cys Ser Val Gln Thr
            100                 105                 110

Lys Gln His Thr Lys Thr Thr Gln Val Tyr Leu Ile Val Gln Val Pro
        115                 120                 125

Pro Lys Ile Ser Asn Ile Ser Ala Asp Ile Thr Val Asn Glu Gly Ser
    130                 135                 140

Asn Val Thr Leu Met Cys Ile Ala Tyr Gly Arg Pro Glu Pro Met Ile
145                 150                 155                 160

Thr Trp Arg His Leu Thr Pro Thr Ala Arg Asp Phe Glu Gly Glu Glu
                165                 170                 175

Glu Phe Leu Glu Ile Gln Gly Ile Thr Arg Glu Gln Ser Gly Arg Tyr
            180                 185                 190

Glu Cys Lys Ala Ala Asn Glu Val Ala Ser Ala Asp Val Lys Gln Val
        195                 200                 205

Arg Val Thr Val Asn Tyr Pro Pro Ile Ile Thr Glu Ser Lys Ser Asn
    210                 215                 220

Glu Ala Thr Thr Gly Lys Gln Ala Ile Leu Arg Cys Glu Ala Ser Ala
225                 230                 235                 240

Val Pro Ala Pro Asp Phe Glu Trp Tyr Lys Asp Asp Thr Arg Ile Asn
                245                 250                 255

Ser Ala Gln Gly Leu Glu Ile Arg Asn Thr Gly Ser Arg Ser Val Leu
            260                 265                 270

Met Val Ala Asn Val Thr Glu Glu His Tyr Gly Asn Tyr Thr Cys Val
        275                 280                 285

Ala Ala Asn Lys Leu Gly Ile Thr Asn Thr Ser Leu Tyr Leu Tyr Ile
    290                 295                 300

Gly Pro Gly Thr Pro Ile Asp Ser Ala Thr Ser Leu Ala Ala Ser Leu
305                 310                 315                 320

Trp Leu Met Ala Asn Leu Leu Phe Cys Leu Phe Cys Thr Cys
                325                 330
```

```
<210> SEQ ID NO 108
<211> LENGTH: 338
<212> TYPE: PRT
<213> ORGANISM: Canis lupus familiaris

<400> SEQUENCE: 108

Met Leu Gly Ala Arg Arg Pro Pro Arg Ser Gln Leu Pro Leu Val Leu
1               5                   10                  15

Leu Arg Leu Leu Cys Leu Leu Pro Thr Gly Leu Pro Val Arg Ser Val
            20                  25                  30

Asp Phe Asn Arg Gly Thr Asp Asn Ile Thr Val Arg Gln Gly Asp Thr
        35                  40                  45

Ala Ile Leu Arg Cys Val Val Glu Asp Lys Asn Ser Lys Val Ala Trp
    50                  55                  60

Leu Asn Arg Ser Gly Ile Ile Phe Ala Gly His Asp Lys Trp Ser Leu
65                  70                  75                  80

Asp Pro Arg Val Glu Leu Glu Lys Arg His Ser Leu Glu Tyr Ser Leu
                85                  90                  95

Arg Ile Gln Lys Val Asp Val Tyr Asp Glu Gly Ser Tyr Thr Cys Ser
            100                 105                 110

Val Gln Thr Gln His Glu Pro Lys Thr Ser Gln Val Tyr Leu Ile Val
        115                 120                 125

Gln Val Pro Pro Lys Ile Ser Asn Ile Ser Ser Asp Val Thr Val Asn
    130                 135                 140

Glu Gly Ser Asn Val Thr Leu Val Cys Met Ala Asn Gly Arg Pro Glu
145                 150                 155                 160

Pro Val Ile Thr Trp Arg His Leu Thr Pro Thr Gly Arg Glu Phe Glu
                165                 170                 175

Gly Glu Glu Glu Tyr Leu Glu Ile Leu Gly Ile Thr Arg Glu Gln Ser
            180                 185                 190

Gly Lys Tyr Glu Cys Lys Ala Ala Asn Glu Val Ser Ser Ala Asp Val
        195                 200                 205

Arg Gln Val Lys Val Thr Val Asn Tyr Pro Pro Thr Ile Thr Glu Ser
    210                 215                 220

Lys Ser Asn Glu Ala Thr Thr Gly Arg Lys Ala Ser Leu Lys Cys Glu
225                 230                 235                 240

Ala Ser Ala Val Pro Ala Pro Asp Phe Glu Trp Tyr Arg Asp Asp Thr
                245                 250                 255

Arg Ile Asn Ser Ala Asn Gly Leu Glu Ile Lys Ser Thr Glu Gly Gln
            260                 265                 270

Ser Ser Leu Thr Val Thr Asn Val Thr Glu Glu His Tyr Gly Asn Tyr
        275                 280                 285

Thr Cys Val Ala Ala Asn Asn Leu Gly Val Thr Asn Ala Ser Leu Val
    290                 295                 300

Leu Phe Arg Pro Gly Ser Val Arg Gly Ile Asn Gly Ser Ile Ser Leu
305                 310                 315                 320

Ala Val Pro Leu Trp Leu Leu Ala Ala Ser Leu Leu Cys Leu Leu Ser
                325                 330                 335

Lys Cys


<210> SEQ ID NO 109
<211> LENGTH: 338
<212> TYPE: PRT
<213> ORGANISM: Monodelphis domestica

<400> SEQUENCE: 109
```

```
Met Val Gly Arg Val His Pro Asp Arg Lys Gln Leu Pro Leu Val Leu
1               5                   10                  15

Leu Arg Leu Leu Cys Leu Leu Pro Thr Gly Leu Pro Val Arg Gly Val
            20                  25                  30

Asp Phe Thr Arg Gly Thr Asp Asn Ile Thr Val Arg Gln Gly Asp Thr
        35                  40                  45

Ala Ile Leu Arg Cys Tyr Val Glu Asp Lys Ser Ser Lys Val Ala Trp
    50                  55                  60

Leu Asn Arg Ser Gly Ile Ile Phe Ala Gly His Asp Lys Trp Ser Leu
65                  70                  75                  80

Asp Pro Arg Val Glu Leu Glu Lys Arg Thr Ala Leu Glu Tyr Ser Leu
                85                  90                  95

Arg Ile Gln Lys Val Asp Val Tyr Asp Glu Gly Ser Tyr Thr Cys Ser
            100                 105                 110

Val Gln Thr Gln His Gln Pro Lys Thr Ser Gln Val Tyr Leu Ile Val
        115                 120                 125

Gln Val Pro Pro Lys Ile Ser Asn Ile Ser Ser Asp Val Thr Val Asn
    130                 135                 140

Glu Gly Ser Asn Val Thr Leu Val Cys Met Ala Asn Gly Arg Pro Glu
145                 150                 155                 160

Pro Val Ile Thr Trp Arg His Leu Thr Pro Thr Gly Arg Glu Phe Glu
                165                 170                 175

Gly Glu Glu Glu Tyr Leu Glu Ile Leu Gly Ile Thr Arg Glu Gln Ser
            180                 185                 190

Gly Lys Tyr Glu Cys Lys Ala Ala Asn Glu Val Ser Ser Ala Asp Val
        195                 200                 205

Lys Gln Val Lys Val Thr Val Asn Tyr Pro Pro Thr Ile Thr Glu Ser
    210                 215                 220

Lys Ser Asn Glu Ala Thr Thr Gly Arg Gln Ala Ser Leu Lys Cys Glu
225                 230                 235                 240

Ala Ser Ala Val Pro Ala Pro Asp Phe Glu Trp Tyr Arg Asp Asp Thr
                245                 250                 255

Arg Ile Asn Ser Ala Asn Gly Leu Glu Ile Lys Ser Ile Glu Gly Gln
            260                 265                 270

Ser Leu Leu Met Val Thr Asn Val Thr Glu Glu His Tyr Gly Asn Tyr
        275                 280                 285

Thr Cys Val Ala Ala Asn Lys Leu Gly Val Thr Asn Ala Ser Leu Ile
    290                 295                 300

Leu Phe Arg Pro Gly Ser Val Arg Gly Ile Asn Gly Ser Ile Ser Leu
305                 310                 315                 320

Ala Val Pro Leu Trp Leu Leu Ala Ala Ser Leu Phe Cys Leu Leu Ser
                325                 330                 335

Lys Cys
```

<210> SEQ ID NO 110
<211> LENGTH: 338
<212> TYPE: PRT
<213> ORGANISM: Gallus gallus

<400> SEQUENCE: 110

```
Met Val Ala Arg Ala Gln Pro Asp Arg Lys Gln Leu Pro Leu Val Leu
1               5                   10                  15

Leu Arg Leu Leu Cys Leu Leu Pro Thr Gly Leu Pro Val Arg Ser Val
            20                  25                  30
```

```
Asp Phe Thr Arg Gly Thr Asp Asn Ile Thr Val Arg Gln Gly Asp Thr
        35                  40                  45

Ala Ile Leu Arg Cys Phe Val Glu Asp Arg Ser Ser Lys Val Ala Trp
    50                  55                  60

Leu Asn Arg Ser Gly Ile Ile Phe Ala Gly Glu Asp Lys Trp Ser Leu
65                  70                  75                  80

Asp Pro Arg Val Glu Leu Glu Lys Arg Ser Pro Leu Glu Tyr Ser Leu
                85                  90                  95

Arg Ile Gln Lys Val Asp Val Tyr Asp Glu Gly Ser Tyr Thr Cys Ser
            100                 105                 110

Val Gln Thr Gln His His Pro Lys Thr Ser Gln Val Tyr Leu Ile Val
        115                 120                 125

Gln Val Pro Pro Lys Ile Ser Asn Ile Ser Ser Asp Ile Thr Val Asn
    130                 135                 140

Glu Gly Ser Asn Val Thr Leu Val Cys Met Ala Asn Gly Arg Pro Glu
145                 150                 155                 160

Pro Val Ile Thr Trp Arg His Leu Thr Pro Thr Gly Lys Glu Phe Glu
                165                 170                 175

Gly Glu Glu Glu Tyr Leu Glu Ile Leu Gly Ile Thr Arg Glu Gln Ser
            180                 185                 190

Gly Lys Tyr Glu Cys Lys Ala Ala Asn Glu Val Ala Ser Ala Asp Val
        195                 200                 205

Lys Gln Val Arg Val Thr Val Asn Tyr Pro Pro Thr Ile Thr Glu Ser
    210                 215                 220

Lys Ser Asn Glu Ala Ala Thr Gly Arg Gln Ala Leu Leu Arg Cys Glu
225                 230                 235                 240

Ala Ser Ala Val Pro Thr Pro Asp Phe Glu Trp Tyr Arg Asp Asp Thr
                245                 250                 255

Arg Ile Asn Ser Ala Asn Gly Leu Glu Ile Lys Ser Thr Gly Ser Gln
            260                 265                 270

Ser Leu Leu Met Val Ala Asn Val Thr Glu Glu His Tyr Gly Asn Tyr
        275                 280                 285

Thr Cys Val Ala Ala Asn Lys Leu Gly Val Thr Asn Ala Ser Leu Tyr
    290                 295                 300

Leu Tyr Arg Pro Gly Thr Gly Arg Val Asp Asn Gly Ser Val Ser Leu
305                 310                 315                 320

Ala Val Pro Leu Trp Leu Leu Ala Ala Ser Leu Leu Cys Leu Leu Ser
                325                 330                 335

Lys Cys


<210> SEQ ID NO 111
<211> LENGTH: 335
<212> TYPE: PRT
<213> ORGANISM: Taeniopygia guttata

<400> SEQUENCE: 111

Met Arg Thr Tyr Trp Leu His Ser Ile Trp Val Leu Gly Phe Phe Leu
1               5                   10                  15

Ser Leu Phe Ser Leu Gln Gly Leu Pro Val Arg Ser Val Asp Phe Thr
            20                  25                  30

Arg Gly Thr Asp Asn Ile Thr Val Arg Gln Gly Asp Thr Ala Ile Leu
        35                  40                  45

Arg Cys Tyr Val Glu Asp Arg Ser Ser Lys Val Ala Trp Leu Asn Arg
    50                  55                  60
```

```
Ser Gly Ile Ile Phe Ala Gly Glu Asp Lys Trp Ser Leu Asp Pro Arg
65                  70                  75                  80

Val Glu Leu Glu Lys Arg Asn Pro Leu Glu Tyr Ser Leu Arg Ile Gln
                85                  90                  95

Lys Val Asp Val Tyr Asp Glu Gly Ser Tyr Thr Cys Ser Val Gln Thr
            100                 105                 110

Gln His His Pro Lys Thr Ser Gln Val Tyr Leu Ile Val Gln Val Pro
        115                 120                 125

Pro Lys Ile Ser Asn Ile Ser Ser Asp Ile Thr Val Asn Glu Gly Ser
    130                 135                 140

Asn Val Thr Leu Val Cys Met Ala Asn Gly Arg Pro Glu Pro Val Ile
145                 150                 155                 160

Thr Trp Arg His Leu Thr Pro Thr Gly Lys Glu Phe Glu Gly Glu Glu
                165                 170                 175

Glu Tyr Leu Glu Ile Leu Gly Ile Thr Arg Glu Gln Ser Gly Lys Tyr
            180                 185                 190

Glu Cys Lys Ala Ala Asn Glu Val Ala Ser Ala Asp Val Lys Gln Val
        195                 200                 205

Arg Val Thr Val Asn Tyr Pro Pro Thr Ile Thr Glu Ser Lys Ser Asn
    210                 215                 220

Glu Ala Ala Thr Gly Arg Gln Ala Leu Leu Arg Cys Glu Ala Ser Ala
225                 230                 235                 240

Val Pro Thr Pro Asp Phe Glu Trp Tyr Arg Asp Asp Thr Arg Ile Asn
                245                 250                 255

Ser Ala Asn Gly Leu Glu Ile Lys Ser Thr Gly Ser Gln Ser Leu Leu
            260                 265                 270

Met Val Ala Asn Val Thr Glu Glu His Tyr Gly Asn Tyr Thr Cys Val
        275                 280                 285

Ala Ala Asn Lys Leu Gly Val Thr Asn Ala Ser Leu Tyr Leu Tyr Arg
    290                 295                 300

Pro Gly Thr Gly Arg Val Asp Asn Gly Ser Met Ser Leu Ala Val Pro
305                 310                 315                 320

Leu Trp Leu Leu Ala Ala Ser Leu Leu Cys Leu Leu Ser Lys Cys
                325                 330                 335


<210> SEQ ID NO 112
<211> LENGTH: 334
<212> TYPE: PRT
<213> ORGANISM: Xenopus tropicalis

<400> SEQUENCE: 112

Met Arg Pro Cys Leu Leu His Ser Ile Trp Met Leu Gly Phe Val Leu
1               5                   10                  15

Cys Leu Leu Ser Leu Gln Gly Leu Pro Val Arg Ser Gly Asp Phe Asn
            20                  25                  30

Arg Ser Thr Asp Asn Ile Thr Val Arg Gln Gly Asp Thr Ala Ile Leu
        35                  40                  45

Arg Cys Phe Val Glu Asp Arg Ser Ser Arg Val Ala Trp Leu Asn Arg
    50                  55                  60

Ser Gly Ile Ile Phe Ala Gly Asp Asp Lys Trp Ser Leu Asp Pro Arg
65                  70                  75                  80

Val Glu Leu Glu Lys Arg Ser Leu Leu Glu Tyr Ser Leu Arg Ile Gln
                85                  90                  95

Lys Val Asp Val Ser Asp Glu Gly Pro Tyr Thr Cys Ser Val Gln Thr
```

```
            100                 105                 110

Lys Gln His Thr Lys Thr Thr Gln Val Tyr Leu Ile Val Gln Val Pro
        115                 120                 125

Pro Lys Ile Ser Asn Ile Ser Ala Asp Ile Thr Val Asn Glu Gly Ser
    130                 135                 140

Asn Val Thr Leu Met Cys Ile Ala Tyr Gly Arg Pro Glu Pro Met Ile
145                 150                 155                 160

Thr Trp Arg His Leu Thr Pro Thr Ala Arg Asp Phe Glu Gly Glu Glu
                165                 170                 175

Glu Phe Leu Glu Ile Gln Gly Ile Thr Arg Glu Gln Ser Gly Arg Tyr
            180                 185                 190

Glu Cys Lys Ala Ala Asn Glu Val Ala Ser Ala Asp Val Lys Gln Val
        195                 200                 205

Arg Val Thr Val Asn Tyr Pro Pro Ile Ile Thr Glu Ser Lys Ser Asn
    210                 215                 220

Glu Ala Thr Thr Gly Lys Gln Ala Ile Leu Arg Cys Glu Ala Ser Ala
225                 230                 235                 240

Val Pro Ala Pro Asp Phe Glu Trp Tyr Lys Asp Asp Thr Arg Ile Asn
                245                 250                 255

Ser Ala Gln Gly Leu Glu Ile Arg Asn Thr Gly Ser Arg Ser Val Leu
            260                 265                 270

Met Val Ala Asn Val Thr Glu Glu His Tyr Gly Asn Tyr Thr Cys Val
        275                 280                 285

Ala Ala Asn Lys Leu Gly Ile Thr Asn Thr Ser Leu Tyr Leu Tyr Ile
    290                 295                 300

Gly Pro Gly Thr Pro Ile Asp Ser Ala Thr Ser Leu Ala Ala Ser Leu
305                 310                 315                 320

Trp Leu Met Ala Asn Leu Leu Phe Cys Leu Phe Cys Thr Cys
                325                 330


<210> SEQ ID NO 113
<211> LENGTH: 337
<212> TYPE: PRT
<213> ORGANISM: Oreochromis niloticus

<400> SEQUENCE: 113

Met Gln Val Gly Arg Lys Ser Cys Trp Arg Gln Leu Gln Ala Ser Phe
1               5                   10                  15

Phe Arg Leu Leu Cys Leu Ile Pro Thr Gly Phe Pro Val Arg Ser Val
            20                  25                  30

Asp Met Gln Arg Ala Thr Asp Asn Ile Thr Ile Arg Gln Gly Asp Thr
        35                  40                  45

Ala Ile Ile Arg Cys Tyr Val Asp Asp Lys Val Ser Lys Val Ala Trp
    50                  55                  60

Leu Asn Arg Ser Asn Ile Ile Phe Ala Gly Gln Asp Lys Trp Ser Leu
65                  70                  75                  80

Asp Pro Arg Val Asp Leu Val Thr Lys Gly Gln Leu Glu Tyr Ser Leu
                85                  90                  95

Arg Ile Gln Lys Val Asp Val Tyr Asp Glu Gly Ser Tyr Thr Cys Ser
            100                 105                 110

Ile Gln Thr Lys Gln Gln Pro Lys Thr Ser Gln Val Tyr Leu Ile Val
        115                 120                 125

Gln Val Pro Ala Ser Ile Tyr Gln Val Ser Asn Asp Ile Thr Val Asn
    130                 135                 140
```

```
Glu Gly Ser Asn Val Thr Leu Ser Cys Leu Ala Asn Gly Arg Pro Asp
145                 150                 155                 160

Pro Ala Ile Thr Trp Arg Leu Leu Asn Pro Ser Ala Glu Pro Leu Asp
                165                 170                 175

Gly Glu Glu Tyr Leu Asp Ile Ile Gly Ile Met Arg Thr Gln Ala Gly
            180                 185                 190

Arg Tyr Glu Cys Lys Ala Ser Asn Asp Val Ala Thr Pro Asp Val Lys
        195                 200                 205

Tyr Val Asn Val Ile Val Asn Tyr Pro Pro Thr Ile Lys Lys Thr Gln
    210                 215                 220

Ser Ser Glu Thr Pro Val Gly Arg Asn Gly Thr Leu Arg Cys Glu Val
225                 230                 235                 240

Thr Ala Val Pro Thr Pro Glu Phe Glu Trp Tyr Arg Asp Asp Lys Arg
                245                 250                 255

Leu Ala Asn Thr Gln Ser Ile Thr Ile Gln Thr Ser Gly Thr Thr Thr
            260                 265                 270

Ser Leu Thr Ile Ala Asn Ile Thr Glu Glu Asp Tyr Gly Asn Tyr Thr
        275                 280                 285

Cys Val Ala Ser Asn Arg Leu Gly Val Gln Asn Ala Ser Leu Phe Leu
    290                 295                 300

Tyr Arg Pro Gly Thr Gly Arg Asp Ile Asn Gly Ser Ala Cys Val Ser
305                 310                 315                 320

Gln Ser Leu Trp Leu Leu Leu Ala Ser Phe Ala Cys Leu Phe Leu Lys
                325                 330                 335

Cys


<210> SEQ ID NO 114
<211> LENGTH: 164
<212> TYPE: PRT
<213> ORGANISM: Homo sapiens

<400> SEQUENCE: 114

Leu Pro Ser Cys Lys Glu Asp Glu Tyr Pro Val Gly Ser Glu Cys Cys
1               5                   10                  15

Pro Lys Cys Ser Pro Gly Tyr Arg Val Lys Glu Ala Cys Gly Glu Leu
            20                  25                  30

Thr Gly Thr Val Cys Glu Pro Cys Pro Pro Gly Thr Tyr Ile Ala His
        35                  40                  45

Leu Asn Gly Leu Ser Lys Cys Leu Gln Cys Gln Met Cys Asp Pro Ala
    50                  55                  60

Met Gly Leu Arg Ala Ser Arg Asn Cys Ser Arg Thr Glu Asn Ala Val
65                  70                  75                  80

Cys Gly Cys Ser Pro Gly His Phe Cys Ile Val Gln Asp Gly Asp His
                85                  90                  95

Cys Ala Ala Cys Arg Ala Tyr Ala Thr Ser Ser Pro Gly Gln Arg Val
            100                 105                 110

Gln Lys Gly Gly Thr Glu Ser Gln Asp Thr Leu Cys Gln Asn Cys Pro
        115                 120                 125

Pro Gly Thr Phe Ser Pro Asn Gly Thr Leu Glu Glu Cys Gln His Gln
    130                 135                 140

Thr Lys Cys Ser Trp Leu Val Thr Lys Ala Gly Ala Gly Thr Ser Ser
145                 150                 155                 160

Ser His Trp Val
```

```
<210> SEQ ID NO 115
<211> LENGTH: 562
<212> TYPE: PRT
<213> ORGANISM: Artificial Sequence
<220> FEATURE:
<223> OTHER INFORMATION: Synthetic Construct

<400> SEQUENCE: 115

Met Ala Pro Arg Ser Ala Arg Arg Pro Leu Leu Leu Leu Leu Leu Leu
1               5                   10                  15

Leu Leu Leu Gly Leu Met His Cys Ala Ser Ala Ala Met Phe Met Val
            20                  25                  30

Lys Asn Gly Asn Gly Thr Ala Cys Ile Met Ala Asn Phe Ser Ala Ala
        35                  40                  45

Phe Ser Val Asn Tyr Asp Thr Lys Ser Gly Pro Lys Asn Met Thr Leu
    50                  55                  60

Asp Leu Pro Ser Asp Ala Thr Val Val Leu Asn Arg Ser Ser Cys Gly
65                  70                  75                  80

Lys Glu Asn Thr Ser Asp Pro Ser Leu Val Ile Ala Phe Gly Arg Gly
                85                  90                  95

His Thr Leu Thr Leu Asn Phe Thr Arg Asn Ala Thr Arg Tyr Ser Val
            100                 105                 110

Gln Leu Met Ser Phe Val Tyr Asn Leu Ser Asp Thr His Leu Phe Pro
        115                 120                 125

Asn Ala Ser Ser Lys Glu Ile Lys Thr Val Glu Ser Ile Thr Asp Ile
    130                 135                 140

Arg Ala Asp Ile Asp Lys Lys Tyr Arg Cys Val Ser Gly Thr Gln Val
145                 150                 155                 160

His Met Asn Asn Val Thr Val Thr Leu His Asp Ala Thr Ile Gln Ala
                165                 170                 175

Tyr Leu Ser Asn Ser Ser Phe Ser Arg Gly Glu Thr Arg Cys Glu Gln
            180                 185                 190

Asp Arg Pro Ser Pro Thr Thr Ala Pro Pro Ala Pro Pro Ser Pro Ser
        195                 200                 205

Pro Ser Pro Val Pro Lys Ser Pro Ser Val Asp Lys Tyr Asn Val Ser
    210                 215                 220

Gly Thr Asn Gly Thr Cys Leu Leu Ala Ser Met Gly Leu Gln Leu Asn
225                 230                 235                 240

Leu Thr Tyr Glu Arg Lys Asp Asn Thr Thr Val Thr Arg Leu Leu Asn
                245                 250                 255

Ile Asn Pro Asn Lys Thr Ser Ala Ser Gly Ser Cys Gly Ala His Leu
            260                 265                 270

Val Thr Leu Glu Leu His Ser Glu Gly Thr Thr Val Leu Leu Phe Gln
        275                 280                 285

Phe Gly Met Asn Ala Ser Ser Ser Arg Phe Phe Leu Gln Gly Ile Gln
    290                 295                 300

Leu Asn Thr Ile Leu Pro Asp Ala Arg Asp Pro Ala Phe Lys Ala Ala
305                 310                 315                 320

Asn Gly Ser Leu Arg Ala Leu Gln Ala Thr Val Gly Asn Ser Tyr Lys
                325                 330                 335

Cys Asn Ala Glu Glu His Val Arg Val Thr Lys Ala Phe Ser Val Asn
            340                 345                 350

Ile Phe Lys Val Trp Val Gln Ala Phe Lys Val Glu Gly Gly Gln Phe
        355                 360                 365

Gly Ser Val Glu Glu Cys Leu Leu Asp Glu Asn Ser Leu Glu Met Gly
```

```
    370                 375                 380

Ala Pro Thr Leu Pro Pro Ala Trp Gln Pro Phe Leu Lys Asp His Arg
385                 390                 395                 400

Ile Ser Thr Phe Lys Asn Trp Pro Phe Leu Glu Gly Cys Ala Cys Thr
                405                 410                 415

Pro Glu Arg Met Ala Glu Ala Gly Phe Ile His Cys Pro Thr Glu Asn
            420                 425                 430

Glu Pro Asp Leu Ala Gln Cys Phe Phe Cys Phe Lys Glu Leu Glu Gly
        435                 440                 445

Trp Glu Pro Asp Asp Asp Pro Ile Glu Glu His Lys Lys His Ser Ser
    450                 455                 460

Gly Cys Ala Phe Leu Ser Val Lys Lys Gln Phe Glu Glu Leu Thr Leu
465                 470                 475                 480

Gly Glu Phe Leu Lys Leu Asp Arg Glu Arg Ala Lys Asn Lys Ile Ala
                485                 490                 495

Lys Glu Thr Asn Asn Lys Lys Lys Glu Phe Glu Glu Thr Ala Lys Lys
            500                 505                 510

Val Arg Arg Ala Ile Glu Gln Leu Ala Ala Met Asp Glu Phe Thr Leu
        515                 520                 525

Ile Pro Ile Ala Val Gly Gly Ala Leu Ala Gly Leu Val Leu Ile Val
    530                 535                 540

Leu Ile Ala Tyr Leu Val Gly Arg Lys Arg Ser His Ala Gly Tyr Gln
545                 550                 555                 560

Thr Ile


<210> SEQ ID NO 116
<211> LENGTH: 558
<212> TYPE: PRT
<213> ORGANISM: Artificial Sequence
<220> FEATURE:
<223> OTHER INFORMATION: Synthetic Construct

<400> SEQUENCE: 116

Met Ala Pro Arg Ser Ala Arg Arg Pro Leu Leu Leu Leu Leu Leu Leu
1               5                   10                  15

Leu Leu Leu Gly Leu Met His Cys Ala Ser Ala Met Gly Ala Pro Thr
            20                  25                  30

Leu Pro Pro Ala Trp Gln Pro Phe Leu Lys Asp His Arg Ile Ser Thr
        35                  40                  45

Phe Lys Asn Trp Pro Phe Leu Glu Gly Cys Ala Cys Thr Pro Glu Arg
    50                  55                  60

Met Ala Glu Ala Gly Phe Ile His Cys Pro Thr Glu Asn Glu Pro Asp
65                  70                  75                  80

Leu Ala Gln Cys Phe Phe Cys Phe Lys Glu Leu Glu Gly Trp Glu Pro
                85                  90                  95

Asp Asp Asp Pro Ile Glu Glu His Lys Lys His Ser Ser Gly Cys Ala
            100                 105                 110

Phe Leu Ser Val Lys Lys Gln Phe Glu Glu Leu Thr Leu Gly Glu Phe
        115                 120                 125

Leu Lys Leu Asp Arg Glu Arg Ala Lys Asn Lys Ile Ala Lys Glu Thr
    130                 135                 140

Asn Asn Lys Lys Lys Glu Phe Glu Glu Thr Ala Lys Lys Val Arg Arg
145                 150                 155                 160

Ala Ile Glu Gln Leu Ala Ala Met Asp Ala Met Phe Met Val Lys Asn
                165                 170                 175
```

```
Gly Asn Gly Thr Ala Cys Ile Met Ala Asn Phe Ser Ala Ala Phe Ser
            180                 185                 190

Val Asn Tyr Asp Thr Lys Ser Gly Pro Lys Asn Met Thr Leu Asp Leu
        195                 200                 205

Pro Ser Asp Ala Thr Val Val Leu Asn Arg Ser Ser Cys Gly Lys Glu
    210                 215                 220

Asn Thr Ser Asp Pro Ser Leu Val Ile Ala Phe Gly Arg Gly His Thr
225                 230                 235                 240

Leu Thr Leu Asn Phe Thr Arg Asn Ala Thr Arg Tyr Ser Val Gln Leu
                245                 250                 255

Met Ser Phe Val Tyr Asn Leu Ser Asp Thr His Leu Phe Pro Asn Ala
            260                 265                 270

Ser Ser Lys Glu Ile Lys Thr Val Glu Ser Ile Thr Asp Ile Arg Ala
        275                 280                 285

Asp Ile Asp Lys Lys Tyr Arg Cys Val Ser Gly Thr Gln Val His Met
    290                 295                 300

Asn Asn Val Thr Val Thr Leu His Asp Ala Thr Ile Gln Ala Tyr Leu
305                 310                 315                 320

Ser Asn Ser Ser Phe Ser Arg Gly Glu Thr Arg Cys Glu Gln Asp Arg
                325                 330                 335

Pro Ser Pro Thr Thr Ala Pro Pro Ala Pro Pro Ser Pro Ser Pro Ser
            340                 345                 350

Pro Val Pro Lys Ser Pro Ser Val Asp Lys Tyr Asn Val Ser Gly Thr
        355                 360                 365

Asn Gly Thr Cys Leu Leu Ala Ser Met Gly Leu Gln Leu Asn Leu Thr
    370                 375                 380

Tyr Glu Arg Lys Asp Asn Thr Thr Val Thr Arg Leu Leu Asn Ile Asn
385                 390                 395                 400

Pro Asn Lys Thr Ser Ala Ser Gly Ser Cys Gly Ala His Leu Val Thr
                405                 410                 415

Leu Glu Leu His Ser Glu Gly Thr Thr Val Leu Leu Phe Gln Phe Gly
            420                 425                 430

Met Asn Ala Ser Ser Ser Arg Phe Phe Leu Gln Gly Ile Gln Leu Asn
        435                 440                 445

Thr Ile Leu Pro Asp Ala Arg Asp Pro Ala Phe Lys Ala Ala Asn Gly
    450                 455                 460

Ser Leu Arg Ala Leu Gln Ala Thr Val Gly Asn Ser Tyr Lys Cys Asn
465                 470                 475                 480

Ala Glu Glu His Val Arg Val Thr Lys Ala Phe Ser Val Asn Ile Phe
                485                 490                 495

Lys Val Trp Val Gln Ala Phe Lys Val Glu Gly Gly Gln Phe Gly Ser
            500                 505                 510

Val Glu Glu Cys Leu Leu Asp Glu Asn Ser Met Leu Ile Pro Ile Ala
        515                 520                 525

Val Gly Gly Ala Leu Ala Gly Leu Val Leu Ile Val Leu Ile Ala Tyr
    530                 535                 540

Leu Val Gly Arg Lys Arg Ser His Ala Gly Tyr Gln Thr Ile
545                 550                 555
```

<210> SEQ ID NO 117
<211> LENGTH: 370
<212> TYPE: PRT
<213> ORGANISM: Artificial Sequence
<220> FEATURE:

<223> OTHER INFORMATION: Synthetic Construct

<400> SEQUENCE: 117

```
Met Ala Pro Arg Ser Ala Arg Arg Pro Leu Leu Leu Leu Leu Leu Leu
1               5                   10                  15

Leu Leu Leu Gly Leu Met His Cys Ala Ser Ala Met Gly Ala Pro Thr
            20                  25                  30

Leu Pro Pro Ala Trp Gln Pro Phe Leu Lys Asp His Arg Ile Ser Thr
        35                  40                  45

Phe Lys Asn Trp Pro Phe Leu Glu Gly Cys Ala Cys Thr Pro Glu Arg
    50                  55                  60

Met Ala Glu Ala Gly Phe Ile His Cys Pro Thr Glu Asn Glu Pro Asp
65                  70                  75                  80

Leu Ala Gln Cys Phe Phe Cys Phe Lys Glu Leu Glu Gly Trp Glu Pro
                85                  90                  95

Asp Asp Asp Pro Ile Glu Glu His Lys Lys His Ser Ser Gly Cys Ala
            100                 105                 110

Phe Leu Ser Val Lys Lys Gln Phe Glu Glu Leu Thr Leu Gly Glu Phe
        115                 120                 125

Leu Lys Leu Asp Arg Glu Arg Ala Lys Asn Lys Ile Ala Lys Glu Thr
    130                 135                 140

Asn Asn Lys Lys Lys Glu Phe Glu Glu Thr Ala Lys Lys Val Arg Arg
145                 150                 155                 160

Ala Ile Glu Gln Leu Ala Ala Met Asp Ala Met Phe Met Val Lys Asn
                165                 170                 175

Gly Asn Gly Thr Ala Cys Ile Met Ala Asn Phe Ser Ala Ala Phe Ser
            180                 185                 190

Val Asn Tyr Asp Thr Lys Ser Gly Pro Lys Asn Met Thr Leu Asp Leu
        195                 200                 205

Pro Ser Asp Ala Thr Val Val Leu Asn Arg Ser Ser Cys Gly Lys Glu
    210                 215                 220

Asn Thr Ser Asp Pro Ser Leu Val Ile Ala Phe Gly Arg Gly His Thr
225                 230                 235                 240

Leu Thr Leu Asn Phe Thr Arg Asn Ala Thr Arg Tyr Ser Val Gln Leu
                245                 250                 255

Met Ser Phe Val Tyr Asn Leu Ser Asp Thr His Leu Phe Pro Asn Ala
            260                 265                 270

Ser Ser Lys Glu Ile Lys Thr Val Glu Ser Ile Thr Asp Ile Arg Ala
        275                 280                 285

Asp Ile Asp Lys Lys Tyr Arg Cys Val Ser Gly Thr Gln Val His Met
    290                 295                 300

Asn Asn Val Thr Val Thr Leu His Asp Ala Thr Ile Gln Ala Tyr Leu
305                 310                 315                 320

Ser Asn Ser Ser Phe Ser Arg Gly Glu Thr Arg Cys Glu Gln Asp Leu
                325                 330                 335

Ile Pro Ile Ala Val Gly Gly Ala Leu Ala Gly Leu Val Leu Ile Val
            340                 345                 350

Leu Ile Ala Tyr Leu Val Gly Arg Lys Arg Ser His Ala Gly Tyr Gln
        355                 360                 365

Thr Ile
    370
```

<210> SEQ ID NO 118
<211> LENGTH: 375

```
<212> TYPE: PRT
<213> ORGANISM: Artificial Sequence
<220> FEATURE:
<223> OTHER INFORMATION: Synthetic Construct

<400> SEQUENCE: 118

Met Ala Pro Arg Ser Ala Arg Arg Pro Leu Leu Leu Leu Leu Leu Leu
1               5                   10                  15

Leu Leu Leu Gly Leu Met His Cys Ala Ser Ala Ala Met Phe Met Val
            20                  25                  30

Lys Asn Gly Asn Gly Thr Ala Cys Ile Met Ala Asn Phe Ser Ala Ala
        35                  40                  45

Phe Ser Val Asn Tyr Asp Thr Lys Ser Gly Pro Lys Asn Met Thr Leu
    50                  55                  60

Asp Leu Pro Ser Asp Ala Thr Val Val Leu Asn Arg Ser Ser Cys Gly
65                  70                  75                  80

Lys Glu Asn Thr Ser Asp Pro Ser Leu Val Ile Ala Phe Gly Arg Gly
                85                  90                  95

His Thr Leu Thr Leu Asn Phe Thr Arg Asn Ala Thr Arg Tyr Ser Val
            100                 105                 110

Gln Leu Met Ser Phe Val Tyr Asn Leu Ser Asp Thr His Leu Phe Pro
        115                 120                 125

Asn Ala Ser Ser Lys Glu Ile Lys Thr Val Glu Ser Ile Thr Asp Ile
    130                 135                 140

Arg Ala Asp Ile Asp Lys Lys Tyr Arg Cys Val Ser Gly Thr Gln Val
145                 150                 155                 160

His Met Asn Asn Val Thr Val Thr Leu His Asp Ala Thr Ile Gln Ala
                165                 170                 175

Tyr Leu Ser Asn Ser Ser Phe Ser Arg Gly Glu Thr Arg Cys Glu Gln
            180                 185                 190

Asp Leu Glu Met Gly Ala Pro Thr Leu Pro Pro Ala Trp Gln Pro Phe
        195                 200                 205

Leu Lys Asp His Arg Ile Ser Thr Phe Lys Asn Trp Pro Phe Leu Glu
    210                 215                 220

Gly Cys Ala Cys Thr Pro Glu Arg Met Ala Glu Ala Gly Phe Ile His
225                 230                 235                 240

Cys Pro Thr Glu Asn Glu Pro Asp Leu Ala Gln Cys Phe Phe Cys Phe
                245                 250                 255

Lys Glu Leu Glu Gly Trp Glu Pro Asp Asp Asp Pro Ile Glu Glu His
            260                 265                 270

Lys Lys His Ser Ser Gly Cys Ala Phe Leu Ser Val Lys Lys Gln Phe
        275                 280                 285

Glu Glu Leu Thr Leu Gly Glu Phe Leu Lys Leu Asp Arg Glu Arg Ala
    290                 295                 300

Lys Asn Lys Ile Ala Lys Glu Thr Asn Asn Lys Lys Lys Glu Phe Glu
305                 310                 315                 320

Glu Thr Ala Lys Lys Val Arg Arg Ala Ile Glu Gln Leu Ala Ala Met
                325                 330                 335

Asp Glu Phe Thr Leu Ile Pro Ile Ala Val Gly Gly Ala Leu Ala Gly
            340                 345                 350

Leu Val Leu Ile Val Leu Ile Ala Tyr Leu Val Gly Arg Lys Arg Ser
        355                 360                 365

His Ala Gly Tyr Gln Thr Ile
    370                 375
```

<210> SEQ ID NO 119
<211> LENGTH: 527
<212> TYPE: PRT
<213> ORGANISM: Artificial Sequence
<220> FEATURE:
<223> OTHER INFORMATION: Synthetic Construct

<400> SEQUENCE: 119

```
Met Ala Pro Arg Ser Ala Arg Arg Pro Leu Leu Leu Leu Leu Leu Leu
1               5                   10                  15

Leu Leu Leu Gly Leu Met His Cys Ala Ser Ala Ala Met Phe Met Val
            20                  25                  30

Lys Asn Gly Asn Gly Thr Ala Cys Ile Met Ala Asn Phe Ser Ala Ala
        35                  40                  45

Phe Ser Val Asn Tyr Asp Thr Lys Ser Gly Pro Lys Asn Met Thr Leu
    50                  55                  60

Asp Leu Pro Ser Asp Ala Thr Val Val Leu Asn Arg Ser Ser Cys Gly
65                  70                  75                  80

Lys Glu Asn Thr Ser Asp Pro Ser Leu Val Ile Ala Phe Gly Arg Gly
                85                  90                  95

His Thr Leu Thr Leu Asn Phe Thr Arg Asn Ala Thr Arg Tyr Ser Val
            100                 105                 110

Gln Leu Met Ser Phe Val Tyr Asn Leu Ser Asp Thr His Leu Phe Pro
        115                 120                 125

Asn Ala Ser Ser Lys Glu Ile Lys Thr Val Glu Ser Ile Thr Asp Ile
    130                 135                 140

Arg Ala Asp Ile Asp Lys Lys Tyr Arg Cys Val Ser Gly Thr Gln Val
145                 150                 155                 160

His Met Asn Asn Val Thr Val Thr Leu His Asp Ala Thr Ile Gln Ala
                165                 170                 175

Tyr Leu Ser Asn Ser Ser Phe Ser Arg Gly Glu Thr Arg Cys Glu Gln
            180                 185                 190

Asp Leu Glu Met Gly Ala Pro Thr Leu Pro Pro Ala Trp Gln Pro Phe
        195                 200                 205

Leu Lys Asp His Arg Ile Ser Thr Phe Lys Asn Trp Pro Phe Leu Glu
    210                 215                 220

Gly Cys Ala Cys Thr Pro Glu Arg Met Ala Glu Ala Gly Phe Ile His
225                 230                 235                 240

Cys Pro Thr Glu Asn Glu Pro Asp Leu Ala Gln Cys Phe Phe Cys Phe
                245                 250                 255

Lys Glu Leu Glu Gly Trp Glu Pro Asp Asp Asp Pro Ile Glu Glu His
            260                 265                 270

Lys Lys His Ser Ser Gly Cys Ala Phe Leu Ser Val Lys Lys Gln Phe
        275                 280                 285

Glu Glu Leu Thr Leu Gly Glu Phe Leu Lys Leu Asp Arg Glu Arg Ala
    290                 295                 300

Lys Asn Lys Ile Ala Lys Glu Thr Asn Asn Lys Lys Lys Glu Phe Glu
305                 310                 315                 320

Glu Thr Ala Lys Lys Val Arg Arg Ala Ile Glu Gln Leu Ala Ala Met
                325                 330                 335

Asp Glu Phe Thr Cys Leu Leu Ala Ser Met Gly Leu Gln Leu Asn Leu
            340                 345                 350

Thr Tyr Glu Arg Lys Asp Asn Thr Thr Val Thr Arg Leu Leu Asn Ile
        355                 360                 365
```

-continued

```
Asn Pro Asn Lys Thr Ser Ala Ser Gly Ser Cys Gly Ala His Leu Val
    370                 375                 380

Thr Leu Glu Leu His Ser Glu Gly Thr Thr Val Leu Leu Phe Gln Phe
385                 390                 395                 400

Gly Met Asn Ala Ser Ser Ser Arg Phe Phe Leu Gln Gly Ile Gln Leu
                405                 410                 415

Asn Thr Ile Leu Pro Asp Ala Arg Asp Pro Ala Phe Lys Ala Ala Asn
            420                 425                 430

Gly Ser Leu Arg Ala Leu Gln Ala Thr Val Gly Asn Ser Tyr Lys Cys
        435                 440                 445

Asn Ala Glu Glu His Val Arg Val Thr Lys Ala Phe Ser Val Asn Ile
    450                 455                 460

Phe Lys Val Trp Val Gln Ala Phe Lys Val Glu Gly Gly Gln Phe Gly
465                 470                 475                 480

Ser Val Glu Glu Cys Leu Leu Asp Glu Asn Ser Met Leu Ile Pro Ile
                485                 490                 495

Ala Val Gly Gly Ala Leu Ala Gly Leu Val Leu Ile Val Leu Ile Ala
            500                 505                 510

Tyr Leu Val Gly Arg Lys Arg Ser His Ala Gly Tyr Gln Thr Ile
        515                 520                 525
```

LAMP CONSTRUCTS

CROSS-REFERENCE TO RELATED APPLICATIONS

This application is a § 371 National Stage Application of PCT/US18/28753 filed on Apr. 22, 2018, which claims priority to U.S. 62/488,741 filed on Apr. 22, 2017, U.S. 62/549,119 filed on Aug. 23, 2017, and U.S. 62/549,033 filed on Aug. 23, 2017, which are all incorporated by reference in their entirety.

BACKGROUND OF THE INVENTION

Field of the Invention

The invention relates to improved LAMP Constructs and their use in treating subjects suffering from infectious disease, diabetes, allergies, hyperproliferative disorders and/or cancer. Additionally, improved LAMP constructs described herein can be used to generate antibodies in non-human vertebrates preferably where the genome of the non-human vertebrates comprise at least partially human immunoglobulin regions and/or humanized immunoglobulin regions. Prime boost protocols utilizing the LAMP improved Constructs described herein are also described.

Discussion of the Related Art

In the following discussion, certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

DNA vaccines are new and promising candidates for the development of both prophylactic and therapeutic vaccines. They are proven to be safe and the lack of immune responses to a vector backbone may be a definitive advantage if repetitive cycles of vaccination are required to achieve clinical benefits. However, one perceived disadvantage of conventional DNA vaccines is their low immunogenicity in humans. A key limiting step in the immunogenicity of epitope-based DNA vaccines may be the access of epitopes to the MHC II presentation pathway to T cells, which is likely a stochastic process in the case of a vaccine without targeting technology.

U.S. Pat. No. 5,633,234 describes chimeric proteins comprising an antigenic domain of modified influenza hemagglutinin (HA) and a cytoplasmic endosomal/lysosomal targeting signal which effectively target antigens to that compartment. The antigenic domain was processed and peptides from it presented on the cell surface in association with major histocompatibility (MHC) class II molecules. The cytoplasmic tail of LAMP-1 was used to form the endosomal/lysosomal targeting domain of the chimeric protein.

U.S. Pat. No. 8,318,173 extended these initial observations to describe chimeric proteins (and the corresponding DNAs that encode these proteins) comprising the HIV-1 Gag protein inserted between the full lumenal domain and a transmembrane domain of LAMP-1. This construct was introduced into dendritic cells which were then reported to target the MHC II pathway.

This approach has proved useful in increasing cellular and humoral responses to several virus antigens, human papillomavirus E7, dengue virus membrane protein, HIV-1 gp160 membrane protein, HIV-1 p55 Gag, West Nile membrane protein, hepatitis C virus NS3 protein and cytomegalovirus pp65 (see, e.g., Bonini, et al., J. Immunol. 166: 5250-5257, 2001). The enhanced immune response can be attributed to co-localization of LAMP with MHC II and the more efficient processing and delivery of antigenic peptides. In addition, LAMP-targeting is reported to result in the presentation of an increased number of immunogenic epitopes, thus inducing a qualitatively broadened immune response compared to untargeted antigen. For example, Fernandes et al., 2000, Eur. J. Immunol. 30(8): 2333-43, demonstrated an increase in the number of presented peptides of a LAMP-trafficked OVA antigen encoded in a vaccinia vector. Of 12 peptides generated from exogenously supplied OVA, 9 were presented by an OVA/LAMP chimera, as compared to only 2 by the construct without LAMP.

While it has been determined that the cytoplasmic domain of LAMP is necessary (in conjunction with a signal sequence and transmembrane domain), it is not always sufficient for endosomal/lysosomal trafficking of all antigens. Instead, the full lumenal domain of LAMP has been shown to be also required for the trafficking of proteins to the lysosomal vesicular pathway.

However, even with the presence of the complete lumenal domain and the complete transmembrane/cytoplasmic tail of LAMP ("complete LAMP Constructs"), it has increasingly been found that the efficacy of a particular antigen to raise an immune response is highly dependent on the particular sequence used in these constructs. In fact, different antigenic fragments of the same protein when inserted into the complete LAMP constructs have been found to not elicit the same immune response. Sometimes the antigen fragment generates an immune response and other times it does not. These observations make the ability to predict ahead of time which particular antigenic sequence from a protein of interest will raise an immune response difficult with the complete LAMP Constructs.

Moreover, in generating the complete LAMP Constructs, it has been repeatedly observed that the full lumenal domain is required to properly express and process an antigen. For example, in Godinho et al., PLoS ONE9(6): 9(6): e99887. doi:10.1371/journal.pone.0099887, the authors reported that the complete and intact lumenal domain was the necessary minimal region needed to target an antigen to the lysosomes and that fragments of the lumenal domain did not work. See, id. at page 6.

Specifically, the Godinho authors showed that by completely removing the first luminal domain and some of the second luminal domain (i.e., T1-Lum/gag construct), both protein expression and antibody response is decreased. Similarly, removing 25% of first luminal domain but having an intact second luminal domain (i.e., T2-lum/gag), both protein expression and antibody response comparatively increased but still less than the results obtained with the complete LAMP construct.

Moreover, the authors acknowledged that the ability to raise an immune response is dependent upon the particular antigen and the epitopes used in these complete LAMP Constructs. For example, on page 9, column 2, the authors state "accordingly, previous studies demonstrated that DNA vaccines that generate Gag secreted as VLP, or in a soluble form, induce different levels of T and B cell activation, which were also different from the response induced by cytoplasmic Gag." However, insertion of an antigenic sequence between the full lumenal domain of LAMP and the full transmembrane/cytoplasmic domain of LAMP as has been described in the literature results in such large polynucleotide sequences that it becomes either too costly to produce at commercial levels or impractical from a scientific perspective.

Thus, there is a need to design new and improved LAMP Constructs that can be used as vaccines to effectively treat, for example, allergies, infectious disease, diabetes, hyperproliferative disorders and/or cancer. Moreover, once improved, these new LAMP Constructs can be used to generate antibodies.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

It is an object of this invention to provide novel constructs ("improved LAMP Constructs") comprising specific fragments and/or variants of LAMP domains that effectively present an antigen(s) of interest to the immune system to generate an enhanced immune response. These improved LAMP Constructs effectively direct the antigens to the lysosomal/endosomal compartment where they are processed and presented to major histocompatibility complex (MHC) class II molecules so that helper T cells are preferentially stimulated and/or antibodies are generated.

The improved LAMP Constructs and methods described herein may elicit an immune response in a subject. The immune response may be an immune response to the epitopes of the antigens in the improved LAMP Construct (e.g., vaccine). Vaccines arm the immune system of the subject such that the immune system may detect and destroy that which contains the antigens of the vaccines in the subject. The improved LAMP Constructs and methods described herein may elicit a Th1 immune response in the subject. Th1 immune responses may include secretion of inflammatory cytokines (e.g., IFNγ, TNFa) by a subset of immune cells (e.g., antigen specific T-cells). In some cases, the inflammatory cytokines activate another subtype of immune cells (e.g., cytotoxic T-cells) which may destroy that which contains the antigen in the subject.

In some cases, the epitopes and/or antigens used in the improved LAMP Constructs and methods described herein may be recognized by the immune system of a subject to elicit a Th1 immune response and release Type I cytokines. The Th1 response may be initiated by the interaction between the epitope and the T-cell, more specifically, the major histocompatibility complex (MHC) expressed by the T-cell. For example, high affinity binding of an epitope to an MHC receptor may stimulate a Th1 response. MHC receptors may be at least one of a plurality of types of MHC receptors. The MHC receptors engaged on a T-cell may vary across individuals in a population.

In some cases, the immune response is a Type 1 immune response. In some cases, the immune response is characterized by a ratio of Type I cytokine production to Type II cytokine production that is greater than 1. In some cases, the immune response is characterized by a ratio of Type I cytokine production to Type II cytokine production that is less than 1. In some cases, the immune response is characterized by a ratio of IFNy production to IL-10 production that is greater than 1. In some cases, the immune response is characterized by a ratio of IFNy production to IL-10 production that is less than 1.

It is yet another object of this invention to provide improved methods of treatment for cancer and/or hyperproliferative disorders by eliciting an anti-tumor immune response through stimulation of helper T cells.

The improved LAMP Constructs described herein can also be used to treat allergies, such as for example, food allergies (e.g., peanut allergens, such as Ara H1, H2 and/or H3), or environmental allergens, such as for example pollen (tree pollen, such as for example CRY J1 or CRY J2), dog dander, cat saliva, or dust mites. Other diseases and/or disorders that can be treated using the improved LAMP Constructs described herein include, for example, infectious disease and diabetes.

The invention further provides a nucleic acid molecule encoding any of the improved LAMP Constructs described herein. The invention also provides an improved LAMP Construct comprising an antigen to generate antibodies. The improved LAMP Construct can comprise a nucleic acid wherein the nucleic acid molecule is operably linked to an expression control sequence. In one preferred aspect, the improved LAMP Construct is a vaccine vector, suitable for vaccinating a patient. In another aspect, the invention provides a delivery vehicle comprising the improved LAMP Construct for facilitating the introduction of the nucleic acid molecule encoding the antigen into a cell. The delivery vehicle may be lipid-based (e.g., a liposome formulation), viral-based (e.g., comprising viral proteins encapsulating the nucleic acid molecule), or cell-based.

In preferred embodiments, the invention provides an injectable composition comprising an improved LAMP Construct comprising an antigen of interest for eliciting an immune response (e.g., generation of antibodies) in a mammal to an antigen. In preferred embodiments, this vaccine generates a preferential Th1 response to a Th2 response. The improved LAMP Constructs comprise at least one epitope of an antigen.

The invention also provides a cell comprising any of the improved LAMP Constructs described herein which can be used to generate an immune response. In one aspect, the cell is an antigen presenting cell. The antigen presenting cell may be a professional antigen presenting cell (e.g., a dendritic cell, macrophage, B cell, and the like) or an engineered antigen presenting cell (e.g., a non-professional antigen presenting cell engineered to express molecules required for antigen presentation, such as MHC class II molecules). The molecules required for antigen presentation may be derived from other cells, e.g., naturally occurring, or may themselves be engineered (e.g. mutated or modified to express desired properties, such as higher or lower affinity for an antigenic epitope). In one aspect, the antigen presenting cell does not express any co-stimulatory signals and the antigen is an auto-antigen.

The invention additionally provides a kit comprising a plurality of cells comprising any of the improved LAMP Constructs described herein. At least two of the cells express different MHC class II molecules, and each cell comprises the same LAMP Construct. In one aspect, a kit is provided comprising an improved LAMP Construct and a cell for receiving the vector.

The invention also provides a transgenic animal comprising at least one of the cells and/or at least one of the improved LAMP Constructs described herein. The invention also provides a transgenic animal comprising at least one of the cells described herein.

The invention further provides a method for generating an immune response in an animal (e.g., a human or a non-human vertebrate) to an antigen, comprising: administering to the animal a cell as described above, wherein the cell expresses, or can be induced to express, the improved LAMP Construct in the animal. In one aspect, the cell comprises an MHC class II molecule compatible with MHC proteins of the animal, such that the animal does not generate an immune response against the MHC class II molecule. In one preferred aspect, the animal is a human.

In one further aspect, the invention provides a method for eliciting an immune response to an antigen, comprising administering to an animal, such as a human or a non-human vertebrate, any of the improved LAMP Constructs described herein. Preferably, the improved LAMP Construct is infectious for a cell of the animal. For example, the improved LAMP Construct may be a viral vector, such as a vaccinia improved LAMP Construct.

Prime boost protocols are also contemplated. For example, the invention further provides a method for generating an immune response in an animal to an antigen, comprising priming the animal with an improved LAMP Construct comprising an antigen as described herein followed by at least one boosting of the animal with the antigen or a related antigen (e.g., a second antigen derived from the same or highly similar protein sequence). Mixtures of antigens can be used in either or both the priming and the boosting step. Use of an improved LAMP Construct for the prime step followed by an antigen boost step has been shown to significantly produce higher titers, indicating the power of LAMP in enhancing antibody response.

In a further aspect, a cell is obtained from a patient, the improved LAMP Construct described herein is introduced into the cell and the cell or progeny of the cell is reintroduced into the patient. In one aspect, the cell is a stem cell-capable of differentiating into an antigen presenting cell. Treatments of human patients as well as veterinary use are specifically contemplated.

The present invention also comprises methods of generating antibodies in a non-human vertebrate wherein the non-human vertebrate is injected with an improved LAMP Construct comprising an antigen of interest as described herein. The antigen of interest is then efficiently presented to the immune system with the help of LAMP in the non-human vertebrate to raise antibodies against the antigen.

Specifically, by combining presentation of the antigen of interest with LAMP, the antigen is then effectively transported to the cytoplasmic endosomal/lysosomal compartments, where the antigen can be processed and peptides from it presented on the cell surface in association with major histocompatibility (MHC) class II molecules.

These generated antibodies can be isolated from the blood of the vertebrate (as polyclonals) and then further isolated to generate monoclonal antibodies using standard techniques.

In preferred embodiments, the genome of the non-human vertebrate comprises an introduced partially human immunoglobulin region, said introduced region comprising human immunoglobulin variable region locus coding sequences and non-coding sequences based on the endogenous immunoglobulin variable region locus of the non-human vertebrate. Preferably, non-human vertebrate's genome has at least part or all of the endogenous immunoglobulin region removed.

In further preferred embodiments, the production of human monoclonal antibodies in the non-human vertebrate requires that the host have at least one locus that will express human heavy chain immunoglobulin proteins and one locus that will express human light chain immunoglobulin proteins.

In some aspects, the partially human immunoglobulin variable region locus comprises human $V_H$ coding sequences and non-coding $V_H$ sequences based on the endogenous $V_H$ region of the non-human vertebrate. In these aspects, the partially human immunoglobulin variable region locus further comprises human D and J gene coding sequences and non-coding D and J gene sequences based on the endogenous genome of the non-human vertebrate host.

In other aspects, the immunoglobulin region comprises an introduced region comprising human $V_L$ coding sequences and non-coding $V_L$ sequences based on the endogenous $V_L$ region of the non-human vertebrate. More preferably, the introduced partially human immunoglobulin region comprising human $V_L$ coding sequences further comprises human J gene coding sequences and non-coding J gene sequences based on the endogenous genome of the non-human vertebrate host.

In certain aspects, the vertebrate is a mammal, and preferably the mammal is a rodent, e.g., a mouse or rat. In other aspects, the vertebrate is avian, e.g., a chicken. Other non-human vertebrates include rabbits, llamas, camels, a cow, a guinea pig, a hamster, a dog, a cat, a horse, a non-human primate, a simian (e.g. a monkey or ape), a monkey (e.g. marmoset, baboon, rhesus macaque), or an ape (e.g. gorilla, chimpanzee, orangutan, gibbon).

In further embodiments, the partially human immunoglobulin region comprises human $V_H$ gene coding regions, and further comprises i) human D and J gene coding sequences and ii) non-coding D and J gene and pre-DJ sequences based on the endogenous genome of the non-human vertebrate host. In other aspects, the $V_H$ gene coding regions derive (at least partially) from other sources—e.g., they could be rationally or otherwise designed sequences, sequences that are a combination of human and other designed sequences, or sequences from other species, such as nonhuman primates.

In yet another specific aspect, the partially human immunoglobulin region comprises human $V_L$ gene coding regions, and further comprises i) human J gene coding sequences and ii) non-coding J gene sequences based on the endogenous genome of the non-human vertebrate host. In a specific aspect, the partially human immunoglobulin region comprises human $V_H$ coding regions, human D and J gene coding sequences, and non-coding D and J gene and pre-DJ sequences based on the endogenous genome of the non-human vertebrate host.

The methods described herein can be used in the production and/or optimization of antibodies, including fully human antibodies, humanized antibodies, chimeric antibodies, for diagnostic and therapeutic uses. Hybridomas producing such antibodies are also a further object of the invention.

These and other aspects, objects and features are described in more detail below.

BRIEF DESCRIPTION OF THE FIGURES

The objects and features of the invention can be better understood with reference to the following detailed description and accompanying drawings.

FIG. 1 illustrates the general scheme of different types of improved LAMP Constructs (identified as ILC-1, ILC-2, ILC-3, ILC-4, ILC-5 and ILC-6) that can be used as described herein.

FIG. 3 provides alignment of LAMP-1 proteins found in other species as compared to human LAMP-1 (SEQ ID NO:1). The equivalent domains of these other species can be used to generate the improved LAMP Constructs described herein and are readily identifiable by comparing the domains identified for human LAMP-1 in FIG. 2 and FIG. 3 to the alignments shown in FIG. 3.

FIG. 4 provides alignment of LAMP-2 proteins found in other species as compared to human LAMP-2 (SEQ ID NO:2). The equivalent domains of these other species can be used to generate the improved LAMP Constructs described herein and are readily identifiable by comparing the domains identified for human LAMP-2 in FIG. 2 and FIG. 4 to the alignments shown in FIG. 4.

FIG. 5 provides alignment of LAMP-3 proteins found in other species as compared to human LAMP-3 (SEQ ID NO:3). The equivalent domains of these other species can be used to generate the improved LAMP Constructs described herein and are readily identifiable by comparing the domains identified for human LAMP-3 in FIG. 2 and FIG. 5 to the alignments shown in FIG. 5.

FIG. 6 provides alignment of LIMP-2 proteins found in other species as compared to human LIMP-2 (SEQ ID NO:4). The equivalent domains of these other species can be used to generate the improved LAMP Constructs described herein and are readily identifiable by comparing the domains identified for human LIMP-2 in FIG. 2 and FIG. 6 to the alignments shown in FIG. 6.

FIG. 7 provides alignment of LIMBIC proteins found in other species as compared to human LIMBIC (SEQ ID NO:67). The equivalent domains of these other species can be used to generate the improved LAMP Constructs described herein and are readily identifiable by comparing the domains identified for human LIMBIC in FIG. 2 and FIG. 7 to the alignments shown in FIG. 7.

FIG. 8 provides alignment of Endolyn proteins found in other species as compared to human Endolyn (SEQ ID NO:5). The equivalent domains of these other species can be used to generate the improved LAMP Constructs described herein and are readily identifiable by comparing the domains identified for human Endolyn in FIG. 2 and FIG. 8 to the alignments shown in FIG. 8.

FIG. 9 provides alignment of Macrosailin proteins found in other species as compared to human Macrosailin (SEQ ID NO:80). The equivalent domains of these other species can be used to generate the improved LAMP Constructs described herein and are readily identifiable by comparing the domains identified for human Macrosailin in FIG. 2 and FIG. 9 to the alignments shown in FIG. 9.

FIG. 10 provides alignment of LAMP-5 proteins found in other species as compared to human LAMP-5 (SEQ ID NO:93). The equivalent domains of these other species can be used to generate the improved LAMP Constructs described herein and are readily identifiable by comparing the domains identified for human LAMP-5 in FIG. 2 and FIG. 10 to the alignments shown in FIG. 10.

Figure ii shows results obtained when mice were immunized with HVEM-LAMP, HVEM, or LAMP on day 0, 7, and 14. On day 28, mice were bled and serum samples were isolated. HVEM specific IgG was examined by ELISA. Data represent geometric mean of antibody titers ±geometric SD, n=6. **p value <0.01

FIG. 12 shows results obtained when mice were immunized with HVEM-LAMP, HVEM, or LAMP on day 0, 7, and 14. On day 35, mice were boosted with 5 μg HVEM protein in the presence of alum adjuvant. Mice were bled on day 49 and serum samples were isolated. HVEM specific IgG was examined by ELISA. Data represent geometric mean of antibody titers ±geometric SD, n=6. *p value <0.001; *p value <0.0001.

Figure 13:
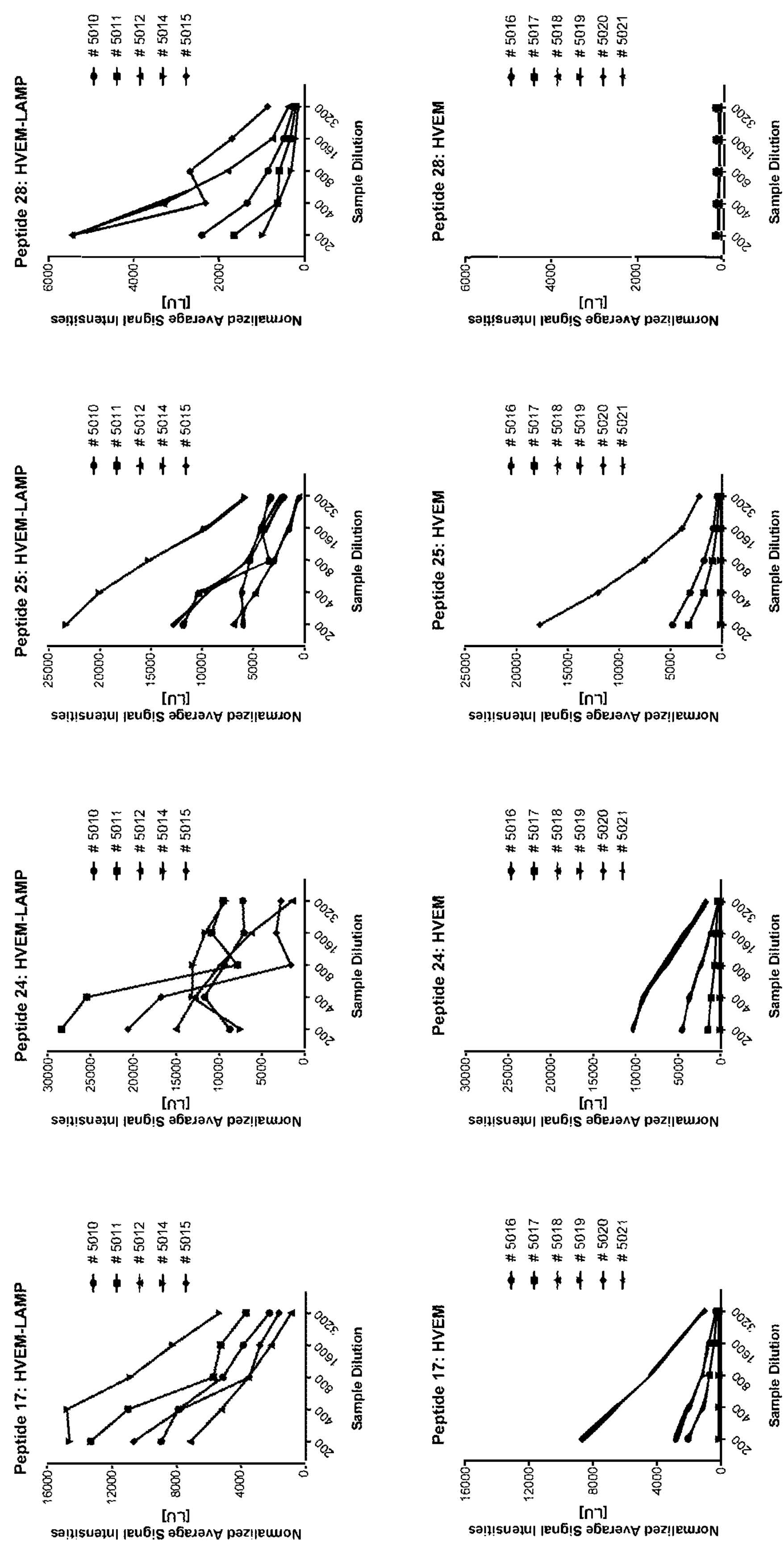

FIG. 13 shows that LAMP alters the binding affinity of epitopes in CRD3/4 of HVEM.

Figure 14:
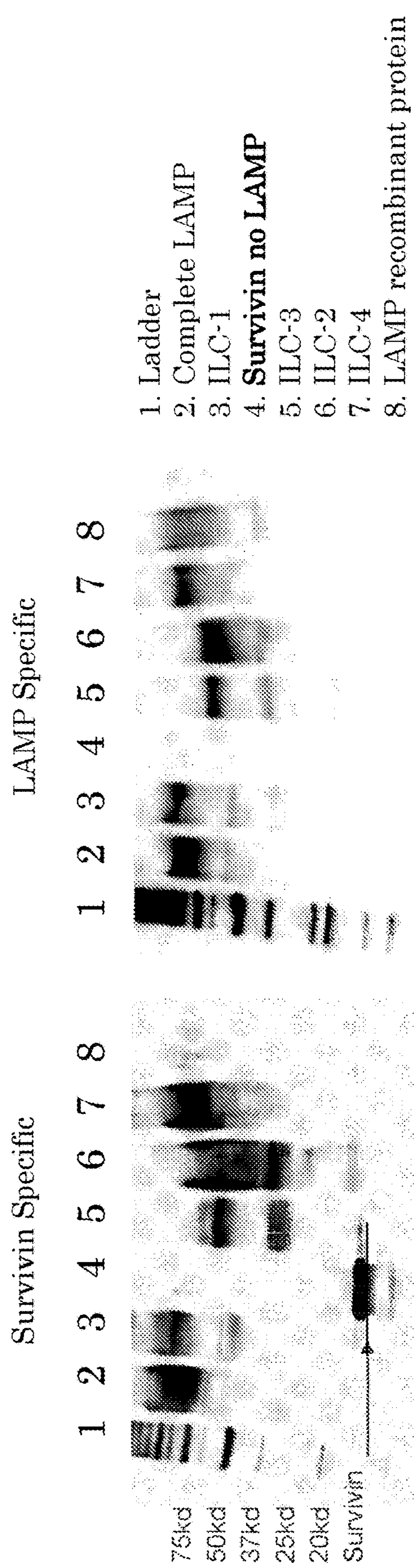

FIG. 14 confirms protein expression of tested improved LAMP Constructs. In each of FIGS. 14-17, the labels "complete LAMP Construct", ILC-1, ILC-2, ILC-3 and ILC-4 correspond to the constructs as depicted in FIG. 1.

Figure 15:
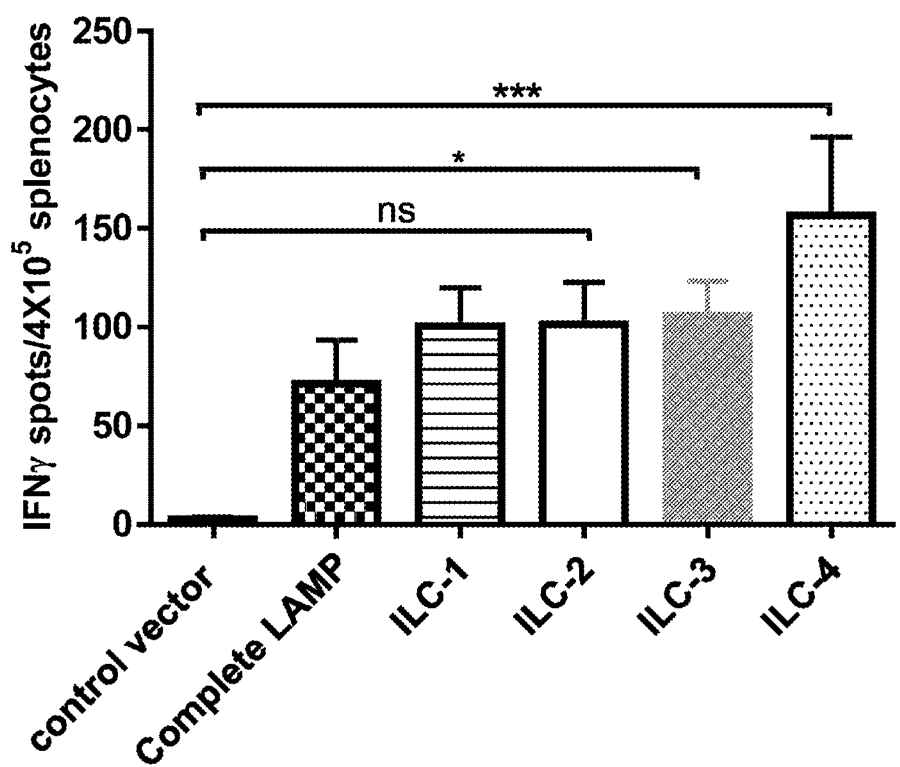

FIG. 15 shows that the improved LAMP Constructs induce Th1 effector T cells producing INFγ.

Figure 16:
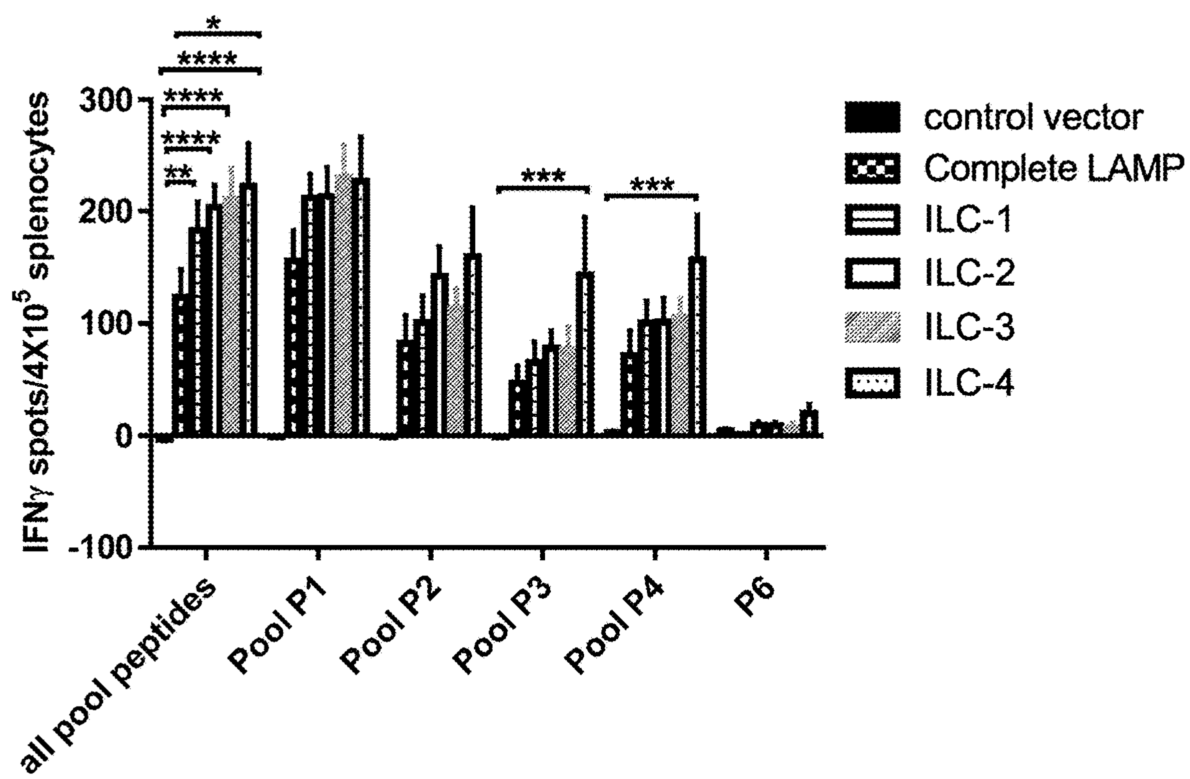

FIG. 16 shows a particular improved LAMP construct (e.g., ILC-4 as shown in FIG. 1) elicited a significantly higher T cell response against all survivin peptide pools.

Figure 17:
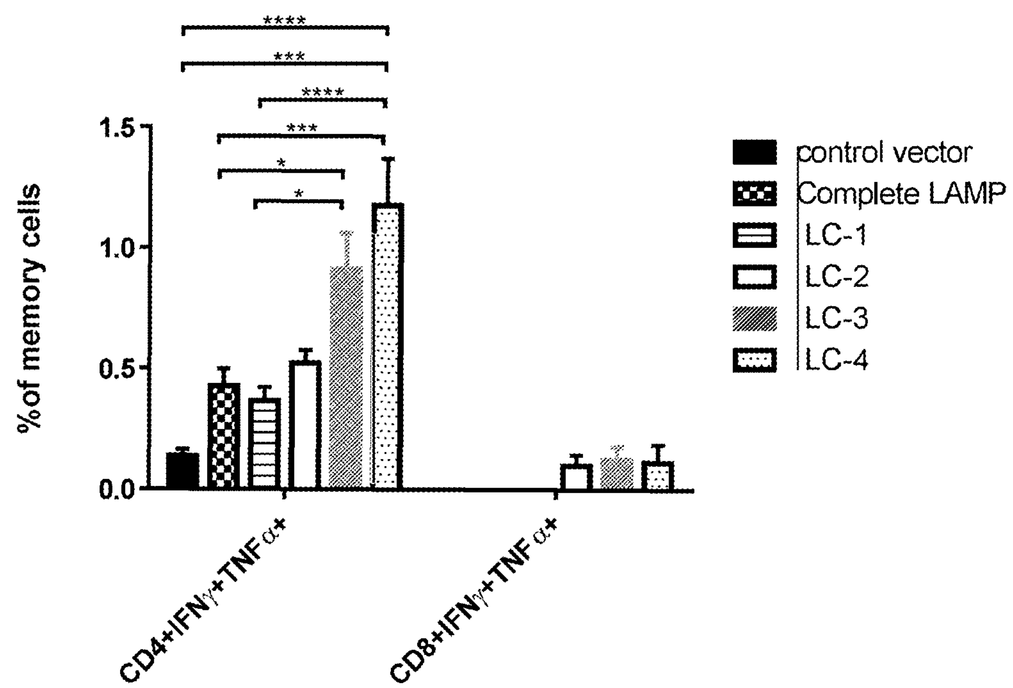

FIG. 17 shows that CD4 T cells are the major source of IFNγ producing cells and that the improved LAMP Constructs demonstrate an increase in the CD4 effector memory cell population over the Complete LAMP construct.

Figure 18:
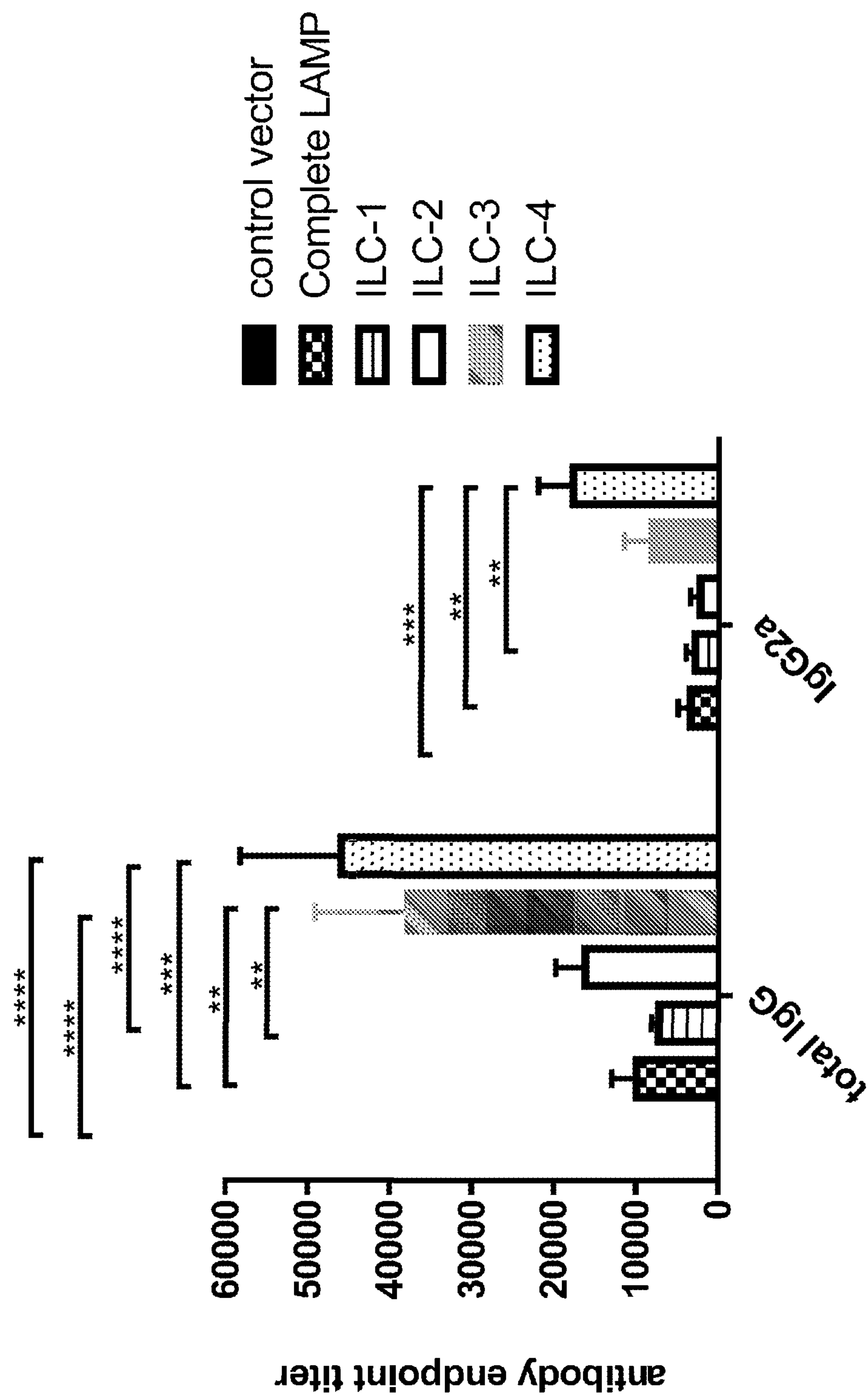

FIG. 18 shows that the improved LAMP Constructs produced stronger Survivin-specific total IgG response in BALB/c mice.

FIG. 19 provides the amino acid sequence of each LAMP construct tested. The signal sequence of each construct is depicted as lower case and underlined letters; the Survivin sequence is depicted in capitalized, white letters, shaded in black; the luminal domain is depicted in italics and capitalized letters and the transmembrane/cytolosolic domain is depicted in capitalized letter and shaded in grey, and in ILC-4, the second homology domain is bolded. Additional amino acids (LE and EF) may be included as part of the cloning linkers.

DETAILED DESCRIPTION

The invention provides improved LAMP Constructs and nucleic acids encoding these which can be used to generate vaccines and/or used to raise antibodies. The improved LAMP Constructs can be used to modulate or enhance an immune response. In one preferred aspect, the invention provides a method for treating a patient with an allergy, infectious disease, diabetes, cancer or a hyperproliferative disorder by providing an improved LAMP Construct described herein. The improved LAMP Constructs can also be used to raise antibodies in non-human vertebrates, and in preferably, non-human mammals.

Definitions

The following definitions are provided for specific terms which are used in the following written description.

As used in the specification and claims, the singular form "a", "an" and "the" include plural references unless the context clearly dictates otherwise. For example, the term "a cell" includes a plurality of cells, including mixtures thereof. The term "a nucleic acid molecule" includes a plurality of nucleic acid molecules.

As used herein, the term "comprising" is intended to mean that the improved LAMP Constructs and methods include the recited elements, but do not exclude other elements. "Consisting essentially of", when used to define improved LAMP Constructs and methods, shall mean excluding other elements of any essential significance to the combination. Thus, an improved LAMP Construct consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the improved LAMP Constructs of this invention. Embodiments defined by each of these transition terms are within the scope of this invention.

The term "about" or "approximately" means within an acceptable range for the particular value as determined by one of ordinary skill in the art, which will depend in part on how the value is measured or determined, e.g., the limitations of the measurement system. For example, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5 fold, and more preferably within 2 fold, of a value. Unless otherwise stated, the term 'about' means within an acceptable error range for the particular value, such as ±1-20%, preferably ±1-10% and more preferably ±1-5%.

Where a range of values is provided, it is understood that each intervening value, between the upper and lower limit of that range and any other stated or intervening value in that stated range is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either both of those included limits are also included in the invention.

As used herein, "the lysosomal/endosomal compartment" refers to membrane-bound acidic vacuoles containing LAMP molecules in the membrane, hydrolytic enzymes that function in antigen processing, and MHC class II molecules for antigen recognition and presentation. This compartment functions as a site for degradation of foreign materials internalized from the cell surface by any of a variety of mechanisms including endocytosis, phagocytosis and pinocytosis, and of intracellular material delivered to this compartment by specialized autolytic phenomena (de Duve, Eur. J. Biochem. 137: 391, 1983). The term "endosome" as used herein and in the claims encompasses a lysosome.

As used herein, a "lysosome-related organelle" refers to any organelle which comprises lysosymes and includes, but is not limited to, MIIC, CIIV, melanosomes, secretory granules, lytic granules, platelet-dense granules, basophil granules, Birbeck granules, phagolysosomes, secretory lysosomes, and the like. Preferably, such an organelle lacks mannose 6-phosphate receptors and comprises LAMP, but may or may not comprise an MHC class II molecule. For reviews, see, e.g., Blott and Griffiths, Nature Reviews, Molecular Cell Biology, 2002; Dell'*Angelica*, et al., The FASEB Journal 14: 1265-1278, 2000.

As used herein, the terms "polynucleotide" and "nucleic acid molecule" are used interchangeably to refer to polymeric forms of nucleotides of any length. The polynucleotides may contain deoxyribonucleotides, ribonucleotides, and/or their analogs. Nucleotides may have any three-dimensional structure, and may perform any function, known or unknown. The term "polynucleotide" includes, for example, single-, double-stranded and triple helical molecules, a gene or gene fragment, exons, introns, mRNA, tRNA, rRNA, ribozymes, antisense molecules, cDNA, recombinant polynucleotides, branched polynucleotides, aptamers, plasmids, vectors, isolated DNA of any sequence, isolated RNA of any sequence, nucleic acid probes, and primers. A nucleic acid molecule may also comprise modified nucleic acid molecules (e.g., comprising modified bases, sugars, and/or internucleotide linkers).

As used herein, the term "peptide" refers to a compound of two or more subunit amino acids, amino acid analogs, or peptidomimetics. The subunits may be linked by peptide bonds or by other bonds (e.g., as esters, ethers, and the like).

As used herein, the term "amino acid" refers to either natural and/or unnatural or synthetic amino acids, including glycine and both D or L optical isomers, and amino acid analogs and peptidomimetics. A peptide of three or more amino acids is commonly called an oligopeptide if the peptide chain is short. If the peptide chain is long (e.g., greater than about 10 amino acids), the peptide is commonly called a polypeptide or a protein. While the term "protein" encompasses the term "polypeptide", a "polypeptide" may be a less than full-length protein.

As used herein a "LAMP polypeptide" refers to the mammalian lysosomal associated membrane proteins human LAMP-1, human LAMP-2, human LAMP-3, human LIMP-2, human Endolyn, human LIMBIC, human LAMP-5, or human Macrosailin as described herein, as well as orthologs (such as, for example, the LAMP proteins shown in FIGS. 3-10), and allelic variants.

As used herein, "expression" refers to the process by which polynucleotides are transcribed into mRNA and/or translated into peptides, polypeptides, or proteins. If the polynucleotide is derived from genomic DNA, expression may include splicing of the mRNA transcribed from the genomic DNA.

As used herein, "under transcriptional control" or "operably linked" refers to expression (e.g., transcription or translation) of a polynucleotide sequence which is controlled by an appropriate juxtaposition of an expression control element and a coding sequence. In one aspect, a DNA sequence is "operatively linked" to an expression control sequence when the expression control sequence controls and regulates the transcription of that DNA sequence.

As used herein, "coding sequence" is a sequence which is transcribed and translated into a polypeptide when placed under the control of appropriate expression control sequences. The boundaries of a coding sequence are determined by a start codon at the 5' (amino) terminus and a translation stop codon at the 3' (carboxyl) terminus. A coding sequence can include, but is not limited to, a prokaryotic sequence, cDNA from eukaryotic mRNA, a genomic DNA sequence from eukaryotic (e.g., mammalian) DNA, and even synthetic DNA sequences. A polyadenylation signal and transcription termination sequence will usually be located 3' to the coding sequence.

As used herein, two coding sequences "correspond" to each other if the sequences or their complementary sequences encode the same amino acid sequences.

As used herein, "signal sequence" denotes the endoplasmic reticulum translocation sequence. This sequence encodes a signal peptide that communicates to a cell to direct a polypeptide to which it is linked (e.g., via a chemical bond) to an endoplasmic reticulum vesicular compartment, to enter an exocytic/endocytic organelle, to be delivered either to a cellular vesicular compartment, the cell surface or to secrete the polypeptide. This signal sequence is sometimes clipped off by the cell in the maturation of a protein. Signal sequences can be found associated with a variety of proteins native to prokaryotes and eukaryotes.

As used herein, "trafficking" denotes movement or progression of the polypeptide encoded by the improved LAMP Construct through cellular organelles or compartments in the pathway from the rough endoplasmic reticulum to the endosomal/lysosomal compartment or related organelles where antigen processing and binding to MHC II occurs.

As used herein, an "improved LAMP Construct" and an "improved LAMP Construct comprising an antigen" and an "improved LAMP Construct comprising an antigen of interest" are used interchangeably. The different arrangements of the improved LAMP Constructs are illustrated in FIG. 1 as ILC1-ILC6. Morever, the use of an "improved LAMP Construct" encompasses both the polynucleotide sequence of the improved LAMP Construct as well as the protein encoded by the polynucleotide sequence of the improved LAMP Construct.

As used herein, an "improved LAMP Construct delivery vehicle" is defined as any molecule or group of molecules or macromolecules that can carry an improved LAMP Construct into a host cell (e.g., such as genes or gene fragments, antisense molecules, ribozymes, aptamers, and the like) and which occurs in association with an improved LAMP Construct as described herein.

As used herein, "improved LAMP Construct delivery," or "improved LAMP Construct transfer," refers to the introduction of the improved LAMP Construct into a host cell, irrespective of the method used for the introduction. The introduced improved LAMP Constructs may be stably or transiently maintained in the host cell. Stable maintenance typically requires that the introduced improved LAMP Construct either contains an origin of replication compatible with the host cell or integrates into a replicon of the host cell such as an extrachromosomal replicon (e.g., a plasmid) or a nuclear or mitochondrial chromosome.

As used herein, a "viral improved LAMP Construct" refers to a virus or viral particle that comprises the improved LAMP Construct to be delivered into a host cell, either in vivo, ex vivo or in vitro. Examples of viral improved LAMP Constructs include, but are not limited to, adenovirus vectors, adeno-associated virus vectors, retroviral vectors, and the like. In aspects where gene transfer is mediated by an adenoviral vector, an improved LAMP Construct includes the adenovirus genome or part thereof, and a selected, non-adenoviral gene, in association with adenoviral capsid proteins.

As used herein, "adenoviral-mediated gene transfer" or "adenoviral transduction" refers to the process by which an improved LAMP Construct is transferred into a host cell by virtue of the adenovirus entering the cell. Preferably, the improved LAMP Construct is able to replicate and/or integrate and be transcribed within the cell.

As used herein, "adenovirus particles" are individual adenovirus virions comprised of an external capsid and an improved LAMP Construct, where the capsid is further comprised of adenovirus envelope proteins. The adenovirus envelope proteins may be modified to comprise a fusion polypeptide which contains a polypeptide ligand covalently attached to the viral protein, e.g., for targeting the adenoviral particle to a particular cell and/or tissue type.

As used herein, the term "administering" or "immunizing" or "injecting" an improved LAMP Construct refers to transducing, transfecting, microinjecting, electroporating, or shooting the cell with the improved LAMP Construct. In some aspects, improved LAMP Constructs are introduced into a target cell by contacting the target cell with a delivery cell (e.g., by cell fusion or by lysing the delivery cell when it is in proximity to the target cell).

As used herein, the phrase "prime boost" describes the use of an improved LAMP Construct described herein used to prime a T-cell response followed by the use of a second improved LAMP Construct comprising an antigen, a DNA vaccine comprising an antigen or a recombinant antigen to boost the response. These heterologous prime-boost immunizations elicit immune responses of greater height and breadth than can be achieved by priming and boosting with the same vector. The priming with an improved LAMP Construct comprising an antigen initiates memory cells; the boost step expands the memory response. Preferably, use of the two different agents do not raise responses against each other and thus do not interfere with each other's activity. Mixtures of antigens are specifically contemplated in the prime and/or boost step. Boosting can occur one or multiple times.

As used herein, "hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

As used herein, a polynucleotide or polynucleotide region (or a polypeptide or polypeptide region) which has a certain percentage (for example, at least about 50%, at least about 60%, at least about 70%, at least about 80%, at least about 85%, at least about 90%, at least about 95%, at least about 99%) of "sequence identity" to another sequence means that, when maximally aligned, using software programs routine in the art, that percentage of bases (or amino acids) are the same in comparing the two sequences.

Two sequences are "substantially homologous" or "substantially similar" when at least about 50%, at least about 60%, at least about 70%, at least about 75%, and preferably at least about 80%, and most preferably at least about 90 or 95% of the nucleotides match over the defined length of the DNA sequences. Similarly, two polypeptide sequences are "substantially homologous" or "substantially similar" when at least about 50%, at least about 60%, at least about 66%, at least about 70%, at least about 75%, and preferably at least about 80%, and most preferably at least about 90 or 95% of the amino acid residues of the polypeptide match over a defined length of the polypeptide sequence. Sequences that are substantially homologous can be identified by comparing the sequences using standard software available in sequence data banks. Substantially homologous nucleic acid sequences also can be identified in a Southern hybridization experiment under, for example, stringent conditions as defined for that particular system. Defining appropriate hybridization conditions is within the skill of the art. For example, stringent conditions can be: hybridization at 5×SSC and 50% formamide at 42° C., and washing at 0.1×SSC and 0.1% sodium dodecyl sulfate at 60° C. Further examples of stringent hybridization conditions include: incubation temperatures of about 25 degrees C. to about 37 degrees C.; hybridization buffer concentrations of about 6×SSC to about 10×SSC; formamide concentrations of about 0% to about 25%; and wash solutions of about 6×SSC. Examples of moderate hybridization conditions include: incubation temperatures of about 40 degrees C. to about 50 degrees C.; buffer concentrations of about 9×SSC to about 2×SSC; formamide concentrations of about 30% to about 50%; and wash solutions of about 5×SSC to about 2×SSC. Examples of high stringency conditions include: incubation temperatures of about 55 degrees C. to about 68 degrees C.; buffer concentrations of about 1×SSC to about 0.1×SSC; formamide concentrations of about 55% to about 75%; and wash solutions of about 1×SSC, 0.1×SSC, or deionized water. In general, hybridization incubation times are from 5 minutes to 24 hours, with 1, 2, or more washing steps, and wash incubation times are about 1, 2, or 15 minutes. SSC is 0.15 M NaCl and 15 mM citrate buffer. It is understood that equivalents of SSC using other buffer systems can be employed. Similarity can be verified by sequencing, but preferably, is also or alternatively, verified by function (e.g., ability to traffic to an endosomal compartment, and the like), using assays suitable for the particular domain in question.

The terms “percent (%) sequence similarity”, “percent (%) sequence identity”, and the like, generally refer to the degree of identity or correspondence between different nucleotide sequences of nucleic acid molecules or amino acid sequences of polypeptides that may or may not share a common evolutionary origin (see Reeck et al., supra). Sequence identity can be determined using any of a number of publicly available sequence comparison algorithms, such as BLAST, FASTA, DNA Strider, GCG (Genetics Computer Group, Program Manual for the GCG Package, Version 7, Madison, Wis.), etc.

To determine the percent identity between two amino acid sequences or two nucleic acid molecules, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are, or are about, of the same length. The percent identity between two sequences can be determined using techniques similar to those described below, with or without allowing gaps. In calculating percent sequence identity, typically exact matches are counted.

The determination of percent identity between two sequences can be accomplished using a mathematical algorithm. A non-limiting example of a mathematical algorithm utilized for the comparison of two sequences is the algorithm of Karlin and Altschul, Proc. Natl. Acad. Sci. USA 1990, 87:2264, modified as in Karlin and Altschul, Proc. Natl. Acad. Sci. USA 1993, 90:5873-5877. Such an algorithm is incorporated into the NBLAST and XBLAST programs of Altschul et al, J. Mol. Biol. 1990; 215: 403. BLAST nucleotide searches can be performed with the NBLAST program, score=100, wordlength=12, to obtain nucleotide sequences homologous to sequences of the invention. BLAST protein searches can be performed with the XBLAST program, score=50, wordlength=3, to obtain amino acid sequences homologous to protein sequences of the invention. To obtain gapped alignments for comparison purposes, Gapped BLAST can be utilized as described in Altschul et al, Nucleic Acids Res. 1997, 25:3389. Alternatively, PSI-Blast can be used to perform an iterated search that detects distant relationship between molecules. See Altschul et al. (1997) supra. When utilizing BLAST, Gapped BLAST, and PSI-Blast programs, the default parameters of the respective programs (e.g., XBLAST and NBLAST) can be used. See ncbi.nlm.nih.gov/BLAST/on the World-WideWeb.

Another non-limiting example of a mathematical algorithm utilized for the comparison of sequences is the algorithm of Myers and Miller, CABIOS 1988; 4: 11-17. Such an algorithm is incorporated into the ALIGN program (version 2.0), which is part of the GCG sequence alignment software package. When utilizing the ALIGN program for comparing amino acid sequences, a PAM120 weight residue table, a gap length penalty of 12, and a gap penalty of 4 can be used.

In a preferred embodiment, the percent identity between two amino acid sequences is determined using the algorithm of Needleman and Wunsch (J. Mol. Biol. 1970, 48:444-453), which has been incorporated into the GAP program in the GCG software package (Accelrys, Burlington, Mass.; available at accelrys.com on the WorldWideWeb), using either a Blossum 62 matrix or a PAM250 matrix, a gap weight of 16, 14, 12, 10, 8, 6, or 4, and a length weight of 1, 2, 3, 4, 5, or 6. In yet another preferred embodiment, the percent identity between two nucleotide sequences is determined using the GAP program in the GCG software package using a NWSgapdna.CMP matrix, a gap weight of 40, 50, 60, 70, or 80, and a length weight of 1, 2, 3, 4, 5, or 6. A particularly preferred set of parameters (and the one that can be used if the practitioner is uncertain about what parameters should be applied to determine if a molecule is a sequence identity or homology limitation of the invention) is using a Blossum 62 scoring matrix with a gap open penalty of 12, a gap extend penalty of 4, and a frameshift gap penalty of 5.

Another non-limiting example of how percent identity can be determined is by using software programs such as those described in Current Protocols In Molecular Biology (F. M. Ausubel et al., eds., 1987) Supplement 30, section 7.7.18, Table 7.70.1. Preferably, default parameters are used for alignment. A preferred alignment program is BLAST, using default parameters. In particular, preferred programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: http://www.ncbi.nlm.nih.gov/cgi-bin/BLAST.

Statistical analysis of the properties described herein may be carried out by standard tests, for example, t-tests, ANOVA, or Chi squared tests. Typically, statistical significance will be measured to a level of p=0.05 (5%), more preferably p=0.01, p=0.001, p=0.0001, p=0.000001

“Conservatively modified variants” of domain sequences also can be provided. With respect to particular nucleic acid sequences, conservatively modified variants refer to those nucleic acids which encode identical or essentially identical amino acid sequences, or where the nucleic acid does not encode an amino acid sequence, to essentially identical sequences. Specifically, degenerate codon substitutions can be achieved by generating sequences in which the third position of one or more selected (or all) codons is substituted with mixed-base and/or deoxyinosine residues (Batzer, et al., 1991, Nucleic Acid Res. 19: 5081; Ohtsuka, et al., 1985, J. Biol. Chem. 260: 2605-2608; Rossolini et al., 1994, Mol. Cell. Probes 8: 91-98).

The term "biologically active fragment", "biologically active form", "biologically active equivalent" of and "functional derivative" of a wild-type protein, possesses a biological activity that is at least substantially equal (e.g., not significantly different from) the biological activity of the wild type protein as measured using an assay suitable for detecting the activity.

As used herein, "in vivo" nucleic acid delivery, nucleic acid transfer, nucleic acid therapy" and the like, refer to the introduction of an improved LAMP Construct directly into the body of an organism, such as a human or non-human mammal, whereby the improved LAMP Construct is introduced to a cell of such organism in vivo.

As used herein, the term "in situ" refers to a type of in vivo nucleic acid delivery in which the improved LAMP Construct is brought into proximity with a target cell (e.g., the nucleic acid is not administered systemically). For example, in situ delivery methods include, but are not limited to, injecting an improved LAMP Construct directly at a site (e.g., into a tissue, such as a tumor or heart muscle), contacting the improved LAMP Construct with cell(s) or tissue through an open surgical field, or delivering the improved LAMP Constructs to a site using a medical access device such as a catheter.

As used herein, the term "isolated" or "purified" means separated (or substantially free) from constituents, cellular and otherwise, in which the polynucleotide, peptide, polypeptide, protein, antibody, or fragments thereof, are normally associated with in nature. For example, with respect to an improved LAMP Construct, an isolated polynucleotide is one that is separated from the 5' and 3' sequences with which it is normally associated in the chromosome. As is apparent to those of skill in the art, a non-naturally occurring polynucleotide, peptide, polypeptide, protein, antibody, or fragments thereof, does not require "isolation" to distinguish it from its naturally occurring counterpart. By substantially free or substantially purified, it is meant at least 50% of the population, preferably at least 70%, more preferably at least 80%, and even more preferably at least 90%, are free of the components with which they are associated in nature.

As used herein, a "target cell" or "recipient cell" refers to an individual cell or cell which is desired to be, or has been, a recipient of the improved LAMP Constructs described herein. The term is also intended to include progeny of a single cell, and the progeny may not necessarily be completely identical (in morphology or in genomic or total DNA complement) to the original parent cell due to natural, accidental, or deliberate mutation. A target cell may be in contact with other cells (e.g., as in a tissue) or may be found circulating within the body of an organism.

As used herein, a "subject" is a vertebrate, preferably a mammal, more preferably a human. Mammals include, but are not limited to, murines, simians, humans, farm animals, sport animals, and pets. In other preferred embodiments, the "subject" is a rodent (e.g. a rat, a mouse, a rabbit, a llama, camels, a cow, a guinea pig, a hamster, a dog, a cat, a horse, a non-human primate, a simian (e.g. a monkey or ape), a monkey (e.g. marmoset, baboon, rhesus macaque), or an ape (e.g. gorilla, chimpanzee, orangutan, gibbon). In other embodiments, non-human mammals, especially mammals that are conventionally used as models for demonstrating therapeutic efficacy in humans (e.g. murine, primate, porcine, canine, or rabbit animals) may be employed.

The terms "cancer," "neoplasm," and "tumor," are used interchangeably and in either the singular or plural form, refer to cells that have undergone a malignant transformation that makes them pathological to the host organism. Primary cancer cells transformation that makes them pathological to the host organism. Primary cancer cells (that is, cells obtained from near the site of malignant transformation) can be readily distinguished from non-cancerous cells by well-established techniques, particularly histological examination. The definition of a cancer cell, as used herein, includes not only a primary cancer cell, but any cell derived from a cancer cell ancestor. This includes metastasized cancer cells, and in vitro cultures and cell lines derived from cancer cells. When referring to a type of cancer that normally manifests as a solid tumor, a "clinically detectable" tumor is one that is detectable on the basis of tumor mass, e.g., by procedures such as CAT scan, MR imaging, X-ray, ultrasound or palpation, and/or which is detectable because of the expression of one or more cancer-specific antigens in a sample obtainable from a patient.

In preferred embodiments, the cancer (including all stages of progression, including hyperplasia) is an adenocarcinoma, sarcoma, skin cancer, melanoma, bladder cancer, brain cancer, breast cancer, uterine cancer, ovarian cancer, prostate cancer, lung cancer (including, but not limited to NSCLC, SCLC, squamous cell cancer), colorectal cancer, anal cancer, rectal cancer, cervical cancer, liver cancer, head and neck cancer, oral cancer, salivary gland cancer, esophageal cancer, pancreas cancer, pancreatic ductal adenocarcinoma (PDA), renal cancer, stomach cancer, kidney cancer, multiple myeloma or cerebral cancer.

The improved LAMP Constructs described herein can also be used to treat allergies, such as for example, food allergies (e.g., peanut allergens, such as Ara H1, H2 and/or H3), or environmental allergens, such as for example pollen (tree pollen, such as for example CRY J1 or CRY J2), dog dander, cat saliva, or dust mites. Other diseases and/or disorders include, for example, infectious disease and diabetes.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. Compositions comprising the improved LAMP Constructs also can include stabilizers and preservatives. For examples of carriers, stabilizers and adjuvants, see Martin Remington's Pharm. Sci., 15th Ed. (Mack Publ. Co., Easton (1975)).

A cell has been "transformed", "transduced", or "transfected" by the improved LAMP Constructs when such nucleic acids have been introduced inside the cell. Transforming DNA may or may not be integrated (covalently linked) with chromosomal DNA making up the genome of the cell. In prokaryotes, yeast, and mammalian cells for example, the improved LAMP Constructs may be maintained on an episomal element, such as a plasmid. In a eukaryotic cell, a stably transformed cell is one in which the improved LAMP Constructs have become integrated into a chromosome so that it is inherited by daughter cells through chromosome replication. This stability is demonstrated by the ability of the eukaryotic cell to establish cell lines or clones comprised of a population of daughter cells containing the improved LAMP Constructs. A "clone" is a population of cells derived from a single cell or common ancestor by mitosis. A "cell line" is a clone of a primary cell that is capable of stable growth in vitro for many generations (e.g., at least about 10).

As used herein, an "effective amount" is an amount sufficient to affect beneficial or desired results, e.g., such as an effective amount of the improved LAMP Construct transfer and/or expression, and/or the attainment of a desired therapeutic endpoint. An effective amount can be administered in one or more administrations, applications or dosages. In one aspect, an effective amount of an improved LAMP Construct is an amount sufficient to transform/transduce/transfect at least one cell in a population of cells comprising at least two cells.

As used herein, a "therapeutically effective amount" is used herein to mean an amount sufficient to prevent, correct and/or normalize an abnormal physiological response. In one aspect, a "therapeutically effective amount" is an amount sufficient to reduce by at least about 30 percent, more preferably by at least 50 percent, most preferably by at least 90 percent, a clinically significant feature of pathology, such as for example, allergic response, size of a tumor mass, antibody production, cytokine production, fever or white cell count, etc.

An "antibody" is any immunoglobulin, including antibodies and fragments thereof, that binds a specific antigen. The term encompasses polyclonal, monoclonal, and chimeric antibodies (e.g., bispecific antibodies). An "antibody combining site" is that structural portion of an antibody molecule comprised of heavy and light chain variable and hypervariable regions that specifically binds antigen. Exemplary antibody molecules are intact immunoglobulin molecules, substantially intact immunoglobulin molecules, and those portions of an immunoglobulin molecule that contains the paratope, including Fab, Fab', F(ab')2 and F(v) portions, which portions are preferred for use in the therapeutic methods described herein. Thus, the term antibody encompasses not only whole antibody molecules, but also antibody fragments as well as variants (including derivatives such as fusion proteins) of antibodies and antibody fragments. Examples of molecules which are described by the term "antibody" in this application include, but are not limited to: single chain Fvs (scFvs), Fab fragments, Fab' fragments, F(ab')2, disulfide linked Fvs (sdFvs), Fvs, and fragments comprising or alternatively consisting of, either a VL or a VH domain. The term "single chain Fv" or "scFv" as used herein refers to a polypeptide comprising a VL domain of an antibody linked to a VH domain of an antibody. See Carter (2006) Nature Rev. Immunol. 6:243.

Additionally, antibodies of the invention include, but are not limited to, monoclonal, multi-specific, bi-specific, human, humanized, mouse, or chimeric antibodies, single chain antibodies, camelid antibodies, Fab fragments, F(ab') fragments, anti-idiotypic (anti-Id) antibodies (including, e.g., anti-Id antibodies to antibodies of the invention), domain antibodies and epitope-binding fragments of any of the above. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule.

Most preferably, the antibodies are human antibodies. As used herein, "human" antibodies include antibodies having the amino acid sequence of a human immunoglobulin and include antibodies isolated from human immunoglobulin libraries and xenomice or other organisms that have been genetically engineered to produce human antibodies. The improved LAMP Constructs described herein can be used in combination with known techniques for generating human antibodies and human monoclonal antibodies as described in the exemplified protocols, see, e.g., PCT publications WO98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598; and Lonberg and Huszar, Int. Rev. Immunol. 13:65-93 (1995).

Human antibodies or "humanized" chimeric monoclonal antibodies can be produced using the improved LAMP Constructs in combination with techniques described herein or otherwise known in the art. For example, standard methods for producing chimeric antibodies are known in the art. See, for review the following references: Morrison, Science 229:1202 (1985); Oi et al., BioTechniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985).

The antibodies of the present invention may be monovalent, bivalent, trivalent or multivalent. For example, monovalent scFvs can be multimerized either chemically or by association with another protein or substance. A scFv that is fused to a hexahistidine tag or a Flag tag can be multimerized using Ni-NTA agarose (Qiagen) or using anti-Flag antibodies (Stratagene, Inc.). Additionally, the improved LAMP Constructs can be used to generate monospecific, bispecific, trispecific or of greater multispecificity for the encoded antigen(s) contained in the improved LAMP Construct. See, e.g., PCT publications WO93/17715; WO 92/08802; WO 91/00360; WO 92/05793; Tutt, et al., J. Immunol. 147:60-69 (1991); U.S. Pat. Nos. 4,474,893; 4,714,681; 4,925,648; 5,573,920; 5,601,819; Kostelny et. al., J. Immunol. 148:1547-1553 (1992).

An "epitope" is a structure, usually made up of a short peptide sequence or oligosaccharide, that is specifically recognized or specifically bound by a component of the immune system. T-cell epitopes have generally been shown to be linear oligopeptides. Two epitopes correspond to each other if they can be specifically bound by the same antibody. Two epitopes correspond to each other if both are capable of binding to the same B cell receptor or to the same T cell receptor, and binding of one antibody to its epitope substantially prevents binding by the other epitope (e.g., less than about 30%, preferably, less than about 20%, and more preferably, less than about 10%, 5%, 1%, or about 0.1% of the other epitope binds). In the present invention, multiple epitopes can make up an antigen.

The term "antigen" or "antigen of interest" as used herein covers any polypeptide sequence encoded by a polynucleotide sequence cloned into the improved LAMP Construct which is used to elicit an innate or adaptive immune response. An "antigen" encompasses both a single antigen as well as multiple antigenic sequences (derived from the same or different proteins) cloned into the improved LAMP Construct.

The term "antigen presenting cell" as used herein includes any cell which presents on its surface an antigen in association with a major histocompatibility complex molecule, or portion thereof, or, alternatively, one or more non-classical MHC molecules, or a portion thereof. Examples of suitable APCs are discussed in detail below and include, but are not limited to, whole cells such as macrophages, dendritic cells, B cells, hybrid APCs, and foster antigen presenting cells.

As used herein an "engineered antigen-presenting cell" refers to an antigen-presenting cell that has a non-natural molecular moiety on its surface. For example, such a cell may not naturally have a costimulator on its surface or may have an additional artificial costimulator in addition to a natural costimulator on its surface, or may express a non-natural class II molecule on its surface. In preferred embodiments, the engineered antigen-presenting cell has the antigen expressed from the improved LAMP Construct on its surface.

As used herein, "immune effector cells" refers to cells capable of binding an antigen and which mediate an immune response. These cells include, but are not limited to, T cells, B cells, monocytes, macrophages, NK cells and cytotoxic T lymphocytes (CTLs), for example CTL lines, CTL clones, and CTLs from tumor, inflammatory, or other infiltrates.

As used herein, "partially human" refers to a nucleic acid having sequences from both a human and a non-human vertebrate. In the context of partially human sequences, the partially human nucleic acids have sequences of human immunoglobulin coding regions and sequences based on the non-coding sequences of the endogenous immunoglobulin region of the non-human vertebrate. The term "based on" when used with reference to endogenous non-coding sequences from a non-human vertebrate refers to sequences that correspond to the non-coding sequence and share a relatively high degree of homology with the non-coding sequences of the endogenous loci of the host vertebrate, e.g., the non-human vertebrate from which the ES cell is derived. Preferably, the non-coding sequences share at least an 80%, more preferably 90% homology with the corresponding non-coding sequences found in the endogenous loci of the non-human vertebrate host cell into which a partially human molecule comprising the non-coding sequences has been introduced.

The term "immunoglobulin variable region" as used herein refers to a nucleotide sequence that encodes all or a portion of a variable region of an antibody molecule or all or a portion of a regulatory nucleotide sequence that controls expression of an antibody molecule. Immunoglobulin regions for heavy chains may include but are not limited to all or a portion of the V, D, J, and switch regions, including introns. Immunoglobulin region for light chains may include but are not limited to the V and J regions, their upstream flanking sequences, introns, associated with or adjacent to the light chain constant region gene.

By "transgenic animal" is meant a non-human animal, usually a mammal, having an exogenous nucleic acid sequence present as an extrachromosomal element in a portion of its cells or stably integrated into its germ line DNA (i.e., in the genomic sequence of most or all of its cells). In generating a transgenic animal comprising human sequences, a partially human nucleic acid is introduced into the germ line of such transgenic animals by genetic manipulation of, for example, embryos or embryonic stem cells of the host animal according to methods well known in the art.

A "vector" includes plasmids and viruses and any DNA or RNA molecule, whether self-replicating or not, which can be used to transform or transfect a cell.

As used herein, a "genetic modification" refers to any addition, deletion or disruption to a cell's normal nucleotides. Art recognized methods include viral mediated gene transfer, liposome mediated transfer, transformation, transfection and transduction, e.g., viral-mediated gene transfer such as the use of the improved LAMP Constructs based on DNA viruses such as adenovirus, adeno-associated virus and herpes virus, as well as retroviral based vectors.

The practice of the present invention employs, unless otherwise indicated, conventional molecular biology, microbiology, and recombinant DNA techniques within the skill of the art. Such techniques are explained fully in the literature. See, e.g., Maniatis, Fritsch & Sambrook, In Molecular Cloning: A Laboratory Manual (1982); DNA Cloning: A Practical Approach, Volumes I and II (D. N. Glover, ed., 1985); Oligonucleotide Synthesis (M. J. Gait, ed., 1984); Nucleic Acid Hybridization (B. D. Hames & S. J. Higgins, eds., 1985); Transcription and Translation (B. D. Hames & S. I. Higgins, eds., 1984); Animal Cell Culture (R. I. Freshney, ed., 1986); Immobilized Cells and Enzymes (IRL Press, 1986); B. Perbal, A Practical Guide to Molecular Cloning (1984).

Figure 2B:
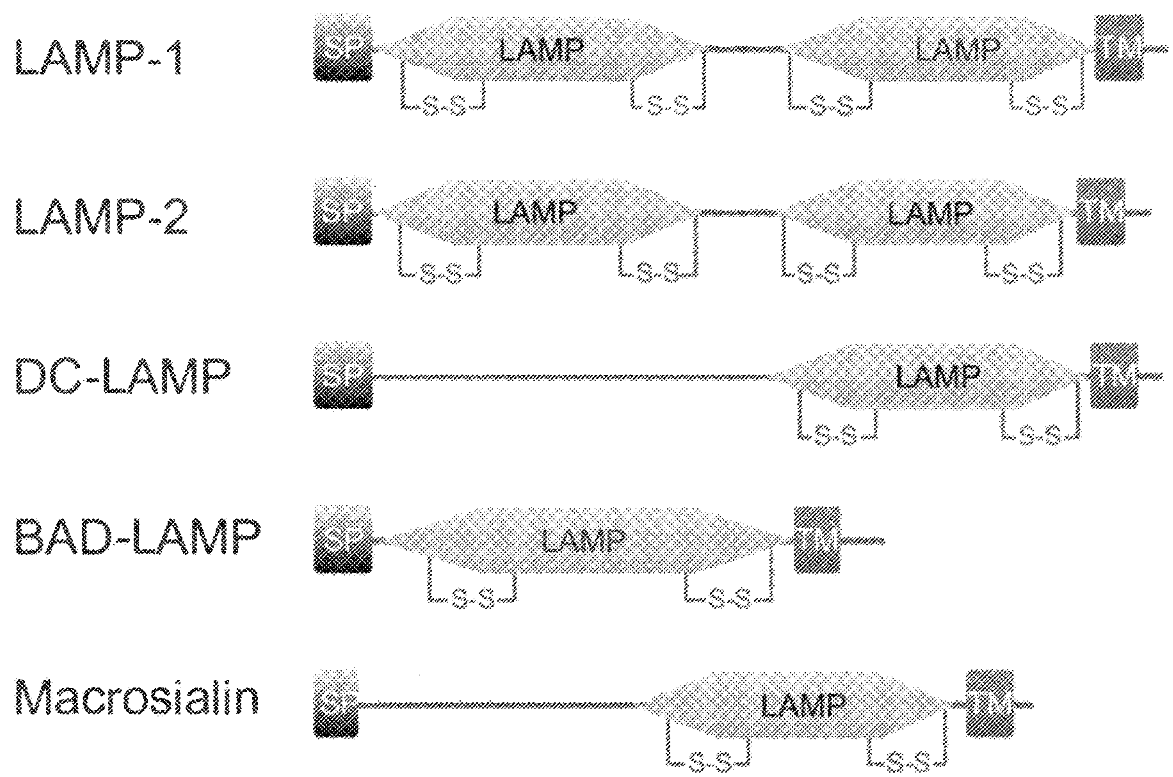
FIG. 2A illustrates the domains of the LAMP proteins defined herein while FIG. 2B defines the specific amino acid boundaries of these domains for human LAMP-1 (SEQ ID NO:1), human LAMP-2 (SEQ ID NO:2), human LAMP-3 (SEQ ID NO:3), human LIMP-2 (SEQ ID NO:4), human Endolyn (SEQ ID NO:5), human Macrosailin (SEQ ID NO:80), human LAMP-5 (SEQ ID NO:93) and human LIMBIC (SEQ ID NO:67). As described herein the LAMP lumenal domains, homology domains, transmembrane domains, the cytoplasmic tail and the signal sequences can be used to generate the improved LAMP Constructs ILC-1, ILC-2, ILC-3, ILC-4, ILC-5 and ILC-6 as described herein.

Unless defined otherwise, all technical and scientific terms used herein have the same meaning as commonly understood by one of ordinary skill in the art to which this invention belongs. All publications mentioned herein are incorporated by reference for the purpose of describing and disclosing devices, formulations and methodologies that may be used in connection with the presently described invention LAMP Constructs LAMP-1, as deduced from a cDNA clone (Chen, et al., J. Biol. Chem. 263: 8754, 1988) consists of a polypeptide core of about 382 amino acids with a large (346-residue) lumenal amino-terminal domain followed by a 24-residue hydrophobic transmembrane region and short (12-residue) carboxyl-terminal cytoplasmic tail. See, FIGS. 2A and 2B. The lumenal domain is highly glycosylated, being substituted with about 20 asparagine linked complex-type oligosaccharides and consists of two approximately 160-residue "homology domains" that are separated by a proline/serine-rich hinge region. Each of these "homology domains" contains 4 uniformly spaced cysteine residues, disulfide bonded to form four 36-38-residue loops symmetrically placed within the two halves of the lumenal domain (Arterburn, et al., J. Biol. Chem. 265: 7419, 1990; see, also Chen, et al., J. Biol. Chem. 25: 263(18): 8754-8, 1988). FIG. 2A schematically shows the conserved domains between LAMP-1, LAMP-2, LAMP-3, Endolyn, LIMBIC, LAMP5, or Macrosailin.

Previously reported LAMP constructs comprise the following elements in this specific arrangement:

(a) a full lumenal domain of LAMP-1 protein, the antigen and then the full transmembrane/cytoplasmic tail of LAMP-1 protein; or (b) the antigen and the full transmembrane/cytoplasmic tail of a LAMP-1 protein. In example (a), the antigenic sequence is inserted in between the full lumenal domain of a LAMP-1 protein and the LAMP-1 full transmembrane domain/cytoplasmic tail. Both constructs have been shown to successfully target an antigenic sequence to the lysosome/endosome and will be referred to as "complete LAMP Constructs" as shown in FIG. 1 as compared to the improved LAMP Constructs ILC1-ILC6 described herein. The improved LAMP Constructs described herein do not include the complete LAMP Constructs described in the prior art.

Although it has been widely reported in the literature that fragments smaller than the full lumenal domain of LAMP-1 were not effective in generating a robust immune response (see, e.g. Godinho et al.) the inventors unexpectedly discovered that specific fragments, in certain arrangements, did in fact effectively present antigens to the immune system, generating a robust immune response, including the generation of a different repitoire of antibodies. For example, the inventors have identified that the minimal LAMP lumenal domain fragment that is effective for generating a robust immune response is not the full lumenal domain (as widely reported in the literature) but rather a single Homology Domain of the Lumenal Domain of a LAMP Protein.

For example, constructs can comprise, not the full lumenal domain, but instead a single Homology Domain of the Lumenal Domain of a LAMP Protein. As used herein, the "Homology Domain" comprises at least the 4 uniformly spaced cysteine residues shown in FIGS. 3-10. These cysteine resides are labeled 1, 2, 3, and 4 (and in LIMP-2 and Macrosailin—five cysteines are identified, LIMBIC—six cysteines are identified and Endolyn—eight cysteines are identified) in each Homology Domain as shown in FIGS. 3-10 and are defined herein as the "Cysteine Conserved Fragment." Additional amino acids can be included to either the N-terminus end and/or the C-terminus end of the Cysteine Conserved Fragment to generate, up to and including a full Homology Domain of a LAMP protein. These additional added amino acids can be derived from the Homology Domain from which the Cysteine Conserved Fragment is derived or from other LAMP Protein Homology Domains. Thus, as used herein, a LAMP Homology Domain comprises and/or consists of one Cysteine Conserved Fragment. At least two LAMP Homology Domains make up the Lumenal Domain of LAMP-1, LAMP-2, LAMP-3, or Endolyn.

Specifically, in one preferred embodiment, the improved LAMP Construct comprises at least one antigen of interest fused to the N-terminus of the lumenal domain of a LAMP protein, at least one homology domain of a LAMP protein, or at least one Cysteine Conserved Fragment of a LAMP protein. See, for example ILC-2 and ILC-6 of FIG. 1. In preferred embodiments, these constructs also comprise a transmembrane domain of a LAMP protein, and/or the cytosolic tail of a LAMP protein. In other preferred embodiments, when an antigen contains a transmembrane domain, the transmembrane domain of a LAMP protein and/or the cytosolic tail of a LAMP protein is unnecessary. In preferred embodiments, two homology domains are included in the improved LAMP Construct (e.g., MC-1 of FIG. 1). In further preferred embodiments, the two homology domains are derived from a LAMP-1, LAMP-2, LAMP-3, or an Endolyn protein. Alternatively, the two homology domains are derived from different LAMP proteins. In these constructs comprising two homology domains, a LAMP hinge domain may also be included. The improved LAMP Constructs described in this paragraph are unexpected in view of the prior art as the antigen has always been placed in between the full lumenal LAMP-1 domain and the full LAMP-1 transmembrane/cytoplasmic tail, as fragments of the lumenal domain have not been reported to be effective in generating a robust immume response.

In another preferred embodiment, the improved LAMP Construct comprises at least one antigen of interest fused to the C-terminus of a single homology domain of a LAMP protein or a single Cysteine Conserved Fragment of a LAMP protein. See, for example, ILC-3 and ILC-5 of FIG. 1. In preferred embodiments, these constructs also comprise a transmembrane domain of a LAMP protein, and/or the cytosolic tail of a LAMP protein. In other preferred embodiments, when an antigen contains a transmembrane domain, the transmembrane domain of a LAMP protein and/or the cytosolic tail of a LAMP protein is unnecessary. The improved LAMP Constructs described in this paragraph are unexpected in view of the prior art as described above.

In another preferred embodiment, the improved LAMP Construct comprises at least one antigen of interest fused in between a first homology domain of a LAMP protein and a second homology domain of a LAMP protein (or at least between two Cysteine Conserved Fragments). See, for example, ILC-4 of FIG. 1. In preferred embodiments, these constructs also comprise a transmembrane domain of a LAMP protein, and/or the cytosolic tail of a LAMP protein. In preferred embodiments, the two homology domains are derived from LAMP-1, LAMP-2, LAMP-3, or an Endolyn protein. In these constructs, the antigen may be placed in the LAMP hinge region. Alternatively, two homology domains from two different LAMP proteins may be used. This arrangement of at least one antigen of interest fused in between two LAMP homology domains (including Cysteine Conserved Fragments) is unexpected in view of the prior art as described above.

Each of the improved LAMP Constructs defined above can be generated using the domains defined in the Figures. For example, it is specifically contemplated that the domains included in the improved LAMP Construct illustrated in FIG. 1, for example, can originate from sequences derived from orthologous sequences. See, FIGS. 3-10 for example. It is expressly contemplated that the equivalent domains defined in FIGS. 2A and 2B be used to generate the improved LAMP Constructs illustrated in FIG. 1 for orthologous sequences. Moreover, the orthologous sequences shown in FIGS. 3-10 are representative of the sequences that can be used to generate the domains. It is well within the skill in the art to identify other orthologous sequences and/or isotypes and comparing them to the alignments shown in FIGS. 3-10. Thus, by identifying the equivalent boundaries defined in FIGS. 2A and 2B for a human LAMP protein with the alignments shown in FIGS. 3-10, one can generate the improved LAMP Constructs illustrated in FIG. 1.

As would be well understood by the skilled artisan, the boundaries of each domain are an approximation and may be adjusted at least 1, 2, 3, 4, 5, 6, 7, 8, 9, or 10 amino acids based on cloning considerations and restriction enzyme placement. Therefore, when a particular domain (e.g., a LAMP Homology Domain) is included in the improved LAMP Construct, the amino acids beginning and ending of the domain may be adjust by at least 1, 2, 3, 4, 5, 6, 7, 8, 9, or 10 amino acids as those boundaries defined in FIG. 2B.

Each of the improved LAMP Constructs described above can additionally comprise a signal sequence and/or additional amino acids in between each domain for cloning purposes as is well known in the art. Additionally, the LAMP homologous domains, the LAMP lumenal domain, the LAMP transmembrane domain, and/or the LAMP cytosolic tail domain can originate from the same LAMP protein (e.g., human LAMP-1) or different LAMP proteins (e.g., lumenal domain from human LAMP-1 and transmembrane domain from human LAMP-2, and/or mixing of orthologous domains in the same gene family (e.g., LAMP-1) or different gene family (LAMP-1 and LAMP-2).

Polypeptide variants of the described LAMP Constructs are contemplated. For example, polypeptides at least about 60%, at least about 70%, at least about 75%, at least about 80%, at least about 85%, at least about 90%, at least about 95%, 96%, 97%, 98% or 99% identity to any of the improved LAMP Constructs described herein as well as polynucleotides encoding these variants. Variants of the improved LAMP Constructs retain the ability to function by targeting the antigenic sequence to the lysosome. For example, a modified lumenal sequence must retain the ability to traffic both membrane and non-membrane antigenic materials to an endosomal compartment with at least about 50%, at least about 60%, at least 70%, at least about 80%, at least about 90%, or at least about 100% efficacy compared to the original domain sequence, i.e., an efficacy that results in sufficient antigen presentation by a cell comprising the chimeric sequence for it to mount an immune response. In one aspect, sequences containing a suitable trafficking signal may be identified by constructing an improved LAMP Construct containing the well-characterized antigenic domain of ovalbumin, a transmembrane domain, and the cytoplasmic domain of a protein containing a putative lysosomal/endosomal targeting signal. Efficiency of targeting can be measured by determining the ability of antigen presenting cells, expressing the improved LAMP Construct, to stimulate HA epitope-specific, MHC class II restricted T-cells (see, e.g., Example 5 of U.S. Pat. No. 5,633,234).

Polynucleotides encoding any of the described improved LAMP Constructs are preferred embodiments of the invention, along with polynucleotides at least about 60%, at least about 70%, at least about 75%, at least about 80%, at least about 85%, at least about 90%, at least about 95%, 96%, 97%, 98% or 99% identity to any of the improved LAMP Construct polynucleotides described herein. Variants of the improved LAMP Constructs retain the ability to function by targeting the antigenic sequence to the lysosome. For example, a modified lumenal sequence must retain the ability to traffic both membrane and non-membrane antigenic materials to an endosomal compartment with at least about 50%, at least about 60%, at least 70%, at least about 80%, at least about 90%, or at least about 100% efficacy compared to the original domain sequence, i.e., an efficacy that results in sufficient antigen presentation by a cell comprising the chimeric sequence for it to mount an immune response. In one aspect, sequences containing a suitable trafficking signal may be identified by constructing an improved LAMP Construct containing the well-characterized antigenic domain of ovalbumin, a transmembrane domain, and the cytoplasmic domain of a protein containing a putative lysosomal/endosomal targeting signal. Efficiency of targeting can be measured by determining the ability of antigen presenting cells, expressing the improved LAMP Construct, to stimulate HA epitope-specific, MHC class II restricted T-cells (see, e.g., Example 5 of U.S. Pat. No. 5,633,234).

Assembly of Sequences Encoding Improved LAMP Constructs

Procedures for constructing improved LAMP Constructs comprising the antigen of interest are well known in the art (see e.g., Williams, et al., J. Cell Biol. 111: 955, 1990). DNA sequences encoding the desired segments can be obtained from readily available recombinant DNA materials such as those available from the American Type Culture Collection, 12301 Parklawn Drive, Rockville, Md. 20852, U.S.A., or from DNA libraries that contain the desired DNA.

For example, the DNA segments corresponding to the desired domain sequences can be assembled with appropriate control and signal sequences using routine procedures of recombinant DNA methodology. See, e.g., as described in U.S. Pat. No. 4,593,002, and Langford, et al., Molec. Cell. Biol. 6: 3191, 1986.

A DNA sequence encoding a protein or polypeptide can be synthesized chemically or isolated by one of several approaches. The DNA sequence to be synthesized can be designed with the appropriate codons for the desired amino acid sequence. In general, one will select preferred codons for the intended host in which the sequence will be used for expression. The complete sequence may be assembled from overlapping oligonucleotides prepared by standard methods and assembled into a complete coding sequence. See, e.g., Edge, Nature 292: 756, 1981; Nambair, et al. Science 223: 1299, 1984; Jay, et al., J. Biol. Chem. 259: 6311, 1984.

In one aspect, one or more of the nucleic acids encoding the domain sequences of the improved LAMP Construct are isolated individually using the polymerase chain reaction (M. A. Innis, et al., In PCR Protocols: A Guide to Methods and Applications, Academic Press, 1990). The domains are preferably isolated from publicly available clones known to contain them, but they may also be isolated from genomic DNA or cDNA libraries. Preferably, isolated fragments are bordered by compatible restriction endonuclease sites which allow an improved LAMP Construct encoding the antigen sequence to be constructed. This technique is well known to those of skill in the art. Domain sequences may be fused directly to each other (e.g., with no intervening sequences), or inserted into one another (e.g., where domain sequences are discontinuous), or may be separated by intervening sequences (e.g., such as linker sequences).

The basic strategies for preparing oligonucleotide primers, probes and DNA libraries, as well as their screening by nucleic acid hybridization, are well known to those of ordinary skill in the art. See, e.g., Sambrook, et al., 1989, supra; Perbal, 1984, supra. The construction of an appropriate genomic DNA or cDNA library is within the skill of the art. See, e.g., Perbal, 1984, supra. Alternatively, suitable DNA libraries or publicly available clones are available from suppliers of biological research materials, such as Clonetech and Stratagene, as well as from public depositories such as the American Type Culture Collection.

Selection may be accomplished by expressing sequences from an expression library of DNA and detecting the expressed peptides immunologically. Clones which express peptides that bind to MHC II molecules and to the desired antibodies/T cell receptors are selected. These selection procedures are well known to those of ordinary skill in the art (see, e.g., Sambrook, et al., 1989, supra).

Once a clone containing the coding sequence for the desired polypeptide sequence has been prepared or isolated, the sequence can be cloned into any suitable vector, preferably comprising an origin of replication for maintaining the sequence in a host cell.

Nucleic Acid Delivery Vehicles

In one aspect, a vaccine composition comprising an improved LAMP Construct is introduced into a cell. The cell may be a host cell for replicating the nucleic acid or for expressing the improved LAMP Construct. Preferably, the host cell for expressing the improved LAMP Construct is an antigen presenting cell (described further below).

In preferred embodiments, the improved LAMP Construct further comprises a polynucleotide sequence for insertion into a target cell and an expression control sequence operably linked thereto to control expression of the polynucleotide sequence (e.g., transcription and/or translation) in the cell. Examples include plasmids, phages, autonomously replicating sequences (ARS), centromeres, and other sequences which are able to replicate or be replicated in vitro or in a host cell (e.g., such as a bacterial, yeast, or insect cell) and/or target cell (e.g., such as a mammalian cell, preferably an antigen presenting cell) and/or to convey the sequences encoding the improved LAMP Construct to a desired location within the target cell.

Recombinant expression vectors may be derived from micro-organisms which readily infect animals, including man, horses, cows, pigs, llamas, giraffes, dogs, cats or chickens. Preferred vectors include those which have already been used as live vaccines, such as vaccinia. These recombinants can be directly inoculated into a host, conferring immunity not only to the microbial vector, but also to express foreign antigens. Preferred vectors contemplated herein as live recombinant vaccines include RNA viruses, adenovirus, herpesviruses, poliovirus, and vaccinia and other pox viruses, as taught in Flexner, Adv. Pharmacol. 21: 51, 1990, for example.

Expression control sequences include, but are not limited to, promoter sequences to bind RNA polymerase, enhancer sequences or negative regulatory elements to bind to transcriptional activators and repressors, respectively, and/or translation initiation sequences for ribosome binding. For example, a bacterial expression vector can include a promoter such as the lac promoter and for transcription initiation, the Shine-Dalgarno sequence and the start codon AUG (Sambrook, et al., 1989, supra). Similarly, a eukaryotic expression vector preferably includes a heterologous, homologous, or chimeric promoter for RNA polymerase II, a downstream polyadenylation signal, the start codon AUG, and a termination codon for detachment of a ribosome.

Expression control sequences may be obtained from naturally occurring genes or may be designed. Designed expression control sequences include, but are not limited to, mutated and/or chimeric expression control sequences or synthetic or cloned consensus sequences. Vectors that contain both a promoter and a cloning site into which a polynucleotide can be operatively linked are well known in the art. Such vectors are capable of transcribing RNA in vitro or in vivo, and are commercially available from sources such as Stratagene (La Jolla, Calif.) and Promega Biotech (Madison, Wis.).

In order to optimize expression and/or transcription, it may be necessary to remove, add or alter 5' and/or 3' untranslated portions of the vectors to eliminate extra, or alternative translation initiation codons or other sequences that may interfere with, or reduce, expression, either at the level of transcription or translation. Alternatively, consensus ribosome binding sites can be inserted immediately 5' of the start codon to enhance expression. A wide variety of expression control sequences—sequences that control the expression of a DNA sequence operatively linked to it—may be used in these vectors to express the DNA sequences of this invention. Such useful expression control sequences include, for example, the early or late promoters of SV40, CMV, vaccinia, polyoma, adenovirus, herpes virus and other sequences known to control the expression of genes of mammalian cells, and various combinations thereof.

In one aspect, the improved LAMP Construct comprises an origin of replication for replicating the vector. Preferably, the origin functions in at least one type of host cell which can be used to generate sufficient numbers of copies of the sequence for use in delivery to a target cell. Suitable origins therefore include, but are not limited to, those which function in bacterial cells (e.g., such as *Escherichia* sp., *Salmonella* sp., *Proteus* sp., *Clostridium* sp., *Klebsiella* sp., *Bacillus* sp., *Streptomyces* sp., and *Pseudomonas* sp.), yeast (e.g., such as *Saccharamyces* sp. or *Pichia* sp.), insect cells, and mammalian cells. In one preferred aspect, an origin of replication is provided which functions in the target cell into which the nucleic acid delivery vehicle is introduced (e.g., a mammalian cell, such as a human cell). In another aspect, at least two origins of replication are provided, one that functions in a host cell and one that functions in a target cell.

The improved LAMP Construct may alternatively, or additionally, comprise sequences to facilitate integration of at least a portion of the nucleic acid deliver vector into a target cell chromosome. For example, the improved LAMP Construct may comprise regions of homology to target cell chromosomal DNA. In one aspect, the delivery vector comprises two or more recombination sites which flank a nucleic acid sequence encoding the improved LAMP Construct.

The vector may additionally comprise a detectable and/or selectable marker to verify that the vector has been successfully introduced in a target cell and/or can be expressed by the target cell. These markers can encode an activity, such as, but not limited to, production of RNA, peptide, or protein, or can provide a binding site for RNA, peptides, proteins, inorganic and organic compounds or compositions and the like.

Examples of detectable/selectable markers genes include, but are not limited to: DNA segments that encode products which provide resistance against otherwise toxic compounds (e.g., antibiotics); DNA segments that encode products which are otherwise lacking in the recipient cell (e.g., tRNA genes, auxotrophic markers); DNA segments that encode products which suppress the activity of a gene product; DNA segments that encode products which can be readily identified (e.g., phenotypic markers such as beta-galactosidase, a fluorescent protein (GFP, CFP, YFG, BFP, RFP, EGFP, EYFP, EBFP, dsRed, mutated, modified, or enhanced forms thereof, and the like), and cell surface proteins); DNA segments that bind products which are otherwise detrimental to cell survival and/or function; DNA segments that otherwise inhibit the activity of other nucleic acid segments (e.g., antisense oligonucleotides); DNA segments that bind products that modify a substrate (e.g., restriction endonucleases); DNA segments that can be used to isolate or identify a desired molecule (e.g., segments encoding specific protein binding sites); primer sequences; DNA segments, which when absent, directly or indirectly confer resistance or sensitivity to particular compounds; and/or DNA segments that encode products which are toxic in recipient cells.

The marker gene can be used as a marker for conformation of successful gene transfer and/or to isolate cells expressing transferred genes and/or to recover transferred genes from a cell. For example, in one aspect, the marker gene is used to isolate and purify antigen presenting cells expressing the improved LAMP Constructs.

Substantially similar genes may be provided, e.g., genes with greater than about 50%, greater than about 70%, greater than 80%, greater than about 90%, and preferably, greater than about 95% identity to a known gene. Substantially similar domain sequences may initially be identified by selecting a sequence which specifically hybridizes to a domain sequence of interest under stringent hybridization conditions. Performing assays to determine the suitability of homologous, variant, or modified domain sequences is merely a matter of screening for sequences which express the appropriate activity. Such screening is routine in the art.

The improved LAMP Construct may be provided as naked nucleic acids or in a delivery vehicle associated with one or more molecules for facilitating entry of a nucleic acid into a cell. Suitable delivery vehicles include, but are not limited to: liposomal formulations, polypeptides, polysaccharides, lipopolysaccharides, viral formulations (e.g., including viruses, viral particles, artificial viral envelopes and the like), cell delivery vehicles, and the like.

Lipid-Based Formulations

Delivery vehicles designed to facilitate intracellular delivery of the improved LAMP Constructs must interact with both non-polar and polar environments (in or on, for example, the plasma membrane, tissue fluids, compartments within the cell, and the like). Therefore, preferably, delivery vehicles are designed to contain both polar and non-polar domains or a translocating sequence for translocating an improved LAMP Construct into a cell.

Compounds having polar and non-polar domains are termed amphiphiles. Cationic amphiphiles have polar groups that are capable of being positively charged at, or around, physiological pH for interacting with negatively charged polynucleotides such as DNA.

The improved LAMP Constructs described herein can be provided in formulations comprising lipid monolayers or bilayers to facilitate transfer of the vectors across a cell membrane. Liposomes or any form of lipid membrane, such as planar lipid membranes or the cell membrane of an intact cell, e.g., a red blood cell, can be used. Liposomal formulations can be administered by any means, including administration intravenously or orally.

Liposomes and liposomal formulations can be prepared according to standard methods and are well known in the art, see, e.g., Remington's; Akimaru, 1995, Cytokines Mol. Ther. 1: 197-210; Alving, 1995, Immunol. Rev. 145: 5-31; Szoka, 1980, Ann. Rev. Biophys. Bioeng. 9: 467; U.S. Pat. Nos. 4,235,871; 4,501,728; and 4,837,028. In one aspect, the liposome comprises a targeting molecule for targeting a liposome: improved LAMP Construct complex to a particular cell type. In a particularly preferred aspect, a targeting molecule comprises a binding partner (e.g., a ligand or receptor) for a biomolecule (e.g., a receptor or ligand) on the surface of a blood vessel or a cell found in a target tissue.

Liposome charge is an important determinant in liposome clearance from the blood, with negatively charged liposomes being taken up more rapidly by the reticuloendothelial system (Juliano, 1975, Biochem. Biophys. Res. Commun. 63: 651) and thus having shorter half-lives in the bloodstream. Incorporating phosphatidylethanolamine derivatives enhances the circulation time by preventing liposomal aggregation. For example, incorporation of N-(omega-carboxy)acylamidophosphatidylethanolamines into large unilamellar vesicles of L-alpha-distearoylphosphatidylcholine dramatically increases the in vivo liposomal circulation lifetime (see, e.g., Ahl, 1997, Biochim. Biophys. Acta 1329: 370-382). Liposomes with prolonged circulation half-lives are typically desirable for therapeutic and diagnostic uses. For a general discussion of pharmacokinetics, see, e.g., Remington's, Chapters 37-39, Lee, et al., In Pharmacokinetic Analysis: A Practical Approach (Technomic Publishing AG, Basel, Switzerland 1996).

Typically, liposomes are prepared with about 5 to 15 mole percent negatively charged phospholipids, such as phosphatidylglycerol, phosphatidylserine or phosphatidyl-inositol. Added negatively charged phospholipids, such as phosphatidylglycerol, also serve to prevent spontaneous liposome aggregation, and thus minimize the risk of undersized liposomal aggregate formation. Membrane-rigidifying agents, such as sphingomyelin or a saturated neutral phospholipid, at a concentration of at least about 50 mole percent, and 5 to 15 mole percent of monosialylganglioside can also impart desirably liposome properties, such as rigidity (see, e.g., U.S. Pat. No. 4,837,028).

Additionally, the liposome suspension can include lipid-protective agents which protect lipids against free-radical and lipid-peroxidative damages on storage. Lipophilic free-radical quenchers, such as alpha-tocopherol and water-soluble iron-specific chelators, such as ferrioxianine, are preferred.

The improved LAMP Constructs of the invention can include multilamellar vesicles of heterogeneous sizes. For example, vesicle-forming lipids can be dissolved in a suitable organic solvent or solvent system and dried under vacuum or an inert gas to form a thin lipid film. If desired, the film can be redissolved in a suitable solvent, such as tertiary butanol, and then lyophilized to form a more homogeneous lipid mixture which is in a more easily hydrated powderlike form. This film is covered with an aqueous solution of the peptide or polypeptide complex and allowed to hydrate, typically over a 15 to 60 minute period with agitation. The size distribution of the resulting multilamellar vesicles can be shifted toward smaller sizes by hydrating the lipids under more vigorous agitation conditions or by adding solubilizing detergents such as deoxycholate. The hydration medium preferably comprises the nucleic acid at a concentration which is desired in the interior volume of the liposomes in the final liposome suspension.

Following liposome preparation, the liposomes can be sized to achieve a desired size range and relatively narrow distribution of liposome sizes. One preferred size range is about 0.2 to 0.4 microns, which allows the liposome suspension to be sterilized by filtration through a conventional filter, typically a 0.22 micron filter. Filter sterilization can be carried out on a high throughput basis if the liposomes have been sized down to about 0.2 to 0.4 microns. Several techniques are available for sizing liposome to a desired size (see, e.g., U.S. Pat. No. 4,737,323).

Suitable lipids include, but are not limited to, DOTMA (Felgner, et al., 1987, Proc. Natl. Acad. Sci. USA 84: 7413-7417), DOGS or Transfectain™ (Behr, et al., 1989, Proc. Natl. Acad. Sci. USA 86: 6982-6986), DNERIE or DORIE (Felgner, et al., Methods 5: 67-75), DC-CHOL (Gao and Huang, 1991, BBRC 179: 280-285), DOTAP™ (McLachlan, et al., 1995, Gene Therapy 2: 674-622), Lipofectamine™. and glycerolipid compounds (see, e.g., EP901463 and WO98/37916).

Other molecules suitable for complexing with the improved LAMP Constructs include cationic molecules, such as, polyamidoamine (Haensler and Szoka, 1993, Bioconjugate Chem. 4: 372-379), dendritic polysine (WO95/24221), polyethylene irinine or polypropylene h-nine (WO96/02655), polylysine (U.S. Pat. No. 5,595,897; FR 2 719 316), chitosan (U.S. Pat. No. 5,744,166), DNA-gelatin coarcervates (see, e.g., U.S. Pat. Nos. 6,207,195; 6,025,337; 5,972,707) or DEAE dextran (Lopata, et al., 1984, Nucleic Acid Res. 12: 5707-5717).

Viral-Based Gene Delivery Vehicles

In one aspect, the improved LAMP Construct delivery vehicle comprises a virus or viral particle. In this aspect, preferably, the improved LAMP Construct comprises a viral vector. Viral vectors, such as retroviruses, adenoviruses, adeno-associated viruses and herpes viruses, are often made up of two components, a modified viral genome and a coat structure surrounding it (see, e.g., Smith et al., 1995, Ann. Rev. Microbiol. 49: 807-838), although sometimes viral vectors are introduced in naked form or coated with proteins other than viral proteins. Most current vectors have coat structures similar to a wild-type virus. This structure packages and protects the viral nucleic acid and provides the means to bind and enter target cells.

Preferably, viral vectors comprising the improved LAMP Constructs described herein are modified from wild-type viral genomes to disable the growth of the virus in a target cell while enabling the virus to grow in a host cell (e.g., such as a packaging or helper cell) used to prepare infectious particles. Vector nucleic acids generally essential cis-acting viral sequences for replication and packaging in a helper line and expression control sequences for regulating the expression of a polynucleotide being delivered to a target cell.

Other viral functions are expressed in trans in specific packaging or helper cell lines as are known in the art.

Preferred improved LAMP Constructs are viral vectors derived from a virus selected from the group consisting of herpes viruses, cytomegaloviruses, foamy viruses, lentiviruses, Semliki forrest virus, AAV (adeno-associated virus), poxviruses, adenoviruses and retroviruses. Such viral vectors are well known in the art.

In one preferred aspect, a viral vector used is an adenoviral vector. The adenoviral genome consists of a linear double-stranded DNA molecule of approximately 36 kb carrying more than about thirty genes necessary to complete the viral replication cycle. The early genes are divided into 4 regions (E1 to E4) that are essential for viral replication with the exception of the E3 region, which is believed to modulate the anti-viral host immune response. The E1 region (EIA and EIB) encodes proteins responsible for the regulation of transcription of the viral genome. Expression of the E2 region genes (E2A and E2B) leads to the synthesis of the polypeptides needed for viral replication. The proteins encoded by the E3 region prevent cytolysis by cytotoxic T cells and tumor necrosis factor (Wold and Gooding, 1991, Virology 184: 1-8). The proteins encoded by the E4 region are involved in DNA replication, late gene expression and splicing and host cell shut off (Halbert, et al., 1985, J. Virol. 56: 250-257). The late genes generally encode structural proteins contributing to the viral capsid. In addition, the adenoviral genome carries at cis-acting 5' and 3' ITRs (Inverted Terminal Repeat) and packaging sequences essential for DNA replication. The ITRs harbor origins of DNA replication while the encapsidation region is required for the packaging of adenoviral DNA into infectious particles.

Adenoviral vectors can be engineered to be conditionally replicative (CRAd vectors) in order to replicate selectively in specific cells (e.g., such as proliferative cells) as described in Heise and Kim (2000, J. Clin. Invest. 105: 847-851). In another aspect, an adenoviral vector is replication-defective for the E1 function (e.g., by total or partial deletion or mutagenesis of E1). The adenoviral backbone of the vector may comprise additional modifications (deletions, insertions or mutations in one or more viral genes). An example of an E2 modification is illustrated by the thermosensitive mutation localized on the DBP (DNA Binding Protein) encoding gene (Ensinger et al., 1972, J. Virol. 10: 328-339). The adenoviral sequence may also be deleted of all or part of the E4 region (see, e.g., EP 974 668; Christ, et al., 2000, Human Gene Ther. 11: 415-427; Lusky, et al., 1999, J. Virol. 73: 8308-8319). Additional deletions within the non-essential E3 region may allow the size of the polynucleotide being delivered to be increased (Yeh, et al., 1997, FASEB Journal 11: 615 623). However, it may be advantageous to retain all or part of the E3 sequences coding for polypeptides (e.g., such as gp19k) allowing the virus to escape the immune system (Gooding, et al., 1990, Critical Review of Immunology 10: 53-71) or inflammatory reactions (EP 00440267.3).

Second generation vectors retaining the ITRs and packaging sequences and comprising substantial genetic modifications to abolish the residual synthesis of the viral antigens also may be used in order to improve long-term expression of the expressed gene in the transduced cells (see, e.g., WO94/28152; Lusky, et al., 1998, J. Virol 72: 2022-2032).

The improved LAMP Constructs being introduced into the cell may be inserted in any location of the viral genome, with the exception of the cis-acting sequences. Preferably, it is inserted in replacement of a deleted region (E1, E3 and/or E4), preferably, within a deleted E1 region.

Adenoviruses can be derived from any human or animal source, in particular canine (e.g. CAV-1 or CAV-2 Genbank ref. CAVIGENOM and CAV77082, respectively), avian (Genbank ref. AAVEDSDNA), bovine (such as BAV3; Reddy, et al., 1998, J. Virol. 72: 1394 1402), murine (Genbank ref. ADRMUSMAVI), ovine, feline, porcine or simian sources or alternatively, may be a hybrid virus. Any serotype can be employed. However, the human adenoviruses of the C sub-group are preferred, especially adenoviruses 2 (Ad2) and 5 (Ad5). Such viruses are available, for example, from the ATCC.

Adenoviral particles or empty adenoviral capsids also can be used to transfer improved LAMP Constructs by a virus-mediated cointernalization process as described in U.S. Pat. No. 5,928,944. This process can be accomplished in the presence of cationic agent(s) such as polycarbenes or lipid vesicles comprising one or more lipid layers.

Adenoviral particles may be prepared and propagated according to any conventional technique in the field of the art (e.g., WO96/17070) using a complementation cell line or a helper virus, which supplies in trans the missing viral genes necessary for viral replication. The cell lines 293 (Graham et al., 1977, J. Gen. Virol. 36: 59-72) and PERC6 (Fallaux et al., 1998, Human Gene Therapy 9: 1909-1917) are commonly used to complement E1 deletions. Other cell lines have been engineered to complement defective vectors (Yeh, et al., 1996, J. Virol. 70: 559-565; Kroughak and Graham, 1995, Human Gene Ther. 6: 1575-1586; Wang, et al., 1995, Gene Ther. 2: 775-783; Lusky, et al., 1998, J. Virol. 72: 2022-203; EP 919627 and WO 97/04119). The adenoviral particles can be recovered from the culture supernatant but also from the cells after lysis and optionally further purified according to standard techniques (e.g., chromatography, ultracentrifugation, as described in WO96/27677, WO 98/00524 WO 98/26048 and WO 00/50573).

Cell-type specific targeting may be achieved with vectors derived from adenoviruses having a broad host range by the modification of viral surface proteins. For example, the specificity of infection of adenoviruses is determined by the attachment to cellular receptors present at the surface of permissive cells. In this regard, the fiber and penton present at the surface of the adenoviral capsid play a critical role in cellular attachment (Defer, et al., 1990, J. Virol. 64: 3661-3673). Thus, cell targeting of adenoviruses can be carried out by genetic modification of the viral gene encoding fiber and/or penton, to generate modified fiber and/or penton capable of specific interaction with unique cell surface receptors. Examples of such modifications are described in Wickarn, et al., 1997, J. Virol. 71: 8221-8229; Arriberg, et al., 1997, Virol. Chem 268: 6866-6869; Roux, et al., 1989, Proc. Natl. Acad. Sci. USA 86: 9079-9083; Miller and Vile, 1995, FASEB J. 9: 190-199; WO 93/09221, and in WO 95/28494.

In a particularly preferred aspect, adeno-associated viral sequences are used as vectors. Vectors derived from the human parvovirus AAV-2 (adeno-associated virus type 2) are among the most promising gene delivery vehicles currently being developed. Several of the features of this system for packaging a single-stranded DNA suggest it as a possible alternative to naked DNA for delivery. A primary attractive feature, in contrast to other viral vectors such as vaccinia or adenovirus, is that AAV vectors do not express any viral genes. The only viral DNA sequences included in the vaccine construct are the 145 bp inverted terminal repeats (ITR). Thus, as in immunization with naked DNA, the only gene expressed is that of the antigen, or antigen chimera. Additionally, AAV vectors are known to transduce both dividing and non-dividing cells, such as human peripheral blood monocyte-derived dendritic cells, with persistent transgene expression, and with the possibility of oral and intranasal delivery for generation of mucosal immunity. Moreover, the amount of DNA required appears to be much less by several orders of magnitude, with maximum responses at doses of 1010 to loll particles or copies of DNA in contrast to naked DNA doses of 50 ug or about 1015 copies.

In one aspect, AAV vectors are packaged by co-transfection of a suitable cell line (e.g., human 293 cells) with the DNA contained in the AAV ITR chimeric protein encoding constructs and an AAV helper plasmid ACG2 containing the AAV coding region (AAV rep and cap genes) without the ITRs. The cells are subsequently infected with the adenovirus Ad5. Vectors can be purified from cell lysates using methods known in the art (e.g., such as cesium chloride density gradient ultracentrifugation) and are validated to ensure that they are free of detectable replication-competent AAV or adenovirus (e.g., by a cytopathic effect bioassay). AAV titer may be determined by quantitative PCR with virus DNA samples prepared after digestion with proteinase K. Preferably, vector titers produced by such a method are approximately $5\times10^{12}$ to $1\times10^{13}$ DNase resistant particles per ml.

In other aspects, retroviral vectors are used. Retroviruses are a class of integrative viruses which replicate using a virus-encoded reverse transcriptase, to replicate the viral RNA genome into double stranded DNA which is integrated into chromosomal DNA of the infected cells (e.g., target cells). Such vectors include those derived from murine leukemia viruses, especially Moloney (Gilboa, et al., 1988, Adv. Exp. Med. Biol. 241: 29) or Friend's FB29 strains (WO 95/01447). Generally, a retroviral vector is deleted of all or part of the viral genes gag, pol and env and retains 5' and 3' LTRs and an encapsidation sequence. These elements may be modified to increase expression level or stability of the retroviral vector. Such modifications include the replacement of the retroviral encapsidation sequence by one of a retrotransposon such as VL30 (see, e.g., U.S. Pat. No. 5,747,323). Preferably, the improved LAMP Construct is inserted downstream of the encapsidation sequence, preferably in opposite direction relative to the retroviral genome. Cell specific targeting may be achieved by the conjugation of antibodies or antibody fragments to the retroviral envelope protein as is known in the art.

Retroviral particles are prepared in the presence of a helper virus or in an appropriate complementation (packaging) cell line which contains integrated into its genome the retroviral genes for which the retroviral vector is defective (e.g. gag/pol and env). Such cell lines are described in the prior art (Miller and Rosman, 1989, BioTechniques 7: 980; Danos and Mulligan, 1988, Proc. Natl. Acad. Sci. USA 85: 6460; Markowitz, et al., 1988, Virol. 167: 400). The product of the env gene is responsible for the binding of the viral particle to the viral receptors present on the surface of the target cell and, therefore determines the host range of the retroviral particle. in the context of the invention, it is advantageous to use a packaging cell line, such as the PA317 cells (ATCC CRL 9078) or 293E16 (WO97/35996) containing an amphotropic envelope protein, to allow infection of human and other species' target cells. The retroviral particles are preferably recovered from the culture supernatant and may optionally be further purified according to standard techniques (e.g. chromatography, ultracentrifugation).

Other suitable viruses include poxviruses. The genome of several members of poxyiridae has been mapped and sequenced. A poxyiral vector may be obtained from any member of the poxyiridae, in particular canarypox, fowlpox and vaccinia virus. Suitable vaccinia viruses include, but are not limited to, the Copenhagen strain (Goebel, et al., 1990, Virol. 179: 247-266; Johnson, et al., 1993, Virol. 196: 381-401), the Wyeth strain and the modified Ankara (MVA) strain (Antoine, et al., 1998, Virol. 244: 365-396). The general conditions for constructing a vaccinia virus vector are known in the art (see, e.g., EP 83 286 and EP 206 920; Mayr et al., 1975, Infection 3: 6-14; Sutter and Moss, 1992, Proc. Natl. Acad. Sci. USA 89: 10847-10851). Preferably, the polynucleotide of interest is inserted within a non-essential locus such as the noncoding intergenic regions or any gene for which inactivation or deletion does not significantly impair viral growth and replication.

Poxyiral particles are prepared as described in the art (Piccini, et al., 1987, Methods of Enzymology 153: 545-563; U.S. Pat. Nos. 4,769,330; 4,772,848; 4,603,112; 5,100,587 and 5,179,993). Generally, a donor plasmid is constructed, amplified by growth in *E. coli* and isolated by conventional procedures. Then, it is introduced into a suitable cell culture (e.g. chicken embryo fibroblasts) together with a poxvirus genome, to produce, by homologous recombination, poxyiral particles. These can be recovered from the culture supernatant or from the cultured cells after a lysis step (e.g., chemical lysis, freezing/thawing, osmotic shock, sonication and the like). Consecutive rounds of plaque purification can be used to remove contaminating wild type virus. Viral particles can then be purified using the techniques known in the art (e.g., chromatographic methods or ultracentrifugation on cesium chloride or sucrose gradients).

The use of vaccinia as a live virus vaccine in the global campaign to eradicate smallpox made vaccinia an obvious choice for development as a live recombinant vaccine vector. Live recombinant vaccinia viruses expressing close to 100 different foreign proteins have been reported, and a number of these are effective experimental vaccines (reviewed by Moss and Flexner, 1987). Vaccinia is particularly versatile as an expression vector because of its large genomic size, capability of accepting at least 25,000 base pairs of foreign DNA, and its ability to infect most eukaryotic cell types, including insect cells (ibid.). Unlike other DNA viruses, poxviruses replicate exclusively in the cytoplasm of infected cells, reducing the possibility of genetic exchange of recombinant viral DNA with the host chromosome. Recombinant vaccinia vectors have been shown to properly process and express proteins from a variety of sources including man, other mammals, parasites, RNA and DNA viruses, bacteria and bacteriophage.

The expression of DNA encoding a foreign protein is controlled by host virus regulatory elements, including upstream promoter sequences and, where necessary, RNA processing signals. Insertion of foreign DNA into nonessential regions of the vaccinia virus genome has been carried out by homologous recombination (Panicali, et al., Proc. Nat'l. Acad. Sci, USA, 79: 4927, 1982; Mackett, et al., Proc. Nat'l. Acad. Sci. USA, 79: 7415, 1982).

Expression of antigens by the improved LAMP Construct may occur because of transcriptional regulatory elements at or near the site of insertion or by more precise genetic engineering. Plasmid vectors that greatly facilitate insertion and expression of foreign genes have been constructed (Mackett, et al., J. Virol, 49: 857, 1982). These vectors contain an expression site, composed of a vaccinia transcriptional promoter and one or more unique restriction endonuclease sites for insertion of the foreign coding sequence flanked by DNA from a nonessential region of the vaccinia genome. The choice of promoter determines both the time (e.g., early or late) and level of expression, whereas the flanking DNA sequence determines the site of homologous recombination.

Only about one in a thousand virus particles produced by this procedure is a recombinant. Although recombinant virus plaques can be identified by DNA hybridization, efficient selection procedures have been developed. By using segments of nonessential vaccinia virus thymidine kinase (TK) gene as flanking sequences, the foreign gene recombines into the TK locus and by insertion inactivates the TK gene. Selection of TK virus is achieved by carrying out the virus plaque assay in TK cells in the presents of 5-bromodeoxyuridine. Phosphorylation of the nucleoside analogue and consequent lethal incorporation into viral DNA occurs only in cells infected with TK+ parental virus. Depending on the efficiency of the transfection and recombination, up to 80 of the plaques are desired recombinants, and the rest are spontaneous TK mutants.

Plasmid vectors that contain the *E. coli* beta-galactosidase gene, as well as an expression site for a second gene, permit an alternative method of distinguishing recombinant from parental virus (Chakrabarti, et al., Mol. Cell. Biol., 5: 3403, 1985). Plaques formed by such recombinants can be positively identified by the blue color that forms upon addition of an appropriate indicator. By combining both TK selection and beta-galactosidase expression, recombinant virus is readily and quickly isolated. The recombinants are then amplified by propagation in suitable cell lines and expression of the inserted gene is checked by appropriate enzymological, immunological or physical procedures.

An upper limit to the amount of genetic information that can be added to the vaccinia virus genome is not yet known. However, the addition of nearly 25,000 base pairs of foreign DNA had no apparent deleterious effect on virus yield (Smith, et al., Gene, 25:21, 1983). Were it necessary, large segments of the vaccinia virus genome could be deleted to provide additional capacity (Moss, et al., J. Virol. 40: 387, 1981).

Viral capsid molecules may include targeting moieties to facilitate targeting and/or entry into cells. Suitable targeting molecules, include, but are not limited to: chemical conjugates, lipids, glycolipids, hormones, sugars, polymers (e.g. PEG, polylysine, PEI and the like), peptides, polypeptides (see, e.g., WO94/40958), vitamins, antigens, lectins, antibodies and fragments thereof. Preferably, such targeting molecules recognize and bind to cell-specific markers, tissue-specific markers, cellular receptors, viral antigens, antigenic epitopes or tumor-associated markers.

Compositions comprising an improved LAMP Construct based on viral particles may be formulated in the form of doses of between 10 and $10^{14}$ i.u. (infectious units), and preferably, between 10 and $10^{11}$ i.u. The titer may be determined by conventional techniques. The doses of LAMP Constructs are preferably comprised between 0.01 and 10 mg/kg, more especially between 0.1 and 2 mg/kg.

Self-Replicating RNA

Self-replicating RNA virus vectors can also be constructed using the improved LAMP Constructs as described herein. For example, alphaviruses, flavivuses, measle virus and rhabdoviruses can be used to generate self-replicating RNA virus vaccines. Preferred strains of self-replicating RNA viruses include, but are not limited to rabies virus (RABV), vesicular stomatisitis virus (VSV), West Nile virus, Kunjin virus, Semliki Forest virus (SFV), Sindbis virus (SIN) and/or Venezuelan equine encephalitis virus (VEE).

Self-replicating RNA viruses express the native antigen upon delivery into tissue, thus mimicking live attenuated vaccines without having the risk of reversion to pathogenicity. They also stimulate the innate immune system, thus potentiating responses. See, e.g., Ljungberg, K. "*Self-replicating alphavirus RNA vaccines*," Expert Rev Vaccines (2):177-94 (2015); Lundstrom, K., "*Oncolytic Alphaviruses in Cancer Immunotherapy*", Vaccines 5:9 (2017); Lundstrom, K. "*Replicon RNA Viral Vectors as Vaccines*," Vaccines 4:39 (2016) (hereby incorporated by reference in their entirety). Use of self-replicating vaccines comprising the improved LAMP Constructs described herein can also be used in prime-boost protocols.

Moreover, self-replicating RNA viruses can also be encapsulated by liposomes, as described herein, to improve delivery and targeting. Immunization with self-replicating RNA viruses comprising the improved LAMP Constructs described herein may provide higher transient expression levels of antigens resulting in generation of neutralizing antibody responses and protection against lethal challenges under safe conditions.

Cell-Based Delivery Vehicles

The improved LAMP Constructs according to the invention can be delivered to target cells by means of other cells ("delivery cells) which comprise the constructs. Methods for introducing constructs into cells are known in the art and include microinjection of DNA into the nucleus of a cell (Capechi, et al., 1980, Cell 22: 479-488); transfection with $CaPo_4$ (Chen and Okayama, 1987, Mol. Cell Biol. 7: 27452752), electroporation (Chu, et al., 1987, Nucleic Acid Res. 15: 1311-1326); lipofection/liposome fusion (Feigner, et al., 1987, Proc. Natl. Acad. Sci. USA 84: 7413-7417) and particle bombardment (Yang, et al., 1990, Proc. Natl. Acad. Sci. USA 87: 9568-9572). Suitable cells include autologous and non-autologous cells, and may include xenogenic cells. Delivery cells may be induced to deliver their contents to the target cells by inducing their death (e.g., by providing inducible suicide genes to these cells).

Accessory Molecules

The compositions comprising the improved LAMP Constructs according to the invention may comprise one or more accessory molecules for facilitating the introduction of an improved LAMP Construct into a cell and/or for enhancing a particular therapeutic effect and/or enhancing antibody production.

In addition, the composition comprising the improved LAMP Construct according to the present invention may include one or more stabilizing substance(s), such as lipids, nuclease inhibitors, hydrogels, hyaluronidase (WO98/53853), collagenase, polymers, chelating agents (EP 890362), in order to inhibit degradation within the animal/human body and/or improve transfection/infection of the vector into a target cell. Such substances may be used alone or in combination (e.g., cationic and neutral lipids).

It has also been shown that adenovirus proteins are capable of destabilizing endosomes and enhancing the uptake of DNA into cells. The mixture of adenoviruses to solutions containing a lipid-complexed DNA vector or the binding of DNA to polylysine covalently attached to adenoviruses using protein cross-linking agents may substantially improve the uptake and expression of an improved LAMP Construct (see, e.g., Curiel, et al., 1992, Am. I. Respir. Cell. Mol. Biol. 6: 247-252).

Host Cells

Improved LAMP Constructs according to the invention can be expressed in a variety of host cells, including, but not limited to: prokaryotic cells (e.g., *E. coli, Staphylococcus* sp., *Bacillus* sp.); yeast cells (e.g., *Saccharomyces* sp.); insect cells; nematode cells; plant cells; amphibian cells (e.g., *Xenopus*); avian cells; and mammalian cells (e.g., human cells, mouse cells, mammalian cell lines, primary cultured mammalian cells, such as from dissected tissues).

The molecules can be expressed in host cells isolated from an organism, host cells which are part of an organism, or host cells which are introduced into an organism. In one aspect, improved LAMP Constructs are expressed in host cells in vitro, e.g., in culture. In another aspect, improved LAMP Constructs are expressed in a transgenic organism (e.g., a transgenic mouse, rat, rabbit, pig, primate, etc.) that comprises somatic and/or germline cells comprising nucleic acids encoding the improved LAMP Constructs. Methods for constructing transgenic animals are well known in the art and are routine.

Improved LAMP Constructs also can be introduced into cells in vitro, and the cells (e.g., such as stem cells, hematopoietic cells, lymphocytes, and the like) can be introduced into the host organism. The cells may be heterologous or autologous with respect to the host organism. For example, cells can be obtained from the host organism, improved LAMP Constructs introduced into the cells in vitro, and then reintroduced into the host organism.

Antigen Presenting Cells

In a preferred aspect of the invention, an improved LAMP Construct as described herein is introduced into a natural or engineered antigen presenting cell.

The term "antigen presenting cell" (APC) as used herein intends any cell which presents on its surface an antigen in association with a major histocompatibility complex molecule, preferably a class II molecule, or portion thereof. Examples of suitable APCs are discussed in detail below and include, but are not limited to, whole cells such as macrophages, dendritic cells, B cells, hybrid APCs, and foster antigen presenting cells. Methods of making hybrid APCs are described and known in the art.

Dendritic cells (DCs) are potent antigen-presenting cells. It has been shown that DCs provide all the signals required for T cell activation and proliferation. These signals can be categorized into two types. The first type, which gives specificity to the immune response, is mediated through interaction between the T-cell receptor/CD3 ("TCR/CD3") complex and an antigenic peptide presented by a major histocompatibility complex ("MHC" defined above) class I or II protein on the surface of APCs. This interaction is necessary, but not sufficient, for T cell activation to occur. In fact, without the second type of signals, the first type of signals can result in T cell anergy. The second type of signals, called co-stimulatory signals, is neither antigen-specific nor MHC-restricted, and can lead to a full proliferation response of T cells and induction of T cell effector functions in the presence of the first type of signals.

Several molecules have been shown to enhance co-stimulatory activity. These include, but are not limited to, heat stable antigen (HSA), chondroitin sulfate-modified MHC invariant chain (Ii-CS), intracellular adhesion molecule I (ICAM-1), and B7 co-stimulatory molecule on the surface of APCs and its counter-receptor CD28 or CTLA-4 on T cells.

Other important co-stimulatory molecules are CD40, CD54, CD80, CD86. As used herein, the term "co-stimulatory molecule" encompasses any single molecule or combination of molecules which, when acting together with a peptide/MHC complex bound by a TCR on the surface of a T cell, provides a co-stimulatory effect which achieves activation of the T cell that binds the peptide. The term thus encompasses B7, or other co-stimulatory molecule(s) on an APC, fragments thereof (alone, complexed with another molecule(s), or as part of a fusion protein) which, together with peptide/MHC complex, binds to a cognate ligand and result in activation of the T cell when the TCR on the surface of the T cell specifically binds the peptide. Co-stimulatory molecules are commercially available from a variety of sources, including, for example, Beckman Coulter.

In one aspect of the invention, the method described in Romani et al., J. Immunol. Methods 196: 135-151, 1996, and Bender et al, J. Immunol. Methods 196: 121-135, 1996, are used to generate both immature and mature dendritic cells from the peripheral blood mononuclear cells (PBMCs) of a mammal, such as a murine, simian or human. Briefly, isolated PBMCs are pre-treated to deplete T- and B-cells by means of an immunomagnetic technique. Lymphocyte-depleted PBMC are then cultured for in RPMI medium 9 e.g., about 7 days), supplemented with human plasma (preferably autologous plasma) and GM-CSF/IL-4, to generate dendritic cells. Dendritic cells are nonadherent when compared to their monocyte progenitors. Thus, on approximately day 7, non-adherent cells are harvested for further processing.

The dendritic cells derived from PBMC in the presence of GM-CSF and IL-4 are immature, in that they can lost the nonadherence property and revert back to macrophage cell fate if the cytokine stimuli are removed from the culture. The dendritic cells in an immature state are very effective in processing native protein antigens for the MHC class II restricted pathway (Romani, et al., J. Exp. Med. 169:1169, 1989). Further maturation of cultured dendritic cells is accomplished by culturing for 3 days in a macrophage-conditioned medium (CM), which contains the necessary maturation factors. Mature dendritic cells are less able to capture new proteins for presentation but are much better at stimulating resting T cells (both CD4 and CD8) to grow and differentiate.

Mature dendritic cells can be identified by their change in morphology, such as the formation of more motile cytoplasmic processes; by their nonadherence; by the presence of at least one of the following markers: CD83, CD68, HLA-DR or CD86; or by the loss of Fc receptors such as CD 115 (reviewed in Steinman, Annu. Rev. Immunol. 9: 271, 1991). Mature dendritic cells can be collected and analyzed using typical cytofluorography and cell sorting techniques and devices, such as FACScan and FACStar. Primary antibodies used for flow cytometry are those specific to cell surface antigens of mature dendritic cells and are commercially available. Secondary antibodies can be biotinylated Igs followed by FITC- or PE-conjugated streptavidin.

Alternatively, others have reported that a method for upregulating (activating) dendritic cells and converting monocytes to an activated dendritic cell phenotype. This method involves the addition of calcium ionophore to the culture media convert monocytes into activated dendritic cells. Adding the calcium 21 ionophore A23187, for example, at the beginning of a 24-48 hour culture period resulted in uniform activation and dendritic cell phenotypic conversion of the pooled "monocyte plus DC" fractions: characteristically, the activated population becomes uniformly CD 14 (Leu M3) negative, and upregulates HLA-DR, HLA-DQ, ICAM-1,137.1, and 137.2. Furthermore, this activated bulk population functions as well on a small numbers basis as a further purified. Specific combination(s) of cytokines have been used successfully to amplify (or partially substitute) for the activation/conversion achieved with calcium ionophore: these cytokines include but are not limited to G-CSF, GM-CSF, IL-2, and IL-4. Each cytokine when given alone is inadequate for optimal upregulation.

The second approach for isolating APCs is to collect the relatively large numbers of precommitted APCs already circulating in the blood. Previous techniques for isolating committed APCs from human peripheral blood have involved combinations of physical procedures such as metrizamide gradients and adherence/nonadherence steps (Freudenthal et al. PNAS 87: 7698-7702, 1990); Percoll gradient separations (Mehta-Damani, et al., J. Immunol. 153: 996-1003, 1994); and fluorescence activated cell sorting techniques (Thomas et al., J. Immunol. 151: 6840-52, 1993).

There are many other methods routine in the art for isolating professional antigen presenting cells (or their precursors) and that such methods and others which may be developed are not limiting and are encompassed within the scope of the invention.

In one embodiment, the APCs and therefore the cells presenting one or more antigens are autologous. In another embodiment, the APCs presenting the antigen are allogeneic, i.e., derived from a different subject.

As discussed herein, improved LAMP Constructs can be introduced into APCs using the methods described above or others known in the art, including, but not limited to, transfection, electroporation, fusion, microinjection, viral-based delivery, or cell based delivery. Arthur et al., Cancer Gene Therapy 4(1): 17-25, 1997, reports a comparison of gene transfer methods in human dendritic cells.

Known, partial and putative human leukocyte antigen (HLA), the genetic designation for the human MHC, amino acid and nucleotide sequences, including the consensus sequence, are published (see, e.g., Zemmour and Parham, Immunogenetics 33: 310-320, 1991), and cell lines expressing HLA variants are known and generally available as well, many from the American Type Culture Collection ("ATCC"). Therefore, using PCR, MHC class II-encoding nucleotide sequences are readily operatively linked to an expression vector of this invention that is then used to transform an appropriate cell for expression therein.

Professional APCs can be used, such as macrophages, B cells, monocytes, dendritic cells, and Langerhans cells. These are collected from the blood or tissue of 1) an autologous donor; 2) a heterologous donor having a different HLA specificity then the host to be treated; or 3) from a xenogeneic donor of a different species using standard procedures (Coligan, et. al., Current Protocols in Immunology, sections 3 and 14, 1994). The cells may be isolated from a normal host or a patient having an infectious disease, cancer, autoimmune disease, or allergy.

Professional APCs may be obtained from the peripheral blood using leukopheresis and "FICOLL/HYPAQUE" density gradient centrifugation (stepwise centrifugation through Ficoll and discontinuous Percoll density gradients). Procedures are utilized which avoid the exposure of the APCs to antigens which could be internalized by the APCs, leading to activation of T cells not specific for the antigens of interest.

Cells which are not naturally antigen presenting can be engineered to be antigen presenting by introducing sequences encoding appropriate molecules. For example, nucleic acid sequences encoding MHC class II molecules, accessory molecules, co-stimulatory molecules and antigen processing assisting molecules can be introduced after direct synthesis, cloning, purification of DNA from cells containing such genes, and the like. One expedient means to obtain genes for encoding the molecules used in the improved LAMP Constructs and methods described herein is by polymerase chain reaction (PCR) amplification on selected nucleic acid templates with selected oligonucleotide primer pairs. For example, epithelial cells, endothelial cells, tumor cells, fibroblasts, activated T cells, eosinophils, keratinocytes, astrocytes, microglial cells, thymic cortical epithelial cells, Schwann cells, retinal pigment epithelial cells, myoblasts, vascular smooth muscle cells, chondrocytes, enterocytes, thyrocytes and kidney tubule cells can be used. These may be primary cells recently explanted from a host and not extensively passaged in cell culture to form an established cell line, or established cell lines that are relatively homogeneous and capable of proliferating for many generations or indefinitely.

Cells that are not professional APCs are isolated from any tissue of an autologous donor; a heterologous donor or a xenogeneic donor, where they reside using a variety of known separation methods (Darling, Animal Cells: Culture and Media. J. Wiley, New York, 1994; Freshney, Culture of Animal Cells. Alan R. Liss, Inc., New York, 1987). Non-autologous cells, e.g., heterologous or xenogeneic cells, can be engineered ex vivo to express HLA class I and class II molecules that match known human HLA specificities. These cells can then be introduced into a human subject matching the HLA specificity of the engineered cells. The cells are further engineered ex vivo to express one or more LAMP Constructs according to the invention.

The engineered cells are maintained in cell culture by standard cell culture methods (Darling, Animal Cells: Culture and Media". J. Wiley, New York, 1994; Freshney, Culture of Animal Cells". Alan R. Liss, Inc., New York, 1987). Cell lines for use in the present invention are obtained from a variety of sources (e.g., ATCC Catalogue of Cell Lines & Hybidomas, American Type Culture Collection, 8th edition, 1995), or are produced using standard methods (Freshney, Culture of Immortalized Cells, Wiley-Liss, New York, 1996). Non-transformed cell lines are preferred for use in human subjects.

In one aspect, CD34+ precursors that are differentiating under the influence of GM-CSF into dendritic cells are obtained from the body of a subject and nucleic acids encoding LAMP Constructs according to the invention are introduced into the cells, which are then injected into the subject. Utilizing the improved LAMP Constructs as described herein will enhance the association of peptides derived from a particular antigen with MHC class II molecules on the transduced antigen presenting cells, resulting in significantly more potent systemic T cell dependent immune responses and/or antibody production. While the antigen presenting cells transfected in this strategy are preferably autologous cells, any MHC class II cells that effectively present antigen in the host may be used as described above.

Peptide Vaccines

Also within the scope of this invention are peptide vaccines encoded by the improved LAMP Construct Preferably, the antigen is processed within the compartment/organelle (or subsequent compartment/organelle to which it is delivered) to generate an epitope bound to an MHC class II molecule capable of modulating an immune response.

The peptide vaccines encoded by the improved LAMP Constructs may also may be bound in a membranous structure to facilitate its administration to the body of an organism. For example, the peptide vaccine encoded by the improved LAMP Construct may be incorporated into liposomes, as described in U.S. Pat. No. 4,448,765.

When a protein or polypeptide is to be used as an immunogen, it may be produced by expression of any one or more of the improved LAMP Constructs described herein in a recombinant cell or it may be prepared by chemical synthesis. For example, the Merrifield technique (Journal of American Chemical Society, vol. 85, pp. 2149-2154, 1968), can be used.

Methods of Producing Antibodies Using LAMP Constructs

The improved LAMP Constructs as polynucleotides, the encoded proteins of the improved LAMP Constructs, and/or cells (such as antigen presenting cells which express the improved LAMP Constructs described herein) can be used to generate antibodies by methods well known by the skilled artisan, such as, for example, methods described in the art. See, for instance, Sutcliffe et al., supra; Wilson et al., supra; Chow et al., Proc. Natl. Acad. Sci. USA 82:910-914 (1985); and Bittle et al., J. Gen. Virol. 66:2347-2354 (1985). If in vivo immunization is used, animals may be immunized with a protein encoded by the improved LAMP Construct and/or a polynucleotide comprising the improved LAMP Construct comprising an antigen as described herein. Priming with improved LAMP Constructs as polynucleotides, the encoded proteins of the improved LAMP Constructs, and/or cells (such as antigen presenting cells which express the improved LAMP Constructs described herein) followed by boosting with an antigen is a preferred embodiment of the invention. In further preferred embodiments, priming with an improved LAMP Construct as described herein followed by boosting with an antigen is specifically contemplated and can be used to generate an even more robust immune response, especially in view of antibody repertoire diversity and titer.

The improved LAMP Construct comprising the antigen may be injected into the non-human vertebrate to raise antibodies. Preparation and injection of LAMP Constructs into non-human vertebrates can be accomplished according to principles of immunization of animals that are well known to those skilled in the art.

The use of an improved LAMP Construct to effectively present the antigen involves, in one aspect, the antigen being processed by LAMP in Antigen Presenting Cells after endocytosis and fusion of the endosome with a lysosome. The endosome then merges with an exocytic vesicle from the Golgi apparatus containing class II MHC molecules, to which the resultant peptides bind. The MHC-peptide complex then trafficks to the plasma membrane where the antigen is available for display to $CD4^+$ T cells.

Animals such as rabbits, rats, mice, llamas, camels, and/or cows can be immunized with the improved LAMP Construct comprising an antigen and/or a polynucleotide encoding the improved LAMP Construct comprising an antigen. Additional animals suitable for immunization include, non-human mammals, such as a rodent (e.g. a guinea pig, a hamster, a rat, a mouse), murine (e.g. a mouse), canine (e.g. a dog), feline (e.g. a cat), equine (e.g. a horse), a primate, simian (e.g. a monkey or ape), a monkey (e.g. marmoset, baboon, rhesus macaque), an ape (e.g. gorilla, chimpanzee, orangutan, gibbon).

For instance, intraperitoneal and/or intradermal injection of emulsions containing about 100 micrograms of an improved LAMP Construct comprising an antigen or carrier protein and Freund's adjuvant or any other adjuvant known for stimulating an immune response may be used. Several booster injections (such as with the recombinant antigen protein) may be needed, for instance, at intervals of about two weeks, to provide a useful titer of an anti-antigen antibody which can be detected, for example, by ELISA assay using free antigen adsorbed, directly or indirectly (e.g., via a biotinylated AviTag), to a solid surface. The titer of anti-antigen antibodies in serum from an immunized animal may be increased by selection of anti-antibodies, for instance, by adsorption to the antigen on a solid support and elution of the selected antibodies according to methods well known in the art.

Alternatively, a polynucleotide encoding the improved LAMP Construct comprising an antigen can also be directly introduced into animals. See, for example, U.S. Pat. Nos. 5,676,954; 6,875,748; 5,661,133; Sahin et al., Nat Rev Drug Discov, 2014 October; 13(10):759-80; Kariko et al., Mol Ther, 2008 November; 16(11):1833-40; Kariko et al., Nucleic Acid Res, 2011, November; 39(21):e142; U.S. Pat. No. 6,511,832. In one example, an improved LAMP Construct comprising an antigen is directly injected into a non-human vertebrate. Injection into the animals can occur via intramuscular, intradermal, intranasal, subcutaneous, intravenous, intratracheal, and intrathecal deliveries. Follow-on boosting with a recombinant antigen can also be include in generating the antibodies.

Additionally, antibodies generated by the disclosed methods can be affinity matured using display technology, such as for example, phage display, yeast display or ribosome display. In one example, single chain antibody molecules ("scFvs") displayed on the surface of phage particles are screened to identify those scFvs that immunospecifically bind to the antigen and/or the starting protein. The present invention encompasses both scFvs and portions thereof that are identified to immunospecifically bind to the antigen and/or the starting protein. Such scFvs can routinely be "converted" to immunoglobulin molecules by inserting, for example, the nucleotide sequences encoding the VH and/or VL domains of the scFv into an expression vector containing the constant domain sequences and engineered to direct the expression of the immunoglobulin molecule.

Recombinant expression of the raised antibodies (including scFvs and other molecules comprising, or alternatively consisting of, antibody fragments or variants thereof (e.g., a heavy or light chain of an antibody of the invention or a portion thereof or a single chain antibody of the invention)) using the improved LAMP Construct comprising an antigen and/or a polynucleotide encoding the improved LAMP Construct comprising an antigen of the invention, requires construction of an expression vector(s) containing a polynucleotide that encodes the antibody or fragment or variant thereof. Once a polynucleotide encoding an antibody molecule (e.g., a whole antibody, a heavy or light chain of an antibody, or variant or portion thereof (preferably, but not necessarily, containing the heavy or light chain variable domain)), of the invention has been obtained, the vector(s) for the production of the antibody molecule may be produced by recombinant DNA technology using techniques well known in the art. Thus, methods for preparing an antibody by expressing a polynucleotide containing an antibody encoding nucleotide sequence are described herein. Methods which are well known to those skilled in the art can be used to construct expression vectors containing the antibody coding sequences and appropriate transcriptional and translational control signals. These methods include, for example, in vitro recombinant DNA techniques, synthetic techniques, and in vivo genetic recombination and are described herein. The invention, thus, provides replicable vectors comprising a nucleotide sequence encoding the anti-antigen antibody obtained and isolated as described herein (e.g., a whole antibody, a heavy or light chain of an antibody, a heavy or light chain variable domain of an antibody, or a portion thereof, or a heavy or light chain CDR, a single chain Fv, or fragments or variants thereof), operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy chain, the entire light chain, or both the entire heavy and light chains.

The expression vector(s) can be transferred to a host cell by conventional techniques and the transfected cells are then cultured by conventional techniques to produce either the anti-antigen antibody. Thus, the invention includes host cells containing polynucleotide(s) encoding the anti-antigen antibody (e.g., whole antibody, a heavy or light chain thereof, or portion thereof, or a single chain antibody of the invention, or a fragment or variant thereof), operably linked to a heterologous promoter. In preferred embodiments, for the expression of entire antibody molecules, vectors encoding both the heavy and light chains may be co-expressed in the host cell for expression of the entire immunoglobulin molecule, as detailed below.

A variety of host-expression vector systems may be utilized to express anti-antigen antibody. Such host-expression systems represent vehicles by which the coding sequences of interest may be produced and subsequently purified, but also represent cells which may, when transformed or transfected, with the appropriate nucleotide coding sequences, express the anti-antigen antibody. These include, but are not limited to, microorganisms such as bacteria (e.g., *E. coli, B. subtilis*) transformed with recombinant bacteriophage DNA, plasmid DNA or cosmid DNA expression vectors containing sequences; yeast (e.g., *Saccharomyces, Pichia*) transformed with recombinant yeast expression vectors containing coding sequences; insect cell systems infected with recombinant virus expression vectors (e.g., baculovirus) containing coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, are used for the expression of the anti-antigen antibody. For example, mammalian cells such as Chinese hamster ovary cells (CHO), in conjunction with a vector such as the major intermediate early gene promoter element from human cytomegalovirus is an effective expression system (Foecking et al., Gene 45:101 (1986); Cockett et al., Bio/Technology 8:2 (1990)).

In bacterial systems, a number of expression vectors may be advantageously selected depending upon the intended use. For example, when a large quantity of a protein is to be produced (for either antibody production or encoded polypeptides of the improved LAMP Construct), vectors which direct the expression of high levels of fusion protein products that are readily purified may be desirable. Such vectors include, but are not limited to, the *E. coli* expression vector pUR278 (Ruther et al., EMBO 1. 2:1791 (1983)), in which the coding sequence may be ligated individually into the vector in frame with the lac Z coding region so that a fusion protein is produced; pIN vectors (Inouye & Inouye, Nucleic Acids Res. 13:3101-3109 (1985); Van Heeke & Schuster, J. Biol. Chem. 24:5503-5509 (1989)); and the like. pGEX vectors may also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or Factor Xa protease cleavage sites so that the cloned target gene product can be released from the GST moiety.

In an insect system, *Autographa californica* nuclear polyhedrosis virus (AcNPV) may be used as a vector to express an anti-antigen antibody or the encoded polypeptides of the improved LAMP Construct. The virus grows in *Spodoptera frugiperda* cells. Coding sequences may be cloned individually into non-essential regions (for example, the polyhedrin gene) of the virus and placed under control of an AcNPV promoter (for example, the polyhedrin promoter).

In mammalian host cells, a number of viral-based expression systems may be utilized express an anti-antigen antibody or the encoded polypeptides of the improved LAMP Construct. In cases where an adenovirus is used as an expression vector, the coding sequence of interest may be ligated to an adenovirus transcription/translation control complex, e.g., the late promoter and tripartite leader sequence. This chimeric gene may then be inserted in the adenovirus genome by in vitro or in vivo recombination.

Insertion in a non-essential region of the viral genome (e.g., region E1 or E3) will result in a recombinant virus that is viable and capable of expressing the anti-antigen antibody or the encoded polypeptides of the improved LAMP Construct in infected hosts (e.g., see Logan & Shenk, Proc. Natl. Acad. Sci. USA 8 1:355-359 (1984)).

Specific initiation signals may also be required for efficient translation of inserted coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Bittner et al., Methods in Enzymol. 153:51-544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed, to this end, eukaryotic host cells which possess the cellular machinery for proper processing of the primary transcript, glycosylation, and phosphorylation of the gene product may be used. Such mammalian host cells include, but are not limited to, CHO, VERY, BHK, Hela, COS, NSO, MDCK, 293, 3T3, W138, and in particular, breast cancer cell lines such as, for example, BT483, Hs578 T, HTB2, BT20 and T47D, and normal mammary gland cell line such as, for example, CRL7030 and HsS78 Bst.

For long-term, high-yield production of recombinant proteins, stable expression is preferred. For example, cell lines which stably express the express an anti-antigen antibody or the encoded polypeptides of the improved LAMP Construct may be engineered. Rather than using expression vectors which contain viral origins of replication, host cells can be transformed with a polynucleotide controlled by appropriate expression control elements (e.g., promoter, enhancer, sequences, transcription terminators, polyadenylation sites, etc.), and a selectable marker. Following the introduction of the foreign polynucleotide, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the anti-antigen antibody or the encoded polypeptides of the improved LAMP Construct.

A number of selection systems may be used, including but not limited to, the herpes simplex virus thymidine kinase (Wigler et al., Cell 11:223 (1977)), hypoxanthineguanine phosphoribosyltransferase (Szybalska & Szybalski, Proc. Natl. Acad. Sci. USA 48:202 (1992)), and adenine phosphoribosyltransferase (Lowy et al., Cell 22:817 (1980)) genes can be employed in tk-, hgprt- or aprt-cells, respectively. Also, antimetabolite resistance can be used as the basis of selection for the following genes: dhfr, which confers resistance to methotrexate (Wigler et al., Natl. Acad. Sci. USA 77:357 (1980); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 (Goldspiel et al., Clinical Pharmacy, 12: 488-505 (1993); Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62: 191-217 (1993); TIB TECH 11(5):155-215 (May; 1993)); and hygro, which confers resistance to hygromycin (Santerre et al., Gene 30:147 (1984)). Methods commonly known in the art of recombinant DNA technology may be routinely applied to select the desired recombinant clone, and such methods are described, for example; in Ausubel et al. (eds.), Current Protocols in Molecular Biology, John Wiley & Sons, N Y (1993); Kriegler, Gene Transfer and Expression, A Laboratory Manual, Stockton Press, N Y (1990); and in Chapters 12 and 13, Dracopoli et al. (eds), Current Protocols in Human Genetics, John Wiley & Sons, N Y (1994); Colberre-Garapin et al., J. Mol. Biol. 150:1 (1981).

The expression levels of either an anti-antigen antibody or the encoded polypeptides of the improved LAMP Construct can be increased by vector amplification (for a review, see Bebbington and Hentschel, *The Use Of Vectors Based On Gene Amplification For The Expression Of Cloned Genes In Mammalian Cells In DNA Cloning*, Vol. 3. (Academic Press, New York, 1987)). When a marker in the vector system expressing an anti-antigen antibody or the encoded polypeptides of the improved LAMP Construct is amplifiable, an increase in the level of inhibitor present in the host cell culture will increase the number of copies of the marker gene. Since the amplified region is associated with the coding sequence, production of the anti-antigen antibody express or the encoded polypeptides of the improved LAMP Construct will also increase (Crouse et al., Mol. Cell. Biol. 3:257 (1983)).

Other elements that can be included in vector sequences include heterologous signal peptides (secretion signals), membrane anchoring sequences, introns, alternative splice sites, translation start and stop signals, inteins, biotinylation sites and other sites promoting post-translational modifications, purification tags, sequences encoding fusions to other proteins or peptides, separate coding regions separated by internal ribosome reentry sites, sequences encoding "marker" proteins that, for example, confer selectability (e.g., antibiotic resistance) or sortability (e.g., fluorescence), modified nucleotides, and other known polynucleotide cis-acting features not limited to these examples.

The host cell may be co-transfected with two expression vectors of the invention, for example, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain is preferably placed before the heavy chain to avoid an excess of toxic free heavy chain (Proudfoot, Nature 322:52 (1986); Kohler, Proc. Natl. Acad. Sci. USA 77:2197 (1980)). The coding sequences for the heavy and light chains may comprise cDNA or genomic DNA or synthetic DNA sequences.

Once an anti-antigen antibody or the encoded polypeptides of the improved LAMP Construct has been produced by recombinant expression, it may be purified by any method known in the art for purification of a protein, for example, by chromatography (e.g., ion exchange, affinity (particularly by Protein A affinity and immunoaffinity for the specific antigen), and sizing column chromatography), centrifugation, differential solubility, or by any other standard technique for the purification of proteins. Further, an anti-antigen antibody or the encoded polypeptides of the improved LAMP Construct may be fused to heterologous polypeptide sequences described herein or otherwise known in the art to facilitate purification.

In one example, the anti-antigen antibody or the encoded polypeptides of the improved LAMP Construct may be fused with the constant domain of immunoglobulins (IgA, IgE, IgG, IgM), or portions thereof (CH1, CH2, CH3, or any combination thereof and portions thereof), or albumin (including but not limited to recombinant human albumin or fragments or variants thereof (see, e.g., U.S. Pat. No. 5,876,969, issued Mar. 2, 1999, EP Patent 0 413 622, and U.S. Pat. No. 5,766,883, issued Jun. 16, 1998), resulting in chimeric polypeptides. Such fusion proteins may facilitate purification and may increase half-life in vivo. This has been shown for chimeric proteins consisting of the first two domains of the human CD4-polypeptide and various domains of the constant regions of the heavy or light chains of mammalian immunoglobulins. See, e.g., EP394,827; Traunecker et al., Nature, 331:84-86 (1988). Enhanced delivery of an antigen across the epithelial barrier to the immune system has been demonstrated for antigens (e.g., insulin) conjugated to an FcRn binding partner such as IgG or Fe fragments (see, e.g., PCT Publications WO96/22024 and WO 99/04813). IgG Fusion proteins that have a disulfide-linked dimeric structure due to the IgG portion disulfide bonds have also been found to be more efficient in binding and neutralizing other molecules than monomeric polypeptides or fragments thereof alone. See, e.g., Fountoulakis et al., J. Biochem., 270:3958-3964 (1995). Nucleic acids encoding the anti-antigen antibody or the encoded polypeptides of the improved LAMP Construct described herein can also be recombined with a gene of interest as an epitope tag (e.g., the hemagglutinin ("HA") tag or flag tag) to aid in detection and purification of the expressed polypeptide. For example, a system described by Janknecht et al. allows for the ready purification of non-denatured fusion proteins expressed in human cell lines (Janknecht et al., 1991, Proc. Natl. Acad. Sci. USA 88:8972-897). In this system, the gene of interest is subcloned into a vaccinia recombination plasmid such that the open reading frame of the gene is translationally fused to an amino-terminal tag consisting of six histidine residues. The tag serves as a matrix-binding domain for the fusion protein. Extracts from cells infected with the recombinant vaccinia virus are loaded onto Ni2+ nitriloacetic acid-agarose column and histidine-tagged proteins can be selectively eluted with imidazole-containing buffers.

Administration

Vaccine material according to this invention may contain the immune stimulatory improved LAMP Constructs described herein or may be recombinant microorganisms, or antigen presenting cells which express the immune stimulatory improved LAMP Constructs. Preparation of improved LAMP Constructs containing vaccine material according to this invention and administration of such improved LAMP Constructs for immunization of individuals are accomplished according to principles of immunization that are well known to those skilled in the art.

Large quantities of these materials may be obtained by culturing recombinant or transformed cells containing replicons that express the improved LAMP Constructs described herein. Culturing methods are well-known to those skilled in the art and are taught in one or more of the documents cited above. The improved LAMP Construct vaccines are generally produced by culture of recombinant or transformed cells and formulated in a pharmacologically acceptable solution or suspension, which is usually a physiologically-compatible aqueous solution, or in coated tablets, tablets, capsules, suppositories or ampules, as described in the art, for example in U.S. Pat. No. 4,446,128, incorporated herein by reference. Administration may be any suitable route, including oral, rectal, intranasal or by injection where injection may be, for example, transdermal, subcutaneous, intramuscular or intravenous.

The improved LAMP Constructs are administered to a mammal in an amount sufficient to induce an immune response in the mammal. A minimum preferred amount for administration is the amount required to elicit antibody formation to a concentration at least 4 times that which existed prior to administration. A typical initial dose for administration would be 10-5000 micrograms when administered intravenously, intramuscularly or subcutaneously, or $10^5$ to $10^{11}$ plaque forming units of a recombinant vector, although this amount may be adjusted by a clinician doing the administration as commonly occurs in the administration of vaccines and other agents which induce immune responses. A single administration may usually be sufficient to induce immunity, but multiple administrations may be carried out to assure or boost the response.

The improved LAMP Construct vaccines may be tested initially in a non-human mammal (e.g., a mouse or primate). For example, assays of the immune responses of inoculated mice can be used to demonstrate greater antibody, T cell proliferation, and cytotoxic T cell responses to the improved LAMP Constructs than to wild type antigen. Improved LAMP Constructs can be evaluated in Rhesus monkeys to determine whether the vaccine formulation that is highly effective in mice will also elicit an appropriate monkey immune response. In one aspect, each monkey receives a total of 5 mg DNA per immunization, delivered IM and divided between 2 sites, with immunizations at day 0 and at weeks 4, 8, and 20, with an additional doses optional. Antibody responses, ADCC, CD4+ and CD8+ T-cell cytokine production, CD4+ and CD8+ T-cell antigen-specific cytokine staining can be measured to monitor immune responses to the vaccine.

Further description of suitable methods of formulation and administration according to this invention may be found in U.S. Pat. No. 4,454,116 (constructs), U.S. Pat. No. 4,681,762 (recombinant bacteria), and U.S. Pat. Nos. 4,592,002 and 4,920,209 (recombinant viruses).

Cancer Immunotherapy: Candidates for Prevention and Treatment

Candidates for cancer immunotherapy would be any patient with a cancer treated with either an improved LAMP Construct as described herein. Examples include patients with documented Epstein-Barr virus associated lymphomas, patients with HPV associated cervical carcinomas, patients with chronic HCV, or patients with a defined re-arrangement or mutation in an oncogene or tumor suppressor gene.

In preferred embodiments, cancers that can be treated using the vaccines described herein include, but are not limited to all stages of progression, including hyperplasia of an adenocarcinoma, sarcoma, skin cancer, melanoma, bladder cancer, brain cancer, breast cancer, uterine cancer, ovarian cancer, prostate cancer, lung cancer (including, but not limited to NSCLC, SCLC, squamous cell cancer), colorectal cancer, anal cancer, rectal cancer, cervical cancer, liver cancer, head and neck cancer, oral cancer, salivary gland cancer, esophageal cancer, pancreas cancer, pancreatic ductal adenocarcinoma (PDA), renal cancer, stomach cancer, kidney cancer, multiple myeloma or cerebral cancer.

It is envisioned that therapy with a vaccine composition comprising the improved LAMP Constructs could be utilized at any period during the course of the individual's cancer, once it is identified. It is also possible that in high risk patients, vaccination in order to prevent the subsequent emergence of a cancer.

Procedure for Therapy

In one embodiment, the improved LAMP Constructs could be injected into the patient at any suitable time during the course of their malignancy. For example, the improved LAMP Constructs would be injected at a stage when the tumor burden was low. In an alternative embodiment in which the improved LAMP Construct is introduced into the individual's antigen presenting cells, precursors to the antigen presenting cells or mature antigen presenting cells are drawn either from the individual's bone marrow or peripheral blood by vena puncture. These cells are established in culture followed by transduction with the improved LAMP Construct. Once transduction had occurred, these antigen presenting cells are injected back into the patient.

In a particularly preferred embodiment, the invention provides a method of treatment for a cancer patient having low tumor burden, such as early in the disease, after resection of a neoplastic tumor, or when the burden of tumor cells is otherwise reduced. In this method, a cell population containing autologous stem cells capable of differentiation into antigen presenting cells which will express MHC class II molecules is obtained from the patient. These cells are cultured and transformed by introducing an improved LAMP Construct to deliver the antigen to be associated with an MHC class II molecule either within the compartment/organelle or within another compartment/organelle to which the antigen is delivered.

The transfected stem cell population is then reintroduced into the patient, where the stem cells differentiate into antigen presenting cells which express MHC class II molecules complexed with $T_h$ epitopes from the antigen. The immune response to the antigen will be enhanced by enhanced stimulation of the helper T cell population.

More generally, in one embodiment, this invention provides a vaccine composition comprising the improved LAMP Construct for modulating an immune response in a mammal to an antigen (i.e., stimulating, enhancing, or reducing such a response).

Kits

The invention further comprises kits to facilitate performing the methods described herein. In one aspect, a kit comprises an improved LAMP Construct as described herein and a cell for receiving the improved LAMP Construct. The kit may additionally comprise one or more nucleic acids for engineering the cell into a professional APC. In one aspect, however, the cell is a professional APC. The cell may or may not express co-stimulatory molecules. In a preferred aspect, when the cell does not express co-stimulatory molecules, the antigen encoded by the improved LAMP Construct is an autoantigen. In another aspect, a panel of cells is provided expressing different MHC molecules (e.g., known to be expressed in human beings). In a further aspect, the kit comprises reagents to facilitate entry of the improved LAMP Constructs into a cell (e.g., lipid-based formulations, viral packaging materials, cells, and the like). In still a further aspect, one or more T cell lines specific for the antigen encoded by the improved LAMP Construct is provided, to verify the ability of the improved LAMP Construct to elicit, modulate, or enhance an immune response.

EXAMPLES

The invention will now be further illustrated with reference to the following examples. It will be appreciated that what follows is by way of example only and that modifications to detail may be made while still falling within the scope of the invention.

Example 1—Construction of LAMP Constructs

The improved LAMP Constructs illustrated in FIG. 1 can be constructed using standard molecular biology techniques well known to the skilled artisan. For example, plasmids comprising the polynucleotides can be designed to generate the different structures ILC-1 to ILC-6 shown in FIG. 1. The LAMP domains illustrated in FIG. 1 can be derived from the amino acid sequences shown in FIGS. 3-10. Preferably the LAMP domains are derived from the human LAMP proteins shown in FIGS. 3-10. It is envisioned that the corresponding domains can also be cloned from the orthologous sequences by identifying the equivalent domains when compared to the human sequence. An antigen of interest (including one or more antigens of interest) can be cloned into the described LAMP Constructs either individually or in combination.

Example 2—Immune Response Evaluation of Mice to LAMP Constructs

The ability of the improved LAMP Constructs as described in Example 1 can be tested for their ability to modulate an immune response. For example, Female BALB/c mice can be immunized i.d with 50 ug of the improved LAMP Constructs and 5 ug of GMCSF in 100 ul PBS using nanopass on day 0, 14 and 28. Experiment will then be terminated 4 weeks after the last dose.

Splenocytes (3×105/well) are stimulated with antigenic protein (10 ug/ml) in T cell media (RPMI with 10% heat inactivated FBS, 1% penicillin/streptomycin, and 1×2-ME), supernatants are collected 72 h after. Supernatants are diluted (400 ul supernatant +200 ul T cell media) and cytokines are evaluated by ELISA. IL-10 or IL-4 production can be measured via ELISPOT assay.

Example 3—Improved Antigen Presentation Using LAMP Constructs

Survivin is the smallest member of the Inhibitor of Apoptosis (IAP) family of proteins, involved in inhibition of apoptosis and regulation of cell cycle. These functional attributes make Survivin a unique protein exhibiting divergent functions i.e. regulating cell proliferation and cell death. Expression of Survivin in tumors correlates with not only inhibition of apoptosis and a decreased rate of cell death, but also resistance to chemotherapy and aggressiveness of tumors [1-6]. Therefore, Survivin is an important target for cancer vaccines and therapeutics [7-9]. Survivin has also been found to be prominently expressed on both human and embryonic stem cells and many somatic stem cell types indicating its yet unexplored role in stem cell generation and maintenance.

Cancer is a heterogeneous group of diseases where abnormal cell growth with potential to invade other body parts takes control of normal homeostasis and becomes fatal if not timely and rightly treated. Immunotherapy specifically targets tumor cells thereby avoiding collateral damage to non-tumor cells and inducing anti-tumor response. This anti-tumor response also has the potential to eradicate tumor at distant sites in the body which may not be possible by surgical resection. Induction or enhancement of anti-tumor immune response is a formidable challenge in cancer because tumor cells use multiple evasion strategies and avoid being detected or eliminated by immune cells.

The aim of this project is to evaluate in vivo immune response of all new generation of LAMP Constructs injected by I.D. in BALB/c mice. Specifically, mice were immunized with 50 μg of the tested constructs defined in the legend of FIG. 1 by intradermal injection. No adjuvants were added at this experiment. Six mice per group were administrated with vaccines every 7 days with total three dose in one month. Immune response was monitored 14 days after the last immunization.

The tested LAMP constructs were generated as described herein and the sequence of each tested construct is shown in FIG. 19. Survivin protein was purchased from MyBiosource (San Diego, Calif.). Survivin peptides were from GenScript (Piscataway, N.J.). Anti-survivin and m-IgGk-BP-HRP were bought from Santa Cruz Biotechnology (Dallas, Tex.), and mouse Monoclonal anti-LAMP-1/CD107a were from OriGene Technologies (Rockville, Md.). ELISPOT antibody pairs for IFNγ were from Biolegend. Fluorescently coupled CD3, CD4, CD8, CD44, CD62L, IFNγ, TNFα, granzyme B, CD69 monoclonal antibodies and Zombie aqua fixable viability kit were purchased from BioLegend (San Diego, Calif.). Goat anti-mouse IgG2a-HRP and goat anti-mouse IgG-HRP were purchased from Southern Biotechnologies (Birmingham, Ala.). Streptavidin-HRP was purchased from Thermo Fisher (Waltham, Mass.). SureBlue TMB microwell peroxidase substrate and TMB stop solution were purchased from KPL (Gaithersburg, Md.).

50 μg of each construct was used in a total volume of 100 ul per mouse per dose for Pharmajet. Mice were immunized with the vaccine by i.d. delivery on days 0, 7, and 14. Mice were bled on days 28 for serum collection. Serum was collected and stored in −30° C. Spleens were collected on day 28 at the termination of experiment and processed for ELISPOT and FACS to evaluate survivin specific T cell responses.

Measurement of plasma survivin-specific total IgG by ELISA.

The murine antibody response to survivin was assessed by indirect ELISA. ELISA plates (MaxiSorp) were coated with 2 μg/ml survivin (1-142) protein in carbonate-bicarbonate buffer overnight and then blocked with 2% BSA in PBS. Plasma samples were diluted moo in blocking buffer. Samples were detected with goat anti-mouse IgG-HRP (Southern Biotech, Birmingham, Ala.). Reaction was developed with SureBlue TMB Substrate and stopped with TMB Stop Solution from KPL (Gaithersburg, Md.). Plates were read (OD450) by using Epoch ELISA reader (BioTek, Winooski, Vt.).

Evaluation of antigen-specific T cell response.

To assess antigen-specific T cell response in the vaccinated mice, splenocytes from vaccinated mice were evaluated for antigen-specific IFNγ production by Enzyme-linked immunospot (ELISPOT). For ELISPOT assays, 96-well nitrocellulose plates (Millipore), were coated overnight at 4° C. with 100 μl/well of capture monoclonal antibody in PBS. The plates were washed three times with 200 μl/well PBS and blocked with 200 μl/well T cell media for at least 2 hrs at room temperature. Splenocytes were plated at $3\times10^5$ cells/well and co-cultured with 2 μg/mlpooled peptides of Survivin (Table 1) or concavalin A (0.125 μg/ml) or medium alone in a total volume of 200 μl/well T cell media (RPMI-1640 with L-Glutamine and HEPES (ATCC), 1% penicillin, 1% streptomycin, and $5\times10^{-5}$ M β-ME) at $3\times10^5$ cells/well for 48 h at 37° C. in 5% CO2. The plates were washed two times with 200 μl/well PBS and two times with 200 μl/well PBS-T (0.05% Tween/PBS). Diluted detection antibodies (50 μl/well in PBS-T/0.5% BSA) were added and plates were incubated for 2 hrs with shaking at room temperature. Plates were washed four times with PBS. Streptavidin-alkaline phosphatase diluted in PBS (50 μl/well) were added and incubated for 2 h. Plates were washed with PBS four times and developed with 50 μl/well of 3-Amino-9-Ethylcarbazole (AEC, BD Bioscience) substrate for 10 min. Color development was stopped by washing under running tap water. After drying 72 h at room temperature in dark, colored spots were counted using an AID ELISPOT High-Resolution Reader System and AID ELISPOT Software version 3.5 (Autoimmun Diagnostika GmbH).

TABLE 1

| Pooled peptides from Genscript | |
|---|---|
| Pooled P1 | Sur1-15, Sur11-25, Sur 21-35, Sur31-45, sur 41-55 |
| Pooled P2 | Sur51-65, sur61-75, sur71-85, sur81-95 |
| Pooled P3 | Sur91-105, sur 101-115, sur111-125, sur121-135, sur131-142 |
| Pooled P4 | Sur31-45, sur41-55 and sur51-65 |

Western blots.

293T cells were transfected with the tested constructs using lipofectamine 2000 reagents (Invitrogen). Transfected cells were washed with PBS and suspended in 200 μl of RIPA lysis buffer with halt proteinase inhibitors (Thermo Scientific, Waltham, Mass.). Lysates were centrifuges (700 g for 15 minutes at 4° C.), followed by measurement of protein concentration in the clarified supernatants using Pierce BCA protein Assay kit (ThermoFisher Scientific, Waltham, Mass.). 10 μg of protein was electrophoresed in pre-cast (4-20%) SDS-PAGE gels (BioRad, Hercules, Calif.), and transferred onto nitrocellulose membranes (BioRad) and immunoblotted with mAbs to hLAMP. Membranes were blocked with Detection™ block buffer (KPL) and probed with rabbit anti-human LAMP (Sino Biological Inc., Beijing, China) or anti-survivin antibody and goat anti-rabbit-HRP antibody, and then developed with TMB (KPL).

Flow cytometry.

Cells were first labelled with Zombie aqua fixable viability dye in PBS (1:500 dilution), followed by surface antibodies (1:100 dilution) in staining buffer (4% FBS, 2% rat serum, 2% mouse serum in PBS). For intracellular staining cells were stained with Zombie aqua, followed by surface staining, fixation with 4% paraformaldehyde, and stained with intracellular antibody in permeabilization buffer (PBS with 1% FCS 0.1% saponin). Samples were analyzed on a CytoFlex flow cytometer (Beckman Coulter) and analyzed using Kaluza software (Beckman Coulter).

Statistics.

Two-Way ANOVA test was performed using GraphPad Prism 6.0 software or R file to evaluate the statistical significance. Each mouse's RPMI result was deducted from the results of the antigen activation.

Study Design.

| | 18-ONC-019 Survivin Pharmajet validation in Balb/c mice (serum) | | | | | | | | IN | PJ = yes | DNA = yes | |
|---|---|---|---|---|---|---|---|---|---|---|---|---|
| T/W Group | Treatment | Concentration | Dose | Route | #Mice | Vol. | Mice ID | Eartag Feb. 16, 2018 | D-0 Feb. 26, 2018 | D-7 Mar. 5, 2018 | D-14 Mar. 12, 2018 | D-28 Mar. 26, 2018 |
| A | Control Vector | 2.52 mg/ml | 50 ug | Pharamajet | 6 | 100 ul | 7896-7901 | Eartag/ Pre few per group pool | 1st Immunization | 2nd Immunization | 3rd Immunization | Harvest spleen and serum |
| B | Survivin + LAMP | 3.4 mg/ml | 50 ug | Pharamajet | 6 | 100 ul | 7902-7907 | | | | | |
| C | Survivin preluminal LAMP | 5.88 mg/ml | 50 ug | Pharamajet | 6 | 100 ul | 7908-7913 | | | | | |
| D | LAMP-luminal-D1-survivin | 2 mg/ml | 50 ug | Pharamajet | 6 | 100 ul | 7914-7919 | | | | | |
| E | Survivin-LAMP-luminal domain 1 | 2 mg/ml | 50 ug | Pharamajet | 6 | 100 ul | 7997-8002 | | | | | |

-continued

| | 18-ONC-019 Survivin Pharmajet validation in Balb/c mice (serum) | | | | | | | | IN | PJ = yes | DNA = yes | |
|---|---|---|---|---|---|---|---|---|---|---|---|---|
| T/W Group | Treatment | Concentra-tion | Dose | Route | #Mice | Vol. | Mice ID | Eartag Feb. 16, 2018 | D-0 Feb. 26, 2018 | D-7 Mar. 5, 2018 | D-14 Mar. 12, 2018 | D-28 Mar. 26, 2018 |
| F | LAMP-hinge-survivin | 2 mg/ml | 50 ug | Pharama-jet | 6 | 100 ul | 8003-8008 | | | | | |

FIG. 14: Validation of the plasmids:

293T cells were transfected with the plasmids for 3 days. Transfected cells were lysed, and then electrophoresed in pre-cast SDS-PAGE gel. The proteins were transferred to nitrocellulose membranes and immunoblotted with mAbs to human LAMP (OriGene, #TA337108) or survivin Santa Cruz #17779). Molecular weight of LAMP=100 KD, Survivin=16 KD. FIG. 13 shows that all tested LAMP constructs produced appropriately sized protein.

FIGS. 15 and 16: Tested LAMP Constructs induce Th1 effector T cells producing IFNγ. Female BALB/c mice were immunized i.d with 50 μg of the indicated constructs in 100 μl PBS via Pharmajet device on day 0, 7 and 14. Experiment was terminated 14 days after the last dose. Splenocytes ($3\times10^5$/well) were stimulated with survivin pooled peptides (4 μg/ml) in T cell media (RPMI with 10% heat inactivated FBS, 1% penicillin/streptomycin, and 1×13-ME), for 48 h. A. IFNγ production by spots. B. IFNγ production induced by all pooled peptides (bar figure from A). n=6 per group. Two way ANOVA (R file) was used for statistical analysis. FIG. 14 shows that all tested LAMP constructs induced a robust T cell response as shown by IFNγ production.

We unexpectedly found that after 3 dose of the improved LAMP Constructs (one week apart), a robust Th1 type response elicited by tested LAMP Constructs, especially ILC-4 where the hinge sequence was replaced by survivin gene. More interestingly, improved LAMP Construct ILC-4 appears to recognize the survivin epitopes from N-terminal to C-terminal, and induce T cell response against human survivin peptide sequence which is 100% identical to the mouse. We also found longer (72 hrs) stimulation of frozen-thawed splenocyte cells with survivin peptides, ILC-4 showed significant higher IFNγ production than the first generation of LAMP-survivin (see FIG. 19). Specifically, FIG. 16 shows that the all improved LAMP Constructs tested showed higher T cell response with ILC-4 having the best activity as this constructed elicited a significantly higher T cell response against all survivin peptides pools. Moreover, contrary to what was known in the art, removal of the second homology domain of the luminal domain created an improved LAMP construct that elicited a more robust immune response as compared to the complete LAMP construct (see, results for ILC-2 and ILC-3). Frozen splenocytes (4×105/well) were stimulated with pooled peptides 4 (4 μg/ml) in T cell media (RPMI with 10% heat inactivated FBS, 1% penicillin/streptomycin, and 1×β-ME), for 48 h. n=6 per group. Two way ANOVA was used for statistical analysis. *p<0.05, p<0.01, *p<0.005, ****p<0.0001

FIG. 17. CD4 T cells are the major source of IFNγ producing cells.

Female BALB/c mice were immunized i.d with 50 μg of the indicated vaccines in 100 μl PBS via Pharmajet device on day 0, 7 and 14. Experiment was terminated 14 days after the last dose. Splenocytes ($1\times10^6$/well) were stimulated with pooled peptides 1 (4 μg/ml) in T cell media (RPMI with 10% heat inactivated FBS, 1% penicillin/streptomycin, and 1×13-ME) over night, followed by adding monesin and brefeldin A and culturing for additional 5 h. Cells were harvested and stained by Zombie, surface marker, and intracellular staining according to ITI staining protocol. Cells are gated on memory CD4 T cells (CD4+CD44+CD62L−) or CD8 T cells (CD8+CD44+CD62L−). Data is representative of one mouse in each group. While there is an increase in CD8 effector memory cells in vaccinated mice with the various constructs, IFNγ production is more pronounced in the CD4 T cell population.

FIG. 18: Improved LAMP Constructs produced stronger survivin-specific total IgG response in BALB/c mice.

Female BALB/c mice were immunized i.d with 50 μg of the indicated vaccines in 100 μl PBS via Pharmajet device on day 0, 7 and 14. Experiment was terminated 14 days after the last dose. Mice were bleed on days 28. Serum was separated and stored in −30° C. Total IgG and IgG2a were determined in serum by ELISA. Briefly, ELISA plates were coated with 2 μg/ml survivin (1-142aa), blocked with PBS/2% BSA, serum (1:100 dilution in blocking buffer) were evaluated by HRP-conjugated goat anti mouse IgG (1:6000) and IgG2a (1:11000). n=6 mice per group. p<0.01, *p<0.005, **p<0.0001. Importantly and contrary to what was known in the art, FIG. 18** shows that fragments of the luminal domain worked better than use of the complete luminal domain (i.e., compare complete LAMP construct with constructs ILC-2 and IL-3). Moreover and unexpectedly, insertion of the antigen between the two homology domains of the luminal domain generated the strongest antibody response (see, ILC-4).

REFERENCES RELIED ON IN THIS SECTION

1. Kami K, Doi R, Koizumi M, Toyoda E, Mori T, Ito D, et al. Survivin expression is a prognostic marker in pancreatic cancer patients. Surgery. 2004; 136(2):443-8. doi: 10.1016/j.surg.2004.05.023. PubMed PMID: 15300213.
2. Zhang S Q, Qiang S Y, Yang W B, Jiang J T, Ji Z Z. [Expression of survivin in different stages of carcinogenesis and progression of breast cancer]. Ai Zheng. 2004; 23(6):697-700. PubMed PMID: 15191674.
3. Zhang X, Zhong L, Hu K, Li Q. [Expression of survivin and its correlation with apoptosis in non-small cell lung cancer]. Zhongguo Fei Ai Za Zhi. 2004; 7(2):138-41. doi: 10.3779/j.issn.1009-3419.2004.02.14. PubMed PMID: 21215009.
4. Kishi H, Igawa M, Kikuno N, Yoshino T, Urakami S, Shiina H. Expression of the survivin gene in prostate cancer: correlation with clinicopathological characteristics, proliferative activity and apoptosis. J Urol. 2004; 171(5):1855-60. doi: 10.1097/01.ju.0000120317.88372.03. PubMed PMID: 15076293.
5. Asanuma K, Tsuji N, Endoh T, Yagihashi A, Watanabe N. Survivin enhances Fas ligand expression via up-regulation of specificity protein 1-mediated gene transcription in colon cancer cells. J Immunol. 2004; 172(6):3922-9. PubMed PMID: 15004200.

6. Miyachi K, Sasaki K, Onodera S, Taguchi T, Nagamachi M, Kaneko H, et al. Correlation between survivin mRNA expression and lymph node metastasis in gastric cancer. Gastric Cancer. 2003; 6(4):217-24. doi: 10.1007/s10120-003-0255-2. PubMed PMID: 14716515.
7. Badana A K, Chintala M, Gavara M M, Naik S, Kumari S, Kappala V R, et al. Lipid rafts disruption induces apoptosis by attenuating expression of LRP6 and survivin in triple negative breast cancer. Biomed Pharmacother. 2017; 97:359-68. doi: 10.1016/j.biopha.2017.10.045. PubMed PMID: 29091885.
8. Cai J P, Wang Y D, Zhang X, Xue H Z. [Expression of P16 and survivin in liver cancer and their clinical significance]. Zhonghua Gan Zang Bing Za Zhi. 2017; 25(10): 778-80. doi: 10.3760/cma.j.issn.1007-3418.2017.10.013. PubMed PMID: 29108210.
9. Cho H J, Kim H R, Park Y S, Kim Y H, Kim D K, Park S I. Prognostic value of survivin expression in stage III non-small cell lung cancer patients treated with platinum-based therapy. Surg Oncol. 2015; 24(4):329-34. doi: 10.1016/j.suronc.2015.09.001. PubMed PMID: 26690822.
10. Godinho R M, Matassoli F L, Lucas C G, Rigato P O, Goncalves J L, Sato M N, et al. Regulation of HIV-Gag expression and targeting to the endolysosomal/secretory pathway by the luminal domain of lysosomal-associated membrane protein (LAMP-1) enhance Gag-specific immune response. PLoS One. 2014; 9 (6): e99887. doi: 10.1371/journal.pone.0099887. PubMed PMID: 24932692; PubMed Central PMCID: PMCPMC4059647.

Example 4: Therapeutic Treatment of LAMP Constructs

Female BALB/c mice can be inoculated s.c with syngeneic 7000 4 T1 mammary carcinoma cells on day 0. Vaccine 50 ug and 5 ug of GMCSF in 100 ul PBS is given i.d using nanopass once the tumors are palpable. Primary tumors are measured with a caliper and tumor volume is calculated using the formula p/6 (length×width)3/2. Average tumor volume as a function of days after tumor inoculation can be measured. A Kaplan-Meier plot can be used to show overall survival at the point of termination.

Example 5—Prime/Boost Protocol

Herpesvirus entry mediator (HVEM), also known as tumor necrosis factor receptor superfamily member 14 (TNFRSF14) or CD270, is a human cell surface receptor of the TNF-receptor superfamily. In recent years, HVEM has been found highly expressed on hematopoietic cells and a variety of parenchymal cells, such as breast, melanoma, colorectal, and ovarian cancer cells, as well as gut epithelium. HVEM is a bidirectional protein, either inhibiting or stimulating T cells, through binding to BTLA or LIGHT (TNFSF14).

We generated a DNA vaccine encoding HVEM-LAMP to generate an antibody which could block the inhibitory function of HVEM for tumor therapeutic applications. We hypothesized that LAMP will promote the antibody response by enhancing the affinity of HVEM specific antibodies and/or expanding the repertoire of B cell epitopes in the HVEM protein. In this study, we compared the immunogenicity of HVEM encoding plasmid with and without LAMP. The HVEM sequence:

```
HVEM amino acids 39-202
                                          (SEQ ID NO: 114)
LPSCKEDEYPVGSECCPKCSPGYRVKEACGELTGTVCEPCPPGTYIAHLN

GLSKCLQCQMCDPAMGLRASRNCSRTENAVCGCSPGHFCIVQDGDHCAAC

RAYATSSPGQRVQKGGTESQDTLCQNCPPGTFSPNGTLEECQHQTKCSWL

VTKAGAGTSSSHWV
```

Plasmids encoding HVEM-LAMP and HVEM and recombinant HVEM protein were designed by ITI and produced by NTC (Lincoln, Nebr.). Polynucleotides encoding the following HVEM sequence was cloned into the improved LAMP Constructs described herein:

Goat anti-mouse IgG-HRP was purchased from Southern Biotechnologies (Birmingham, Ala.). SureBlue TMB microwell peroxidase substrate and TMB stop solution were purchased from KPL (Gaithersburg, Md.). ELISPOT plates were ordered from EMD Millipore (Billerica, Mass., Cat. No. MAIPS4510). IFN-γ antibody pair used in ELISPOT was purchased from BioLegend (San Diego, Calif.) and clones AN18 and R46 A2 were used as coating and detection, respectively. Streptavidin-HRP and AEC substrate were purchased from BD Biosciences (San Jose, Calif.).

Six to eight week old female Balb/c mice were purchased from Harlan Laboratories (Frederick, Mass.) and maintained at animal facility in Immunomic Therapeutics, Inc. (Rockville, Mass.). Mice (n=6) were treated with ion/dose of HVEM-LAMP, HVEM, or LAMP vector control by Ichor electroporation IM delivery at days 0, 7, and 14. On day 35, mice were boosted with 5 μg HVEM protein in the presence of Alum by i.p. injection. On day 28 and 49, mice were bled and sera were isolated for antibody detection. Mice were sacrificed on day 56 and splenocytes were tested for IFN-γ production by ELISPOT.

ELISA procedure was followed by Su et al., J of Immunol Res; (10):1-15 (2016). Plates were coated with 5 μg/ml HVEM protein. Data were analyzed by using Microsoft Excel and Prism 6 software.

The primary aim of this study was to compare the antibody profiles between HVEM-LAMP and HVEM. On day 28, HVEM-LAMP vaccinated mice produced significant higher level of HVEM specific IgG antibody than that of the HVEM group (Figure ii). After a protein boost, the HVEM specific antibody was increased about 1000-fold in HVEM immunized mice and the mean titer was changed from 100 to 108000. This result indicates that the immune memory was induced by the HVEM DNA plasmid. Although HVEM DNA alone only induced a minimal antibody response, protein boost rapidly recalled the immune memory. On the other hand, HVEM-LAMP group again exhibited a significant higher titer than the HVEM and LAMP groups, the mean titer is 5 folds of the HVEM group, indicating the power of LAMP in enhancing antibody response (FIG. 12).

Additionally serum samples (Day 49) from HVEM+LAMP or HVEM alone immunized/HVEM protein boosted mice were pooled and tested for peptide mapping. Twelve peptides were found to be bound to the pooled serum (mouse IgG reaction) and seven of the twelve peptides showed strong binding affinity. HVEM+LAMP alters the binding affinity of peptides 17. 24, 25, and 28 as compared to HVEM alone as shown in FIG. 13. These changes may have physiological effects in protecting tumor growth.

In conclusion, data from this study suggest that two constructs were expressed in vivo and LAMP significantly improved the humoral immune response.

Example 6: Production of an Antibody from a Polypeptide

Anti-antigen antibodies can be prepared by a variety of standard methods of raising antibodies using animal injection. (See, Current Protocols, Chapter 2.) For example, cells expressing an improved LAMP Construct comprising an antigen described herein is administered to a non-human vertebrate to induce the production of sera containing polyclonal antibodies. In a preferred method, a preparation of the LAMP/antigen protein is prepared and purified to render it substantially free of natural contaminants. Such a preparation is then introduced into the non-human vertebrate to produce polyclonal antisera of greater specific activity.

In the most preferred method, the anti-antigen antibodies of the present invention are monoclonal antibodies (or protein binding fragments thereof). Such monoclonal antibodies can be prepared using hybridoma technology. (Kohler et al., Nature 256:495 (1975); Kohler et al., Eur. J. Immunol. 6:511 (1976); Kohler et al., Eur. J. Immunol. 6:292 (1976); Hammerling et al., in: Monoclonal Antibodies and T-Cell Hybridomas, Elsevier, N.Y., pp. 563-681 (1981).) In general, such procedures involve immunizing a non-human vertebrate animal (preferably a rabbit, mouse, cow, camel, llama) with an improved LAMP Construct comprising an antigen, the encoded polypeptide of an improved LAMP Construct comprising an antigen or, more preferably, with an improved LAMP Construct-expressing cell. Such cells may be cultured in any suitable tissue culture medium; however, it is preferable to culture cells in Earle's modified Eagle's medium supplemented with 10% fetal bovine serum (inactivated at about 56 degrees C.), and supplemented with about 10 g/l of nonessential amino acids, about 1,000 U/ml of penicillin, and about 100 ug/ml of streptomycin.

The splenocytes of such non-human vertebrate host (e.g, mice) are extracted and fused with a suitable myeloma cell line. Any suitable myeloma cell line may be employed in accordance with the present invention; however, it is preferable to employ the parent myeloma cell line (SP20), available from the ATCC™. After fusion, the resulting hybridoma cells are selectively maintained in HAT medium, and then cloned by limiting dilution as described by Wands et al. (Gastroenterology 80:225-232 (1981).) The hybridoma cells obtained through such a selection are then assayed to identify clones which secrete antibodies capable of binding the antigen.

It will be appreciated that Fab and F(ab')2 and other fragments of the anti-antigen antibodies may be used according to the methods disclosed herein. Such fragments are typically produced by proteolytic cleavage, using enzymes such as papain (to produce Fab fragments) or pepsin (to produce F(ab')2 fragments). Alternatively, secreted protein-binding fragments can be produced through the application of recombinant DNA technology or through synthetic chemistry.

For in vivo use of antibodies in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art. (See, for review, Morrison, Science 229:1202 (1985); Oi et al., BioTechniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985).)

Example 7: Use of Polvnucleotides to Generate Polyclonal and Monoclonal Antibodies Methods of directly injecting polynucleotides into animals are well described in the art. See, for example, U.S. Pat. Nos. 5,676,954; 6,875,748; 5,661,133. For example, a polynucleotide encoding an improved LAMP Construct comprising an antigen can be injected into the quadriceps muscles of restrained awake mice (female 6-12 week old BALB/c or Nude, nu/nu, from Harlan Sprague Dawley, Indianapolis, Ind.). In one embodiment, 50 μg of a polynucleotide in 50 μl solution using a disposable sterile, plastic insulin syringe and 28G ½ needle (Becton-Dickinson, Franklin Lakes, N.J., Cat. No. 329430) fitted with a plastic collar cut from a micropipette tip can be used to inject the mice, as described in Hartikka, J., et al., Hum. Gene Ther. 7:1205-1217 (1996)).

Alternatively, 6-week old Sprague Dawley female mice (body weight 20-25 grams) can be given 5000 ppm ZnOSO4 in their drinking water beginning 24 hours prior to injection. This amount of zinc has been shown to be able to activate the metallothionein promoter. Each mouse is then injected intravenously through a tail vein puncture with a 25 gauge needle with 30 μg of a polynucleotide encoding an improved LAMP Construct comprising an antigen complexed with 150 μg liposome (Lipofection™) in a total volume of 30 μl. Animal care should be maintained throughout the study and should be performed in compliance with the "Guide for the Use and Care of Laboratory Animals", Institute of Laboratory Animal Resources, Commission on Life Sciences, National Research Council, National Academy Press.

After the injected polynucleotide encoding the improved LAMP Construct comprising an antigen is delivered into the cells in the animal, the antigen is delivered to the endosome/lysosome, processed and presented to the immune system. The improved LAMP Construct comprising an antigen can then stimulate the production of antibodies specific to the antigen. These antibodies can be isolated and used as a polyclonal mixture or further isolated into single species or monoclonals. The process of the immune response and production of antibodies against foreign antigens in vivo are well known in the art.

In a third animal model, Balb/c 3T3 A31 cells are transfected by electroporation with a polynucleotide encoding an improved LAMP Construct comprising an antigen. G418 resistant clones expressing LAMP Construct comprising an antigen are identified by their ability to bind human RBC. To generate polyclonal antibodies, Balb/c mice are immunized twice intraperitoneally, at an interval of 14 days, with $10^7$ cells comprising the improved LAMP Construct comprising an antigen. After a final boost, the immune serum is collected, IgG is purified by protein G Sepharose and passed over an antigen column prepared by coupling 1.0 mg purified antigen to cyanogen bromide activated Sepharose CL-4B. Bound IgG can be eluted with 0.1 M glycine buffer pH 2.5 and neutralized with 0.1 volumes of 0.1 M Tris pH 8.0. To generate a monoclonal antibody (mAb), Balb/c mice are immunized with LAMP Construct comprising an antigen and hybridomas are generated by fusing immune spleen cells with the SP2 myeloma following standard methods (28). A positive well reacting specifically with an antigen can be identified by enzyme-linked immunosorbent assays as described in the art. The hybridoma is cloned three times by limiting dilution to produce an antibody.

Example 8: Immunization of an Improved LAMP Construct Comprising an Antigen

Methods of raising antibodies in mammals are well known in the art. In one example, polyclonal antiserum against LAMP Construct comprising an antigen is raised by immunization of pathogen free rabbits with a total of 500 μg an improved LAMP Construct comprising an antigen over a period of two months. For example, the improved LAMP Construct comprising an antigen can be dissolved in PBS and emulsified with an equal volume of Freund's adjuvant. After the final booster, the serum of the rabbits can be separated to determine the titer of the polyclonal antiserum.

In an additional animal model, groups of 5 mice (C57BL/6J; Jackson Labs) can be subcutaneously immunized with 5 μg of endotoxin-free LAMP Construct comprising an antigen emulsified in alum. Three weeks later, mice are bled and the presence of anti-antigen specific antibodies can be determined by titering the seras by ELISA (direct binding of antibodies in sera to wild type BPTI or APP-KI coated, directly or indirectly (via a biotinylated tag and streptavidin), on the wells).

To obtain monoclonal antibodies, 4-6 week old Balb/c mice can be immunized with an improved LAMP Construct comprising an antigen (for example 4 times with 2 week intervals with 10-100 μg/injection dissolved in Freunds complete adjuvant for the first injection, and Freund's incomplete adjuvant for subsequent immunizations). Splenocytes are isolated and fused with a fusion cell line such as Sp2/0 myeloma cells, followed by limiting dilution. Growing clones are screened using for example an enzyme-linked immunosorbant assay (ELISA). 96 cells plates are coated with an improved LAMP Construct comprising an antigen or with a control protein. The culture supernatant is added, followed by washing and addition of a labeled anti-mouse antibody for detection. After limited dilution cloning of the anti-antigen antibody producing stable hybridomas are obtained. From each cell, supernatant is collected and by affinity chromatography using protein A sepharose columns monoclonal antibodies can be purified.

Variations, modifications, and other implementations of what is described herein will occur to those of ordinary skill in the art without departing from the spirit and scope of the invention and the claims. All of the patents, patent applications, international applications, and references identified are expressly incorporated herein by reference in their entireties.

What is claimed:

1. A lysosomal associated membrane protein ("LAMP") Construct comprising two homology domains of a luminal domain of a LAMP protein, and an antigenic domain heterologous to the LAMP protein, wherein the antigenic domain is placed between the two homology domains.

2. The LAMP Construct of claim 1, wherein the LAMP Construct further comprises a Transmembrane Domain of a LAMP Protein.

3. The LAMP Construct of claim 1, wherein the LAMP Construct further comprises a signal sequence.

4. The LAMP Construct of claim 1, wherein the LAMP Construct further comprises Cytoplasmic Domain of a LAMP Protein.

5. The LAMP Construct of claim 1, wherein the LAMP protein is selected from LAMP-1, LAMP2, LAMP-3, lysosomal integral membrane protein-2 ("LIMP 2"), Macrosailin, Endolyn, LAMP5 or limbic system-associated membrane protein ("LIMBIC").

6. The LAMP Construct of claim 5, wherein the LAMP Protein is selected from any one of SEQ ID NO:1-113.

7. The LAMP Construct of claim 5, wherein the LAMP Protein is at least about 70%, at least about 75%, at least about 80%, at least about 85%, at least about 90%, at least about 95%, 96%, 97%, 98% or 99% identical to SEQ ID NO:1-113.

8. The LAMP Construct of claim 1, wherein the LAMP Construct comprises LAMP-1 Homology Domain 1 and LAMP-1 Homology Domain 2.

9. The LAMP Construct of claim 1, wherein the antigenic domain is Survivin or Herpesvirus entry mediator ("HVEM").

10. The LAMP Construct of claim 9, wherein the LAMP Construct comprises SEQ ID NO: 119.

11. A polynucleotide encoding the LAMP Construct of claim 1.

12. The polynucleotide of claim 11, wherein the polynucleotide is DNA.

13. The polynucleotide of claim 11, wherein the polynucleotide is mRNA.

14. A host cell comprising the polynucleotide of any one of claims 11.

15. A composition comprising the LAMP Construct of claim 1.

16. A composition comprising the polynucleotide of claim 11.

17. A composition comprising the host cell of claim 14.

18. A method of treating a subject having a disease or a disorder, wherein the method comprises administering to a subject in need thereof the LAMP Construct of claim 1 in an amount sufficient to reduce or treat the disease or disorder.

19. The method of claim 18, wherein the method comprises a priming step and at least one boosting step.

20. The method of claim 19, wherein the LAMP Construct as defined in claim 1 is used in the priming step.

21. The method of claim 19, wherein the boosting step comprises administration of an antigen, a polynucleotide encoding a LAMP Construct, a polypeptide encoded by an LAMP Construct, or a cell comprising the LAMP Construct.

22. The method of claim 19, wherein the antigen used to prime is the same that is used to boost.

23. The method of claim 19, wherein the antigen used to prime is derived from the same protein as a second antigen used to boost.

* * * * *

UNITED STATES PATENT AND TRADEMARK OFFICE

CERTIFICATE OF CORRECTION

PATENT NO. : 11,203,629 B2
APPLICATION NO. : 16/607082
DATED : December 21, 2021
INVENTOR(S) : Heiland It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 23 days.

Signed and Sealed this
Seventh Day of February, 2023

Katherine Kelly Vidal

Katherine Kelly Vidal
*Director of the United States Patent and Trademark Office*